US010934279B2

(12) United States Patent
Aspnes et al.

(10) Patent No.: US 10,934,279 B2
(45) Date of Patent: *Mar. 2, 2021

(54) GLP-1 RECEPTOR AGONISTS AND USES THEREOF

(71) Applicant: Pfizer Inc., New York, NY (US)

(72) Inventors: Gary Erik Aspnes, Biberach an der Riss (DE); Scott W. Bagley, Mystic, CT (US); John M. Curto, Mystic, CT (US); David James Edmonds, Arlington, MA (US); Mark E. Flanagan, Gales Ferry, CT (US); Kentaro Futatsugi, Sharon, MA (US); David A. Griffith, Sudbury, MA (US); Kim Huard, Berkeley, CA (US); Yajing Lian, Waterford, CT (US); Chris Limberakis, Pawcatuck, CT (US); Allyn T. Londregan, Barrington, RI (US); Alan M. Mathiowetz, Waltham, MA (US); David W. Piotrowski, Waterford, CT (US); Roger B. Ruggeri, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/436,311

(22) Filed: Jun. 10, 2019

(65) Prior Publication Data

US 2019/0382384 A1 Dec. 19, 2019

Related U.S. Application Data

(60) Provisional application No. 62/851,206, filed on May 22, 2019, provisional application No. 62/846,944, filed on May 13, 2019, provisional application No. 62/684,696, filed on Jun. 13, 2018.

(51) Int. Cl.

| | |
|---|---|
| ***C07D 405/12*** | (2006.01) |
| ***C07C 53/06*** | (2006.01) |
| ***C07C 53/10*** | (2006.01) |
| ***C07C 215/40*** | (2006.01) |
| ***C07D 405/14*** | (2006.01) |
| ***C07D 413/14*** | (2006.01) |
| ***C07D 471/04*** | (2006.01) |

(52) U.S. Cl.

CPC ............ *C07D 405/12* (2013.01); *C07C 53/06* (2013.01); *C07C 53/10* (2013.01); *C07C 215/40* (2013.01); *C07D 405/14* (2013.01); *C07D 413/14* (2013.01); *C07D 471/04* (2013.01); *C07B 2200/13* (2013.01)

(58) Field of Classification Search

CPC ........ C07D 405/12; C07C 53/06; C07C 53/10

USPC .......................................................... 546/273

See application file for complete search history.

(56) References Cited

U.S. PATENT DOCUMENTS

| | | | | |
|---|---|---|---|---|
| 5,714,498 | A | 2/1998 | Kulagowski et al. | |
| 6,362,196 | B1 | 3/2002 | Kulagowski | |
| 6,596,722 | B2 | 7/2003 | Moltzen et al. | |
| 7,160,879 | B2 | 1/2007 | DeSimone et al. | |
| 7,425,554 | B2 | 9/2008 | Kawahara et al. | |
| 10,676,465 | B2 * | 6/2020 | Aspnes | C07C 215/40 |
| 10,683,281 | B2 * | 6/2020 | Aspnes | C07D 405/14 |
| 2004/0077654 | A1 | 4/2004 | Bouillot et al. | |
| 2007/0244133 | A1 | 10/2007 | Bower et al. | |
| 2008/0280933 | A1 | 11/2008 | Efremov et al. | |
| 2015/0376198 | A1 | 12/2015 | Roberts et al. | |
| 2017/0275279 | A1 | 9/2017 | Buckner et al. | |
| 2018/0305334 | A1 | 10/2018 | Larsen et al. | |

FOREIGN PATENT DOCUMENTS

| | | | |
|---|---|---|---|
| CA | 3038479 | 3/2018 | |
| WO | 2010/114824 | 10/2010 | |
| WO | 2011/097491 | 8/2011 | |
| WO | WO-2011097491 A1 * | 8/2011 | A61K 2300/00 |

OTHER PUBLICATIONS

Lopez-Rodriguez et al., "Design & synthesis of new benzimidazole-arylpiperazine derivatives acting as mixed 5-HT1A/5-HT3 ligands", Bioorganic and Medicinal Chemistry Letters, vol. 13(9) pp. 3177-3180 (2003).

Lopez-Rodriguez et al.,"Benzimidazole derivatives. Part 5: Design & synthesis of new benzimidazole-arylpiperazine derivatives acting as mixed 5-HT1A/5-HT3 ligands", Bioorganic and Medicinal Chemistry, vol. 12(19), pp. 5181-5191 (2004).

Compound 1; Chemical Abstracts Services (CAS): American Chemical Society, Columbus, Ohio, Aug. 6, 2017; Registry No. 2108925-34-2; Chemical name: (1R,4R)-rel-2-(1,3-benzodioxol-5-yl)-5-[(1-methyl-1H-benzimidazol-2-yl)methyl]-2,5-Diazabicyclo[2.2.1]heptan-3-one.

Compound 2; Chemical Abstracts Services (CAS): American Chemical Society, Columbus, Ohio, Jan. 23, 2014; Registry No. 1527580-20-6; Chemical name: (3R,4R)-rel-1-(1H-benzimidazol-2-ylmethyl)-4-(1,3-benzodioxol-5-yl)-3-piperidinol.

Compound 3; Chemical Abstracts Services (CAS): American Chemical Society, Columbus, Ohio, Jan. 17, 2014; Registry No. 1523524-38-0; Chemical name: (3R,4R)-rel-4-(1,3-benzodioxol-5-yl)-1-[(1-methyl-1H-benzimidazol-2-yl)methyl]-3-piperidinol.

Pfizer Inc./Feng Shao, Notice of Co-Pending Applications, Sep. 16, 2019.

PCT/IB2019/054867 International Search Report and Written Opinion dated Aug. 9, 2019.

* cited by examiner

*Primary Examiner* — Rita J Desai

(74) *Attorney, Agent, or Firm* — Feng Shao

(57) ABSTRACT

Provided herein are 6-carboxylic acids of benzimidazoles and 4-aza-, 5-aza-, and 7-aza-benzimidazoles as GLP-1R agonists, processes to make said compounds, and methods comprising administering said compounds to a mammal in need thereof.

16 Claims, 2 Drawing Sheets

GLP-1 RECEPTOR AGONISTS AND USES THEREOF

This application claims the benefit of priority to U.S. Provisional Patent Application Ser. No. 62/684,696 filed Jun. 13, 2018, to U.S. Provisional Patent Application Ser. No. 62/846,944 filed May 13, 2019, and to U.S. Provisional Patent Application Ser. No. 62/851,206 filed May 22, 2019, the disclosure of each of which is hereby incorporated by reference in its entirety.

FIELD OF INVENTION

Provided herein are 6-carboxylic acids of benzimidazoles and 4-aza-, 5-aza-, and 7-aza-benzimidazoles as GLP-1R agonists, processes to make said compounds, and methods comprising administering said compounds to a mammal in need thereof.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. *Use of Antidiabetic Drugs in the U.S.,* 2003-2012, Diabetes Care 2014, 37, 1367-1374). These may be grouped into six major classes, each acting through a different primary mechanism: (A) Insulin secretogogues, including sulphonyl-ureas (e.g., glipizide, glimepiride, glyburide), meglitinides (e.g., nateglidine, repaglinide), dipeptidyl peptidase IV (DPP—IV) inhibitors (e.g., sitagliptin, vildagliptin, alogliptin, dutogliptin, linagliptin, saxogliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP—IV inhibitors have limited efficacy. Marketed GLP-1R agonists are peptides administered by subcutaneous injection. Liraglutide is additionally approved for the treatment of obesity. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents, and frequent use may also lead to weight gain and carries a risk of hypoglycemia. (F) sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs have limited efficacy and do not address the most important problems, the declining 1-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier, et al. *Biodrugs.* 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. *Diabetes.* 2001. 50; 609-613).

Hoist (*Physiol. Rev.* 2007, 87, 1409) and Meier (*Nat. Rev. Endocrinol.* 2012, 8, 728) describe that GLP-1 receptor agonists, such as GLP-1, liraglutide and exendin-4, have 3 major pharmacological activities to improve glycemic control in patients with T2DM by reducing fasting and post-prandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need for an easily-administered prevention and/or treatment for cardiometabolic and associated diseases.

DETAILED DESCRIPTION OF THE INVENTION

Figure 1:
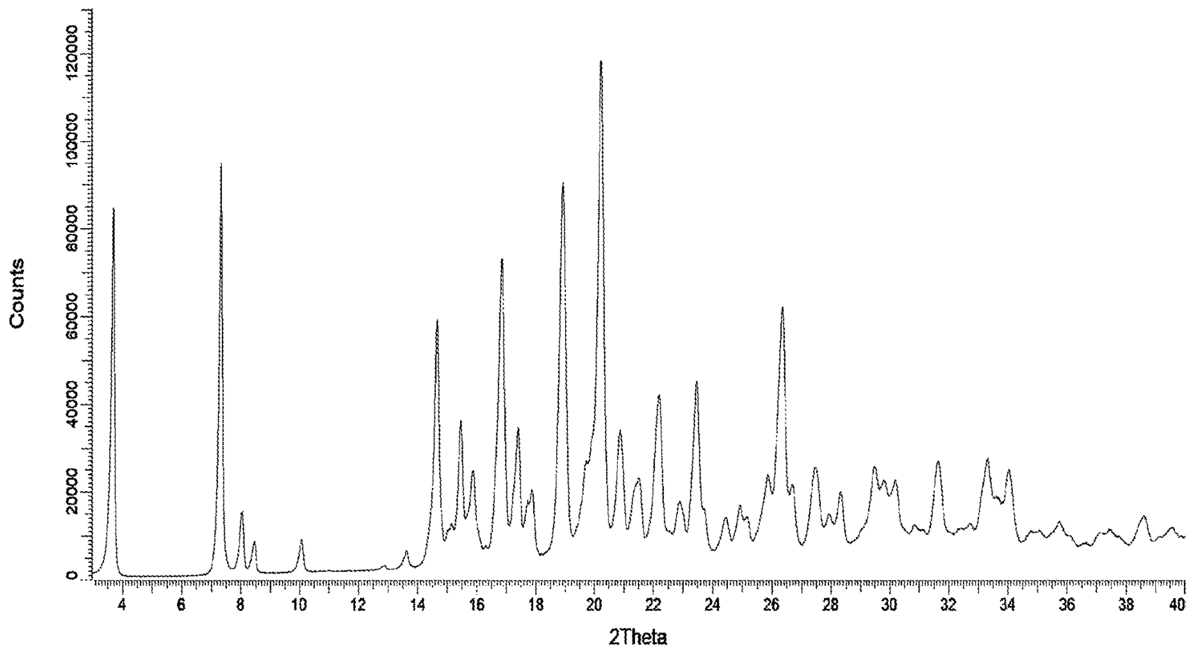
FIG. 1 represents an observed powder X-ray diffraction pattern for an anhydrous (anhydrate) crystal form (Form 1) of tris salt of compound Example 7.

The present invention concerns compounds of Formula I

I

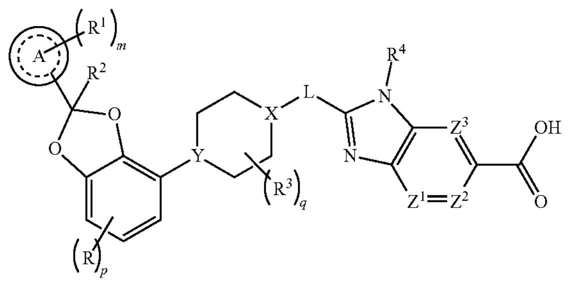

or a pharmaceutically acceptable salt thereof, wherein

R is F, Cl, or —CN;

p is 0 or 1;

Ring A is phenyl or a 6-membered heteroaryl;

m is 0, 1, 2, or 3;

each $R^1$ is independently selected from halogen, —CN, —$C_{1-3}$alkyl, and —$OC_{1-3}$alkyl, wherein the alkyl of $C_{1-3}$alkyl and $OC_{1-3}$alkyl is substituted with 0 to 3 F atoms;

$R^2$ is H or —$C_{1-3}$alkyl, wherein alkyl is substituted with 0 to 1 OH;

each $R^3$ is independently F, —OH, —CN, —$C_{1-3}$alkyl, —$OC_{1-3}$alkyl, and —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;

q is 0, 1, or 2;

X-L is N—$CH_2$, $CHCH_2$, or cyclopropyl;

Y is CH or N;

$R^4$ is —$C_{1-3}$alkyl, —$C_{0-3}$alkylene-$C_{3-6}$cycloalkyl, —$C_{0-3}$ alkylene-$R^5$, or —$C_{1-3}$alkylene-$R^6$, wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, —$SO_2$—N$(R^N)_2$, —C(O)—N$(R^N)_2$, —N(C═O)$(R^N)$, and —N$(R^N)_2$, and wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-OR, and —N$(R^N)_2$;

$R^5$ is a 4- to 6-membered heterocycloalkyl, wherein said heterocycloalkyl may be substituted with 0 to 2 substituents as valency allows independently selected from:

0 to 1 oxo (═O), 0 to 1 —CN, 0 to 2 F atoms, and 0 to 2 substituents independently selected from —$C_{1-3}$ alkyl and —$OC_{1-3}$alkyl, wherein the alkyl of $C_{1-3}$alkyl and $OC_{1-3}$alkyl may be substituted with 0 to 3 substituents as valency allows independently selected from:

0 to 3 F atoms, 0 to 1 —CN, and 0 to 1 —$OR^O$;

$R^6$ is a 5- to 6-membered heteroaryl, wherein said heteroaryl may be substituted with 0 to 2 substituents as valency allows independently selected from:

0 to 2 halogens, 0 to 1 substituent selected from —$OR^O$ and —N$(R^N)_2$, and 0 to 2 —$C_{1-3}$alkyl, wherein the alkyl may be substituted with 0 to 3 substituents as valency allows independently selected from:

0 to 3 F atoms, and 0 to 1 —$OR^O$;

each $R^O$ is independently H, or —$C_{1-3}$alkyl, wherein $C_{1-3}$alkyl may be substituted with 0 to 3 F atoms;

each $R^N$ is independently H, or —$C_{1-3}$alkyl;

$Z^1$, $Z^2$, and $Z^3$ are each —$CR^Z$, or one of $Z^1$, $Z^2$, and $Z^3$ is N and the other two are —$CR^Z$; and each $R^Z$ is independently H, F, Cl, or —$CH_3$.

Another embodiment concerns compounds of Formula II

II

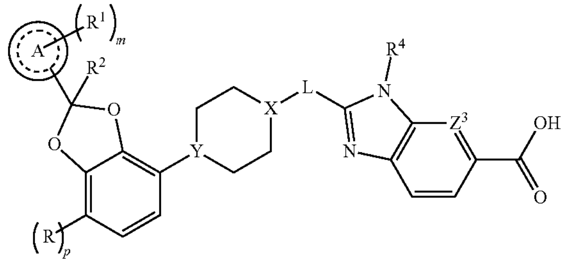

or a pharmaceutically acceptable salt thereof, wherein

R is F;

p is 0 or 1;

Ring A is phenyl or pyridinyl;

m is 0, 1, or 2;

each $R^1$ is independently selected from halogen, —CN, —$C_{1-3}$alkyl, and —$OC_{1-3}$alkyl, wherein the alkyl of $C_{1-3}$alkyl and $OC_{1-3}$alkyl is substituted with 0 to 3 F atoms;

$R^2$ is H or $CH_3$;

X-L is N—$CH_2$, or cyclopropyl;

Y is CH or N;

$Z^3$ is —$CR^Z$ or N; and $R^Z$ is H, F, Cl, or —$CH_3$.

Another embodiment concerns compounds of Formula III

III

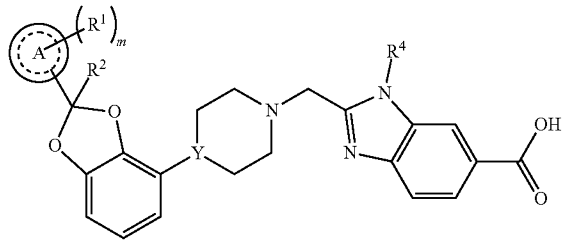

or a pharmaceutically acceptable salt thereof, wherein

Ring A is phenyl or pyridinyl;

m is 0, 1, or 2;

each $R^1$ is independently selected from F, Cl, and —CN;

$R^2$ is H or $CH_3$; and

Y is CH or N.

Another embodiment concerns compounds of Formula IV

IV

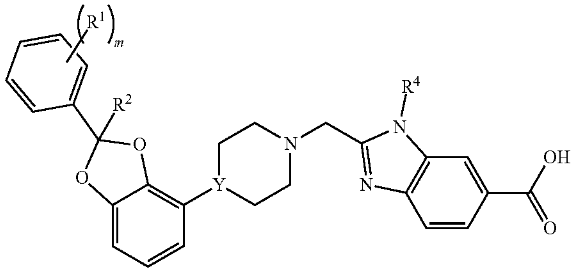

or a pharmaceutically acceptable salt thereof, wherein m is 0, 1, or 2;

each $R^1$ is independently selected from F, Cl, and —CN;

$R^2$ is H or $CH_3$; and

Y is CH or N.

Another embodiment concerns compounds of Formula V

V

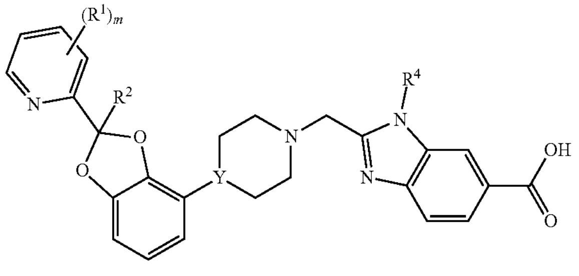

or a pharmaceutically acceptable salt thereof, wherein m is 0 or 1;

$R^1$ is F, Cl, or —CN;

$R^2$ is H or $CH_3$; and

Y is CH or N.

Another embodiment concerns compounds of Formula IV or Formula V, wherein the phenyl or pyridinyl of Ring A has one $R^1$ para substituted relative to carbon of said phenyl or pyridinyl attached to the dioxolane to provide:

IVa

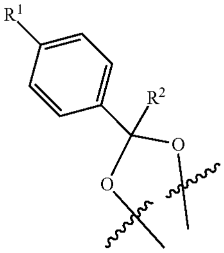

IVb

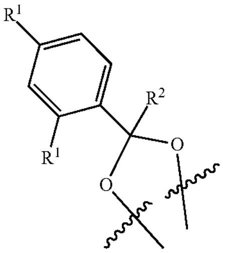

or

Va

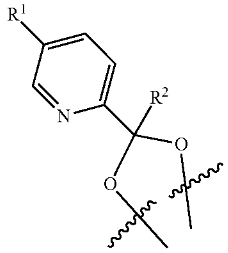

or a pharmaceutically acceptable salt thereof, wherein each $R^1$ is independently selected from F, Cl, and —CN;

$R^2$ is H or $CH_3$; and

Y is CH or N.

Another embodiment concerns compounds of other embodiments herein, e.g., compounds of Formulas I, or II, or a pharmaceutically acceptable salt thereof, wherein X-L is N—$CH_2$; and Y is CH or N. From the embodiments described herein, in such a case, X is N and L is $CH_2$.

Another embodiment concerns compounds of other embodiments herein, e.g., compounds of Formulas I, or II, or a pharmaceutically acceptable salt thereof, wherein X-L is $CHCH_2$; and Y is N. From the embodiments described herein, in such a case, X is CH and L is $CH_2$.

Another embodiment concerns compounds of other embodiments herein, e.g., compounds of Formulas I, or II, or a pharmaceutically acceptable salt thereof, wherein X-L is $CHCH_2$; and Y is CH. From the embodiments described herein, in such a case, X is CH and L is $CH_2$.

Another embodiment concerns compounds of other embodiments herein, e.g., compounds of Formulas I, or II, or a pharmaceutically acceptable salt thereof, wherein X-L is cyclopropyl; and Y is N.

In the embodiments where X-L is cyclopropyl, the compounds of Formulas I, or II would provide:

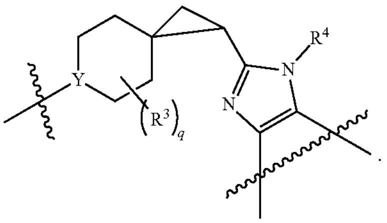

Another embodiment concerns compounds of Formulas I, II, III, IV, or V, wherein $R^4$ is —$CH_2CH_2OCH_3$, $C_{1-3}$alkylene-$R^5$, or $C_{1-3}$alkylene-$R^6$, or a pharmaceutically acceptable salt thereof.

Another embodiment concerns compounds of Formulas II, III, IV, or V, wherein $R^4$ is as defined for compounds of Formula I, or a pharmaceutically acceptable salt thereof.

Another embodiment concerns compounds of Formulas I, II, III, IV, or V, wherein $R^4$ is —$C_{1-3}$alkyl, wherein said alkyl may be substituted as valency allows with 0 to 1 substituent selected from —$C_{0-1}$alkylene-OR, and —$N(R^N)_2$, or a pharmaceutically acceptable salt thereof.

Another embodiment concerns compounds of Formulas I, II, III, IV, or V, wherein $R^4$ is —$(CH_2)_2OCH_3$, or —$(CH_2)_2N(CH_3)_2$, or a pharmaceutically acceptable salt thereof.

Another embodiment concerns compounds of Formulas I, II, III, IV, or V, wherein $R_4$ is —$CH_2$—$R^5$, wherein $R^5$ is the 4- to 5-membered heterocycloalkyl, wherein said heterocycloalkyl may be substituted with 0 to 2 substituents as valency allows independently selected from:

0 to 2 F atoms, and 0 to 1 substituent selected from —$OCH_3$ and —$CH_2OCH_3$;

or a pharmaceutically acceptable salt thereof.

Another embodiment concerns compounds of Formulas I, II, III, IV, or V, wherein the heterocycloalkyl is

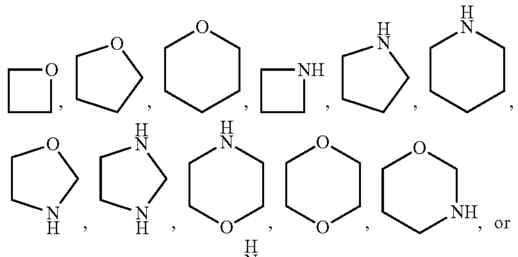

or

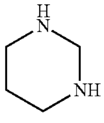

wherein the heterocycloalkyl may be substituted with 0 to 2 substituents as valency allows, e.g., replacing hydrogen, independently selected from:

0 to 1 oxo (O═), 0 to 1 —CN, 0 to 2 F atoms, and 0 to 2 substituents independently selected from —$C_{1-3}$ alkyl and —$OC_{1-3}$alkyl, wherein the alkyl of $C_{1-3}$alkyl and $OC_{1-3}$alkyl may be independently substituted with 0 to 3 substituents as valency allows independently selected from:

0 to 3 F atoms, 0 to 1 —CN, and 0 to 1 —$OR^O$, or a pharmaceutically acceptable salt thereof.

Another embodiment concerns compounds of Formulas I, II, III, IV, or V, wherein the heterocycloalkyl is

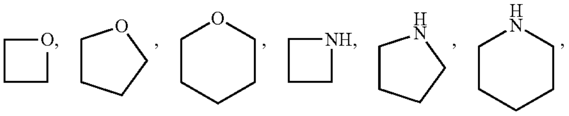

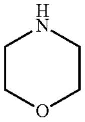

or

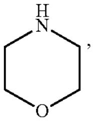

wherein the heterocycloalkyl may be substituted with 0 to 2 substituents as valency allows, e.g., replacing hydrogen, independently selected from:

0 to 1 —CN, 0 to 2 F atoms, and 0 to 2 substituents independently selected from —$C_{1-3}$ alkyl and —$OC_{1-3}$alkyl, wherein the alkyl of $C_{1-3}$alkyl and $OC_{1-3}$alkyl may be independently substituted with 0 to 3 substituents as valency allows independently selected from:

0 to 3 F atoms, 0 to 1 —CN, and 0 to 1 —$OR^O$, or a pharmaceutically acceptable salt thereof.

Another embodiment concerns compounds of Formulas I, II, III, IV, or V, wherein the heterocycloalkyl is

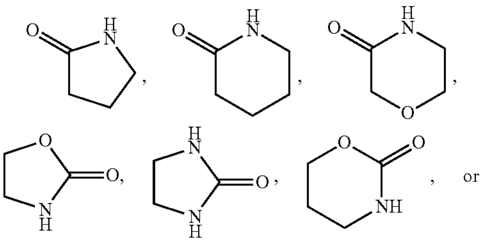

or

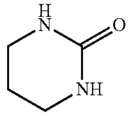

wherein the heterocycloalkyl may be substituted with 0 to 1 substituent as valency allows, e.g., replacing hydrogen, selected from:

—CN,

F atom, and 0 to 1 substituent independently selected from —$C_{1-3}$ alkyl and —$OC_{1-3}$alkyl, wherein the alkyl of $C_{1-3}$alkyl and $OC_{1-3}$alkyl may be substituted with 0 to 3 substituents as valency allows independently selected from:

0 to 3 F atoms, 0 to 1 —CN, and 0 to 1 —$OR^O$, or a pharmaceutically acceptable salt thereof.

Another embodiment concerns compounds of Formulas I, II, III, IV, or V, wherein the heterocycloalkyl is

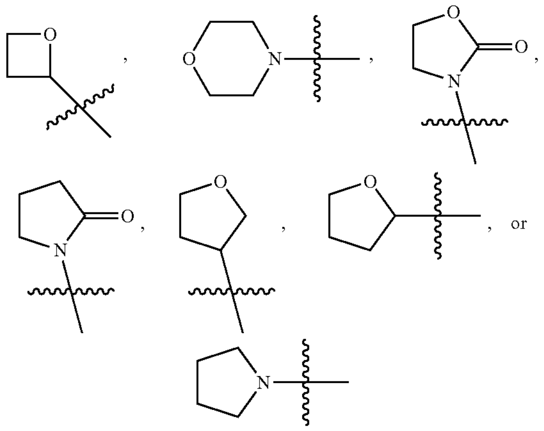

or a pharmaceutically acceptable salt thereof.

Another embodiment concerns compounds of Formulas I, II, III, IV, or V, wherein the heterocycloalkyl is

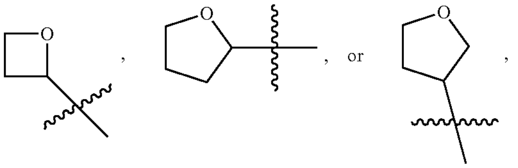 [SMILES: *C1CCO1 ; *C1CCCO1 ; *C1CCOC1]

wherein the heterocycloalkyl may be substituted as valency allows with 0 to 1 methyl, wherein said methyl may be substituted with 0 to 3 F atoms, or a pharmaceutically acceptable salt thereof.

Another embodiment concerns compounds of Formulas I, II, III, IV, or V, wherein the heterocycloalkyl is

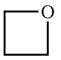

wherein the heterocycloalkyl is unsubstituted.

Another embodiment concerns compounds of Formulas I, II, III, IV, or V, wherein $-CH_2-R^5$ and the nitrogen to which $R^4$ is attached provides:

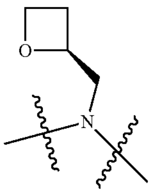 [SMILES: *N(*)C[C@@H]1CCO1]

or a pharmaceutically acceptable salt thereof.

Another embodiment concerns compounds of Formulas I, II, III, IV, or V, wherein $R_4$ is $-CH_2-R^6$, wherein $R^6$ is the 5-membered heteroaryl, wherein said heteroaryl may be substituted with 0 to 2 substituents as valency allows independently selected from:

0 to 2 halogens, wherein the halogen is independently selected from F and Cl, 0 to 1 $-OCH_3$, and 0 to 1 $-CH_3$, $-CH_2CH_3$, $-CF_3$, or $-CH_2CH_2OCH_3$;

or a pharmaceutically acceptable salt thereof.

Another embodiment concerns compounds of Formulas I, II, III, IV, or V, wherein the heteroaryl is

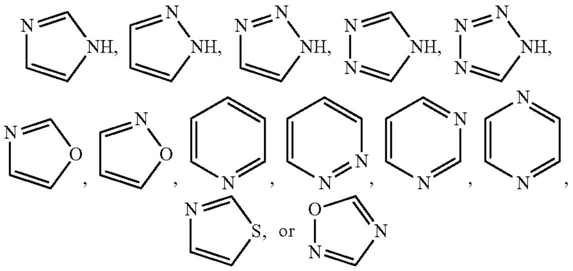

wherein said heteroaryl may be substituted with 0 to 2 substituents as valency allows, e.g., replacing hydrogen, independently selected from:

0 to 2 halogens, wherein the halogen is independently selected from F and Cl, 0 to 1 substituent selected from $-OR^O$ and $-N(R^N)_2$, or 0 to 2 $-C_{1-3}$alkyl, wherein the alkyl may be substituted with 0 to 3 substituents as valency allows independently selected from:

0 to 3 F atoms, and 0 to 1 $-OR^O$;

or a pharmaceutically acceptable salt thereof.

Another embodiment concerns compounds of Formulas I, II, III, IV, or V, wherein the heteroaryl is

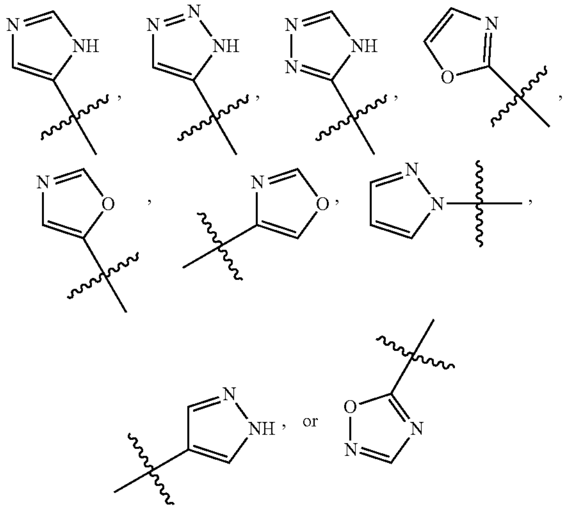

wherein said heteroaryl may be substituted with 0 to 2 substituents as valency allows, e.g., replacing hydrogen, independently selected from:

0 to 2 halogens, wherein the halogen is independently selected from F and Cl, 0 to 1 substituent selected from $-OR^O$ and $-N(R^N)_2$, or 0 to 2 $-C_{1-3}$alkyl, wherein the alkyl may be substituted with 0 to 3 substituents as valency allows independently selected from:

0 to 3 F atoms, and 0 to 1-$OR^O$;

or a pharmaceutically acceptable salt thereof.

Another embodiment concerns compounds of Formulas I, II, III, IV, or V, wherein the heteroaryl is

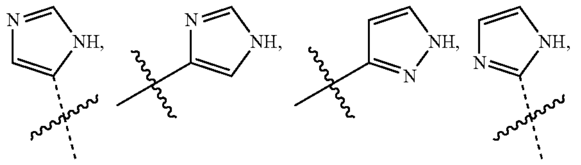

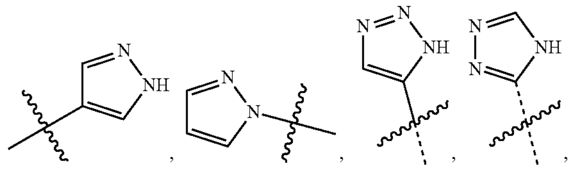

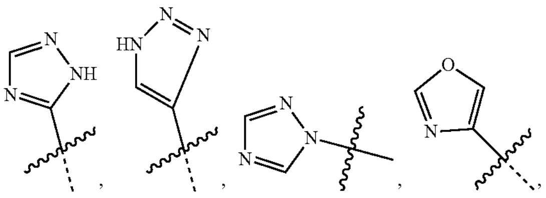

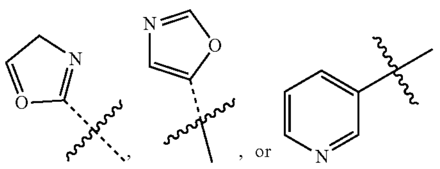

wherein said heteroaryl may be substituted with 0 to 1 substituent as valency allows with —$C_{1-2}$alkyl, wherein the alkyl may be substituted with 0 to 3 substituents as valency allows independently selected from:

0 to 3 F atoms, and 0 to 1 —$OR^O$; and each $R^O$ is independently H, or —$C_{1-3}$alkyl;

or a pharmaceutically acceptable salt thereof. One will recognize that any substituent would replace H on the carbon or nitrogen being substituted. A non-limiting example of substituted heteroaryls are:

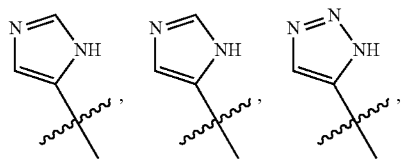

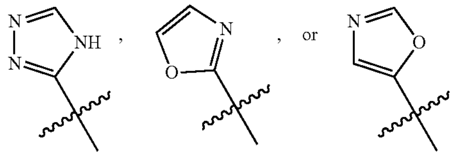

One will recognize that H is replaced with a substituent, e.g., $R^{6s}$ (substituent allowed on any heteroaryl of $R^6$), to provide:

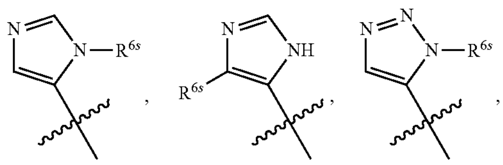

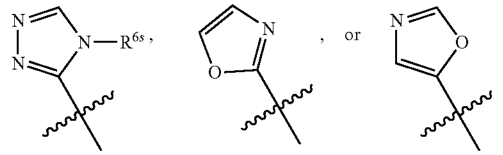

wherein $R^{6s}$ is —$C_{1-2}$alkyl, wherein the alkyl may be substituted with 0 to 3 substituents as valency allows independently selected from:

0 to 3 F atoms, and 0 to 1 —$OR^O$; and each $R^O$ is independently H, or —$C_{1-3}$alkyl;

or a pharmaceutically acceptable salt thereof.

Another embodiment concerns compounds of Formulas I, II, III, IV, or V, wherein the heteroaryl is

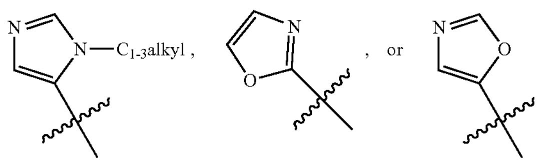

or a pharmaceutically acceptable salt thereof.

Another embodiment concerns compounds of other embodiments herein, e.g., compounds of Formulas I, II, III, IV, or V, wherein $Z^1$, $Z^2$, and $Z^3$ are each $CR^Z$, or a pharmaceutically acceptable salt thereof.

Another embodiment concerns compounds of other embodiments herein, e.g., compounds of Formulas I, II, III, IV, or V, wherein $R^Z$ is H, or a pharmaceutically acceptable salt thereof.

Another embodiment concerns compounds of other embodiments herein, e.g., compounds of Formulas I, II, III, IV, or V, wherein $Z^1$, $Z^2$, and $Z^3$ are each CH, or a pharmaceutically acceptable salt thereof.

Another embodiment concerns compounds of other embodiments herein, e.g., compounds of Formulas I, II, III, IV, or V, wherein $R^3$ is —$CH_3$, or —$CF_3$; and q is 1, or a pharmaceutically acceptable salt thereof.

Another embodiment concerns compounds of other embodiments herein, e.g., compounds of Formulas I, II, III, IV, or V, wherein each $R^1$ is independently F, Cl, or —CN, or a pharmaceutically acceptable salt thereof.

Another embodiment concerns compounds of other embodiments herein, e.g., compounds of Formulas I, II, III, IV, or V, wherein $R_4$ is —$CH_2$—$R^5$, or a pharmaceutically acceptable salt thereof.

Another embodiment concerns compounds of other embodiments herein, e.g., compounds of Formulas I, II, III, IV, or V, wherein $R_4$ is —$CH_2$—$R^6$, or a pharmaceutically acceptable salt thereof.

Another embodiment concerns compounds of other embodiments herein, e.g., compounds of Formulas I, II, III, IV, or V, wherein the compound is the free acid.

Another embodiment concerns any embodiment of compounds of Formulas I, II, III, IV, or V, wherein Ring A and $R^2$ provide:

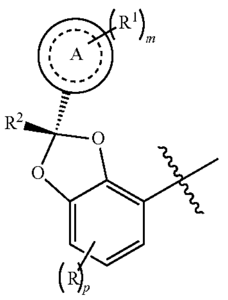

or a pharmaceutically acceptable salt thereof, wherein

R is F, Cl, or —CN;

p is 0 or 1;

m is 0, 1, or 2; and each $R^1$ is independently selected from halogen, —CN, —$C_{1-3}$alkyl, and —$OC_{1-3}$alkyl, wherein the alkyl of $C_{1-3}$alkyl and $OC_{1-3}$alkyl is substituted with 0 to 3 F atoms.

Another embodiment concerns compounds of Formulas I, II, III, IV, or V, wherein $R^2$ is H, or a pharmaceutically acceptable salt thereof.

Another embodiment concerns compounds on the invention, wherein $R^2$ is H, or a pharmaceutically acceptable salt thereof.

Another embodiment concerns compounds on the invention, wherein the compound is 2-({4-[2-(4-chloro-2-fluorophenyl)-1,3-benzodioxol-4-yl] piperidin-1-yl}methyl)-1-[(2S)-oxetan-2-ylmethyl]-1H-benzimidazole-6-carboxylic acid; or 2-({4-[2-(4-chloro-2-fluorophenyl)-1,3-benzodioxol-4-yl] piperidin-1-yl}methyl)-7-fluoro-1-[(2S)-oxetan-2-ylmethyl]-1H-benzimidazole-6-carboxylic acid;

or a pharmaceutically acceptable salt thereof.

Another embodiment concerns compounds on the invention, wherein the compound is 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid; or 2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid; or a pharmaceutically acceptable salt thereof.

Another embodiment concerns compounds on the invention, wherein $R^2$ is $CH_3$, or a pharmaceutically acceptable salt thereof.

Another embodiment concerns compounds on the invention, wherein the compound is 2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid; or 2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

or a pharmaceutically acceptable salt thereof.

Another embodiment concerns compounds on the invention, wherein the compound is 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid; or 2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

or a pharmaceutically acceptable salt thereof.

Another embodiment concerns compounds on the invention, wherein the compound is 2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; or 2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

or a pharmaceutically acceptable salt thereof.

Another embodiment concerns compounds on the invention, wherein the compound is 2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; or 2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

or a pharmaceutically acceptable salt thereof.

Another embodiment concerns compounds on the invention, wherein the compound is 2-({4-[2-(4-Cyano-2-fluorophenyl)-2*-methyl-1,3-benzodioxol-4-yl]piperidin-1-yl}methyl)-1-[(2S)-oxetan-2-ylmethyl]-1H-benzimidazole-6-carboxylic acid, wherein chirality of 2* comes from C56;

2-({4-[2-(5-Chloropyridin-2-yl)-2*-methyl-1,3-benzodioxol-4-yl]piperidin-1-yl}methyl)-1-[(2S)-oxetan-2-ylmethyl]-1H-benzimidazole-6-carboxylic acid, wherein chirality of 2* comes from P9;

2-({4-[2-(4-chloro-2-fluorophenyl)-2*-methyl-1,3-benzodioxol-4-yl]piperidin-1-yl}methyl)-1-[(1-ethyl-1H-imidazol-5-yl)methyl]-1H-benzimidazole-6-carboxylic acid, wherein chirality of 2* comes from 17;

2-({4-[2-(4-chloro-2-fluorophenyl)-7-fluoro-2*-methyl-1,3-benzodioxol-4-yl]piperidin-1-yl}methyl)-1-[(2S)-oxetan-2-ylmethyl]-1H-benzimidazole-6-carboxylic acid, wherein chirality of 2* comes from 96; or 2-({4-[2-(4-cyano-2-fluorophenyl)-2*-methyl 1,3-benzodioxol-4-yl]piperidin-1-yl}methyl)-1-(1,3-oxazol-2-ylmethyl)-1H-benzimidazole-6-carboxylic acid, wherein chirality of 2* comes from C82;

or a pharmaceutically acceptable salt thereof.

Another embodiment includes a compound that is 2-({4-[(2S)-2-(4-chloro-2-fluorophenyl)-1,3-benzodioxol-4-yl]piperid in-1-yl}methyl)-1-[(2S)-oxetan-2-ylmethyl]-1H-benzimidazole-6-carboxylic acid, or a pharmaceutically acceptable salt thereof, wherein the salt is a tris salt.

Another embodiment includes a compound that is 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid, as a free acid.

Another embodiment includes a compound that is

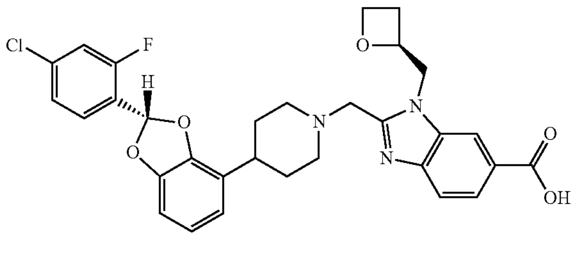 [SMILES: O=C(O)c1ccc2nc(CN3CCC(c4cccc5c4O[C@@H](c4ccc(Cl)cc4F)O5)CC3)n(C[C@@H]3CCO3)c2c1]

or a pharmaceutically acceptable salt thereof.

Another embodiment includes a compound that is 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, or a pharmaceutically acceptable salt, wherein the salt is a tris salt {the tris salt of this compound is also known as: 1,3-dihydroxy-2-(hydroxymethyl)propan-2-aminium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate}.

In some embodiments, the present invention provides a crystal form of anhydrous tris salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid. In some further embodiments, the crystal form of anhydrous (anhydrate) tris salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid is designated as "Form I" that is characterized according to its unique solid state signatures with respect to, for example, powder X-ray diffraction (PXRD), described herein (such as substantially as depicted in FIG. 1). In some embodiments, Form I exhibits a powder X-ray diffraction pattern comprising at least two characteristic peaks, in terms of 26, selected from at 3.7±0.2°; 7.3+0.2°; 8.5+0.2°; 10.1±0.2°; 14.7+0.20; and 16.9±0.2°. In some embodiments, Form I exhibits a powder X-ray diffraction pattern comprising at least three characteristic peaks, in terms of 2θ, selected from at 3.7±0.2°; 7.3+0.2°; 8.5+0.2°; 10.1±0.2°; 14.7±0.2°; and 16.9±0.2°. In some embodiments, Form I exhibits a powder X-ray diffraction pattern comprising at least four characteristic peaks, in terms of 2θ, selected from at 3.7+0.2°; 7.3+0.2°; 8.5+0.2°; 10.1±0.2°; 14.7+0.20; and 16.9±0.2°. In some embodiments, Form I exhibits a powder X-ray diffraction pattern comprising at least five characteristic peaks, in terms of 2θ, selected from at 3.7+0.2°; 7.3+0.2°; 8.5+0.2°; 10.1±0.2°; 14.7+0.20; and 16.9±0.20.

In some embodiments, Form I exhibits a powder X-ray diffraction pattern comprising characteristic peaks, in terms of 2θ, at 3.7±0.2° and 7.3±0.2°.

In some embodiments, Form I exhibits a powder X-ray diffraction pattern comprising peaks, in terms of 2θ, at 3.7±0.2°; 7.3±0.2°; and 14.7±0.2°. In some further embodiments, Form I exhibits the X-ray powder diffraction pattern further comprises at least one peak, in terms of 2θ, selected from at 8.5±0.2°; 10.1±0.2°; and 16.9±0.2°.

In some embodiments, Form I exhibits a powder X-ray diffraction pattern comprising peaks, in terms of 2θ, at 3.7±0.2°; 7.3±0.2°; 14.7±0.2°; and 16.9±0.2°.

In some embodiments, Form I exhibits a powder X-ray diffraction pattern comprising peaks, in terms of 2θ, at 3.7±0.2°; 7.3±0.2°; 8.5±0.2°; 10.1±0.2°; 14.7±0.2°; and 16.9±0.2°.

In some embodiments, Form I exhibits a powder X-ray diffraction pattern substantially as shown in FIG. 1. A list of diffraction peaks expressed in terms of the degree 2θ and relative intensities with a relative intensity of ≥3.0% is provided above in Table X1.

As is well known in the art of powder diffraction, the relative intensities of the peaks (reflections) can vary, depending upon the sample preparation technique, the sample mounting procedure and the particular instrument employed. Moreover, instrument variation and other factors can affect the 2-theta values. Therefore, the XRPD peak assignments can vary by plus or minus about 0.2°.

Another embodiment includes a compound that is 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, as a free acid.

Another embodiment includes a compound that is

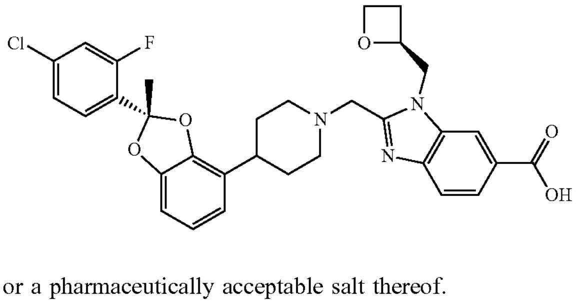

or a pharmaceutically acceptable salt thereof.

Another embodiment includes a compound that is 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; or 2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; as the free acid.

Another embodiment includes a compound that is 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; or 2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; or a pharmaceutically acceptable salt thereof, wherein the salt is a tris salt.

Another embodiment includes a compound that is 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2:

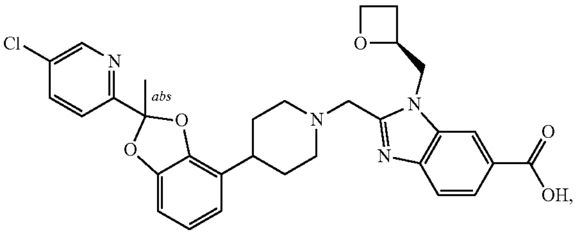

DIAST-X2 or pharmaceutically acceptable salt thereof. In some further embodiments, the present invention provides a compound that is 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or tris salt [i.e. 1,3-dihydroxy-2-(hydroxymethyl)propan-2-amine salt] thereof. The chiral center on the left part of the compound structure is marked as "abs" to indicate that chiral center has only one stereo-configuration (i.e., not a racemate with respect to that chiral center).

Figure 2:
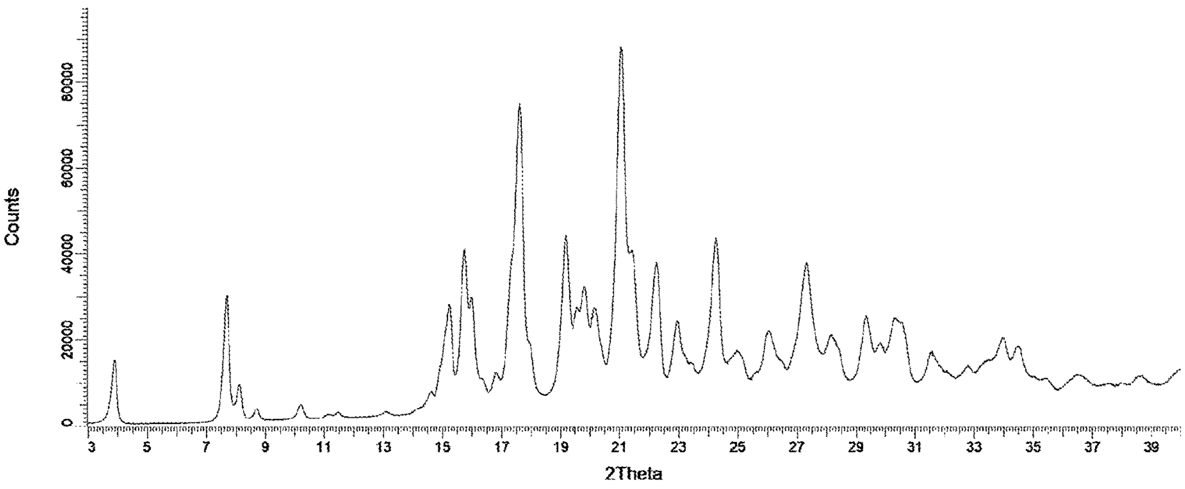
FIG. 2 represents an observed powder X-ray diffraction pattern for an anhydrous (anhydrate) crystal form (Form A) of tris salt of compound Example 10.

In some embodiments, the present invention provides a crystal form of anhydrous tris salt of 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2. In some further embodiments, the crystal form of anhydrous (anhydrate) tris salt of 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, is designated as "Form A" that is characterized according to its unique solid state signatures with respect to, for example, powder X-ray diffraction (PXRD), described herein (such as substantially as depicted in FIG. 2). In some embodiments, Form A exhibits a powder X-ray diffraction pattern comprising at least two characteristic peaks, in terms of 2θ, selected from at 7.7±0.2°; 15.2±0.2°; 15.7±0.2°; and 17.6±0.2°. In some embodiments, Form A exhibits a powder X-ray diffraction pattern comprising at least three characteristic peaks, in terms of 2θ, selected from at 7.7±0.2°; 15.2+0.2°; 15.7±0.2°; and 17.6±0.2°. In some embodiments, Form A exhibits a powder X-ray diffraction pattern comprising characteristic peaks, in terms of 2θ, selected from at 7.7±0.2°; 15.2±0.2°; 15.7±0.2°; and 17.6±0.2°.

In some embodiments, Form I exhibits a powder X-ray diffraction pattern comprising characteristic peaks, in terms of 2θ, at 7.7±0.2° and 17.6±0.2°.

In some embodiments, Form A exhibits a powder X-ray diffraction pattern comprising peaks, in terms of 2θ, at 7.7±0.2°; 15.2±0.2°; and 17.6±0.2°.

In some embodiments, Form I exhibits a powder X-ray diffraction pattern comprising peaks, in terms of 2θ, at 7.7±0.2°; 15.2±0.2°; and 15.7±0.2°.

In some embodiments, Form I exhibits a powder X-ray diffraction pattern comprising peaks, in terms of 2θ, at 7.7±0.2°; 15.2±0.2°; 15.7±0.2°; and 17.6±0.2°.

In some embodiments, Form A exhibits a powder X-ray diffraction pattern substantially as shown in FIG. 2. A list of diffraction peaks expressed in terms of the degree 20 and relative intensities with a relative intensity of ≥3.0% is provided above in Table X2.

As is well known in the art of powder diffraction, the relative intensities of the peaks (reflections) can vary, depending upon the sample preparation technique, the sample mounting procedure and the particular instrument employed. Moreover, instrument variation and other factors can affect the 2-theta values. Therefore, the XRPD peak assignments can vary by plus or minus about 0.2°.

In another embodiment, the invention provides a pharmaceutical composition comprising a compound of Formulas I, II, III, IV, or V, or a pharmaceutically acceptable salt thereof, as defined in any of the embodiments described herein, in admixture with at least one pharmaceutically acceptable excipient. This would include a pharmaceutical composition comprising a compound of Formulas I, II, III, IV, or V, or a pharmaceutically acceptable salt thereof, as defined in any of the embodiments described herein, in admixture with at least one pharmaceutically acceptable excipient and one or more other therapeutic agent discussed herein.

The invention also includes the following embodiments:

a compound of Formulas I, II, III, IV, or V, or a pharmaceutically acceptable salt thereof, as defined in any of the embodiments described herein, for use as a medicament;

a compound of Formulas I, II, III, IV, or V, or a pharmaceutically acceptable salt thereof, as defined in any of the embodiments described herein, for use in the prevention and/or treatment of cardiometabolic and associated diseases discussed herein, including T2DM, pre-diabetes, NASH, and cardiovascular disease;

a method of treating a disease for which an agonist of GLP-1R is indicated, in a subject in need of such prevention and/or treatment, comprising administering to the subject a therapeutically effective amount of a compound of Formulas I, II, III, IV, or V, or a pharmaceutically acceptable salt thereof, as defined in any of the embodiments described herein;

the use of a compound of Formulas I, II, III, IV, or V, or a pharmaceutically acceptable salt thereof, as defined in any of the embodiments described herein, for the manufacture of a medicament for treating a disease or condition for which an agonist of the GLP-1R is indicated;

a compound of Formulas I, II, III, IV, or V, or a pharmaceutically acceptable salt thereof, as defined in any of the embodiments described herein, for use in the treatment of a disease or condition for which an agonist of GLP-1R is indicated; or a pharmaceutical composition for the treatment of a disease or condition for which an agonist of the GLP-1R is indicated, comprising a compound of Formulas I, II, III, IV, or V, or a pharmaceutically acceptable salt thereof, as defined in any of the embodiments described herein.

Every Example or pharmaceutically acceptable salt thereof may be claimed individually or grouped together in any combination with any number of each and every embodiment described herein.

The invention also relates to a pharmaceutical composition comprising a compound of Formulas I, II, III, IV, or V, or a pharmaceutically acceptable salt thereof, as defined in any of the embodiments described herein, for use in the treatment and/or prevention of cardiometabolic and associated diseases discussed herein, including T2DM, pre-diabetes, NASH, and cardiovascular disease.

Another embodiment of the invention concerns a compound of Formulas I, II, III, IV, or V, or a pharmaceutically acceptable salt thereof, as defined in any of the embodiments described herein, for use in the treatment and/or prevention of cardiometabolic and associated diseases including diabetes (T1D and/or T2DM, including pre-diabetes), idiopathic T1D (Type 1 b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, prevention or treatment of Polycystic Ovary Syndrome and treatment of addiction (e.g., alcohol and/or drug abuse).

Abbreviations used herein are as follows:

The term "alkyl", as used herein, means a straight or branched chain monovalent hydrocarbon group of formula $-C_nH_{(2n+1)}$. Non-limiting examples include methyl, ethyl, propyl, butyl, 2-methyl-propyl, 1,1-dimethylethyl, pentyl and hexyl.

The term "alkylene", as used herein, means a straight or branched chain divalent hydrocarbon group of formula $-C_nH_{2n}-$. Non-limiting examples include ethylene, and propylene.

The term "cycloalkyl", as used herein, means a cyclic, monovalent hydrocarbon group of formula $-C_nH_{(2n-1)}$ containing at least three carbon atoms. Non-limiting examples include cyclopropyl, cyclobutyl, cyclopentyl and cyclohexyl.

The term "halogen", as used herein, refers to fluoride, chloride, bromide, or iodide.

The term "heterocycloalkyl", as used herein, refers to a cycloalkyl group in which one or more of the ring methylene groups ($-CH_2-$) has been replaced with a group selected from —O—, —S— or nitrogen, wherein the nitrogen may provide a point of attachment or may be substituted as provided within each embodiment. Where nitrogen provides a point of attachment, a structural drawing of a heterocycloalkyl would have an hydrogen on said nitrogen. Generally, the heterocycloalkyl may be substituted with 0 to 2 substituents as valency allows independently selected from oxo, —CN, halogen, alkyl and —Oalkyl and the alkyl may be further substituted. One will note that when there is 0 substitution, the heterocycloalkyl is unsubstituted.

The term "heteroaryl", as used herein, refers to a monocyclic aromatic hydrocarbon containing from 5 to 6 carbon atoms in which at least one of the ring carbon atoms has been replaced with a heteroatom selected from oxygen, nitrogen and sulfur. Such a heteroaryl group may be attached through a ring carbon atom or, where valency permits, through a ring nitrogen atom. Generally, the heteroaryl may be substituted with 0 to 2 substituents as valency allows independently selected from halogen, OH, alkyl, O-alkyl, and amino (e.g., $NH_2$, NHalkyl, $N(alkyl)_2$), and the alkyl may be further substituted. One will note that when there is 0 substitution, the heteroaryl is unsubstituted.

Room temperature: RT (15 to 25° C.).
Methanol: MeOH.
Ethanol: EtOH.
Isopropanol: iPrOH.
Ethyl acetate: EtOAc.
Tetrahydrofuran: THF.
Toluene: $PhCH_3$.
Cesium carbonate: $Cs_2CO_3$.
Lithium bis(trimethylsilyl)amide: LiHMDS.
Sodium t-butoxide: NaOtBu.
Potassium t-butoxide: KOtBu.
Lithium diisopropylamide: LDA.
Triethylamine: $Et_3N$.
N,N-diisopropylethyl amine: DIPEA.
Potassium carbonate: $K_2CO_3$.
Dimethyl formamide: DMF.
Dimethyl acetamide: DMAc.
Dimethyl sulfoxide: DMSO.
N-Methyl-2-pyrrolidinone: NMP.
Sodium hydride: NaH.
Trifluoroacetic acid: TFA.
Trifluoroacetic anhydride: TFAA.
Acetic anhydride: $Ac_2O$.
Dichloromethane: DCM.
1,2-Dichloroethane: DCE.
Hydrochloric acid: HCl.
1,8-Diazabicyclo[5.4.0]undec-7-ene: DBU.
Borane-dimethylsulfide complex: $BH_3$-DMS.

Borane-tetrahydrofuran complex: $BH_3$-THF.

Lithium aluminum hydride: LAH.

Acetic acid: AcOH.

Acetonitrile: MeCN.

p-Toluenesulfonic acid: pTSA.

Dibenzylidine acetone: DBA.

2,2'-Bis(diphenylphosphino)-1,1'-binaphthalene: BINAP.

1,1'-Ferrocenediyl-bis(diphenylphosphine): dppf.

1,3-Bis(diphenylphosphino)propane: DPPP.

3-Chloroperbenzoic acid: m-CPBA.

Tert-Butyl methyl ether: MTBE.

Methanesulfonyl: Ms.

N-Methylpyrrolidinone: NMP.

Thin layer chromatography: TLC.

Supercritical fluid chromatography: SFC.

4-(Dimethylamino)pyridine: DMAP.

Tert-Butyloxycarbonyl: Boc.

1-[Bis(dimethylamino)methylene]-1H-1,2,3-triazolo[4,5-b]pyridinium 3-oxid hexafluorophosphate: HATU.

Petroleum ether: PE.

2-(1H-Benzotriazole-1-yl)-1,1,3,3-tetramethyluronium hexafluorophosphate: HBTU.

2-Amino-2-(hydroxymethyl)propane-1,3-diol: tris.

tris(dibenzylideneacetone)dipalladium: $Pd_2(dba)_3$ $^1$H Nuclear magnetic resonance (NMR) spectra were in all cases consistent with the proposed structures. Characteristic chemical shifts (6) are given in parts-per-million relative to the residual proton signal in the deuterated solvent ($CHCl_3$ at 7.27 ppm; $CD_2HOD$ at 3.31 ppm; MeCN at 1.94 ppm; DMSO at 2.50 ppm) and are reported using conventional abbreviations for designation of major peaks: e.g. s, singlet; d, doublet; t, triplet; q, quartet; m, multiplet; br, broad. The symbol ^ denotes that the $^1$H NMR peak area was assumed because the peak was partially obscured by water peak. The symbol ^^ denotes that the $^1$H NMR peak area was assumed because the peak was partially obscured by solvent peak.

As used herein, a wavy line, "  " denotes a point of attachment of a substituent to another group.

The compounds and intermediates described below were named using the naming convention provided with ACD/ChemSketch 2012, File Version C10H41, Build 69045 (Advanced Chemistry Development, Inc., Toronto, Ontario, Canada). The naming convention provided with ACD/ChemSketch 2012 is well known by those skilled in the art and it is believed that the naming convention provided with ACD/ChemSketch 2012 generally comports with the IUPAC (International Union for Pure and Applied Chemistry) recommendations on Nomenclature of Organic Chemistry and the CAS Index rules. One will note that the chemical names may have only parentheses or may have parentheses and brackets. The stereochemical descriptors may also be placed at different locations within the name itself, depending on the naming convention. One of ordinary skill in the art will recognize these formatting variations and understand they provide the same chemical structure.

Pharmaceutically acceptable salts of the compounds of Formulas I, II, III, IV, or V include acid addition and base salts.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinafoate salts.

Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-Amino-2-(hydroxymethyl)propane-1,3-diol (tris or tromethamine) and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^-K^+$, or $—SO_3^-Na^+$) or non-ionic (such as $—N^-N^+(CH_3)_3$) polar head group. For more information, see *Crystals and the Polarizing Microscope* by N. H. Hartshorne and A. Stuart, $4^{th}$ Edition (Edward Arnold, 1970).

The compounds of Formula I may exhibit polymorphism and/or one or more kinds of isomerism (e.g. optical, geometric or tautomeric isomerism). The compounds of Formula I may also be isotopically labelled. Such variation is implicit to the compounds of Formula I defined as they are by reference to their structural features and therefore within the scope of the invention.

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

The pharmaceutically acceptable salts of compounds of Formula I may also contain a counterion which is optically active (e.g. d-lactate or I-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, a racemic precursor containing a chiral ester may be separated by enzymatic resolution (see, for example, Int J Mol Sci 29682-29716 by A. C. L. M. Carvaho et. al. (2015)). In the case where the compound of Formula I contains an acidic or basic moiety, a salt may be formed with an optically pure base or acid such as 1-phenylethylamine or tartaric acid. The resulting diastereomeric mixture may be separated by fractional crystallization and one or both of the diastereomeric salts converted to the corresponding pure enantiomer(s) by means well known to a skilled person. Alternatively, the racemate (or a racemic precursor) may be covalently reacted with a suitable optically active compound, for example, an alcohol, amine or benzylic chloride. The resulting diastereomeric mixture may be separated by chromatography and/or fractional crystallization by means well known to a skilled person to give the separated diastereomers as single enantiomers with 2 or more chiral centers. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (SFC with Packed Columns), pp. 223-249 and references cited therein). In some relevant examples herein, columns were obtained from Chiral Technologies, Inc, West Chester, Pa., USA, a subsidiary of Daicel® Chemical Industries, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

It must be emphasised that the compounds of Formula I have been drawn herein in a single tautomeric form, all possible tautomeric forms are included within the scope of the invention.

The present invention includes all pharmaceutically acceptable isotopically-labeled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

One way of carrying out the invention is to administer a compound of Formula I in the form of a prodrug. Thus, certain derivatives of a compound of Formula I which may have little or no pharmacological activity themselves can, when administered into or onto the body, be converted into a compound of Formula I having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, *ACS Symposium Series* (T. Higuchi and W. Stella) and 'Bioreversible Carriers in Drug Design', Pergamon Press, 1987 (Ed. E. B. Roche, American Pharmaceutical Association). Reference can also be made to *Nature Reviews/Drug Discovery,* 2008, 7, 355 and *Current Opinion in Drug Discovery and Development,* 2007, 10, 550.

Prodrugs in accordance with the invention can, for example, be produced by replacing appropriate functionalities present in the compounds of Formula I with certain moieties known to those skilled in the art as 'pro-moieties' as described, for example, in 'Design of Prodrugs' by H. Bundgaard (Elsevier, 1985) and Y. M. Choi-Sledeski and C. G. Wermuth, 'Designing Prodrugs and Bioprecursors' in Practice of Medicinal Chemistry, (Fourth Edition), Chapter 28, 657-696 (Elsevier, 2015).

Thus, a prodrug in accordance with the invention is (a) an ester or amide derivative of a carboxylic acid in a compound of Formula I; (b) an ester, carbonate, carbamate, phosphate or ether derivative of a hydroxyl group in a compound of Formula I; (c) an amide, imine, carbamate or amine derivative of an amino group in a compound form Formula I; (d) an oxime or imine derivative of a carbonyl group in a compound of Formula I; or (e) a methyl, primary alcohol or aldehyde group that can be metabolically oxidized to a carboxylic acid in a compound of Formula I.

Some specific examples of prodrugs in accordance with the invention include:

(i) where the compound of Formula I contains a carboxylic acid functionality (—COOH), an ester thereof, such as a compound wherein the hydrogen of the carboxylic acid functionality of the compound of Formula I is replaced by $C_1$-$C_8$ alkyl (e.g. ethyl) or ($C_1$-$C_8$ alkyl)C(=O)$OCH_2$— (e.g. $^t$BuC(=O)$OCH_2$—);

(ii) where the compound of Formula I contains an alcohol functionality (—OH), an ester thereof, such as a compound wherein the hydrogen of the alcohol functionality of the compound of Formula I is replaced by —CO($C_1$-$C_8$ alkyl) (e.g. methylcarbonyl) or the alcohol is esterified with an amino acid;

(iii) where the compound of Formula I contains an alcohol functionality (—OH), an ether thereof, such as a compound wherein the hydrogen of the alcohol functionality of the compound of Formula I is replaced by ($C_1$-$C_8$ alkyl)C(=O)$OCH_2$— or —$CH_2OP$(=O)$(OH)_2$; (iv) where the compound of Formula I contains an alcohol functionality (—OH), a phosphate thereof, such as a compound wherein the hydrogen of the alcohol functionality of the compound of Formula I is replaced by —P(=O)$(OH)_2$ or —P(=O)$(ONa)_2$ or —P(=O)$(O^-)_2$ $Ca^{2+}$;

(v) where the compound of Formula I contains a primary or secondary amino functionality (—$NH_2$ or —NHR where R≠H), an amide thereof, for example, a compound wherein, as the case may be, one or both hydrogens of the amino functionality of the compound of Formula I is/are replaced by ($C_1$-$C_{10}$)alkanoyl, —$COCH_2NH_2$ or the amino group is derivatised with an amino acid;

(vi) where the compound of Formula I contains a primary or secondary amino functionality (—$NH_2$ or —NHR where R #H), an amine thereof, for example, a compound wherein, as the case may be, one or both hydrogens of the amino functionality of the compound of Formula I is/are replaced by —$CH_2OP$(=O)$(OH)_2$;

(vii) where the carboxylic acid group within compound of Formula I is replaced by a methyl group, a —$CH_2OH$ group or an aldehyde group.

Certain compounds of Formula I may themselves act as prodrugs of other compounds of Formula I. It is also possible for two compounds of Formula I to be joined together in the form of a prodrug. In certain circumstances, a prodrug of a compound of Formula I may be created by internally linking two functional groups in a compound of Formula I, for instance by forming a lactone.

References to compounds of Formula I are taken to include the compounds themselves and prodrugs thereof. The invention includes such compounds of Formula I as well as pharmaceutically acceptable salts of such compounds and pharmaceutically acceptable solvates of said compounds and salts.

Administration and Dosing

Typically, a compound of the invention is administered in an amount effective to treat a condition as described herein. The compounds of the invention can be administered as compound per se, or alternatively, as a pharmaceutically acceptable salt. For administration and dosing purposes, the compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, or topically.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the invention is typically from about 0.001 to about 100 mg/kg (i.e., mg compound of the invention per kg body weight) for the treatment of the indicated conditions discussed herein. In another embodiment, total daily dose of the compound of the invention is from about 0.01 to about 30 mg/kg, and in another embodiment, from about 0.03 to about 10 mg/kg, and in yet another embodiment, from about 0.1 to about 3. It is not uncommon that the administration of the compounds of the invention will be repeated a plurality of times in a day (typically no greater than 4 times). Multiple doses per day typically may be used to increase the total daily dose, if desired.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient.

Intravenously, doses may range from about 0.01 to about 10 mg/kg/minute during a constant rate infusion.

Suitable subjects according to the invention include mammalian subjects. In one embodiment, humans are suitable subjects. Human subjects may be of either gender and at any stage of development.

Pharmaceutical Compositions

In another embodiment, the invention comprises pharmaceutical compositions. Such pharmaceutical compositions comprise a compound of the invention presented with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Co-Administration

The compounds of the invention can be used alone, or in combination with other therapeutic agents. The invention provides any of the uses, methods or compositions as defined herein wherein the compound of any embodiment of Formula I herein, or pharmaceutically acceptable salt thereof, or pharmaceutically acceptable solvate of said compound or salt, is used in combination with one or more other therapeutic agent discussed herein. This would include a pharmaceutical composition for the treatment of a disease or condition for which an agonist of the GLP-1R is indicated, comprising a compound of Formulas I, II, III, IV, or V, or a pharmaceutically acceptable salt thereof, as defined in any of the embodiments described herein, and one or more other therapeutic agent discussed herein.

The administration of two or more compounds "in combination" means that all of the compounds are administered closely enough in time that each may generate a biological effect in the same time frame. The presence of one agent may alter the biological effects of the other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the invention provides methods of treatment that include administering compounds of the present invention in combination with one or more other pharmaceutical agents, wherein the one or more other pharmaceutical agents may be selected from the agents discussed herein.

In one embodiment, the compounds of this invention are administered with an antidiabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of this invention are administered with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues therof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of this invention are administered in combination with one or more of the following: an agent to treat NASH including but not limited to PF-05221304, an FXR agonist (e.g., obeticholic acid), a PPAR α/δ agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976 or PF-05221304), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

Some specific compounds that can be used in combination with the compounds of the present invention for treating diseases or disorders described herein (e.g. NASH) include:

4-(4-(1-Isopropyl-7-oxo-1,4,6,7-tetrahydrospiro[indazole-5,4'-piperidine]-1'-carbonyl)-6-methoxypyridin-2-yl) benzoic acid, which is an example of a selective ACC inhibitor and was prepared as the free acid in Example 9 of U.S. Pat. No. 8,859,577, which is the U.S. national phase of International Application No. PCT/IB2011/054119, the disclosures of which are hereby incorporated herein by reference in their entireties for all purposes. Crystal forms of 4-(4-(1-Isopropyl-7-oxo-1,4,6,7-tetrahydrospiro[indazole-5,4'-piperidine]-1'-carbonyl)-6-methoxypyridin-2-yl)benzoic acid, including an anhydrous mono-tris form (Form 1) and a trihydrate of the mono-tris salt (Form 2), are described in International PCT Application No. PCT/IB2018/058966, the disclosure of which is hereby incorporated herein by reference in its entirety for all purposes;

(S)-2-(5-((3-Ethoxypyridin-2-yl)oxy)pyridin-3-yl)-N—(tetrahydrofuran-3-yl)pyrimidine-5-carboxamide, or a pharmaceutically acceptable salt thereof, and its crystalline solid forms (Form 1 and Form 2) is an example of a DGAT2 inhibitor described in Example 1 of U.S. Pat. No. 10,071,992, the disclosure of which is hereby incorporated herein by reference in its entirety for all purposes;

[(1R,5S,6R)-3-{2-[(2S)-2-methylazetidin-1-yl]-6-(trifluoromethyl)pyrimidin-4-yl}-3-azabicyclo[3.1.0]hex-6-yl] acetic acid, or a pharmaceutically acceptable salt thereof, (including a crystalline free acid form thereof) is an example of a ketohexokinase inhibitor and is described in Example 4 of U.S. Pat. No. 9,809,579, the disclosure of which is hereby incorporated herein by reference in its entirety for all purposes; and the FXR agonist Tropifexor or a pharmaceutically acceptable salt thereof is described in Example 1-1B of U.S. Pat. No. 9,150,568, the disclosure of which is hereby incorporated herein by reference in its entirety for all purposes.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semi-permeable matrices of solid hydrophobic polymers containing the compound of Formulas I, II, III, IV, or V, which matrices are in the form of shaped articles, e.g., films, or microcapsules. Examples of sustained-release matrices include polyesters, hydrogels (for example, poly(2-hydroxy-ethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

Another aspect of the invention provides kits comprising the compound of Formulas I, II, III, IV, or V or pharmaceutical compositions comprising the compound of Formulas I, II, III, IV, or V of the invention. A kit may include, in addition to the compound of Formulas I, II, or III, of the invention or pharmaceutical composition thereof, diagnostic or therapeutic agents. A kit may also include instructions for use in a diagnostic or therapeutic method. In some embodiments, the kit includes the compound of Formulas I, II, III, IV, or V, or a pharmaceutical composition thereof and a diagnostic agent. In other embodiments, the kit includes the compound of Formulas I, II, III, IV, or V, or a pharmaceutical composition thereof.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

Preparation

The compounds of Formulas I, II, III, IV, or V, may be prepared by the general and specific methods described below, using the common general knowledge of one skilled in the art of synthetic organic chemistry. Such common general knowledge can be found in standard reference books such as Comprehensive Organic Chemistry, Ed. Barton and Ollis, Elsevier; Comprehensive Organic Transformations: A Guide to Functional Group Preparations, Larock, John Wiley and Sons; and Compendium of Organic Synthetic Methods, Vol. I-XII (published by Wiley-Interscience). The starting materials used herein are commercially available or may be prepared by routine methods known in the art.

In the preparation of the compounds of Formulas I, II, III, IV, or V, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I compounds.

The Schemes described below are intended to provide a general description of the methodology employed in the preparation of the compounds of the present invention.

Some of the compounds of the present invention may contain single or multiple chiral centers with the stereochemical designation (R) or (S). It will be apparent to one skilled in the art that all of the synthetic transformations can be conducted in a similar manner whether the materials are enantioenriched or racemic. Moreover the resolution to the desired optically active material may take place at any desired point in the sequence using well known methods such as described herein and in the chemistry literature. For example, intermediates (e.g., S4, S7, S8, S24, S40, and S41) and finals (e.g., S25 and S42) may be separated using chiral chromatographic methods. Alternatively, chiral salts may be utilized to isolate enantiomerically enriched intermediates and final compounds.

In the Schemes that follow, the variables X, Y, $Z^1$, $Z^2$, $Z^3$, R, $R^1$, $R^2$, $R^3$, $R^4$, m, p, and q are as described herein for compounds of Formulas I, II, III, IV, or V unless otherwise noted. For simplicity, the variable A is used to denote Ring A and its optional substituent $R^1$. For the Schemes provided below, each $X^1$, $X^2$, $X^3$, and $X^4$ can independently be a leaving group such as any alkyl or aryl sulfonate (e.g., mesylate, tosylate, or triflate), or a halogen or any other group that can be displaced by an amine or utilized in a metal mediated coupling reaction. $X^4$ may also be a protected carboxylic acid (i.e., ester). When the protecting group is identified as $Pg^1$, it can be an alkyl amine protecting group such as benzyl, benzhydryl, allyl, or the like; a carbamate protecting group such as Boc, Cbz, or the like; or an amide protecting group such trifluoroacetamide. When the protecting group is identified as $Pg^2$, it can be an acid protecting group such as methyl, ethyl, benzyl, t-butyl or the like. When the protecting group is identified as $Pg^3$, it can be an alcohol protecting group such as trimethylsilylethoxyethyl; or an acyl group like acetyl, benzoyl or the like; or a trialkylsilyl group such as trimethylsilyl, tert-butyldimethylsilyl, triisopropylsilyl or the like. $R^{2a}$ is H or —$C_{1-2}$alkyl, wherein alkyl may have 0 to 1 OH. $R^{4a}$ is $C_{1-2}$alkyl, $C_{0-2}$alkylene-$C_{3-6}$cycloalkyl, $C_{0-2}$alkylene-$R^5$, or $C_{1-2}$alkylene-$R^6$, wherein said alkyl, alkylene, or cycloalkyl may be independently substituted as valency allows with 0 to 3 F atoms and 0 to 1 substituent independently selected from $C_{0-1}$alkylene-$OR^O$ and —$N(R^N)_2$.

The substituted piperidine S8, where $R^2$=H and Y=CH, may be prepared as discussed in Scheme 1. Aryl or heteroaryl bromide S1 can be treated with an alkyl lithium, for example butyl lithium or tert-butyl lithium, to give an aryl- or heteroaryl-lithium species that may react with aldehyde S2 to give diol S3. Other aryl or heteroaryl organometallic reagents, such as, but not limited to, Grignard reagents, may also be used in the preparation of S3. The reaction is typically conducted at a temperature around −70° C. Diol S3 may then be oxidized with $NaIO_4$ to provide acetal S4 ($R^2$=H). Compound S4 may then be reacted with a substituted boronic acid or boronate ester (S5) in the presence of a palladium catalyst and ligand complex in the manner of a Suzuki reaction (Maluenda and Navarro, Molecules, 2015, 20, 7528-7557) to provide compounds of the general formula S6. Reduction of the olefin to provide compounds of general structure S7 could be performed under an atmosphere of hydrogen (15-100 psi $H_2$) in an alcoholic solvent such as MeOH or EtOH or alternatively an aprotic organic solvent such as EtOAc or THF in the presence of an appropriate catalyst such as palladium on carbon, $Pd(OH)_2$ on carbon (Pearlman's catalyst), $PtO_2$ (Adams catalyst), or tris(triphenylphosphine)rhodium(I) chloride (Wilkinson's catalyst). Transfer hydrogenation reagents, for example ammonium formate or dihydrobenzene, or similar, may be employed using suitable catalyst. Alternatively, the reduction may be accomplished by alternative methods know to those skilled in the art using reagents such as triethyl silane or other silanes, under acid or metallic catalysis, or metallic reductants, such as magnesium or similar. Alternatively, the olefin can be functionalized by methods known to one skilled in the art to introduce $R^3$ groups. For example, the olefin could be hydroborated to produce an alcohol that could be alkylated or further converted to a nitrile, F or alkyl group. Removal of $Pg^1$ could be effected with many methods described in literature to provide amines S8.

Scheme 1

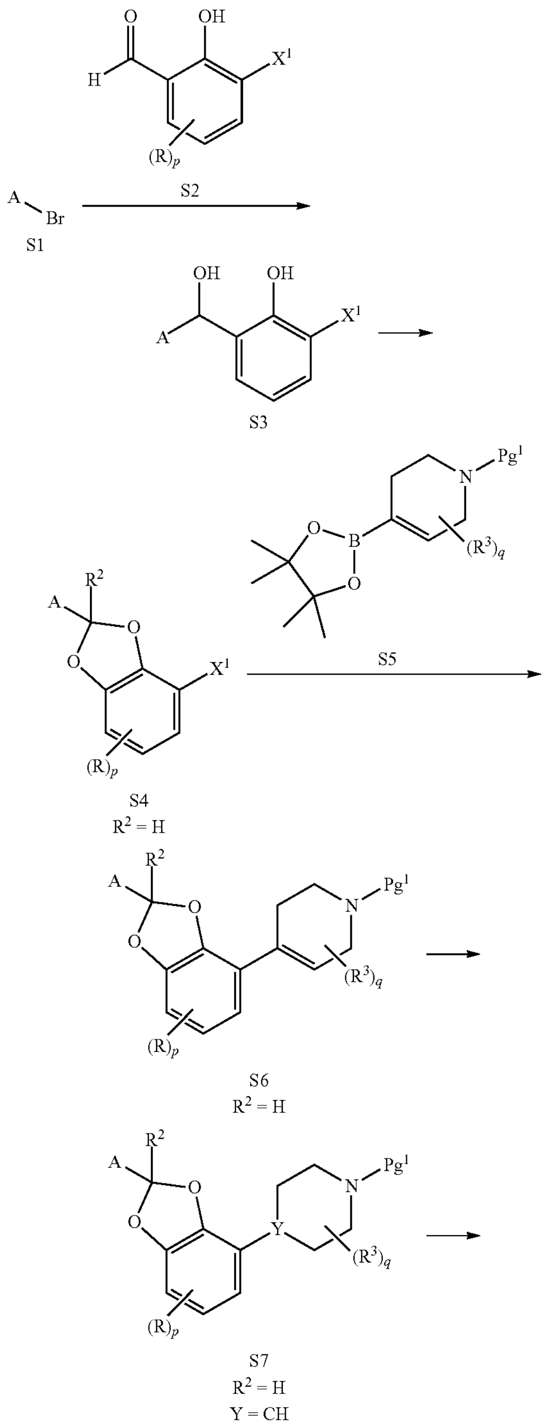

-continued

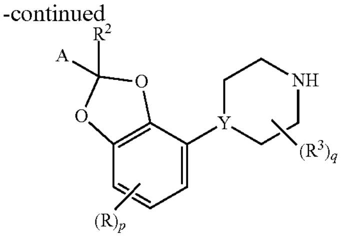

S8
$R^2 = H$
Y = CH

Scheme 2 provides an alternative preparation of compounds of general structure S4. Reaction of appropriately substituted diols of general structure S9 with aldehydes or ketones of general structure S10a in the presence of a an acid such as p-toluenesulfonic acid or pyridinium p-toluenesulfonate in aprotic organic solvent such as toluene or benzene may deliver compounds of the general structure S4. The reaction is typically heated at reflux using a Dean-Stark trap to azeotropically remove water. Diols S9 may also be reacted with cyclic (dotted line exists) or acyclic (dotted line is absent) acetals or ketals of general structure S10b under acidic catalysis. The same is applicable with cyclic or acyclic thioacetals or thioketals of general structure S10c under the influence of mercury salts, mild oxidants or alkylating reagents, to provide compounds S4. Alternatively, diols of general formula S9 may be reacted with appropriately substituted alkyne S11 in an aprotic solvent such as toluene in the presence triruthenium dodecacarbonyl at a temperature around 100° C. to deliver compounds of the general structure S4 where $R^2{=}CH_2R^{2a}$. In cases where $R^2$ contains an alcohol functional group, such as $CH_2OH$, an alcohol protecting group ($Pg^3$), such as acetate, may be incorporated into compounds of general structure S10. The protecting group may then be removed in a subsequent step. Intermediate S4 may then be further modified using methods described for Scheme 1 to provide amines of general structure S8.

Scheme 2

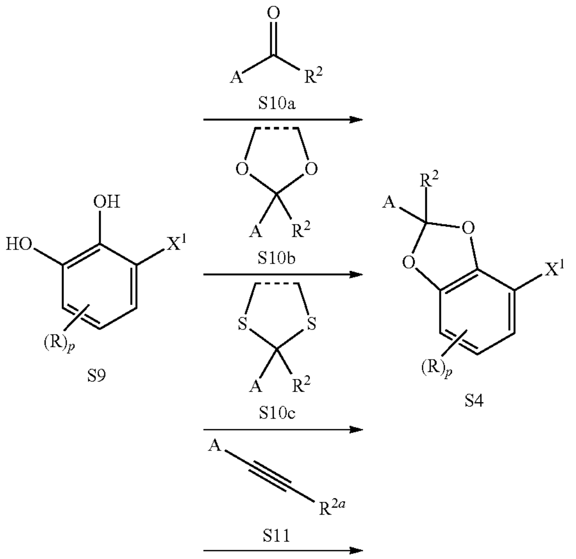

S10a
S10b
S10c
S11
S9
S4

As provided in Scheme 3, conversion of S4 to compounds of general structure S7 where Y═N can be accomplished by such manner as a Buchwald-Hartwig C—N coupling between compounds of the general structure S4 and an appropriately substituted and protected piperazine S12 in the presence of a palladium or copper catalyst and ligand complex. These reactions are generally performed between 0 and 110° C. in aprotic organic solvents such as but not limited to 1,4-dioxane and $PhCH_3$ with added base such as $Cs_2CO_3$, LiHMDS or NaOtBu. Removal of $Pg^1$ could be effected with many methods described in literature to provide amines S8 where Y═N.

Scheme 3

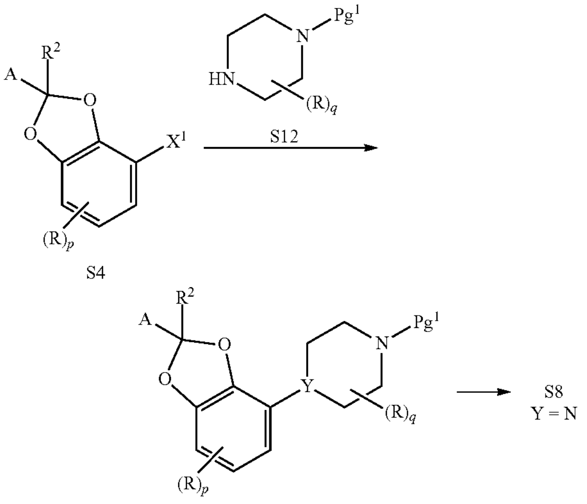

S12
S4
S7
Y = N
S8
Y = N

Amine compounds S8 prepared via methods described in Schemes 1-3 can be alkylated with a protected 2-bromoacetate in the presence of a suitable base such as $K_2CO_3$, $Et_3N$, NaH or LiHMDS in a polar aprotic solvent such as but not limited to DMF, DMAc, DMSO or NMP to deliver compounds of the general structure S13 (X═N, L═$CH_2$). Standard ester hydrolysis can be performed to provide acids S14. If $Pg^2$ is t-butyl, standard acidic deprotection methods such as TFA/DCM, HCl/1,4-dioxane, HCl/EtOAc or other suitable conditions may be used to deliver acids S14. If $Pg^2$ is methyl or ethyl, standard basic deprotection methods such as aqueous NaOH in methanol or ethanol, or other suitable conditions may be used to deliver acids S14.

Scheme 4

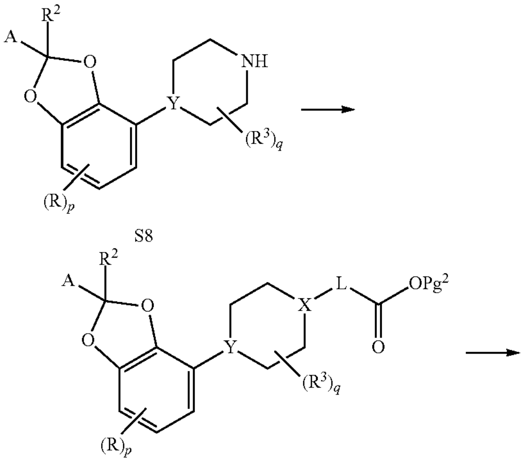

S8
S13
X = N
$L = CH_2$

-continued

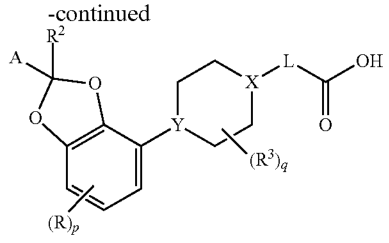

S14
X = N
L = $CH_2$

Compounds of general structure S15 (Scheme 5) can react with amines $R^4NH_2$ in the presence of bases such as sodium-, potassium-, or cesium carbonate, -bicarbonate, hydroxide, acetate, or an organic amine base such as $Et_3N$, DIPEA, DBU, and the like in a polar aprotic solvent such as but not limited to THF, DMF, DMAc, DMSO or NMP or a protic solvent such as water, MeOH, EtOH or iPrOH or a mixture thereof to deliver compounds of the general structure S16. One will note that if an example provides an $R^4$ with a resolved enantiomeric center, the other enantiomer or a racemix mixture thereof could be obtained by selection of the appropriate starting material. Preferred $X^3$ substituents include F, Cl, and Br, preferred $X^4$ groups include Cl, Br, and $—CO_2—Pg^2$. Reduction of the nitro group can be affected by hydrogenation at 1-6 atm $H_2$ with a metal catalyst such as palladium on carbon or Raney nickel in a protic solvent such as MeOH or EtOH or aprotic solvent such as DMF, THF or EtOAc. Alternatively, the nitro group may be reduced with iron, zinc, $SnCl_2$ or other suitable metal in an acidic media such as 1N HCl, AcOH or aqueous $NH_4Cl$ in THF or methanol to provide compounds of general structure S17 (Scheme 5a). Compounds such as S18 may be acylated by acyl halides by standard fashion or by carboxylates via standard amide coupling protocols to provide compounds S19. Reduction to compounds S20 may be performed under standard conditions with reducing agents such as LAH or $BH_3$-THF or $BH_3$-DMS (Scheme 5b).

Scheme 5 a)

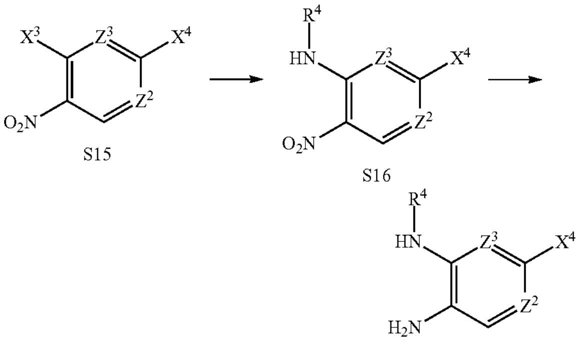

S15

S16

S17

-continued b)

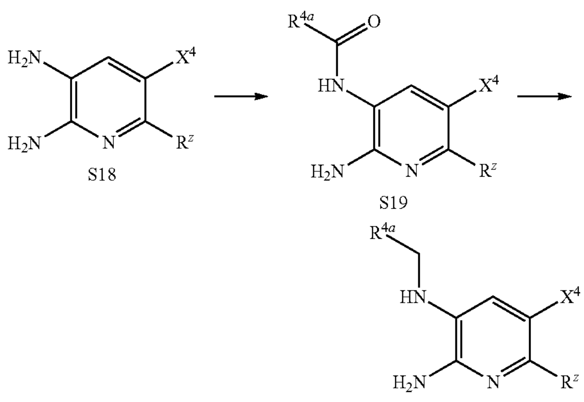

S18

S19

S20

Diamine compounds S17 and S20 prepared via methods described in Schemes 5a and 5b, collectively designated as diamine S21 (Scheme 6), may be acylated with acids of general structure S14 under standard amide coupling protocols to deliver amides S22 which will exist as a mixture from 100% S22a to 100% S22b. This mixture of amines S22 may be cyclized to deliver compounds of general structure S23 by a variety of methods. Amines S22 may be heated with a dehydrating agent such as $T_3P$® or an alkyl alcohol such as n-butanol under microwave conditions (10-60 min at 120-180° C.) to deliver compounds S23. Alternatively, the mixture of compounds S22 may be heated under acidic conditions such as AcOH from 60-100° C. or under basic conditions such as aqueous NaOH or KOH in 1,4-dioxane from 60-100° C. to provide S23. Compounds of general structure S23 ($X^4$═Cl, Br or I) can be converted to esters of structure S24 by palladium-catalyzed carbonylation under a 15-100 psi carbon monoxide atmosphere at a temperature from 20-100 at a temperature from 20-100° C. with an appropriate alcohol such as MeOH or EtOH or other alkyl alcohol. Hydrolysis of ester S24 can be performed as described in Scheme 4 to provide acids S25. For compounds S22 where $X^4$═$CO_2$—$Pg^2$ conversion to ester S24 proceeds under similar conditions as described previously except for use of the basic cyclization method where compound S25 may be isolated directly from the reaction mixture. For compounds S24 where $X^4$ is $CO_2tBu$, deprotection to acid S25 can be performed under acidic conditions described in Scheme 4. Alternatively, for compounds S24 where $Pg^2$ is a $C_1$-$C_8$ alkyl, such as methyl, ethyl, hexyl or octyl, the ester deprotection may be performed with a variety of enzymes including esterases, proteases, peptidases, lipases, and glycosidases which are well known to those skilled in the art. The hydrolysis may also be performed by treating the ester with an aqueous solution of 1,5,7-triazabicyclo[4.4.0]dec-5-ene at RT.

Scheme 6

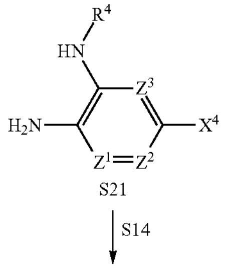

S21

-continued

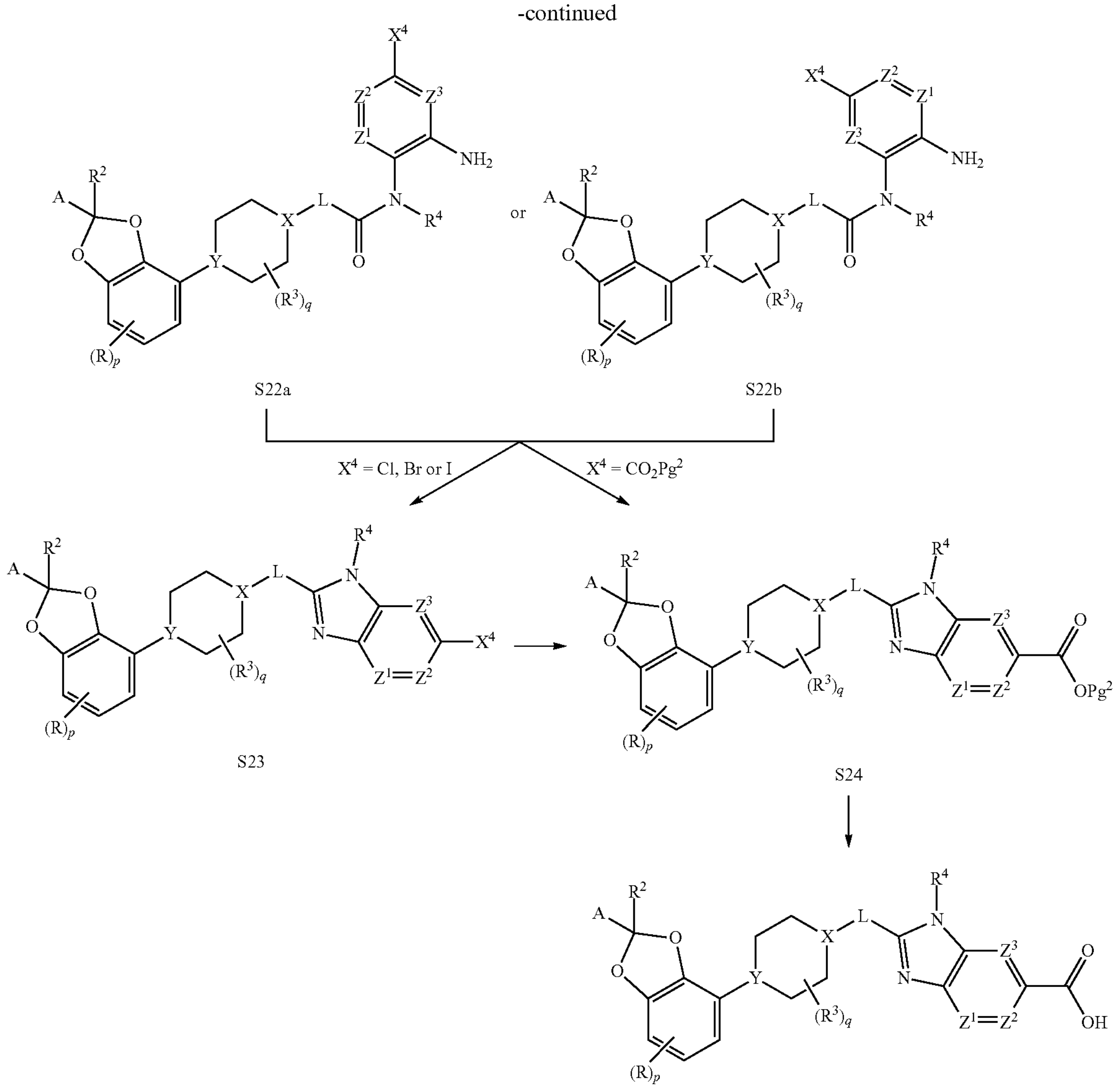

S22a or S22b

S23

S24

S25

Additionally, diamine S21 may be converted to the 2-chloromethyl benzimidazole S26 (Scheme 7) by several methods. Treatment with 2-chloroacetyl chloride or chloroacetic anhydride in an aprotic solvent such as 1,4-dioxane followed by heating at 40-100° C. for 2-18 h can deliver the desired benzimidazole S26 where $Z^1$, $Z^2$ and $Z^3$ are CH. In the cases where $Z^1$, $Z^2$ and $Z^3$ are not all $CR^z$, after treatment with 2-chloroacetyl chloride in an aprotic solvent such as 1,4-dioxane for 30 min to 4 h, the solvent is exchanged for an acidic media such as AcOH or TFA followed by heating at 40-100° C. for 2-18 h to provide the desired compound S26. Diamine S21 can also be treated with chloroacetic anhydride at a temperature between 0 and 80° C. in an aprotic solvent such as, but not limited to 1,4-dioxane, THF or MeCN, followed by heating for 2 to 18 h at 60-100° C. to deliver the desired compound S26. In addition, diamine S21 can be treated with 2-chloro-1,1,1-trimethoxyethane in an aprotic solvent such as, but not limited to 1,4-dioxane, THF or MeCN, or a protic solvent, e.g., MeOH or EtOH, in the presence of an acid catalyst, e.g., pTSA, at 20-100° C. Alternatively, diamines S21 may be heated 100-180° C. with 2-hydroxyacetic acid in an aprotic solvent, such as but not limited to mesitylene, to provide a hydroxymethyl intermediate. Conversion of the hydroxymethyl group to the chloromethyl compound S26 may be accomplished by standard methods, including treatment with $SOCl_2$ in an aprotic solvent. Compounds of general structure S26 can be reacted with compounds S8 in the presence of bases such as sodium-, potassium-, or cesium carbonate, -bicarbonate, NaH or an organic amine base such as $Et_3N$, DIPEA, DBU, and the like in a polar aprotic solvent, such as but not limited to THF, MeCN, DMF, DMAc, DMSO or NMP, to deliver compounds S23 ($X^4$=Cl, Br, I) or compounds S24 ($X^4$=$CO_2$—$Pg^2$) that are then used to obtain compounds S25 via methods described in Scheme 6.

Scheme 7

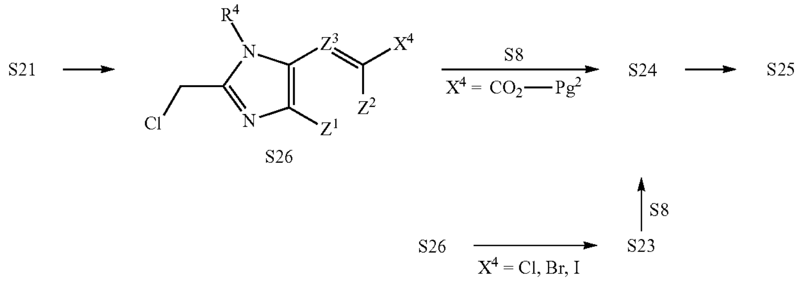

Alternatively (Scheme 8), compounds of general structure S26 can be reacted with appropriately substituted and protected piperazines S12, in the presence of bases such as sodium-, potassium-, or cesium carbonate, —bicarbonate, NaH or an organic amine base such as $Et_3N$, DIPEA, DBU, and the like in a polar aprotic solvent, such as but not limited to THF, MeCN, DMF, DMAc, DMSO or NMP, to provide compounds S27 (Scheme 8). Removal of $Pg^1$ could be effected with many methods described in literature to provide amines S28. Conversion to compounds of general structure S23 ($X^4$=Cl, Br or I) or S24 ($X^4$=$CO_2$—$Pg^2$) can be accomplished by such manner as a Buchwald-Hartwig C—N coupling between compounds of the general structures S4 and as described previously in Scheme 3. Compounds of general structure S23 or S24 can then be used to obtain compounds of structure S25 via methods described in Scheme 6.

Scheme 8

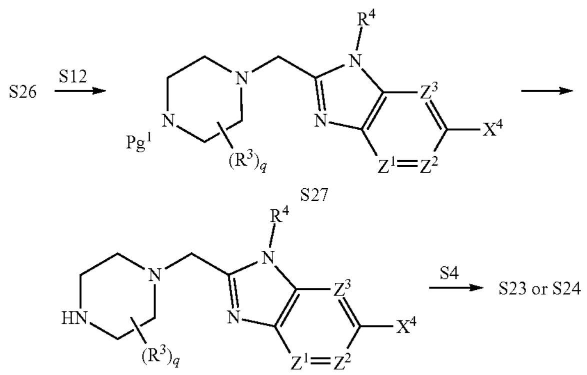

Compounds of general structure S25 may also be prepared as discussed in Scheme 9. Diol S9 can be protected to give S29. The trimethylsilylethoxymethyl group is a preferred protecting group. Protection of the diol as the corresponding acetal, for example the formaldehyde acetal, is also preferred. Compound S29 may then be reacted with a substituted boronic acid or boronate ester (S5) and the olefin then reduced with methods described in Scheme 1 to provide compounds of the general formula S31 where Y=CH. Alternatively, compound S29 may be coupled with piperazines of general structure S12 using methods described in Scheme 3 to provide S31 where Y=N. Compounds of general structure S31 may be deprotected and then coupled with S26 to give compounds of general structure S33 using methods described in Scheme 7. Alternatively, compounds of general structure S33 may be prepared from S32 by conversion of S32 to the corresponding N-acetic acid derivative and subsequent condensations with diamines S21 as described in Schemes 4 and 6. Deprotection of S33 using methods know to those skilled in the art may provide diols of general structure S34 which may then react with alkynes of general structure S11 using methods described in Scheme 2 to provide S23 or S24. Alternatively, S34 may be converted to S23 or S24 using aldehydes, ketones or their derivatives, as discussed in Scheme 2. Compounds of general structure S23 or S24 can then be used to obtain compounds of structure S25 via methods described in Scheme 6.

Scheme 9

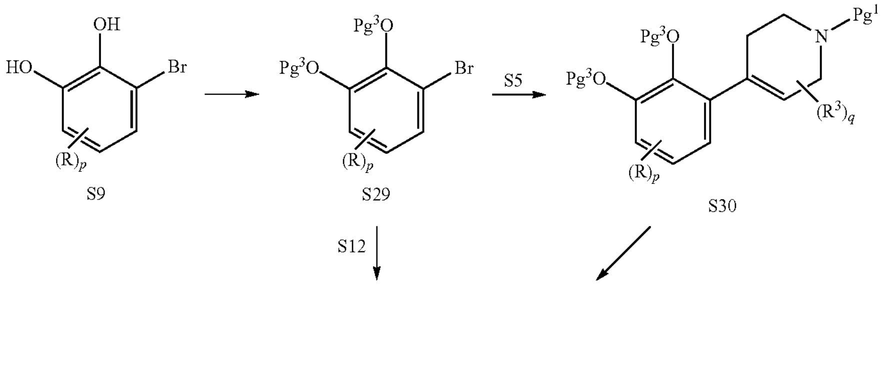

-continued

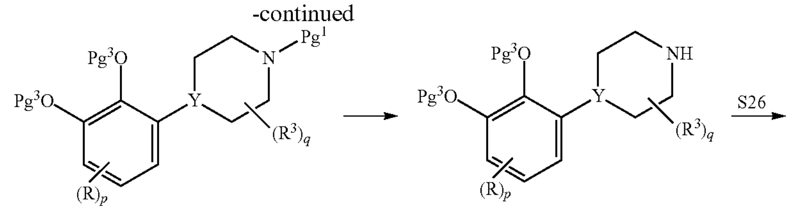

S31 S32

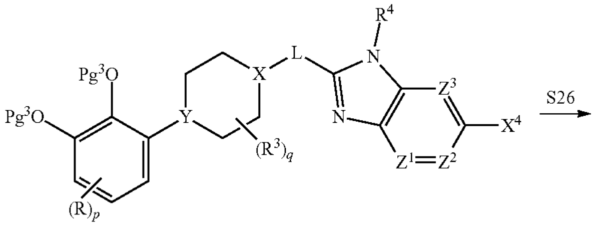

S33

X = N

L = $CH_2$

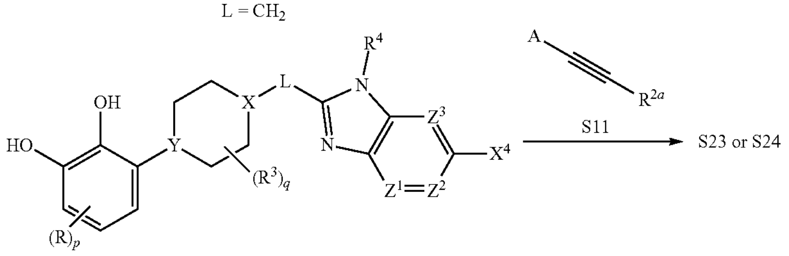

S34

Compounds of general structures S24 and S33 where Y═N and X-L=cyclopropyl may be prepared as discussed in Scheme 10. Protected piperidinone S35 may be homologated to unsaturated ester S36 using methods well known to those skilled in the art. For example, Horner-Wadsworth-Emmons olefination of S42 with a phosphonate, such as ethyl (diethoxyphosphoryl)acetate, that has been deprotonated with a strong base such as lithium, sodium or potassium tert-butoxide, may provide S36. The reaction is typically conducted in an aprotic solvent like THF or DME, at a temperature around 0 to −50° C. Conversion of S36 to the cyclopropane derivative S37 may be accomplished by treatment with sulfoxonium ylid derived from trimethylsulfoxonium iodide and a base, such as potassium tert-butoxide or sodium hydride. Deprotection of S37 and subsequent coupling of the resulting carboxylic acid S38 with S21, where $X^4$=$CO_2Pg^2$, using methods described in Scheme 6 may provide compounds of general formula S39. Deprotection of S39 and coupling with S4 using methods described in Scheme 3 may give compounds of general structure S24 where Y═N and X-L is cyclopropyl. Compounds of general structure S24 can then be used to obtain compounds of structure S25 via methods described in Scheme 6. Alternatively, S40 may be reacted with S29 using methods described in Scheme 3 to provide S33 where Y═N and X-L=cyclopropyl. Compounds of general structure S33 can then be used to obtain compounds of structure S25 via methods described in Scheme 6 and 9.

Scheme 10

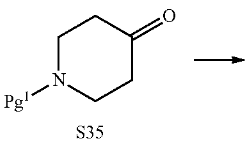

S35

-continued

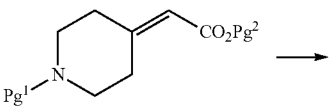

S36

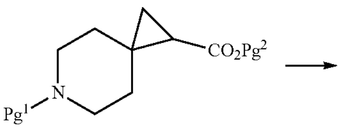

S37

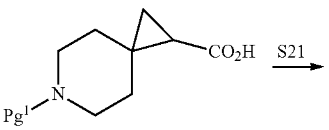

S38

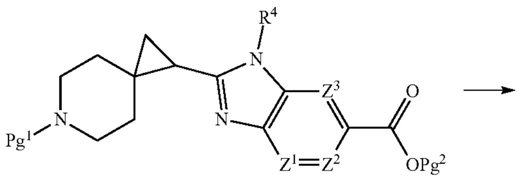

S39

-continued

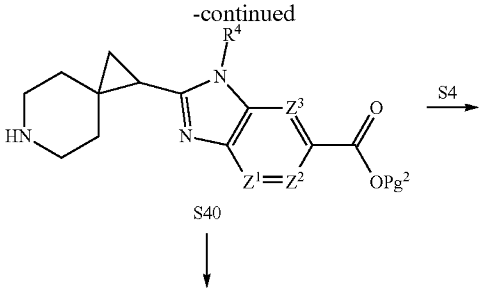

S40

S33
Y = N
X—L = cPr

S24
Y = N
X—L = cPr

Alternatively, compounds of the general structure S25 where Y=N and X-L is cyclopropyl may be prepared as described in Scheme 11. Removal of $Pg^1$ from S37 provides piperidine derivative S43. Coupling of S43 with S4 in a manner similar to that described in Scheme 3 provides S13 where Y=N and X-L is cyclopropyl. Deprotection may then provide compounds of general structure S14 that may then be used to prepare S25 as described in Scheme 6.

Scheme 11

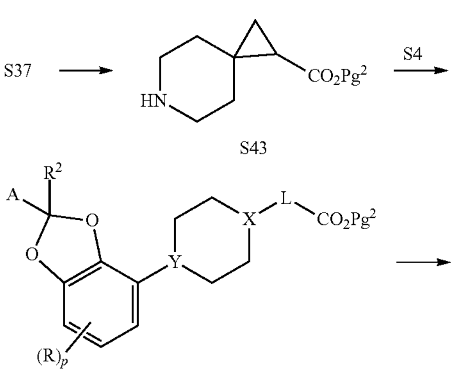

S43

S14
Y = N
X—L = cPr

S13
Y = N
X—L = cPr

EXAMPLES

The following illustrate the synthesis of non-limiting compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv products from EMD Chemicals. In other cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. The symbol * denotes that the chlorine isotope pattern was observed in the mass spectrum. Chiral separations were used to separate enantiomers or diastereomers of some intermediates during the preparation of the compounds of the invention. When chiral separation was done, the separated enantiomers were designated as ENT-1 or ENT-2 (or DIAST-1 or DIAST-2), according to their order of elution. In some embodiments, enantiomers designated as ENT-1 or ENT-2 can be used as starting materials to prepare other enantiomers or diastereomers. In such situations, the resulting enantiomers prepared are designated as ENT-X1 and ENT-X2, respectively, according to their starting materials; similarly, the diastereomers prepared are designated as DIAST-X1 and DIAST-X2, respectively, (or DIAST-according to their starting materials. DIAST-Y and DIAST-Z nomenclature is used similarly, in syntheses employing multiple intermediates.

For compounds with two chiral centers, the stereoisomers at each stereocenter were separated at different times. The designation of ENT-1 or ENT-2 (or DIAST-1 or DIAST-2) of an intermediate or an example refers to the order of elution for the separation done at that step. It is recognized that when stereoisomers at a chiral center are separated in a compound with two or more centers, the separated enantiomers are diastereomers of each other. By way of example, but not limitation, Examples 15 and 16 have two chiral centers. The chiral center of the cyclopropyl moiety was separated when intermediate C36 was separated into ENT-1, giving intermediate P17, and ENT-2, giving intermediate P18. P18 was then used in preparing C70, which had one stereoisomer enriched at the cyclopropyl chiral carbon and a mixture of stereoisomers at the dioxolane carbon. C70 was then separated into DIAST-Y1 at the dioxolane carbon, giving intermediate C71, and DIAST-Y2 at the dioxolane carbon, giving intermediate C72, where these intermediates are enriched in a single stereoisomer. C71 was then used to prepare Example 15, which is identified by name as 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-X1, trifluoroacetate salt [from P18 via C71]. In these preparations, after a mixture is subjected to separation procedures, the chiral center is identified with "abs" near that center, with the understanding that the separated enantiomers may not be enantiomerically pure. Typically, the enriched enantiomer at each chiral center is >90% of the isolated material. Preferably, the enriched enantiomer at each center is >98% of the mixture.

In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

Preparation P1 tert-Butyl 4-[2-(4-chloro-2-fluorophenyl)-1,3-benzodioxol-4-yl]piperidine-1-carboxylate (P1)

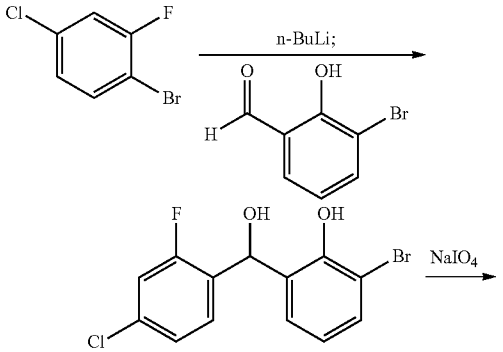

C1

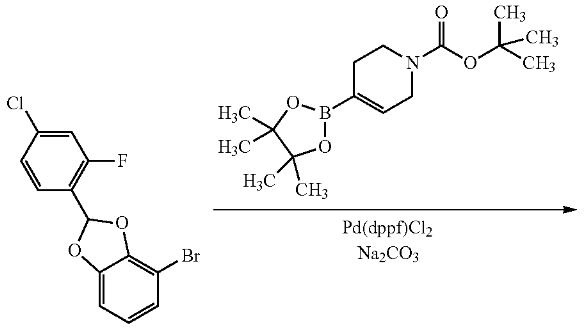

C2

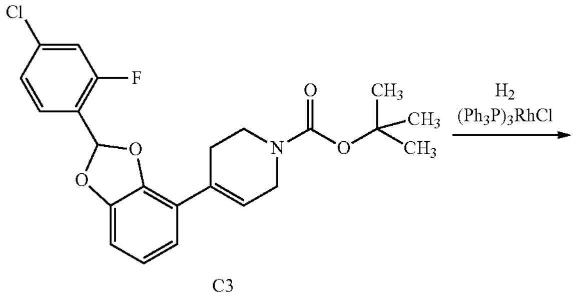

C3

-continued

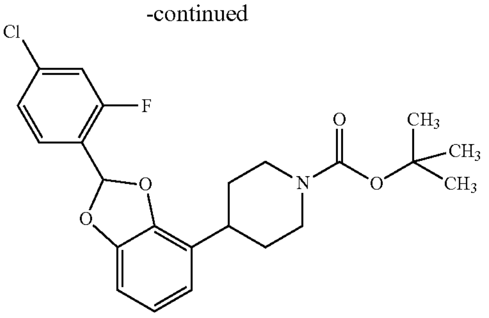

P1

Step 1. Synthesis of 2-bromo-6-[(4-chloro-2-fluorophenyl) (hydroxy)methyl]phenol (C1)

This experiment was carried out in two batches of the same scale. n-Butyllithium (2.5 M solution in hexanes; 32.8 mL, 82.0 mmol) was slowly added to a −70° C. solution of 1-bromo-4-chloro-2-fluorobenzene (17.2 g, 82.1 mmol) in diethyl ether (100 mL), while the temperature of the reaction mixture was maintained below −60° C. After the reaction mixture had been stirred at −70° C. for 20 minutes, a solution of 3-bromo-2-hydroxybenzaldehyde (5.5 g, 27 mmol) in diethyl ether (100 mL) was slowly added, while the reaction temperature was maintained below −60° C. After a further 1 hour of stirring at −70° C., the reaction was quenched by addition of aqueous ammonium chloride solution (50 mL) at −70° C., and the resulting mixture was diluted with water (100 mL). The two batches were combined at this point and extracted with ethyl acetate (400 mL); the organic layer was washed with saturated aqueous sodium chloride solution (200 mL), dried over sodium sulfate, filtered, and concentrated in vacuo. Silica gel chromatography (Gradient: 0% to 7% ethyl acetate in petroleum ether) afforded C1 as a white solid. Combined yield: 15.7 g, 47.4 mmol, 88%. $^1H$ NMR (400 MHz, chloroform-d) δ 7.44 (dd, J=8.0, 1.5 Hz, 1H), 7.37 (dd, J=8.1, 8.1 Hz, 1H), 7.15 (br dd, J=8.5, 2.1 Hz, 1H), 7.12-7.05 (m, 2H), 6.80 (dd, J=7.8, 7.8 Hz, 1H), 6.78 (s, 1H), 6.31 (d, J=4.8 Hz, 1H), 3.02 (brd, J=4.9 Hz, 1H).

Step 2. Synthesis of 4-bromo-2-(4-chloro-2-fluorophenyl)-1,3-benzodioxole (C2)

To a solution of C1 (15.7 g, 47.4 mmol) in methanol (450 mL) was added a solution of sodium periodate (25.4 g, 119 mmol) in water (105 mL), and the reaction mixture was stirred at 30° C. for 16 hours, whereupon it was concentrated in vacuo. After the residue had been diluted with dichloromethane (500 mL), it was washed with water (500 mL). The dichloromethane solution was then dried over sodium sulfate, filtered, and concentrated in vacuo. Purification via silica gel chromatography (Eluent: petroleum ether) provided C2 as a white solid. Yield: 10.0 g, 30.3 mmol, 64%. The following $^1H$ NMR data was obtained from an experiment carried out in the same manner but on smaller scale. $^1H$ NMR (400 MHz, DMSO-$d_6$) δ 7.67-7.61 (m, 2H), 7.50 (s, 1H), 7.43 (br dd, J=8, 2 Hz, 1H), 7.09 (dd, J=8.3, 1.1 Hz, 1H), 7.01 (dd, J=7.9, 1.1 Hz, 1H), 6.86 (dd, J=8.1, 8.1 Hz, 1H).

Step 3. Synthesis of tert-butyl 4-[2-(4-chloro-2-fluorophenyl)-1,3-benzodioxol-4-yl]-3,6-dihydropyridine-1 (2H)-carboxylate (C3)

A reaction flask containing a suspension of C2 (8.00 g, 24.3 mmol), tert-butyl 4-(4,4,5,5-tetramethyl-1,3,2-dioxaborolan-2-yl)-3,6-dihydropyridine-1(2H)-carboxylate (9.01 g, 29.1 mmol), sodium carbonate (5.15 g, 48.6 mmol), and [1,1'-bis(diphenylphosphino)ferrocene]dichloro-palladium (II) [Pd(dppf)$Cl_2$; 888 mg, 1.21 mmol] in 1,4-dioxane (80 mL) and water (32 mL) was evacuated and charged with nitrogen. This evacuation cycle was repeated twice, and then the reaction mixture was stirred at 90° C. for 16 hours. After removal of solvent in vacuo, the residue was partitioned between ethyl acetate (200 mL) and water (200 mL). The organic layer was washed with saturated aqueous sodium chloride solution (100 mL), dried over sodium sulfate, filtered, and concentrated under reduced pressure. Chromatography on silica gel (Gradient: 0% to 4.3% ethyl acetate in petroleum ether) provided the product, which was combined with material from a similar reaction carried out using C2 (2.00 g, 6.07 mmol) to afford C3 as a light-yellow gum. Combined yield: 10.3 g, 23.8 mmol, 78%. $^1H$ NMR (400 MHz, chloroform-d) δ 7.53 (dd, J=8.3, 7.8 Hz, 1H), 7.23-7.16 (m, 3H), 6.88-6.83 (m, 2H), 6.81-6.76 (m, 1H), 6.34-6.28 (br m, 1H), 4.10-4.05 (m, 2H), 3.61 (br dd, J=6, 5 Hz, 2H), 2.59-2.50 (br m, 2H), 1.48 (s, 9H).

Step 4. Synthesis of tert-butyl 4-[2-(4-chloro-2-fluorophenyl)-1,3-benzodioxol-4-yl]piperidine-1-carboxylate (P1)

A solution of C3 (10.3 g, 23.8 mmol) and tris(triphenylphosphine)rhodium(I) chloride (Wilkinson's catalyst; 1.54 g, 1.66 mmol) in methanol (100 mL) was stirred at 50° C. under hydrogen (45 psi) for 18 hours. The reaction mixture was then filtered through a pad of diatomaceous earth, and the filtrate was concentrated under reduced pressure and subjected to silica gel chromatography (Gradient: 0% to 9% ethyl acetate in petroleum ether). The resulting material was combined with that from a similar reaction carried out using C3 (1.67 g, 3.87 mmol) to afford P1 as a colorless gum. Combined yield: 10.3 g, 23.7 mmol, 86%. LCMS m/z 456.1♦ [M+Na$^+$]. $^1H$ NMR (400 MHz, chloroform-d) δ 7.52 (dd, J=8.5, 7.6 Hz, 1H), 7.23-7.17 (m, 2H), 7.16 (s, 1H), 6.83 (dd, J=7.8, 7.8 Hz, 1H), 6.78-6.69 (m, 2H), 4.35-4.10 (br m, 2H), 2.89-2.71 (m, 3H), 1.89-1.77 (m, 2H), 1.77-1.63 (m, 2H), 1.47 (s, 9H).

Preparation P2 tert-Butyl 4-[2-(4-chloro-2-fluorophenyl)-2-methyl-1,3-benzodioxol-4-yl]piperidine-1-carboxylate

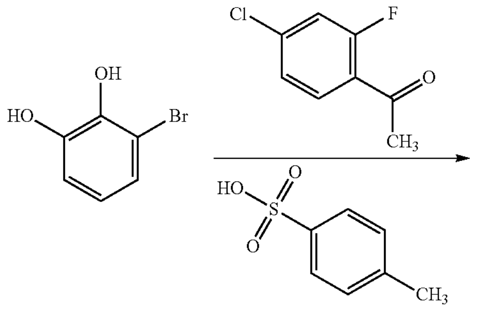

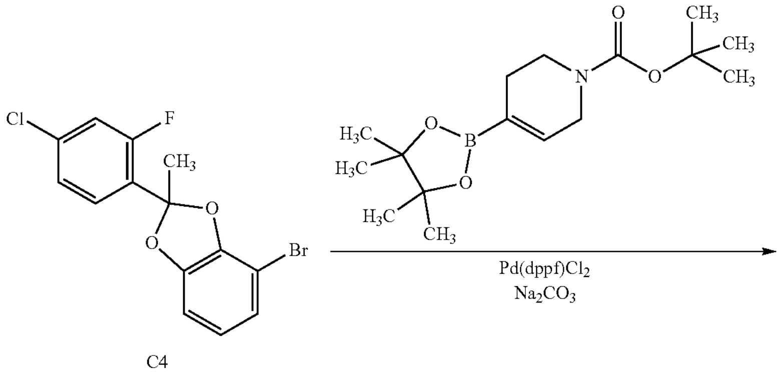

C4

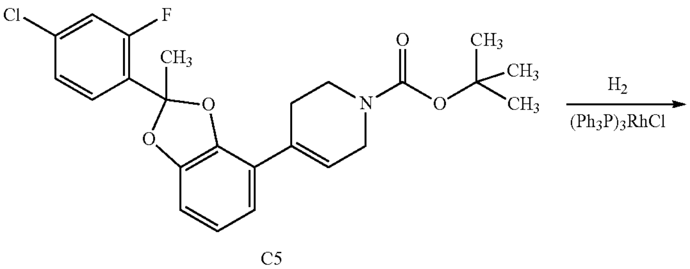

C5

-continued

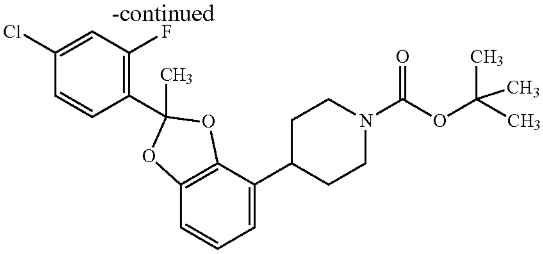

P2

Step 1. Synthesis of 4-bromo-2-(4-chloro-2-fluorophenyl)-2-methyl-1,3-benzodioxole (C4)

To a solution of 3-bromobenzene-1,2-diol (330 g, 1.75 mol) in toluene (1.5 L) were added 1-(4-chloro-2-fluorophenyl)ethanone (316 g, 1.83 mol) and p-toluenesulfonic acid (6.02 g, 35.0 mmol). The reaction apparatus was fitted with a Dean-Stark trap, and the reaction mixture was heated at 140° C. for 60 hours, whereupon the solution was concentrated in vacuo and purified using silica gel chromatography (Eluent: petroleum ether); C4 was obtained as a mixture of yellow oil and solid. Yield: 158 g, 460 mmol, 26%. $^{1}$H NMR (400 MHz, chloroform-d): δ 7.54 (dd, J=8.4, 8.4 Hz, 1H), 7.17-7.10 (m, 2H), 6.95 (dd, J=7.9, 1.4 Hz, 1H), 6.75 (dd, component of ABX pattern, J=7.8, 1.4 Hz, 1H), 6.70 (dd, component of ABX pattern, J=7.9, 7.9 Hz, 1H), 2.11 (d, J=1.1 Hz, 3H).

Step 2. Synthesis of tert-butyl 4-[2-(4-chloro-2-fluorophenyl)-2-methyl-1,3-benzodioxol-4-yl]-3,6-dihydropyridine-1 (2H)-carboxylate (C5)

tert-Butyl 4-(4,4,5,5-tetramethyl-1,3,2-dioxaborolan-2-yl)-3,6-dihydropyridine-1 (2H)-carboxylate (62 g, 200 mmol) and sodium carbonate (100 g, 940 mmol) were added to a solution of C4 (58.0 g, 169 mmol) in 1,4-dioxane (600 mL). After addition of [1,1'-bis(diphenylphosphino)ferrocene]dichloropalladium(II) (6.0 g, 8.2 mmol), the reaction mixture was heated to 90° C. and stirred for 16 hours. Water (500 mL) was then added, and the resulting mixture was extracted with ethyl acetate (2×500 mL). The combined organic layers were washed with saturated aqueous sodium chloride solution (2×500 mL), dried over sodium sulfate, filtered, and concentrated in vacuo. Silica gel chromatography (Gradient: 0% to 9% ethyl acetate in petroleum ether) provided C5 as a yellow oil. Yield: 56.0 g, 126 mmol, 75%. $^{1}$H NMR (400 MHz, chloroform-d) δ 7.50 (dd, J=8.2, 8.2 Hz, 1H), 7.17-7.09 (m, 2H), 6.83-6.77 (m, 2H), 6.74 (dd, component of ABX pattern, J=5.4, 3.6 Hz, 1H), 6.39-6.33 (br m, 1H), 4.14-4.08 (m, 2H), 3.70-3.56 (m, 2H), 2.66-2.45 (m, 2H), 2.07 (d, J=1.1 Hz, 3H), 1.50 (s, 9H).

Step 3. Synthesis of tert-butyl 4-[2-(4-chloro-2-fluorophenyl)-2-methyl-1,3-benzodioxol-4-yl]piperidine-1-carboxylate (P2)

To a solution of C5 (56.0 g, 126 mmol) in methanol (200 mL) was added tris(triphenylphosphine)rhodium(I) chloride (Wilkinson's catalyst; 8.10 g, 8.75 mmol), and the reaction mixture was heated to 50° C. for 18 hours under hydrogen (45 psi). It was then cooled to 25° C. and filtered through diatomaceous earth. The filtrate was concentrated in vacuo, and purified twice using silica gel chromatography (First column—Gradient: 0% to 9% ethyl acetate in petroleum ether; Second column—Gradient: 0% to 2% ethyl acetate in petroleum ether), affording P2 as a yellow solid. Yield: 37.0 g, 82.6 mmol, 66%. LCMS m/z 392.1♦ [(M-2-methylprop-1-ene)+H]$^{+}$. $^{1}$H NMR (400 MHz, chloroform-d) δ 7.51 (dd, J=8.3, 8.0 Hz, 1H), 7.17-7.09 (m, 2H), 6.77 (dd, component of ABC pattern, J=7.8, 7.8 Hz, 1H), 6.70 (dd, component of ABC pattern, J=7.7, 1.3 Hz, 1H), 6.66 (dd, component of ABC pattern, J=7.8, 1.3 Hz, 1H), 4.37-4.13 (br m, 2H), 2.92-2.73 (m, 3H), 2.05 (d, J=1.1 Hz, 3H), 1.90-1.63 (m, 4H), 1.49 (s, 9H).

Preparation P3

4-[(2S)-2-(4-Chloro-2-Fluorophenyl)-2-Methyl-1,3-Benzodioxol-4-Yl]Piperidine, p-Toluenesulfonate Salt (P3)

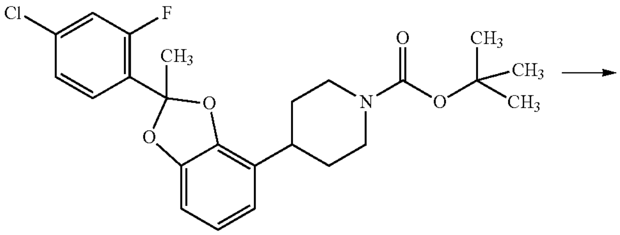

P2

-continued

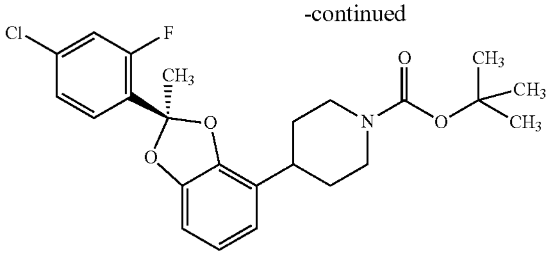

C6

+

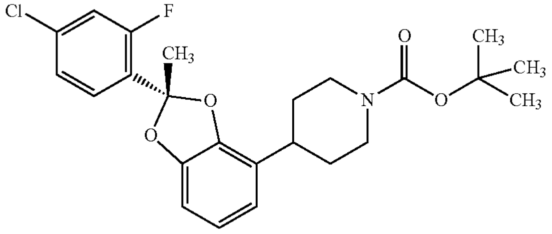

C7

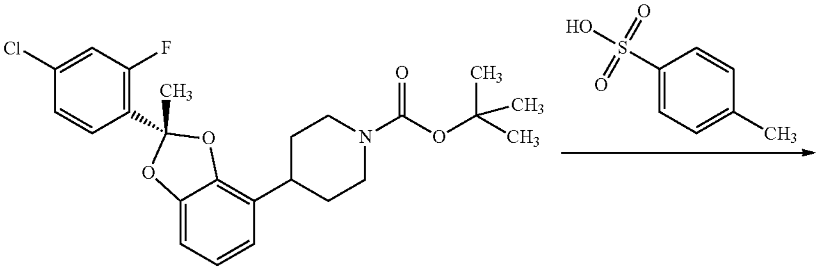

C7

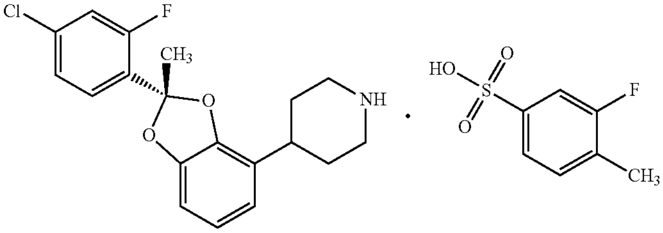

P3

Step 1. Isolation of tert-butyl 4-[(2R)-2-(4-chloro-2-fluorophenyl)-2-methyl-1,3-benzodioxol-4-yl]piperidine-1-carboxylate (C6) and tert-butyl 4-[(2S)-2-(4-chloro-2-fluorophenyl)-2-methyl-1,3-benzodioxol-4-yl]piperidine-1-carboxylate (C7)

Separation of P2 (75.2 g, 168 mmol) into its component enantiomers was carried out via SFC (supercritical fluid chromatography)_[Column: Chiral Technologies Chiralpak AD-H, 5 μm; Mobile phase: 4:1 carbon dioxide/(2-propanol containing 0.2% 1-aminopropan-2-ol)]. The first-eluting compound was designated as C6, and the second-eluting enantiomer as C7. The indicated absolute configurations were assigned on the basis of a single-crystal X-ray structure determination carried out on C8, which was derived from C6 (see below).

C6-Yield: 38.0 g, 84.8 mmol, 50%. Retention time 3.64 minutes [Column: Chiral Technologies Chiralpak AD-H, 4.6×250 mm, 5 μm; Mobile phase A: carbon dioxide; Mobile phase B: 2-propanol containing 0.2% 1-aminopropan-2-ol; Gradient: 5% B for 1.00 minute, then 5% to 60% B over 8.00 minutes; Flow rate: 3.0 mL/minute; Back pressure: 120 bar].

C7-Yield: 36.8 g, 82.2 mmol, 49%. Retention time 4.19 minutes (Analytical SFC conditions identical to those used for C6).

Step 2. Synthesis of 4-[(2S)-2-(4-chloro-2-fluorophenyl)-2-methyl-1,3-benzodioxol-4-yl]piperidine, p-toluenesulfonate salt (P3)

A solution of C7 (1.62 g, 3.62 mmol) in ethyl acetate (36 mL) was treated with p-toluenesulfonic acid monohydrate (791 mg, 4.16 mmol) and heated at 45° C. After 23 hours, the reaction mixture was allowed to cool to room temperature and the solid was collected via filtration. It was rinsed with a mixture of ethyl acetate and heptane (1:1, 2×15 mL) to afford P3 as a white solid. Yield: 1.37 g, 2.63 mmol, 73%. LCMS m/z 348.1♦ $[M+H]^+$. $^1H$ NMR (400 MHz, DMSO-$d_6$) δ 8.53 (v br s, 1H), 8.29 (v br s, 1H), 7.65-7.55 (m, 2H), 7.47 (d, J=8.1 Hz, 2H), 7.35 (dd, J=8.4, 2.0 Hz, 1H), 7.11 (d, J=7.8 Hz, 2H), 6.88-6.81 (m, 2H), 6.75-6.68 (m, 1H), 3.42-3.33 (m, 2H), 3.11-2.93 (m, 3H), 2.29 (s, 3H), 2.03 (s, 3H), 1.98-1.82 (m, 4H).

Conversion of C6 to 4-[(2R)-2-(4-chloro-2-fluorophenyl)-2-methyl-1,3-benzodioxol-4-yl]piperidine, Methanesulfonate Salt (C8) for Determination of Absolute Stereochemistry

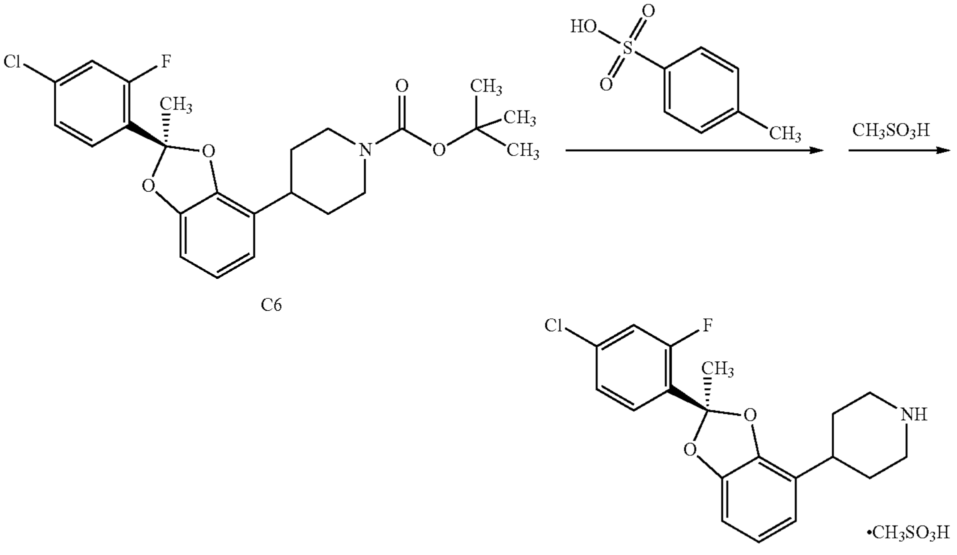

C6

C8 p-Toluenesulfonic acid (377 mg, 2.19 mmol) was added to a solution of C6 (490 mg, 1.09 mmol) in ethyl acetate (5.5 mL), and the reaction mixture was stirred at room temperature overnight. After dilution with additional ethyl acetate, the reaction mixture was washed sequentially with aqueous sodium bicarbonate solution, water, and saturated aqueous sodium chloride solution, dried over sodium sulfate, filtered, and concentrated in vacuo. Yield: 375 mg, 1.08 mmol, 99%. $^1$H NMR (400 MHz, methanol-$d_4$) δ 7.59 (dd, J=8.3. 8.3 Hz, 1H), 7.27 (dd, J=10.9, 2.0 Hz, 1H), 7.20 (br dd, J=8.4, 2.1 Hz, 1H), 6.81-6.75 (m, 1H), 6.74-6.67 (m, 2H), 3.18-3.09 (m, 2H), 2.88-2.77 (m, 1H), 2.77-2.67 (m, 2H), 2.02 (d, J=0.7 Hz, 3H), 1.85-1.73 (m, 4H).

A 0.1 M solution of this free base (4-[(2R)-2-(4-chloro-2-fluorophenyl)-2-methyl-1,3-benzodioxol-4-yl]piperidine) in ethyl acetate was prepared and subjected to a salt screen. Only the methanesulfonate salt formation is described here. A mixture of methanesulfonic acid (25 μL, 39 μmol) and the solution of substrate (0.1 M; 0.25 mL, 25 μmol) was stirred overnight. Sufficient methanol was then added to dissolve the solid present, and ethyl acetate (3 mL) was added. The resulting solution was allowed to evaporate slowly, without stirring, to afford crystals of C8; one of these was used for the single crystal X-ray structure determination described below.

Single-Crystal X-Ray Structural Determination of C8

Single Crystal X-Ray Analysis

Data collection was performed on a Bruker D8 Quest diffractometer at room temperature. Data collection consisted of omega and phi scans.

The structure was solved by intrinsic phasing using SHELX software suite in the orthorhombic class space group $P2_12_12_1$. The structure was subsequently refined by the full-matrix least squares method. All non-hydrogen atoms were found and refined using anisotropic displacement parameters.

Formation of the methanesulfonate salt was confirmed via N1_H1X_O4 proton transfer.

The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned; the method calculates that the probability that the structure is correct is 100%. The Hooft parameter is reported as 0.02 with an esd of 0.0012 and the Parson's parameter is reported as 0.07 with an esd of 0.009. The absolute configuration at C7 was confirmed as (R).

The asymmetric unit is comprised of one molecule of the protonated free base of C8 and one molecule of deprotonated methanesulfonic acid. The final R-index was 4.6%. A final difference Fourier revealed no missing or misplaced electron density.

Pertinent crystal, data collection, and refinement information is summarized in Table A. Atomic coordinates, bond lengths, bond angles, and displacement parameters are listed in Tables B-D.

Software and References

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE A

Crystal data and structure refinement for C8.

| | | |
|---|---|---|
| Empirical formula | $C_{20}H_{23}ClFNO_5S$ | |
| Formula weight | 443.90 | |
| Temperature | 296(2) K | |
| Wavelength | 1.54178 Å | |
| Crystal system | Orthorhombic | |
| Space group | $P2_12_12_1$ | |
| Unit cell dimensions | a = 6.5348(5) Å | α = 90° |
| | b = 9.3688(7) Å | β = 90° |
| | c = 35.214(3) Å | γ = 90° |
| Volume | 2155.9(3) $Å^3$ | |
| Z | 4 | |
| Density (calculated) | 1.368 $Mg/m^3$ | |
| Absorption coefficient | 2.823 $mm^{-1}$ | |
| F(000) | 928 | |
| Crystal size | 0.480 × 0.100 × 0.040 $mm^3$ | |
| Theta range for data collection | 2.509 to 70.483° | |
| Index ranges | −7 <= h <= 7, −11 <= k <= 8, −42 <= l <= 42 | |
| Reflections collected | 16311 | |
| Independent reflections | 4035 [$R_{int}$ = 0.0638] | |
| Completeness to theta = 67.679° | 99.0% | |
| Absorption correction | Empirical | |
| Refinement method | Full-matrix least-squares on $F^2$ | |
| Data/restraints/ parameters | 4035/2/271 | |
| Goodness-of-fit on $F^2$ | 0.832 | |
| Final R indices [I > 2σ(I)] | R1 = 0.0463, wR2 = 0.1227 | |
| R indices (all data) | R1 = 0.0507, wR2 = 0.1294 | |
| Absolute structure parameter | −0.003(18) | |
| Extinction coefficient | 0.0051(6) | |
| Largest diff. peak and hole | 0.256 and −0.305 e · $Å^{-3}$ | |

TABLE B

Atomic coordinates (× $10^4$) and equivalent isotropic displacement parameters ($Å^2$ × $10^3$) for C8. U(eq) is defined as one-third of the trace of the orthogonalized $U^{ij}$ tensor.

| | x | y | z | U(eq) |
|---|---|---|---|---|
| (1) | 3842(2) | 9910(1) | 5317(1) | 57(1) |
| Cl(1) | −1625(2) | −718(1) | 6588(1) | 80(1) |
| O(1) | 6138(4) | 3727(3) | 6876(1) | 53(1) |
| F(1) | 639(5) | 3071(4) | 7503(1) | 89(1) |
| O(2) | 3445(4) | 5043(3) | 7117(1) | 57(1) |
| O(4) | 2909(6) | 11013(4) | 5082(1) | 78(1) |
| O(3) | 3708(7) | 10299(4) | 5708(1) | 83(1) |
| N(1) | 10461(5) | 2909(4) | 5493(1) | 56(1) |
| C(9) | 5652(6) | 4826(4) | 6629(1) | 44(1) |
| C(1) | 3361(7) | 1662(4) | 6697(1) | 53(1) |
| C(6) | 2957(6) | 2523(4) | 7012(1) | 49(1) |
| C(10) | 4075(6) | 5613(4) | 6776(1) | 47(1) |
| C(14) | 6628(6) | 5138(4) | 6294(1) | 47(1) |
| O(5) | 5833(7) | 9578(4) | 5179(1) | 96(1) |
| C(15) | 8265(6) | 4182(4) | 6130(1) | 49(1) |
| C(5) | 1105(7) | 2270(5) | 7190(1) | 59(1) |
| C(16) | 7309(6) | 3048(5) | 5874(1) | 54(1) |
| C(2) | 1971(7) | 670(4) | 6567(1) | 55(1) |
| C(4) | −286(7) | 1288(5) | 7080(1) | 64(1) |
| C(7) | 4448(6) | 3667(4) | 7142(1) | 52(1) |
| C(13) | 5876(8) | 6374(5) | 6113(1) | 60(1) |
| C(11) | 3359(7) | 6819(4) | 6602(1) | 57(1) |
| C(8) | 5296(8) | 3485(6) | 7537(1) | 64(1) |
| C(19) | 9905(7) | 4976(6) | 5902(1) | 67(1) |
| C(17) | 8902(7) | 2063(5) | 5702(1) | 59(1) |
| C(12) | 4316(8) | 7178(5) | 6263(1) | 65(1) |
| C(3) | 150(7) | 497(4) | 6756(1) | 56(1) |
| C(18) | 11476(7) | 3977(6) | 5738(1) | 73(1) |
| C(20) | 2328(14) | 8399(7) | 5260(2) | 117(3) |

TABLE C

Bond lengths [Å] and angles [°] for C8.

| | | | |
|---|---|---|---|
| S(1)—O(5) | 1.423(4) | C(4)—C(3) | 1.389(6) |
| S(1)—O(3) | 1.428(3) | C(4)—H(4) | 0.9300 |
| S(1)—O(4) | 1.458(3) | C(7)—C(8) | 1.506(6) |
| S(1)—C(20) | 1.738(6) | C(13)—C(12) | 1.373(7) |
| Cl(1)—C(3) | 1.729(5) | C(13)—H(13) | 0.9300 |
| O(1)—C(9) | 1.385(4) | C(11)—C(12) | 1.388(7) |
| O(1)—C(7) | 1.449(4) | C(11)—H(11) | 0.9300 |
| F(1)—C(5) | 1.367(4) | C(8)—H(8A) | 0.9600 |
| O(2)—C(10) | 1.376(4) | C(8)—H(8B) | 0.9600 |
| O(2)—C(7) | 1.449(4) | C(8)—H(8C) | 0.9600 |
| N(1)—C(18) | 1.478(6) | C(19)—C(18) | 1.505(7) |
| N(1)—C(17) | 1.486(5) | C(19)—H(19A) | 0.9700 |
| N(1)—H(1X) | 0.99(2) | C(19)—H(19B) | 0.9700 |
| N(1)—H(1Y) | 0.97(2) | C(17)—H(17A) | 0.9700 |
| C(9)—C(10) | 1.369(5) | C(17)—H(17B) | 0.9700 |
| C(9)—C(14) | 1.375(5) | C(12)—H(12) | 0.9300 |
| C(1)—C(2) | 1.378(6) | C(18)—H(18A) | 0.9700 |
| C(1)—C(6) | 1.395(5) | C(18)—H(18B) | 0.9700 |
| C(1)—H(1) | 0.9300 | C(20)—H(20A) | 0.9600 |
| C(6)—C(5) | 1.384(6) | C(20)—H(20B) | 0.9600 |
| C(6)—C(7) | 1.519(6) | C(20)—H(20C) | 0.9600 |
| C(10)—C(11) | 1.369(5) | | |
| C(14)—C(13) | 1.409(6) | O(5)—S(1)—O(3) | 116.2(3) |
| C(14)—C(15) | 1.509(5) | O(5)—S(1)—O(4) | 110.1(2) |
| C(15)—C(16) | 1.527(5) | O(3)—S(1)—O(4) | 109.9(2) |
| C(15)—C(19) | 1.531(6) | O(5)—S(1)—C(20) | 107.6(4) |
| C(15)—H(15) | 0.9800 | O(3)—S(1)—C(20) | 106.6(3) |
| C(5)—C(4) | 1.351(7) | O(4)—S(1)—C(20) | 105.9(4) |
| C(16)—C(17) | 1.518(6) | C(9)—O(1)—C(7) | 105.0(3) |
| C(16)—H(16A) | 0.9700 | C(10)—O(2)—C(7) | 105.2(3) |
| C(16)—H(16B) | 0.9700 | C(18)—N(1)—C(17) | 112.3(3) |

TABLE C-continued

| Bond lengths [Å] and angles [°] for C8. | | | |
|---|---|---|---|
| C(2)—C(3) | 1.372(6) | C(18)—N(1)—H(1X) | 107(3) |
| C(2)—H(2) | 0.9300 | C(17)—N(1)—H(1X) | 113(3) |
| C(18)—N(1)—H(1Y) | 113(3) | C(1)—C(2)—H(2) | 120.3 |
| C(17)—N(1)—H(1Y) | 103(3) | C(5)—C(4)—C(3) | 117.5(4) |
| H(1X)—N(1)—H(1Y) | 108(4) | C(5)—C(4)—H(4) | 121.2 |
| C(10)—C(9)—C(14) | 124.1(3) | C(3)—C(4)—H(4) | 121.2 |
| C(10)—C(9)—O(1) | 109.6(3) | O(1)—C(7)—O(2) | 105.7(3) |
| C(14)—C(9)—O(1) | 126.3(3) | O(1)—C(7)—C(8) | 108.7(3) |
| C(2)—C(1)—C(6) | 121.9(4) | O(2)—C(7)—C(8) | 108.8(3) |
| C(2)—C(1)—H(1) | 119.0 | O(1)—C(7)—C(6) | 108.7(3) |
| C(6)—C(1)—H(1) | 119.0 | O(2)—C(7)—C(6) | 108.6(3) |
| C(5)—C(6)—C(1) | 115.3(4) | C(8)—C(7)—C(6) | 115.8(3) |
| C(5)—C(6)—C(7) | 123.0(3) | C(12)—C(13)—C(14) | 122.4(4) |
| C(1)—C(6)—C(7) | 121.7(4) | C(12)—C(13)—H(13) | 118.8 |
| C(9)—C(10)—C(11) | 122.1(4) | C(14)—C(13)—H(13) | 118.8 |
| C(9)—C(10)—O(2) | 110.3(3) | C(10)—C(11)—C(12) | 115.6(4) |
| C(11)—C(10)—O(2) | 127.5(4) | C(10)—C(11)—H(11) | 122.2 |
| C(9)—C(14)—C(13) | 113.6(4) | C(12)—C(11)—H(11) | 122.2 |
| C(9)—C(14)—C(15) | 122.1(3) | C(7)—C(8)—H(8A) | 109.5 |
| C(13)—C(14)—C(15) | 124.2(3) | C(7)—C(8)—H(8B) | 109.5 |
| C(14)—C(15)—C(16) | 110.4(3) | H(8A)—C(8)—H(8B) | 109.5 |
| C(14)—C(15)—C(19) | 114.1(3) | C(7)—C(8)—H(8C) | 109.5 |
| C(16)—C(15)—C(19) | 108.4(3) | H(8A)—C(8)—H(8C) | 109.5 |
| C(14)—C(15)—H(15) | 107.9 | H(8B)—C(8)—H(8C) | 109.5 |
| C(16)—C(15)—H(15) | 107.9 | C(18)—C(19)—C(15) | 112.2(4) |
| C(19)—C(15)—H(15) | 107.9 | C(18)—C(19)—H(19A) | 109.2 |
| C(4)—C(5)—F(1) | 117.2(4) | C(15)—C(19)—H(19A) | 109.2 |
| C(4)—C(5)—C(6) | 125.0(4) | C(18)—C(19)—H(19B) | 109.2 |
| F(1)—C(5)—C(6) | 117.9(4) | C(15)—C(19)—H(19B) | 109.2 |
| C(17)—C(16)—C(15) | 112.2(3) | H(19A)—C(19)—H(19B) | 107.9 |
| C(17)—C(16)—H(16A) | 109.2 | N(1)—C(17)—C(16) | 110.1(3) |
| C(15)—C(16)—H(16A) | 109.2 | N(1)—C(17)—H(17A) | 109.6 |
| C(17)—C(16)—H(16B) | 109.2 | C(16)—C(17)—H(17A) | 109.6 |
| C(15)—C(16)—H(16B) | 109.2 | N(1)—C(17)—H(17B) | 109.6 |
| H(16A)—C(16)—H(16B) | 107.9 | C(16)—C(17)—H(17B) | 109.6 |
| C(3)—C(2)—C(1) | 119.4(4) | H(17A)—C(17)—H(17B) | 108.2 |
| C(3)—C(2)—H(2) | 120.3 | C(13)—C(12)—C(11) | 122.1(4) |
| C(1)—C(2)—H(2) | 120.3 | C(13)—C(12)—H(12) | 118.9 |
| | | C(11)—C(12)—H(12) | 118.9 |
| C(2)—C(3)—C(4) | 120.8(4) | H(18A)—C(18)—H(18B) | 108.2 |
| C(2)—C(3)—Cl(1) | 119.6(3) | S(1)—C(20)—H(20A) | 109.5 |
| C(4)—C(3)—Cl(1) | 119.6(3) | S(1)—C(20)—H(20B) | 109.5 |
| N(1)—C(18)—C(19) | 109.9(3) | H(20A)—C(20)—H(20B) | 109.5 |
| N(1)—C(18)—H(18A) | 109.7 | S(1)—C(20)—H(20C) | 109.5 |
| C(19)—C(18)—H(18A) | 109.7 | H(20A)—C(20)—H(20C) | 109.5 |
| N(1)—C(18)—H(18B) | 109.7 | H(20B)—C(20)—H(20C) | 109.5 |
| C(19)—C(18)—H(18B) | 109.7 | | |

Symmetry transformations used to generate equivalent atoms.

TABLE D

Anisotropic displacement parameters ($Å^2 \times 10^3$) for C8. The anisotropic displacement factor exponent takes the form: $-2\pi^2[h^2 a^{*2}U^{11} + \ldots + 2\ h\ k\ a^*\ b^*\ U^{12}]$.

| | $U^{11}$ | $U^{22}$ | $U^{33}$ | $U^{23}$ | $U^{13}$ | $U^{12}$ |
|---|---|---|---|---|---|---|
| S(1) | 73(1) | 48(1) | 48(1) | −2(1) | 7(1) | −1(1) |
| Cl(1) | 81(1) | 78(1) | 81(1) | −8(1) | 1(1) | −8(1) |
| O(1) | 54(1) | 50(1) | 56(1) | 14(1) | 10(1) | 17(1) |
| F(1) | 83(2) | 103(2) | 79(2) | −40(2) | 38(2) | −6(2) |
| O(2) | 66(2) | 49(1) | 54(1) | 2(1) | 11(1) | 18(1) |
| O(4) | 87(2) | 84(2) | 64(2) | 19(2) | 17(2) | 21(2) |
| O(3) | 122(3) | 80(2) | 47(1) | −3(1) | 7(2) | −13(2) |
| N(1) | 47(2) | 73(2) | 48(2) | 7(2) | 3(1) | 11(2) |
| C(9) | 51(2) | 38(2) | 44(2) | 2(1) | −7(1) | 2(2) |
| C(1) | 63(2) | 46(2) | 50(2) | 5(2) | 21(2) | 13(2) |
| C(6) | 55(2) | 47(2) | 45(2) | 5(1) | 11(2) | 19(2) |
| C(10) | 55(2) | 39(2) | 46(2) | −5(1) | −4(2) | 6(2) |
| C(14) | 54(2) | 46(2) | 42(2) | 0(1) | −9(2) | −5(2) |
| O(5) | 88(2) | 88(3) | 113(3) | −24(2) | 13(2) | 21(2) |
| C(15) | 47(2) | 61(2) | 40(2) | 3(2) | −3(1) | −2(2) |
| C(5) | 60(2) | 62(2) | 54(2) | −6(2) | 19(2) | 13(2) |
| C(16) | 43(2) | 53(2) | 65(2) | −4(2) | 8(2) | −6(2) |
| C(2) | 72(3) | 49(2) | 45(2) | 2(2) | 16(2) | 14(2) |

TABLE D-continued

Anisotropic displacement parameters ($Å^2 \times 10^3$) for C8. The anisotropic displacement factor exponent takes the form: $-2\pi^2[h^2 a^{*2}U^{11} + \ldots + 2\ h\ k\ a^*\ b^*\ U^{12}]$.

| | $U^{11}$ | $U^{22}$ | $U^{33}$ | $U^{23}$ | $U^{13}$ | $U^{12}$ |
|---|---|---|---|---|---|---|
| C(4) | 57(2) | 68(3) | 65(2) | −3(2) | 23(2) | 6(2) |
| C(7) | 54(2) | 50(2) | 51(2) | 7(2) | 12(2) | 16(2) |
| C(13) | 81(3) | 54(2) | 46(2) | 9(2) | −4(2) | 4(2) |
| C(11) | 70(3) | 46(2) | 54(2) | −8(2) | −14(2) | 17(2) |
| C(8) | 69(3) | 71(3) | 51(2) | 4(2) | 4(2) | 15(2) |
| C(19) | 54(2) | 78(3) | 70(3) | −13(2) | 2(2) | −25(2) |
| C(17) | 54(2) | 57(2) | 67(2) | −3(2) | 8(2) | 3(2) |
| C(12) | 96(3) | 43(2) | 56(2) | 5(2) | −14(2) | 13(2) |
| C(3) | 64(2) | 52(2) | 52(2) | 4(2) | 2(2) | 14(2) |
| C(18) | 43(2) | 103(4) | 73(3) | 7(3) | 3(2) | −18(2) |
| C(20) | 153(7) | 87(4) | 110(5) | −14(4) | −6(5) | −57(5) |

Preparation of P3, di-p-toluoyl-L-tartrate salt

4-[(2S)-2-(4-Chloro-2-Fluorophenyl)-2-Methyl-1,3-Benzodioxol-4-Yl]Piperidine, Di-p-Toluoyl-L-Tartrate Salt (P3, Di-p-Toluoyl-L-Tartrate Salt)

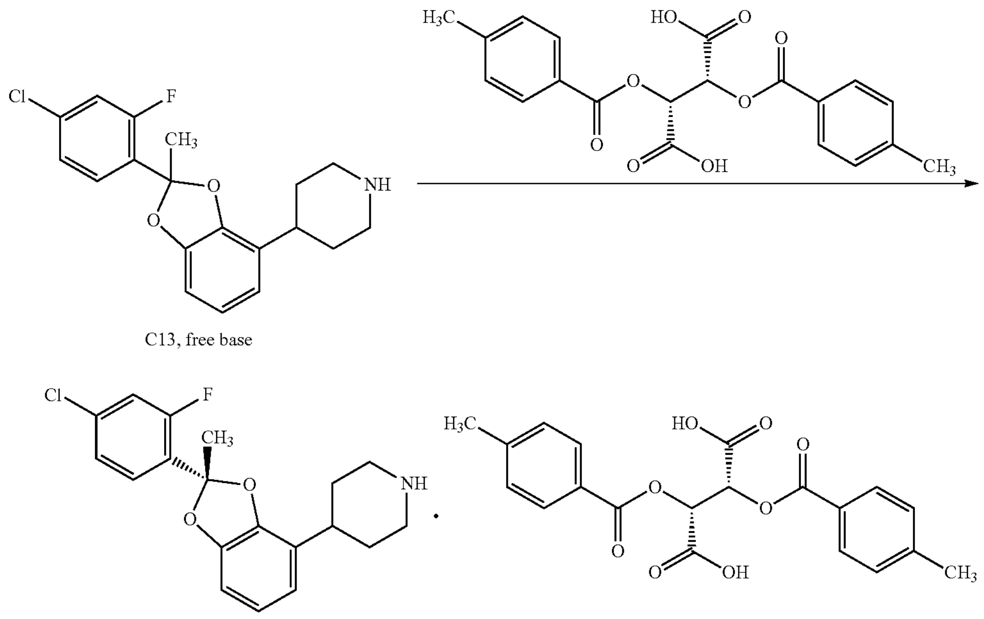

C13, free base

P3, di-p-toluoyl-L-tartrate salt

A solution of C13, free base (519 mg, 1.49 mmol) and di-p-toluoyl-L-tartaric acid (278 mg, 0.719 mmol) in acetonitrile (7.5 mL) was stirred at 50° C. for 1.5 hours. The mixture was allowed to cool to room temperature at 0.2° C./minute. After 15 hours at room temperature, the mixture was heated to 65° C. and charged with acetonitrile (15 mL). The mixture was allowed to cool to room temperature at 0.2° C./minute. After 15 hours at room temperature, the mixture was heated to 54° C. After 3 hours, the solid was collected by filtration, and dried in a vacuum oven at 35° C. under nitrogen, providing P3, di-p-toluoyl-L-tartrate salt as a white solid (217 mg, 0.296 mmol, 20%, 82% ee).

A solution of P3, di-p-toluoyl-L-tartrate salt (217 mg, 0.296 mmol, 82% ee) in acetonitrile (8.0 mL) at 50° C. was allowed to cool to room temperature at 0.2° C./minute. After 15 hours, the solid was collected by filtration, and dried in a vacuum oven at 35° C. under nitrogen, providing P3, di-p-toluoyl-L-tartrate salt as a white solid (190 mg, 0.259 mmol, 88%, 88% ee). LCMS m/z 348.1♦ $[M+H]^+$. $^1H$ NMR (400 MHz, DMSO-$d_6$) δ 8.9-8.5 (br s, 2H), 7.79 (d, J=8.1 Hz, 4H), 7.64-7.54 (m, 2H), 7.34 (dd, J=8.4, 2.1 Hz, 1H), 7.26 (d, J=8.0 Hz, 4H), 6.87-6.78 (m, 2H), 6.69 (dd, J=6.7, 2.5 Hz, 1H), 5.58 (s, 2H), 3.37-3.28 (m, 2H, assumed; partially obscured by water peak), 3.05-2.89 (m, 3H), 2.33 (s, 6H), 2.02 (s, 3H), 1.92-1.80 (m, 4H). Retention time: Peak 1 (4.97 minutes, minor) and Peak 2 (5.31 minutes, Major) {Column: Chiralpak IC—U 3.0×50 mm, 1.6 μm; Mobile phase A: carbon dioxide; Mobile phase B: 0.1% isopropylamine in methanol; Gradient: 10% B for 5.00 minutes, then 45% B for 0.6 minutes; Flow rate: 1.7 mL/minute; Back pressure: 130 bar}.

Preparation P4 tert-Butyl 4-[2-(4-cyano-2-fluorophenyl)-2-methyl-1,3-benzodioxol-4-yl]piperidine-1-carboxylate (P4)

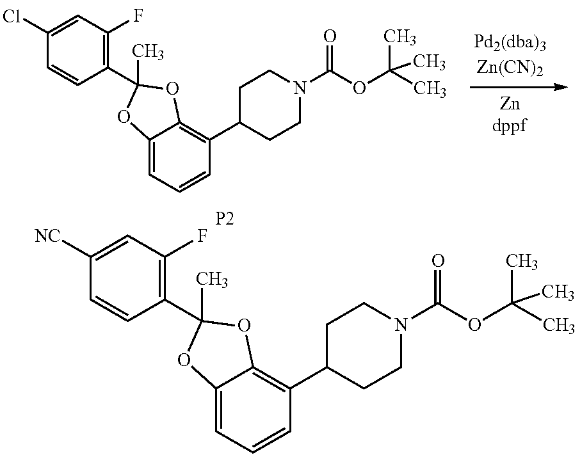

P2

P4

A suspension of P2 (2.00 g, 4.46 mmol), zinc cyanide (734 mg, 6.25 mol), zinc (70.1 mg, 1.07 mmol), 1,1'-bis(diphenylphosphino)ferrocene (dppf; 198 mg, 0.357 mmol) and tris(dibenzylideneacetone)dipalladium(0) (164 mg, 0.179 mmol) in N,N-dimethylacetamide (20 mL) was stirred at 120° C. for 16 hours, whereupon it was filtered. The filtrate was mixed with water (50 mL) and extracted with ethyl acetate (3×50 mL); the combined organic layers were then washed sequentially with water (30 mL) and with saturated aqueous sodium chloride solution (20 mL), and concentrated in vacuo. Silica gel chromatography (Gradient: 0% to 30% ethyl acetate in petroleum ether) afforded a solid, which was treated with acetonitrile (15 mL) and water (15 mL) and subjected to lyophilization. This provided P4 as a light yellow solid. Yield: 1.17 g, 2.67 mmol, 60%. LCMS m/z 461.3 $[M+Na^+]$. $^1H$ NMR (400 MHz, chloroform-d) 7.71 (dd, J=7.7, 7.6 Hz, 1H), 7.45 (dd, J=8.0, 1.6 Hz, 1H), 7.42 (dd, J=10.0, 1.5 Hz, 1H), 6.79 (dd, component of ABC pattern, J=7.7, 7.6 Hz, 1H), 6.72 (dd, component of ABC pattern, J=7.8, 1.3 Hz, 1H), 6.68 (dd, component of ABC pattern, J=7.8, 1.3 Hz, 1H), 4.37-4.14 (br m, 2H), 2.91-2.73 (m, 3H), 2.07 (d, J=1.1 Hz, 3H), 1.89-1.62 (m, 4H), 1.49 (s, 9H).

Preparations P5 and P6

4-Bromo-2-phenyl-1,3-benzodioxole, ENT-1 (P5) and 4-Bromo-2-phenyl-1,3-benzodioxole, ENT-2 (P6)

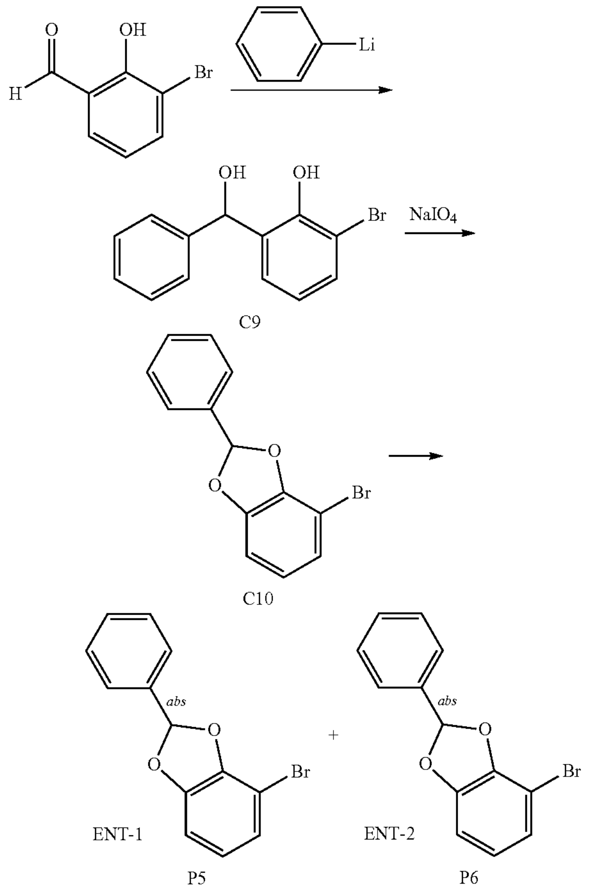

C9

C10

ENT-1 P5 ENT-2 P6

Step 1. Synthesis of 2-bromo-6-[hydroxy(phenyl)methyl]phenol (C9)

Phenyllithium (1.9 M solution in 1-butoxybutane; 78.5 mL, 149 mmol) was slowly added to a −70° C. solution of 3-bromo-2-hydroxybenzaldehyde (10.0 g, 49.7 mmol) in tetrahydrofuran (70 mL), at a rate that maintained the reaction temperature below −60° C. The resulting suspension was stirred at −70° C. for 1 hour, and then allowed to warm to room temperature overnight, whereupon it was poured into a 0° C. aqueous ammonium chloride solution (30 mL). This mixture was extracted with ethyl acetate (3×30 mL), and the combined organic layers were washed with saturated aqueous sodium chloride solution (30 mL), dried over sodium sulfate, filtered, and concentrated in vacuo. Silica gel chromatography (Gradient: 0% to 5% ethyl acetate in petroleum ether) provided C9 as a yellow solid. Yield: 6.11 g, 21.9 mmol, 44%. $^1H$ NMR (400 MHz, chloroform-d) δ 7.45-7.28 (m, 6H), 7.22-7.18 (m, 1H), 7.06 (br d, J=7.7 Hz, 1H), 6.77 (dd, J=7.9, 7.8 Hz, 1H), 6.06 (br s, 1H), 2.89 (br s, 1H).

Step 2. Synthesis of 4-bromo-2-phenyl-1,3-benzodioxole (C10)

To a solution of C9 (6.11 g, 21.9 mmol) in methanol (370 mL) was added a solution of sodium periodate (11.7 g, 54.7 mmol) in water (175 mL). The reaction mixture was stirred at 30° C. for 40 hours, whereupon most of the methanol was removed via concentration in vacuo. The resulting mixture was extracted with dichloromethane (5×100 mL), and the combined organic layers were washed sequentially with aqueous sodium sulfite solution (100 mL) and saturated aqueous sodium chloride solution (100 mL), dried over sodium sulfate, filtered, and concentrated under reduced pressure. Chromatography on silica gel (Eluent: petroleum ether) provided C10 as a colorless oil. Yield: 4.50 g, 16.2 mmol, 74%. LCMS m/z 278.5 (bromine isotope pattern observed) $[M+H]^+$. $^1H$ NMR (400 MHz, chloroform-d) δ 7.62-7.57 (m, 2H), 7.49-7.43 (m, 3H), 7.04 (s, 1H), 7.00 (dd, J=8.0, 1.4 Hz, 1H), 6.79 (dd, component of ABX pattern, J=7.8, 1.4 Hz, 1H), 6.75 (dd, component of ABX pattern, J=7.9, 7.8 Hz, 1H).

Step 3. Isolation of 4-bromo-2-phenyl-1,3-benzodioxole, ENT-1 (P5) and 4-bromo-2-phenyl-1,3-benzodioxole, ENT-2 (P6)

The enantiomers comprising C10 (5.00 g, 18.0 mmol) were separated using SFC [Column: Chiral Technologies ChiralCel OD, 10 μm; Mobile phase: 3:1 carbon dioxide/(methanol containing 0.1% ammonium hydroxide)]. The first-eluting enantiomer was designated as ENT-1 (P5), and the second-eluting enantiomer as ENT-2 (P6); both were obtained as yellow oils.

P5 Yield: 2.20 g, 7.94 mmol, 44%. LCMS m/z 277.0 (bromine isotope pattern observed) $[M+H]^+$. $^1H$ NMR (400 MHz, chloroform-d) δ 7.63-7.55 (m, 2H), 7.51-7.42 (m, 3H), 7.04 (s, 1H), 7.00 (dd, J=8.0, 1.3 Hz, 1H), 6.80 (dd, component of ABX pattern, J=7.8, 1.4 Hz, 1H), 6.75 (dd, component of ABX pattern, J=7.9, 7.8 Hz, 1H). Retention time 3.28 minutes (Column: Chiral Technologies ChiralCel OD-H, 4.6×150 mm, 5 μm; Mobile phase A: carbon dioxide; Mobile phase B: methanol containing 0.05% diethylamine; Gradient: 5% to 40% B over 5.5 minutes; Flow rate: 2.5 mL/minute).

P6 Yield: 2.00 g, 7.22 mmol, 40%. LCMS m/z 276.9 (bromine isotope pattern observed) $[M+H]^+$. $^1H$ NMR (400 MHz, chloroform-d) δ 7.63-7.55 (m, 2H), 7.50-7.42 (m, 3H), 7.04 (s, 1H), 7.00 (dd, J=8.0, 1.4 Hz, 1H), 6.80 (dd, component of ABX pattern, J=7.8, 1.4 Hz, 1H), 6.75 (dd, component of ABX pattern, J=7.9, 7.9 Hz, 1H). Retention time 3.73 minutes (Analytical conditions identical to those used for P5).

Preparation P7 tert-Butyl 4-[2-(5-chloropyridin-2-yl)-2-methyl-1,3-benzodioxol-4-yl]piperidine-1-carboxylate (P7)

Step 1. Synthesis of 2-(4-bromo-2-methyl-1,3-benzodioxol-2-yl)-5-chloropyridine (C11)

A mixture of 5-chloro-2-ethynylpyridine (1.80 g, 13.1 mmol), 3-bromobenzene-1,2-diol (2.47 g, 13.1 mmol), and triruthenium dodecacarbonyl (167 mg, 0.261 mmol) in toluene (25 mL) was degassed for 1 minute and then heated at 100° C. for 16 hours. The reaction mixture was diluted with ethyl acetate (30 mL) and filtered through a pad of diatomaceous earth; the filtrate was concentrated in vacuo and purified using silica gel chromatography (Gradient: 0% to 1% ethyl acetate in petroleum ether) to provide C11 as a yellow oil. Yield: 1.73 g, 5.30 mmol, 40%. LCMS m/z 325.6 (bromine-chlorine isotope pattern observed) $[M+H]^+$. $^1H$

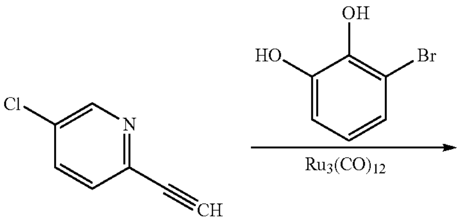

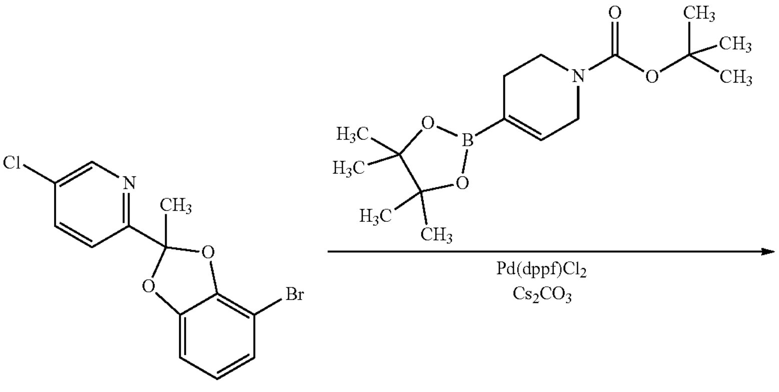

C11

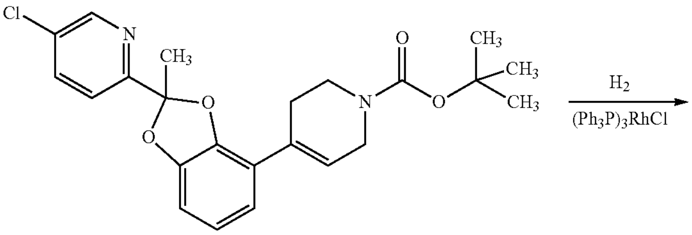

C12

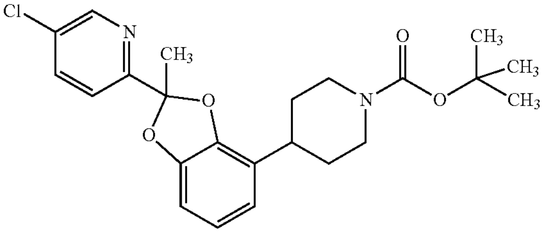

P7

NMR (400 MHz, chloroform-d) δ 8.63 (dd, J=2.4, 0.7 Hz, 1H), 7.71 (dd, component of ABX pattern, J=8.4, 2.4 Hz, 1H), 7.60 (dd, component of ABX pattern, J=8.4, 0.7 Hz, 1H), 6.97 (dd, J=8.0, 1.4 Hz, 1H), 6.76 (dd, component of ABX pattern, J=7.8, 1.4 Hz, 1H), 6.72 (dd, component of ABX pattern, J=8.0, 7.8 Hz, 1H), 2.10 (s, 3H).

Step 2. Synthesis of tert-butyl 4-[2-(5-chloropyridin-2-yl)-2-methyl-1,3-benzodioxol-4-yl]-3,6-dihydropyridine-1(2H)-carboxylate (C12)

[1,1'-Bis(diphenylphosphino)ferrocene]dichloropalladium(II) (388 mg, 0.530 mmol) was added to a suspension of C11 (1.73 g, 5.30 mmol), tert-butyl 4-(4,4,5,5-tetramethyl-1,3,2-dioxaborolan-2-yl)-3,6-dihydropyridine-1(2H)-carboxylate (1.64 g, 5.30 mmol), and cesium carbonate (5.18 g, 15.9 mmol) in 1,4-dioxane (35 mL) and water (6 mL). The reaction mixture was stirred at 90° C. for 4 hours, whereupon it was diluted with ethyl acetate (30 mL) and water (5 mL). The organic layer was concentrated in vacuo and the residue was subjected to silica gel chromatography (Gradient: 0% to 5% ethyl acetate in petroleum ether), affording C12 as a yellow gum. Yield: 1.85 g, 4.31 mmol, 81%. LCMS m/z 451.0♦ $[M+Na^+]$. $^1H$ NMR (400 MHz, chloroform-d) δ 8.62 (dd, J=2.5, 0.8 Hz, 1H), 7.69 (dd, component of ABX pattern, J=8.4, 2.4 Hz, 1H), 7.57 (dd, component of ABX pattern, J=8.4, 0.8 Hz, 1H), 6.84-6.79 (m, 2H), 6.78-6.73 (m, 1H), 6.39-6.33 (br m, 1H), 4.13-4.07 (m, 2H), 3.68-3.58 (m, 2H), 2.60-2.51 (br m, 2H), 2.07 (s, 3H), 1.49 (s, 9H).

Step 3. Synthesis of tert-butyl 4-[2-(5-chloropyridin-2-yl)-2-methyl-1,3-benzodioxol-4-yl]piperidine-1-carboxylate (P7)

A solution of C12 (2.61 g, 6.08 mmol) and tris(triphenylphosphine)rhodium(I) chloride (Wilkinson's catalyst; 563 mg, 0.608 mmol) in methanol (100 mL) was degassed under vacuum and then purged with hydrogen; this evacuation-purge cycle was carried out a total of three times. The reaction mixture was then stirred at 60° C. under hydrogen (50 psi) for 16 hours, whereupon it was filtered. The filtrate was concentrated in vacuo, and the residue was purified using silica gel chromatography (Gradient: 0% to 10% ethyl acetate in petroleum ether); the resulting material was combined with material from a similar hydrogenation carried out on C12 (110 mg, 0.256 mmol) to provide P7 as a light-yellow gum. Combined yield: 2.05 g, 4.76 mmol, 75%. LCMS m/z 431.3♦ $[M+H]^+$. $^1H$ NMR (400 MHz, chloroform-d) δ 8.62 (d, J=2.3 Hz, 1H), 7.69 (dd, component of ABX pattern, J=8.4, 2.4 Hz, 1H), 7.57 (d, half of AB quartet, J=8.4 Hz, 1H), 6.79 (dd, component of ABC pattern, J=7.8, 7.7 Hz, 1H), 6.72 (dd, component of ABC pattern, J=7.8, 1.3 Hz, 1H), 6.68 (br d, component of ABC pattern, J=7.9 Hz, 1H), 4.32-4.12 (br m, 2H), 2.91-2.73 (m, 3H), 2.05 (s, 3H), 1.90-1.62 (m, 4H), 1.48 (s, 9H).

Preparations P8 and P9 tert-Butyl 4-[2-(5-chloropyridin-2-yl)-2-methyl-1,3-benzodioxol-4-yl]piperidine-1-carboxylate, ENT-1 (P8) and tert-Butyl 4-[2-(5-chloropyridin-2-yl)-2-methyl-1,3-benzodioxol-4-yl]piperidine-1-carboxylate, ENT-2 (P9)

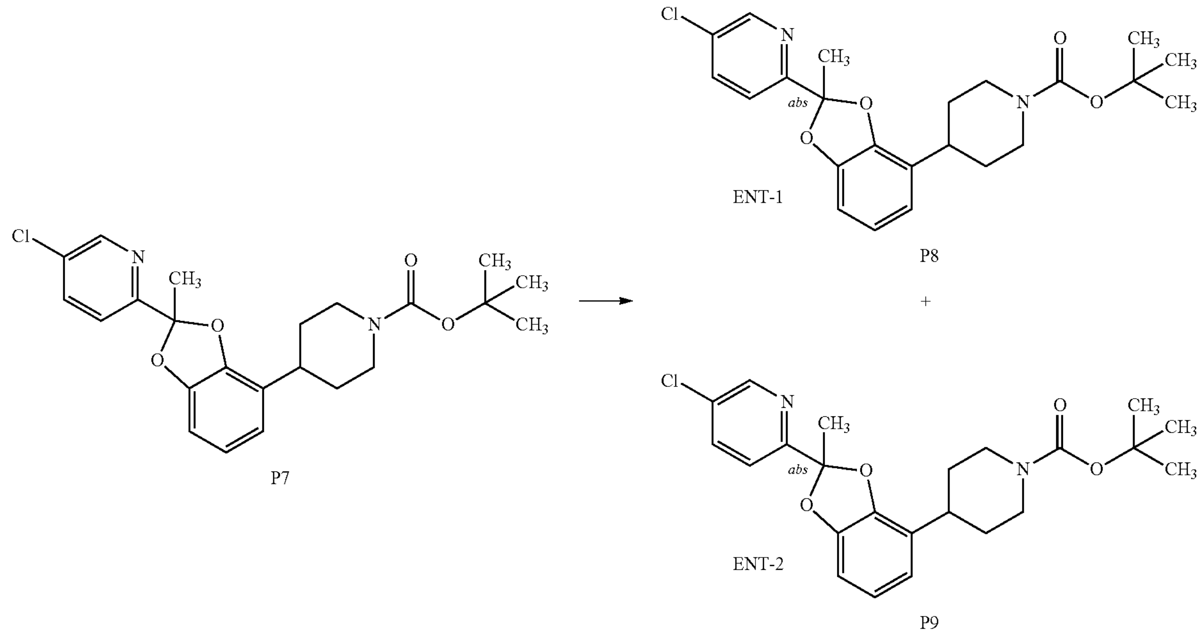

ENT-1

P8

+

ENT-2

P9

P7

Separation of P7 (500 mg, 1.16 mmol) into its component enantiomers was effected using SFC {Column: Phenomenex Lux Amylose-1, 5 μm; Mobile phase: 9:1 carbon dioxide/[2-propanol containing 0.2% (7 M ammonia in methanol)]}. The first-eluting enantiomer was designated as ENT-1 (P8), and the second-eluting enantiomer as ENT-2 (P9).

P8 Yield: 228 mg, 0.529 mmol, 46%. Retention time 4.00 minutes {Column: Phenomenex Lux Amylose-1, 4.6×250 mm, 5 μm; Mobile phase A: carbon dioxide; Mobile phase B: [2-propanol containing 0.2% (7 M ammonia in methanol)]; Gradient: 5% B for 1.00 minute, then 5% to 60% B over 8.00 minutes; Flow rate: 3.0 mL/minute; Back pressure: 120 bar}.

P9 Yield: 229 mg, 0.531 mmol, 46%. Retention time 4.50 minutes (Analytical conditions identical to those used for P8).

Preparation P10

{4-[2-(4-Chloro-2-fluorophenyl)-2-methyl-1,3-benzodioxol-4-yl]piperidin-1-yl}acetic acid (P10)

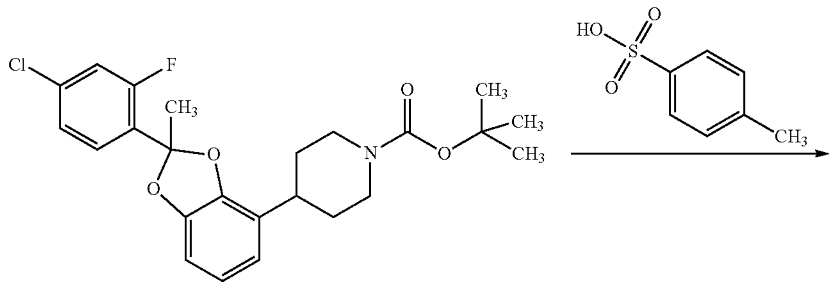

P2

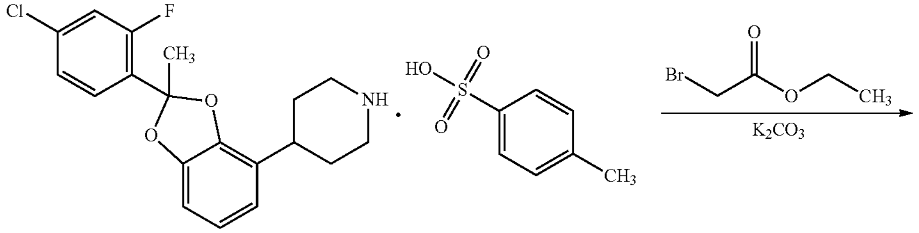

C13

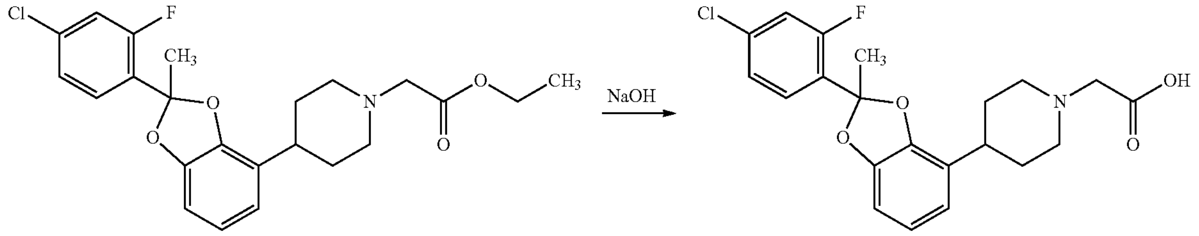

C14

P10

Step 1. Synthesis of 4-[2-(4-Chloro-2-Fluorophenyl)-2-Methyl-1,3-Benzodioxol-4-Yl]Piperidine, p-Toluenesulfonate Salt (C13)

A solution of P2 (5.0 g, 11 mmol) and p-toluenesulfonic acid (4.81 g, 27.9 mmol) in ethyl acetate (100 mL) was stirred at 60° C. for 2 hours, whereupon it was concentrated in vacuo to afford C13 as a yellow gum. This material was taken directly into the following step. LCMS m/z 347.9♦ $[M+H]^+$.

Step 2. Synthesis of ethyl {4-[2-(4-chloro-2-fluorophenyl)-2-methyl-1,3-benzodioxol-4-yl]piperidin-1-yl}acetate (C14)

Potassium carbonate (7.71 g, 55.8 mmol) and ethyl bromoacetate (1.86 g, 11.2 mmol) were added to a solution of C13 (from the previous step; 511 mmol) in acetonitrile (150 mL), and the reaction mixture was stirred at 55° C. for 16 hours. It was then filtered, and the filtrate was concentrated in vacuo and purified using silica gel chromatography (Gradient: 0% to 30% ethyl acetate in petroleum ether) to afford C14 as a yellow gum. By $^1H$ NMR analysis, this material was not entirely pure. Yield: 3.57 g, 8.23 mmol, 75% over 2 steps. $^1H$ NMR (400 MHz, chloroform-d), C14 peaks only: δ 7.52 (dd, J=8.4, 8.0 Hz, 1H), 7.17-7.07 (m, 2H), 6.77 (dd, component of ABC pattern, J=7.8, 7.8 Hz, 1H), 6.72-6.67 (m, 2H), 4.21 (q, J=7.1 Hz, 2H), 3.27 (s, 2H), 3.07 (m, 2H), 2.70 (tt, J=12.1, 3.8 Hz, 1H), 2.35 (ddd, J=11.5, 11.5, 2.7 Hz, 2H), 2.04 (d, J=1.1 Hz, 3H), 2.02-1.76 (m, 4H), 1.29 (t, J=7.1 Hz, 3H).

Step 3. Synthesis of {4-[2-(4-chloro-2-fluorophenyl)-2-methyl-1,3-benzodioxol-4-yl]piperidin-1-yl}acetic acid (P10)

A solution of C14 (3.57 g, 8.23 mmol) and aqueous sodium hydroxide solution (3 M; 13.7 mL, 41.1 mmol) in a mixture of methanol (80 mL) and tetrahydrofuran (40 mL) was stirred at 25° C. for 16 hours. After removal of solvents in vacuo, the aqueous residue was acidified to pH 7 by addition of 1 M hydrochloric acid, and then extracted with a mixture of dichloromethane and methanol (10:1, 2×100 mL). The combined organic layers were dried over sodium sulfate, filtered, and concentrated under reduced pressure to provide P10 as a yellow solid. Yield: 2.95 g, 7.27 mmol, 88%. LCMS m/z 406.2♦ $[M+H]^+$. $^1H$ NMR (400 MHz, methanol-$d_4$) δ 7.61 (dd, J=8.3, 8.3 Hz, 1H), 7.29 (dd, J=10.9, 2.0 Hz, 1H), 7.22 (ddd, J=8.4, 2.0, 0.8 Hz, 1H), 6.82 (dd, component of ABC pattern, J=8.3, 7.1 Hz, 1H), 6.78-6.72 (m, 2H), 3.65-3.54 (br m, 2H), 3.51 (s, 2H), 3.04-2.88 (m, 3H), 2.23-2.07 (m, 2H), 2.07-1.93 (m, 2H), 2.04 (d, J=1.1 Hz, 3H).

Preparation P11

Methyl 2-(chloromethyl)-1-(2-methoxyethyl)-1H-benzimidazole-6-carboxylate (P11)

stirred at room temperature under 15 psi hydrogen for 18 hours. The black suspension was filtered through diatomaceous earth and the filter cake was washed with methanol (500 mL). The combined filtrates were concentrated in vacuo to give C16 (26.5 g, quantitative) as a brown oil, which solidified on standing. $^1$H NMR (400 MHz, chloroform-d) δ 7.48 (dd, 1H), 7.36 (d, 1H), 6.69 (d, 1H), 3.87 (s, 3H), 3.77 (br s, 2H), 3.68 (t, 2H), 3.41 (s, 3H), 3.32 (t, 2H); LCMS m/z 224.7 [M+H]$^+$.

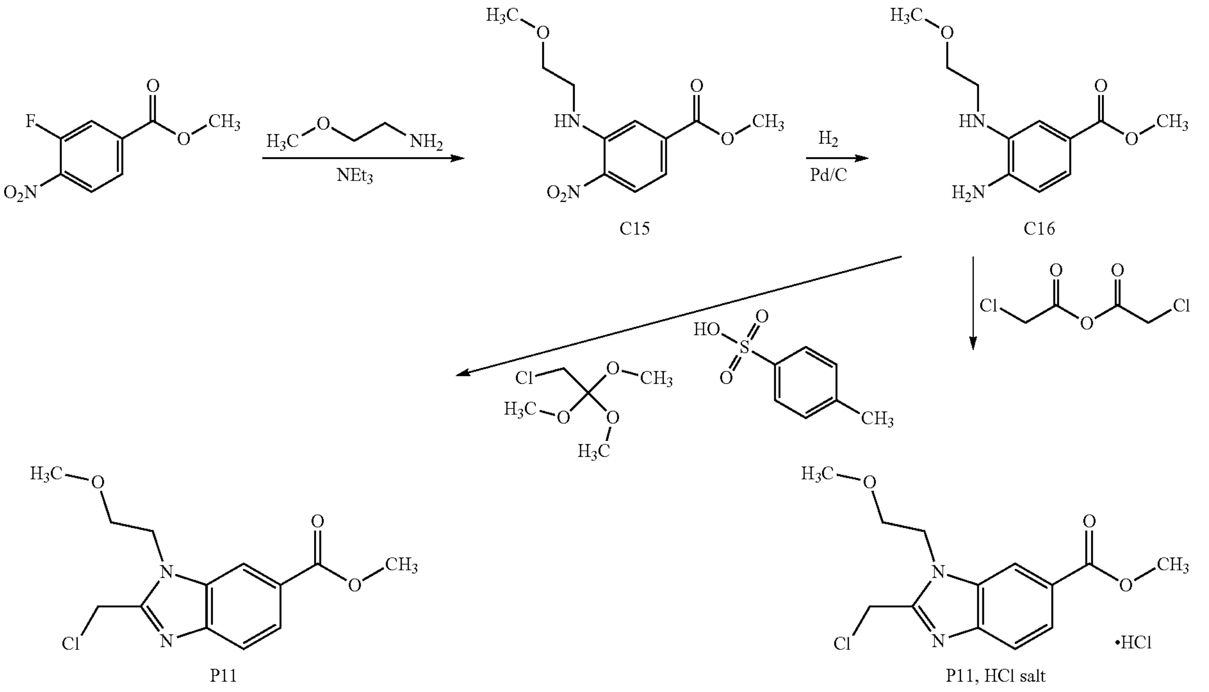

Step 1. Synthesis of methyl 3-[(2-methoxyethyl)amino]-4-nitrobenzoate (C15)

To a colorless solution of methyl 3-fluoro-4-nitrobenzoate (50 g, 250 mmol) in tetrahydrofuran (400 mL) was added triethylamine (40.7 g, 402 mmol, 55.8 mL) followed by addition of 2-methoxyethanamine (30.2 g, 402 mmol) in tetrahydrofuran (100 mL), drop-wise, at room temperature. The resultant yellow solution was stirred at 55° C. for 18 hours. The solution was cooled to room temperature and concentrated under reduced pressure to remove tetrahydrofuran. The resultant yellow solid was dissolved in ethyl acetate (800 mL) and washed with saturated aqueous ammonium chloride solution (250 mL). The aqueous phase was separated and extracted with ethyl acetate (200 mL). The combined organic layers were washed with saturated aqueous sodium chloride solution (3×250 mL), dried over sodium sulfate, filtered, and concentrated under reduced pressure to yield C15 (60.2 g, 94%) as a yellow solid. $^1$H NMR (600 MHz, chloroform-d) δ 8.23 (d, 1H), 8.17 (br s, 1H), 7.58 (d, 1H), 7.25 (dd, 1H), 3.95 (s, 3H), 3.69-3.73 (m, 2H), 3.56 (m, 2H), 3.45 (s, 3H); LCMS m/z 255.4 [M+H]$^+$.

Step 2. Synthesis of methyl 4-amino-3-[(2-methoxyethyl) amino]benzoate (C16)

To solution of C15 (30 g, 118 mmol) in methanol (500 mL) was added Pd/C (10 g, 94 mmol). This reaction was Step 3. Synthesis of methyl 2-(chloromethyl)-1-(2-methoxyethyl)-1H-benzimidazole-6-carboxylate (P11)

To a solution of C16 (5.00 g, 22.3 mmol) in tetrahydrofuran (100 mL) was added 2-chloro-1,1,1-trimethoxyethane (3.31 mL, 24.6 mmol), followed by p-toluenesulfonic acid monohydrate (84.8 mg, 0.446 mmol). The reaction mixture was heated at 45° C. for 5 hours, whereupon it was concentrated in vacuo; the residual oil was dissolved in ethyl acetate (10 mL) and heated until a solution formed. This was slowly stirred while cooling to room temperature overnight. The precipitate was collected via filtration and washed with heptane to afford P11 as a gray solid. Yield: 5.73 g, 20.3 mmol, 91%. $^1$H NMR (600 MHz, chloroform-d) δ 8.12 (br s, 1H), 8.01 (br d, J=8.6 Hz, 1H), 7.79 (d, J=8.4 Hz, 1H), 4.96 (s, 2H), 4.52 (t, J=5.1 Hz, 2H), 3.96 (s, 3H), 3.74 (t, J=5.1 Hz, 2H), 3.28 (s, 3H).

Step 4. Synthesis of methyl 2-(chloromethyl)-1-(2-methoxyethyl)-1H-benzimidazole-6-carboxylate, hydrochloride salt (P11, HCl salt)

A solution of C16 (5.0 g, 24 mmol) in 1,4-dioxane (100 mL) was heated to 100° C., a solution of chloroacetic anhydride (4.1 g, 24.5 mmol) in 1,4-dioxane (60 mL) was added via addition funnel over a period of 10 hours, and the reaction mixture was stirred for another 12 hours at 100° C. The following day, the reaction was cooled to room temperature and the 1,4-dioxane was removed under reduced pressure. The crude reaction mixture was dissolved in ethyl acetate and washed with saturated aqueous sodium bicarbonate solution. The ethyl acetate layer was separated, dried over sodium sulfate, and filtered. A solution of 4 M hydrogen chloride in 1,4-dioxane (1.1 equiv.) was added to the ethyl acetate solution with constant stirring. The hydrochloride salt of P11 precipitated out as a pale yellow solid. The suspension was stirred for 1 hour and the hydrochloride salt of P11 was then collected by filtration to give a yellow solid (6.1 g, 86%). $^1$H NMR (600 MHz, $CD_3OD$) 6 8.64 (s, 1H), 8.30 (d, 1H), 7.92 (d, 1H), 5.32 (s, 2H), 4.84 (m, 2H), 3.99 (s, 3H), 3.83 (t, 2H), 3.31 (s, 3H). LCMS m/z 283.2 [M+H]$^+$.

Preparation P12

Methyl 1-(2-methoxyethyl)-2-(piperazin-1-ylmethyl)-1H-benzimidazole-6-carboxylate (P12)

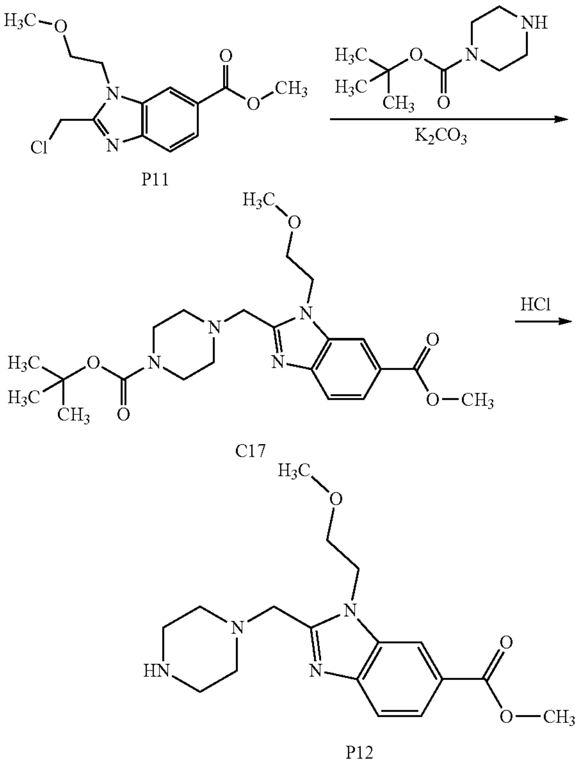

P11

C17

P12

Step 1. Synthesis of methyl 2-{[4-(tert-butoxycarbonyl)piperazin-1-yl]methyl}-1-(2-methoxyethyl)-1H-benzimidazole-6-carboxylate (C17)

Compound P11 (1.59 g, 5.62 mmol) was added to a 15° C. mixture of tert-butyl piperazine-1-carboxylate (1.00 g, 5.37 mmol) and potassium carbonate (2.97 g, 21.5 mmol) in acetonitrile (15 mL), and the reaction mixture was stirred at 55° C. for 12 hours. It was then combined with a similar reaction carried out using P11 and tert-butyl piperazine-1-carboxylate (200 mg, 1.07 mmol), and the mixture was filtered. After the filtrate had been concentrated in vacuo, the residue was purified via chromatography on silica gel (Gradient: 0% to 60% ethyl acetate in petroleum ether) to provide C17 as a pale yellow solid. Combined yield: 2.30 g, 5.32 mmol, 83%. LCMS m/z 433.0 [M+H]$^+$. $^1$H NMR (400 MHz, chloroform-d) δ 8.12 (d, J=1.5 Hz, 1H), 7.96 (dd, J=8.4, 1.5 Hz, 1H), 7.73 (d, J=8.5 Hz, 1H), 4.58 (t, J=5.4 Hz, 2H), 3.95 (s, 3H), 3.89 (s, 2H), 3.73 (t, J=5.4 Hz, 2H), 3.46-3.37 (br m, 4H), 3.28 (s, 3H), 2.54-2.44 (br m, 4H), 1.45 (s, 9H).

Step 2. Synthesis of methyl 1-(2-methoxyethyl)-2-(piperazin-1-ylmethyl)-1H-benzimidazole-6-carboxylate (P12)

To a solution of C17 (2.30 g, 5.32 mmol) in dichloromethane (80 mL) was added a solution of hydrogen chloride in ethyl acetate (20 mL). The reaction mixture was stirred at 20° C. for 2 hours, whereupon it was concentrated in vacuo. The residue was diluted with water (20 mL), adjusted to a pH of 9 to 10 by addition of saturated aqueous sodium bicarbonate solution, and extracted with a mixture of ethyl acetate and methanol (10:1, 15×50 mL). The combined organic layers were dried over sodium sulfate, filtered, and concentrated in vacuo to afford P12 as a pale yellow solid. Yield: 1.68 g, 5.05 mmol, 95%. LCMS m/z 332.8 [M+H]$^+$. $^1$H NMR (400 MHz, chloroform-d) δ 8.13 (br s, 1H), 7.96 (br d, J=8.5 Hz, 1H), 7.72 (d, J=8.5 Hz, 1H), 4.59 (t, J=5.5 Hz, 2H), 3.95 (s, 3H), 3.86 (s, 2H), 3.75 (t, J=5.5 Hz, 2H), 3.29 (s, 3H), 2.87 (t, J=4.8 Hz, 4H), 2.50 (br m, 4H).

Preparation P13

6-Bromo-2-(chloromethyl)-1-(2-methoxyethyl)-1H-imidazo[4,5-b]pyridine (P13)

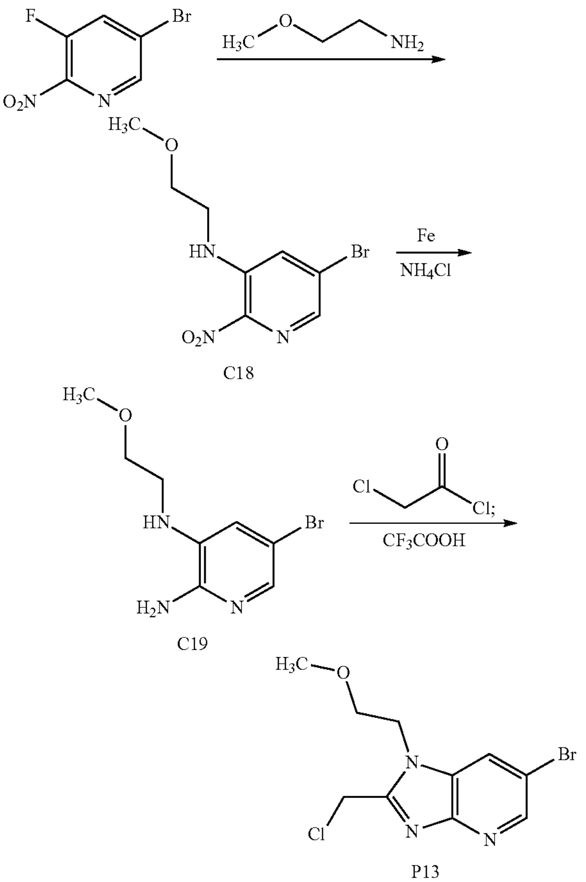

C18

C19

P13

Step 1. Synthesis of 5-bromo-N-(2-methoxyethyl)-2-nitropyridin-3-amine (C18)

A solution of 5-bromo-3-fluoro-2-nitropyridine (400 mg, 1.81 mmol) and 2-methoxyethanamine (408 mg, 5.43 mmol) in tetrahydrofuran (10 mL) was stirred at 25° C. for 2 hours, whereupon it was diluted with ethyl acetate (100 mL) and washed with water (50 mL). The organic layer was washed with saturated aqueous sodium chloride solution (50 mL), dried over magnesium sulfate, filtered, and concentrated to afford C18 as a yellow solid. Yield: 430 mg, 1.56 mmol, 86%.

Step 2. Synthesis of 5-bromo-$N^3$-(2-methoxyethyl)pyridine-2,3-diamine (C19)

A solution of C18 (430 mg, 1.56 mmol), ammonium chloride (833 mg, 15.6 mmol), and iron powder (870 mg, 15.6 mmol) in a mixture of methanol (10 mL) and water (2 mL) was stirred at 80° C. for 30 minutes. The resulting suspension was poured into water (50 mL) and extracted with ethyl acetate (2×50 mL); the combined organic layers were dried over magnesium sulfate, filtered, and concentrated to provide C19 as a brown solid. Yield: 350 mg, 1.42 mmol, 91%. $^1$H NMR (400 MHz, chloroform-d) δ 7.63 (d, J=2.1 Hz, 1H), 6.88 (d, J=2.0 Hz, 1H), 4.33-4.19 (br s, 2H), 3.65 (dd, J=5.6, 4.6 Hz, 2H), 3.40 (s, 3H), 3.22 (br t, J=5 Hz, 2H).

Step 3. Synthesis of 6-bromo-2-(chloromethyl)-1-(2-methoxyethyl)-1H-imidazo[4,5-b]pyridine (P13)

A solution of C19 (400 mg, 1.63 mmol) in 1,4-dioxane (8 mL) was treated with chloroacetyl chloride (0.284 mL, 3.57 mmol) and stirred at room temperature until LCMS analysis indicated complete conversion of C19 to the intermediate amide. After removal of the 1,4-dioxane in vacuo, the residue was dissolved in trifluoroacetic acid (8 mL) and heated at 80° C. for 18 hours, whereupon the reaction mixture was cooled to room temperature and concentrated under reduced pressure. The resulting oil was dissolved in ethyl acetate (50 mL) and neutralized by addition of saturated aqueous sodium bicarbonate solution. The aqueous layer was extracted with ethyl acetate (20 mL), and the combined organic layers were dried over sodium sulfate, filtered, and concentrated in vacuo. Silica gel chromatography (Gradient: 0% to 80% ethyl acetate in heptane) afforded P13 as a solid. Yield: 176 mg, 0.578 mmol, 35%. LCMS m/z 306.1 (bromine-chlorine isotope pattern observed) $[M+H]^+$. $^1$H NMR (600 MHz, chloroform-d) 6 8.58 (br s, 1H), 7.89 (br s, 1H), 4.92 (s, 2H), 4.44 (t, J=5.0 Hz, 2H), 3.71 (t, J=5.0 Hz, 2H), 3.28 (s, 3H).

Preparation P14

Methyl 2-{[4-(2, 3-dihydroxyphenyl)piperidin-1-yl]methyl}-1-(2-methoxyethyl)-1H-benzimidazole-6-carboxylate (P14)

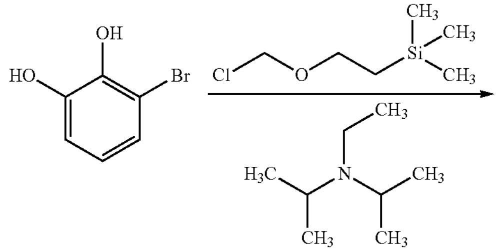

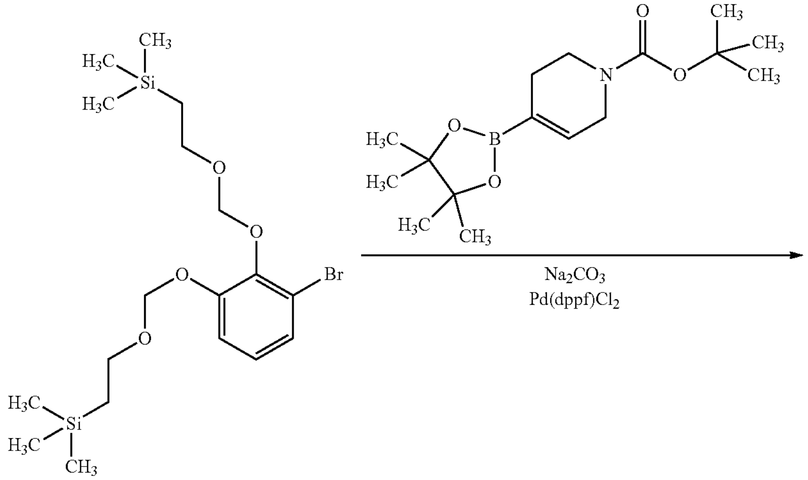

C20

-continued
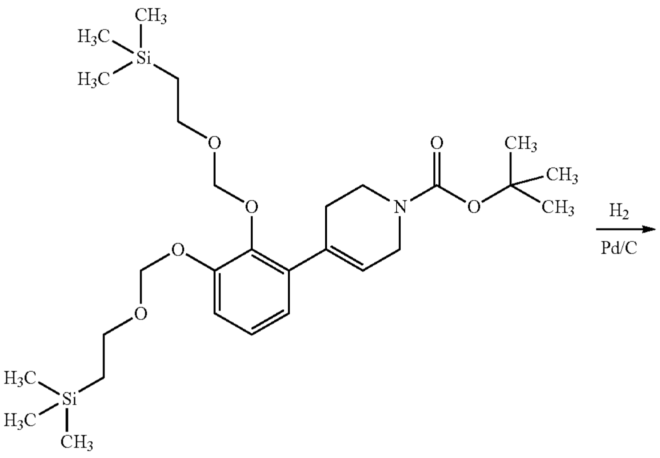
C21
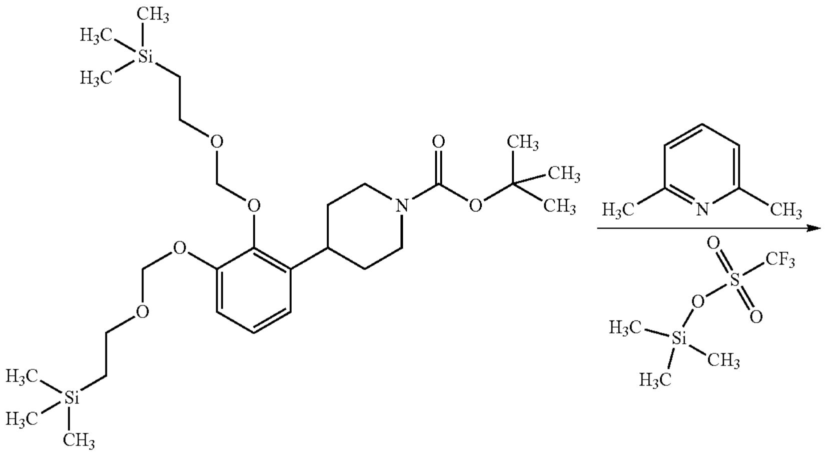
C22
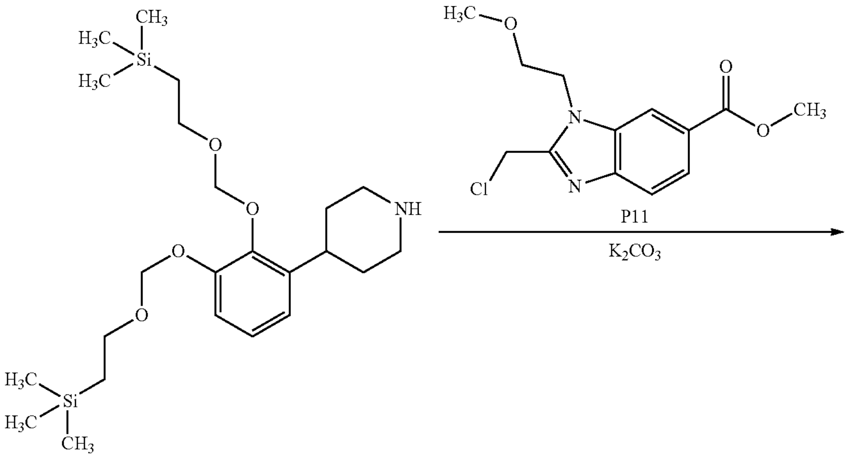
C23

-continued

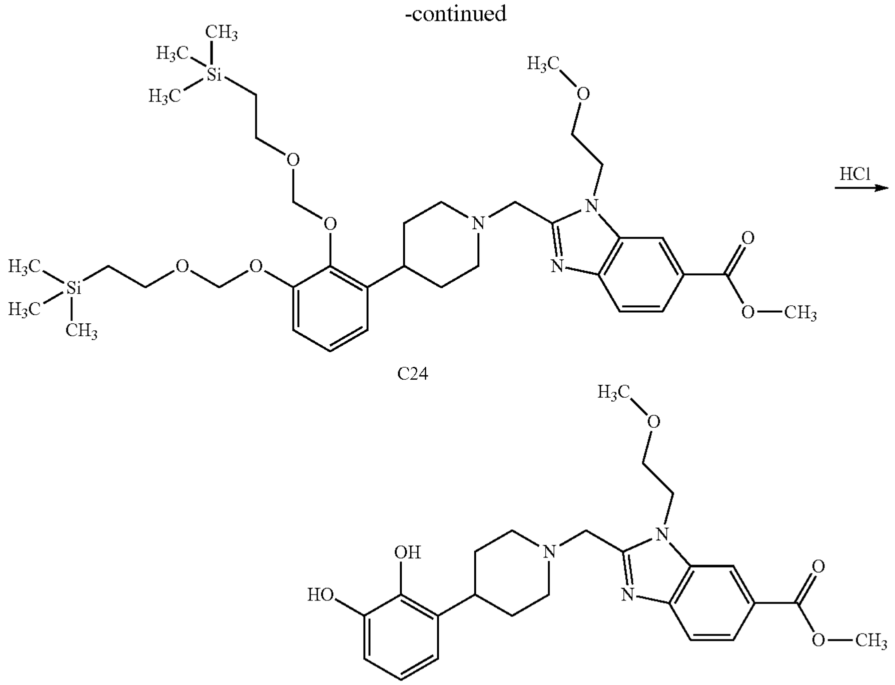

C24

P14

Step 1. Synthesis of [(3-bromobenzene-1,2-diyl)bis (oxymethanediyloxyethane-2, 1-diyl)]bis(trimethylsilane) (C20)

This reaction was carried out in two batches of identical scale. N,N-Diisopropylethylamine (37.8 mL, 217 mmol) was added drop-wise to a solution of 3-bromobenzene-1,2-diol (10.0 g, 52.9 mmol) in tetrahydrofuran (300 mL). After the mixture had been stirred for 10 minutes at 20° C., [2-(chloromethoxy)ethyl](trimethyl)silane (19.2 mL, 108 mmol) was added drop-wise over 5 minutes, and stirring was continued for 16 hours at room temperature (18° C.). N,N-Diisopropylethylamine (27.6 mL, 158 mmol) was again added, followed by drop-wise addition of [2-(chloromethoxy)ethyl](trimethyl)silane (14.0 mL, 79.1 mmol) at room temperature (18° C.). After another 2.5 hours at room temperature, the reaction mixture was filtered, and the filtrate was concentrated in vacuo. At this point, the crude products from the two batches were combined and purified using silica gel chromatography (Gradient: 0% to 7% ethyl acetate in petroleum ether), to afford C20 as a colorless oil. By $^1$H NMR analysis, this material was not entirely pure. Combined yield: 22.9 g, 50.9 mmol, 48%. $^1$H NMR (400 MHz, chloroform-d), C20 peaks only: 67.19 (dd, J=8.1, 1.5 Hz, 1H), 7.12 (dd, J=8.3, 1.4 Hz, 1H), 6.90 (dd, J=8.2. 8.2 Hz, 1H), 5.26-5.19 (m, 4H), 4.00-3.92 (m, 2H), 3.80-3.73 (m, 2H), 1.00-0.91 (m, 4H), 0.03 (s, 9H), 0.00 (s, 9H).

Step 2. Synthesis of tert-butyl 4-(2,3-bis{[2-(trimethylsilyl)ethoxy]methoxy}phenyl)-3,6-dihydropyridine-1 (2H)-carboxylate (C21)

A reaction vessel containing a suspension of C20 (6.11 g, 13.6 mmol), tert-butyl 4-(4,4,5,5-tetramethyl-1,3,2-dioxaborolan-2-yl)-3,6-dihydropyridine-1 (2H)-carboxylate (5.04 g, 16.3 mmol), aqueous sodium carbonate solution (1 M; 40.8 mL, 40.8 mmol), and [1,1'-bis(diphenylphosphino) ferrocene]dichloropalladium(II) (497 mg, 0.679 mmol) in 1,4-dioxane (100 mL) was evacuated and charged with nitrogen. This evacuation cycle was repeated twice, and then the reaction mixture was stirred at 85° C. for 16 hours, whereupon the reaction mixture was diluted with water (40 mL) and extracted with ethyl acetate (3×150 mL). The combined organic layers were dried over sodium sulfate, filtered, and concentrated in vacuo. Purification via silica gel chromatography (Gradient: 0% to 8% methanol in dichloromethane) provided C21 as a yellow oil. Yield: 5.47 g, 9.91 mmol, 73%. $^1$H NMR (600 MHz, chloroform-d) δ 7.10 (br d, J=8.2 Hz, 1H), 6.98 (dd, J=7.9, 7.9 Hz, 1H), 6.81 (br d, J=7.7 Hz, 1H), 5.79 (br s, 1H), 5.23 (s, 2H), 5.07 (s, 2H), 4.03 (br s, 2H), 3.83-3.74 (m, 4H), 3.59 (br s, 2H), 2.52 (br s, 2H), 1.49 (s, 9H), 1.01-0.89 (m, 4H), 0.01 (s, 9H), 0.01 (s, 9H).

Step 3. Synthesis of tert-butyl 4-(2,3-bis{[2-(trimethylsilyl)ethoxy]methoxy}phenyl)piperidine-1-carboxylate (C22)

A solution of C21 (12.5 g, 22.6 mmol) in methanol (300 mL) was treated with 10% palladium on carbon (2.94 g, 2.76 mmol) and hydrogenated for 16 hours at 40 psi and 25° C. LCMS analysis at this point indicated conversion to the product: LCMS m/z 576.0 [M+Na$^+$]. After the reaction mixture had been filtered, and the filter cake had been washed with methanol (2×100 mL), the combined filtrates were concentrated in vacuo to afford C22 as a colorless oil. Yield: 11.2 g, 20.1 mmol, 89%. $^1$H NMR (400 MHz, chloroform-d) δ 7.05-6.97 (m, 2H), 6.83 (dd, J=6.9, 2.5 Hz, 1H), 5.22 (s, 2H), 5.13 (s, 2H), 4.38-4.10 (br m, 2H), 3.90-3.82 (m, 2H), 3.81-3.73 (m, 2H), 3.22 (tt, J=12.2, 3.5 Hz, 1H), 2.79 (br dd, J=12.8, 12.8 Hz, 2H), 1.78 (br d, J=13 Hz, 2H), 1.65-1.52 (m, 2H), 1.48 (s, 9H), 1.04-0.91 (m, 4H), 0.03 (s, 9H), 0.00 (s, 9H).

Step 4. Synthesis of 4-(2,3-bis{[2-(trimethylsilyl)ethoxy]methoxy}phenyl)piperidine (C23)

To a room temperature (15° C.) solution of C22 (7.23 g, 13.0 mmol) in dichloromethane (90 mL) was added 2,6-dimethylpyridine (2.39 g, 22.3 mmol), followed by drop-wise addition of trimethylsilyl trifluoromethanesulfonate (3.80 g, 17.1 mmol). The reaction mixture was stirred at 15° C. for 16 hours, whereupon additional 2,6-dimethylpyridine (909 mg, 8.48 mmol) and trimethylsilyl trifluoromethane-sulfonate (1.45 g, 6.52 mmol) were added. After stirring at room temperature (15° C.) for another 5 hours, LCMS analysis of the reaction mixture indicated the presence of product: LCMS m/z 454.1 $[M+H]^+$. The reaction mixture was concentrated in vacuo, and the residue was washed sequentially with aqueous ammonium chloride solution (3×100 mL) and saturated aqueous sodium chloride solution (100 mL), dried over sodium sulfate, filtered, and concentrated under reduced pressure to afford C23 as a brown oil (6.6 g). This material was taken directly to the following step.

Step 5. Synthesis of methyl 2-{[4-(2,3-bis{[2-(trimethylsilyl)ethoxy]methoxy}phenyl)piperidin-1-yl]methyl}-1-(2-methoxyethyl)-1H-benzimidazole-6-carboxylate (C24)

To a solution of C23 (from the previous step; 6.6 g, 513 mmol) in acetonitrile (150 mL) was added P11 (3.08 g, 10.9 mmol), followed by potassium carbonate (10.1 g, 73.1 mmol), and the reaction mixture was stirred at room temperature (15° C.) for 16 hours. LCMS analysis at this point indicated the presence of the product: LCMS m/z 700.2 $[M+H]^+$. The reaction mixture was filtered, and the filtrate was concentrated in vacuo; purification via silica gel chromatography (Gradient: 34% to 56% ethyl acetate in petroleum ether) afforded C24 as a yellow oil. Yield: 5.4 g, 7.7 mmol, 59% over 2 steps. $^1H$ NMR (400 MHz, chloroform-d) δ 8.16-8.12 (m, 1H), 7.96 (dd, J=8.5, 1.5 Hz, 1H), 7.73 (d, J=8.5 Hz, 1H), 7.04-6.96 (m, 2H), 6.86 (dd, J=6.7, 2.6 Hz, 1H), 5.21 (s, 2H), 5.12 (s, 2H), 4.63 (t, J=5.5 Hz, 2H), 3.95 (s, 3H), 3.93-3.83 (m, 4H), 3.80-3.72 (m, 4H), 3.31 (s, 3H), 3.17-3.06 (m, 1H), 2.99 (br d, J=11.2 Hz, 2H), 2.35-2.22 (m, 2H), 1.81 (br d, half of AB quartet, J=12.6 Hz, 2H), 1.75-1.61 (m, 2H), 1.04-0.91 (m, 4H), 0.05 (s, 9H), −0.01 (s, 9H).

Step 6. Synthesis of methyl 2-{[4-(2,3-dihydroxyphenyl)piperidin-1-yl]methyl}-1-(2-methoxyethyl)-1H-benzimidazole-6-carboxylate (P14)

A solution of hydrogen chloride in 1,4-dioxane (4 M; 96 mL, 384 mmol) was added to a room temperature (18° C.) solution of C24 (6.40 g, 9.14 mmol) in 1,4-dioxane (120 mL). After completion of the addition, the reaction mixture was stirred at room temperature (18° C.) for 16 hours, combined with a similar reaction carried out using C24 (1.00 g, 1.43 mmol), and concentrated in vacuo. The residue was treated with a mixture of dichloromethane and methanol (20:1, 150 mL) and stirred at room temperature (18° C.) for 1 hour, whereupon the solid (4.85 g) was collected via filtration. This material was treated with water (100 mL), and the mixture was adjusted to a pH of 7 to 8 by addition of aqueous sodium bicarbonate solution, stirred at room temperature (18° C.) for 30 minutes, and filtered. The filter cake was washed with water (2×20 mL), then mixed with methanol (100 mL) and concentrated in vacuo. The resulting material was treated with petroleum ether (100 mL) and stirred at room temperature (18° C.) for 30 minutes. After filtration, the filter cake was mixed with toluene (30 mL) and concentrated in vacuo to provide P14 as a gray solid. Combined yield: 2.92 g, 6.64 mmol, 63%. LCMS m/z 440.1 $[M+H]^+$. $^1H$ NMR (400 MHz, DMSO-$d_6$) δ 8.21 (d, J=1.6 Hz, 1H), 7.81 (dd, J=8.5, 1.6 Hz, 1H), 7.66 (d, J=8.5 Hz, 1H), 6.64-6.51 (m, 3H), 4.63 (t, J=5.3 Hz, 2H), 3.88 (s, 3H), 3.84 (s, 2H), 3.75 (t, J=5.3 Hz, 2H), 3.22 (s, 3H), 2.97-2.78 (m, 3H), 2.18 (br dd, J=11, 11 Hz, 2H), 1.75-1.64 (m, 2H), 1.64-1.49 (m, 2H).

Preparation P15 Methyl 2-(chloromethyl)-1-[(2S)-oxetan-2-ylmethyl]-1H-benzimidazole-6-carboxylate (P15)

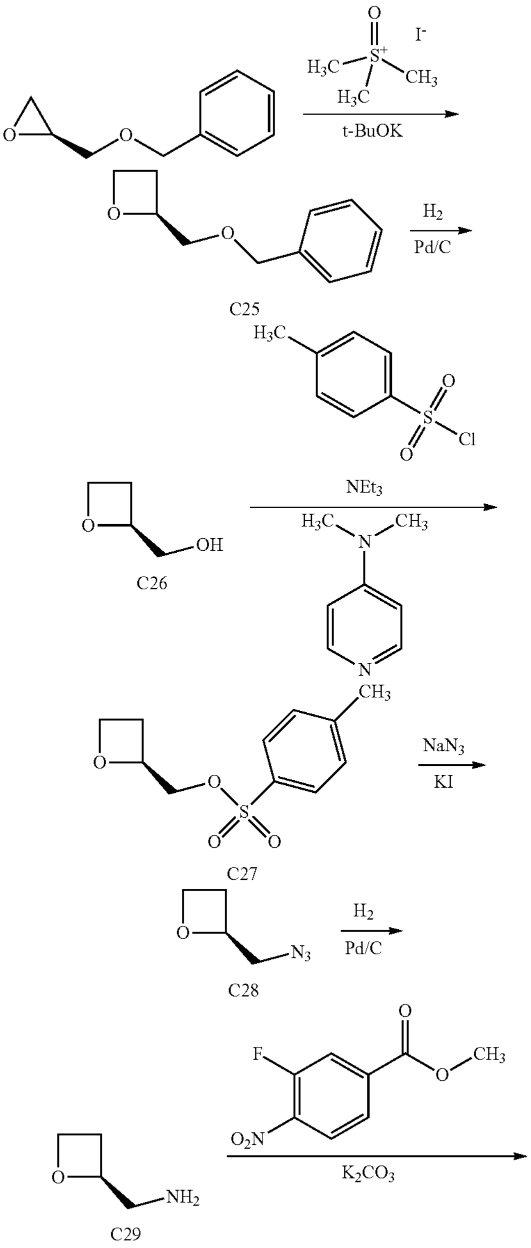

-continued

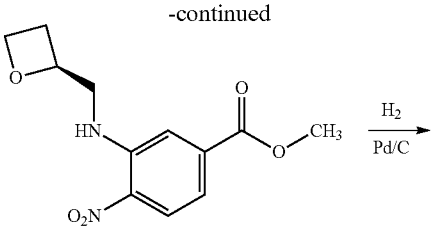

C30

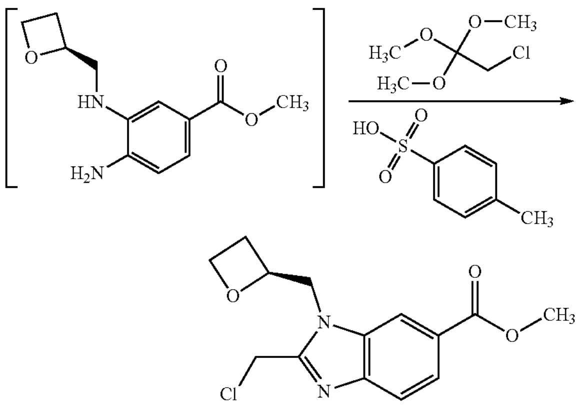

P15

This entire sequence was carried out on large scale. In general, before reactions, as well as after addition of reagents, reactors were evacuated to −0.08 to −0.05 MPa and then filled with nitrogen to normal pressure. This process was generally repeated 3 times, and then oxygen content was assessed to ensure that it was 51.0%. For the processes of extraction and washing of organic layers, mixtures were generally stirred for 15 to 60 minutes and then allowed to settle for 15 to 60 minutes before separation of layers.

Step 1. Synthesis of (2S)-2-[(benzyloxy)methyl]oxetane (C25)

This reaction was carried out in three batches of approximately the same scale. A 2000 L glass-lined reactor was charged with 2-methylpropan-2-ol (774.7 kg). Potassium tert-butoxide (157.3 kg, 1402 mol) was added via a solid addition funnel, and the mixture was stirred for 30 minutes. Trimethylsulfoxonium iodide (308.2 kg, 1400 mol) was then added in the same manner, and the reaction mixture was heated at 55° C. to 65° C. for 2 to 3 hours, whereupon (2S)-2-[(benzyloxy)methyl]oxirane (92.1 kg, 561 mol) was added at a rate of 5 to 20 kg/hour. After the reaction mixture had been maintained at 55° C. to 65° C. for 25 hours, it was cooled to 25° C. to 35° C., and filtered through diatomaceous earth (18.4 kg). The filter cake was rinsed with tert-butyl methyl ether (3×340 kg), and the combined filtrates were transferred to a 5000 L reactor, treated with purified water (921 kg), and stirred for 15 to 30 minutes at 15° C. to 30° C. The organic layer was then washed twice using a solution of sodium chloride (230.4 kg) in purified water (920.5 kg), and concentrated under reduced pressure (≤−0.08 MPa) at 545° C. n-Heptane (187 kg) was added, and the resulting mixture was concentrated under reduced pressure (≤−0.08 MPa) at ≤45° C.; the organic phase was purified using silica gel chromatography (280 kg), with sodium chloride (18.5 kg) on top of the column. The crude material was loaded onto the column using n-heptane (513 kg), and then eluted with a mixture of n-heptane (688.7 kg) and ethyl acetate (64.4 kg). The three batches were combined, providing C25 as an 85% pure light yellow oil (189.7 kg, 906 mmol, 54%). $^1$H NMR (400 MHz, chloroform-d), C25 peaks only: δ 7.40-7.32 (m, 4H), 7.32-7.27 (m, 1H), 4.98 (dddd, J=8.1, 6.7, 4.9, 3.7 Hz, 1H), 4.72-4.55 (m, 4H), 3.67 (dd, component of ABX pattern, J=11.0, 4.9 Hz, 1H), 3.62 (dd, component of ABX pattern, J=11.0, 3.7 Hz, 1H), 2.72-2.53 (m, 2H).

Step 2. Synthesis of (2S)-oxetan-2-ylmethanol (C26)

10% Palladium on carbon (30.7 kg) was added through an addition funnel to a 10° C. to 30° C. solution of 85% pure C25 (from previous step; 185.3 kg, 884.8 mol) in tetrahydrofuran (1270 kg) in a 3000 L stainless steel autoclave reactor. The addition funnel was rinsed with purified water and tetrahydrofuran (143 kg), and the rinses were added to the reaction mixture. After the reactor contents had been purged with nitrogen, they were similarly purged with hydrogen, increasing the pressure to 0.3 to 0.5 MPa and then venting to 0.05 MPa. This hydrogen purge was repeated 5 times, whereupon the hydrogen pressure was increased to 0.3 to 0.4 MPa. The reaction mixture was then heated to 35° C. to 45° C. After 13 hours, during which the hydrogen pressure was maintained at 0.3 to 0.5 MPa, the mixture was vented to 0.05 MPa, and purged five times with nitrogen, via increasing the pressure to 0.15 to 0.2 MPa and then venting to 0.05 MPa. After the mixture had been cooled to 10° C. to 25° C., it was filtered, and the reactor was rinsed with tetrahydrofuran (2×321 kg). The filter cake was soaked twice with this rinsing liquor and then filtered; concentration at reduced pressure (≤−0.06 MPa) was carried out at ≤40° C., affording C26 (62.2 kg, 706 mol, 80%) in tetrahydrofuran (251 kg)

Step 3. Synthesis of (2S)-oxetan-2-ylmethyl 4-methylbenzenesulfonate (C27)

4-(Dimethylamino)pyridine (17.5 kg, 143 mol) was added to a 10° C. to 25° C. solution of C26 (from the previous step; 62.2 kg, 706 mol) in tetrahydrofuran (251 kg) and triethylamine (92.7 kg, 916 mol) in dichloromethane (1240 kg). After 30 minutes, p-toluenesulfonyl chloride (174.8 kg, 916.9 mol) was added in portions at intervals of 20 to 40 minutes, and the reaction mixture was stirred at 15° C. to 25° C. for 16 hours and 20 minutes. Purified water (190 kg) was added; after stirring, the organic layer was washed with aqueous sodium bicarbonate solution (prepared using 53.8 kg of sodium bicarbonate and 622 kg of purified water), and then washed with aqueous ammonium chloride solution (prepared using 230 kg of ammonium chloride and 624 kg of purified water). After a final wash with purified water (311 kg), the organic layer was filtered through a stainless steel Nutsche filter that had been preloaded with silica gel (60.2 kg). The filter cake was soaked with dichloromethane (311 kg) for 20 minutes, and then filtered; the combined filtrates were concentrated at reduced pressure (≤−0.05 MPa) and ≤40° C. until 330 to 400 L remained. Tetrahydrofuran (311 kg) was then added, at 15° C. to 30° C., and the mixture was concentrated in the same manner, to a final volume of 330 to 400 L. The tetrahydrofuran addition and concentration was repeated, again to a volume of 330 to 400 L, affording a light yellow solution of C27 (167.6 kg, 692 mmol, 98%) in tetrahydrofuran (251.8 kg). $^1$H NMR (400 MHz, chloroform-d), C27 peaks only: δ 7.81 (d, J=8.4 Hz, 2H), 7.34 (d, J=8.1 Hz, 2H), 4.91 (ddt, J=8.0, 6.7, 3.9 Hz, 1H), 4.62-4.55

(m, 1H), 4.53-4.45 (m, 1H), 4.14 (d, J=3.9 Hz, 2H), 2.75-2.63 (m, 1H), 2.60-2.49 (m, 1H), 2.44 (s, 3H).

Step 4. Synthesis of (2S)-2-(azidomethyl)oxetane (C28)

N,N-Dimethylformamide (473 kg), sodium azide (34.7 kg, 534 mol), and potassium iodide (5.2 kg, 31 mol) were combined in a 3000 L glass-lined reactor at 10° C. to 25° C. After addition of C27 (83.5 kg, 344.6 mol) in tetrahydrofuran (125.4 kg), the reaction mixture was heated to 55° C. to 65° C. for 17 hours and 40 minutes, whereupon it was cooled to 25° C. to 35° C., and nitrogen was bubbled from the bottom valve for 15 minutes. tert-Butyl methyl ether (623 kg) and purified water (840 kg) were then added, and the resulting aqueous layer was extracted twice with tert-butyl methyl ether (312 kg and 294 kg). The combined organic layers were washed with purified water (2×419 kg) while maintaining the temperature at 10° C. to 25° C., affording C28 (31.2 kg, 276 mol, 80%) in a solution of the above organic layer (1236.8 kg).

Step 5. Synthesis of 1-[(2S)-oxetan-2-yl]methanamine (C29)

10% Palladium on carbon (3.7 kg) was added through an addition funnel to a 10° C. to 30° C. solution of C28 [from the previous step; 1264 kg (31.1 kg of C28, 275 mol)] in tetrahydrofuran (328 kg) in a 3000 L stainless steel autoclave reactor. The addition funnel was rinsed with tetrahydrofuran (32 kg), and the rinse was added to the reaction mixture. After the reactor contents had been purged with nitrogen, they were similarly purged with hydrogen, increasing the pressure to 0.05 to 0.15 MPa and then venting to 0.03 to 0.04 MPa. This hydrogen purge was repeated 5 times, whereupon the hydrogen pressure was increased to 0.05 to 0.07 MPa. The reaction temperature was increased to 25° C. to 33° C., and the hydrogen pressure was maintained at 0.05 to 0.15 MPa for 22 hours, while exchanging the hydrogen every 3 to 5 hours. The mixture was then purged five times with nitrogen, via increasing the pressure to 0.15 to 0.2 MPa and then venting to 0.05 MPa. After filtration, tetrahydrofuran (92 kg and 93 kg) was used to wash the reactor and then soak the filter cake. The combined filtrates were concentrated at reduced pressure (≤−0.07 MPa) and ≤45° C., affording C29 (18.0 kg, 207 mol, 75%) in tetrahydrofuran (57.8 kg). $^1$H NMR (400 MHz, DMSO-$d_6$), C29 peaks only: δ 4.62 (ddt, J=7.6, 6.6, 5.1 Hz, 1H), 4.49 (ddd, J=8.6, 7.3, 5.6 Hz, 1H), 4.37 (dt, J=9.1, 5.9 Hz, 1H), 2.69 (d, J=5.1 Hz, 2H), 2.55-2.49 (m, 1H), 2.39 (m, 1H).

Step 6. Synthesis of methyl 4-nitro-3-{[(2S)-oxetan-2-ylmethyl]amino}benzoate (C30)

Potassium carbonate (58.1 kg, 420 mol) was added to a solution of methyl 3-fluoro-4-nitrobenzoate (54.8 kg, 275 mol) in tetrahydrofuran (148 kg) in a 100 L glass-lined reactor, and the mixture was stirred for 10 minutes. A solution of C29 (29.3 kg, 336 mol) in tetrahydrofuran (212.9 kg) was added, and the reaction mixture was stirred at 20° C. to 30° C. for 12 hours, whereupon ethyl acetate (151 kg) was added, and the mixture was filtered through silica gel (29 kg). The filter cake was rinsed with ethyl acetate (150 kg and 151 kg), and the combined filtrates were concentrated at reduced pressure (≤−0.08 MPa) and ≤45° C. to a volume of 222 to 281 L. After the mixture had been cooled to 10° C. to 30° C., n-heptane (189 kg) was added, stirring was carried out for 20 minutes, and the mixture was concentrated at reduced pressure (≤−0.08 MPa) and ≤45° C. to a volume of 222 L. n-Heptane (181 kg) was again added into the mixture at a reference rate of 100 to 300 kg/hour, and stirring was continued for 20 minutes. The mixture was sampled until residual tetrahydrofuran was ≤5% and residual ethyl acetate was 10% to 13%. The mixture was heated to 40° C. to 45° C. and stirred for 1 hour, whereupon it was cooled to 15° C. to 25° C. at a rate of 5° C. to 10° C. per hour, and then stirred at 15° C. to 25° C. for 1 hour. Filtration using a stainless steel centrifuge provided a filter cake, which was rinsed with a mixture of ethyl acetate (5.0 kg) and n-heptane (34 kg), and then stirred with tetrahydrofuran (724 kg) at 10° C. to 30° C. for 15 minutes; filtration provided a yellow solid largely composed of C30 (57.3 kg, 210 mol, 76%). $^1$H NMR (400 MHz, DMSO-$d_6$) 8.34 (t, J=5.8 Hz, 1H), 8.14 (d, J=8.9 Hz, 1H), 7.63 (d, J=1.7 Hz, 1H), 7.13 (dd, J=8.9, 1.8 Hz, 1H), 4.99 (dddd, J=7.7, 6.7, 5.3, 4.1 Hz, 1H), 4.55 (ddd, J=8.6, 7.3, 5.8 Hz, 1H), 4.43 (dt, J=9.1, 6.0 Hz, 1H), 3.87 (s, 3H), 3.67-3.61 (m, 2H), 2.67 (dddd, J=11.1, 8.6, 7.7, 6.2 Hz, 1H), 2.57-2.47 (m, 1H).

Step 7. Synthesis of methyl 2-(chloromethyl)-1-[(2S)-oxetan-2-ylmethyl]-1H-benzimidazole-6-carboxylate (P15)

A solution of C30 (from the previous step; 51.8 kg, 190 mol) in tetrahydrofuran (678 kg), in a 3000 L autoclave reactor, was treated with 10% palladium on carbon (5.2 kg) at 10° C. to 30° C. The addition pipe was rinsed with tetrahydrofuran (46 kg) and the rinse was added to the reaction mixture. After the reactor contents had been purged with nitrogen, they were similarly purged with hydrogen, increasing the pressure to 0.1 to 0.2 MPa and then venting to 0.02 to 0.05 MPa. This hydrogen purge was repeated 5 times, whereupon the hydrogen pressure was increased to 0.1 to 0.25 MPa. The reaction mixture was stirred at 20° C. to 30° C., and every 2 to 3 hours, the mixture was purged with nitrogen three times, and then purged with hydrogen five times; after each final hydrogen exchange, the hydrogen pressure was increased to 0.1 to 0.25 MPa. After 11.25 hours total reaction time, the reaction mixture was vented to normal pressure, and purged five times with nitrogen, via increasing the pressure to 0.15 to 0.2 MPa and then venting to 0.05 MPa. It was then filtered, and the filter cake was rinsed twice with tetrahydrofuran (64 kg and 63 kg); the combined rinse and filtrate were concentrated under reduced pressure (≤−0.08 MPa) and 540° C. to a volume of 128 to 160 L. Tetrahydrofuran (169 kg) was added, and the mixture was again concentrated to a volume of 128 to 160 L; this process was repeated a total of 4 times, affording a solution of the intermediate methyl 4-amino-3-{[(2S)-oxetan-2-ylmethyl]amino}benzoate.

Tetrahydrofuran (150 kg) was added to this solution, followed by 2-chloro-1,1,1-trimethoxyethane (35.1 kg, 227 mol) and p-toluenesulfonic acid monohydrate (1.8 kg, 9.5 mol). After the reaction mixture had been stirred for 25 minutes, it was heated at 40° C. to 45° C. for 5 hours, whereupon it was concentrated under reduced pressure to a volume of 135 to 181 L. 2-Propanol (142 kg) was added, and the mixture was again concentrated to a volume of 135 to 181 L, whereupon 2-propanol (36.5 kg) and purified water (90 kg) were added, and stirring was continued until a solution was obtained. This was filtered with an in-line liquid filter, and then treated with purified water (447 kg) at a reference rate of 150 to 400 kg/hour at 20° C. to 40° C. After the mixture had been cooled to 20° C. to 30° C., it was stirred for 2 hours, and the solid was collected via filtration with a centrifuge. The filter cake was rinsed with a solution of 2-propanol (20.5 kg) and purified water (154 kg); after drying, P15 was obtained as a white solid (32.1 kg, 109 mol, 57%). $^{1}H$ NMR (400 MHz, chloroform-d) δ 8.14-8.11 (m, 1H), 8.01 (dd, J=8.5, 1.1 Hz, 1H), 7.79 (br d, J=8.6 Hz, 1H), 5.26-5.18 (m, 1H), 5.04 (s, 2H), 4.66-4.58 (m, 2H), 4.53 (dd, component of ABX pattern, J=15.7, 2.7 Hz, 1H), 4.34 (dt, J=9.1, 6.0 Hz, 1H), 3.96 (s, 3H), 2.82-2.71 (m, 1H), 2.48-2.37 (m, 1H).

Preparation P16

Methyl 2-(chloromethyl)-1-methyl-1H-benzimidazole-6-carboxylate (P16)

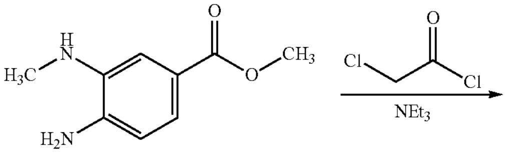

-continued

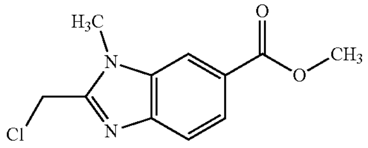

P16

Methyl 4-amino-3-(methylamino)benzoate (206 mg, 1.14 mmol) was dissolved in 1,4-dioxane (11.5 mL) and treated with chloroacetyl chloride (109 μL, 1.37 mmol). The mixture was stirred at 100° C. for 3 hours and cooled to room temperature. Triethylamine (0.8 mL, 7 mmol) and heptane (10 mL) were added and filtered. The filtrate was concentrated under reduced pressure and the crude material was purified by chromatography on silica gel (Eluent: 40% ethyl acetate in heptane) to afford 120 mg of P16 (44%). $^{1}H$ NMR (400 MHz, chloroform-d) δ 8.14 (s, 1H), 8.01 (d, 1H), 7.78 (d, 1H), 4.87 (s, 2H), 3.97 (s, 3H), 3.94 (s, 3H); LCMS m/z 239.1 $[M+H]^+$.

Preparations P17 and P18

Methyl 2-(6-azaspiro[2.5]oct-1-yl)-1-(2-methoxyethyl)-1H-benzimidazole-6-carboxylate, ENT-1 (P17) and Methyl 2-(6-azaspiro[2.5]oct-1-yl)-1-(2-methoxyethyl)-1H-benzimidazole-6-carboxylate, ENT-2 (P18)

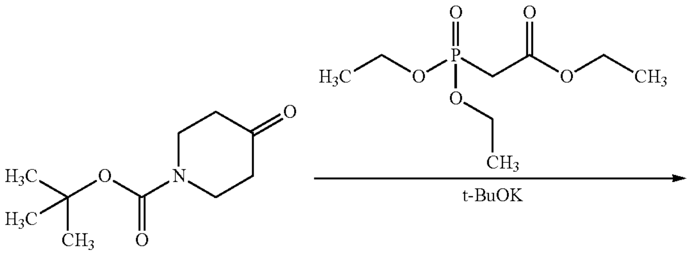

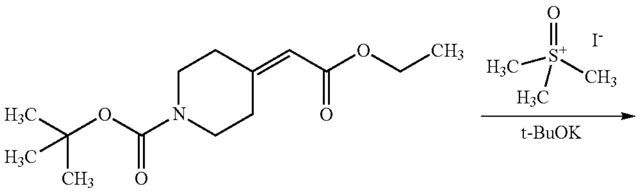

C31

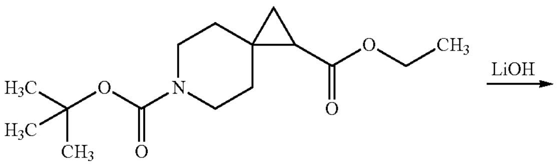

C32

-continued
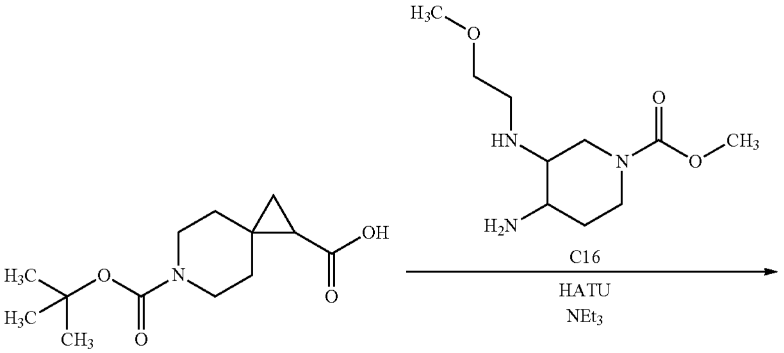
C33
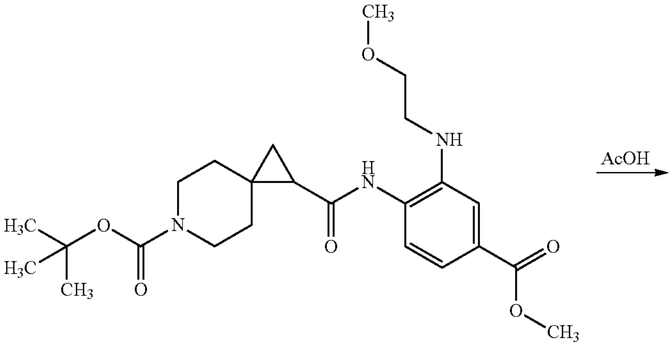
C34
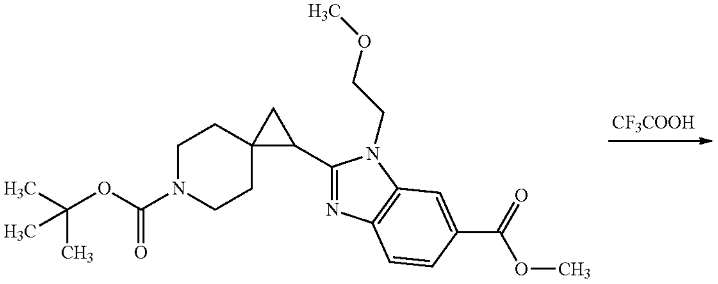
C35
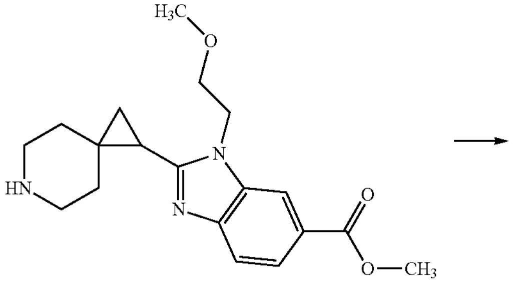
C36
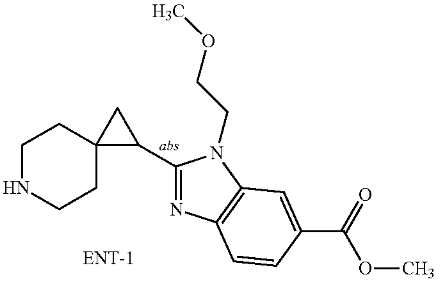
ENT-1
P17
+
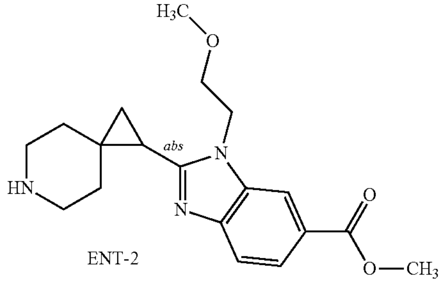
ENT-2
P18

Step 1. Synthesis of tert-butyl 4-(2-ethoxy-2-oxo-ethylidene)piperidine-1-carboxylate (C31)

A solution of potassium tert-butoxide (65.9 g, 587 mmol) in tetrahydrofuran (500 mL) was added to a 0° C. solution of ethyl (diethoxyphosphoryl)acetate (132 g, 589 mmol) in tetrahydrofuran (500 mL), and the resulting suspension was stirred at 0° C. for 1 hour, whereupon it was cooled to −50° C. A solution of tert-butyl 4-oxopiperidine-1-carboxylate (90.0 g, 452 mmol) in tetrahydrofuran (1.5 L) was added drop-wise at −50° C., and the reaction mixture was subsequently allowed to slowly warm to 20° C., and then to stir for 16 hours at 20° C. After addition of water (1 L), the mixture was concentrated in vacuo to remove tetrahydrofuran. The aqueous residue was extracted with ethyl acetate (2×800 mL), and the combined organic layers were washed with saturated aqueous sodium chloride solution (500 mL), dried over sodium sulfate, filtered, and concentrated under reduced pressure. The resulting material was washed several times with petroleum ether (200 mL) to provide C31 as a white solid. Yield: 95.0 g, 353 mmol, 78%. $^1$H NMR (400 MHz, chloroform-d) δ 5.71 (s, 1H), 4.16 (q, J=7.2 Hz, 2H), 3.55-3.43 (m, 4H), 2.94 (br t, J=5.5 Hz, 2H), 2.28 (br t, J=5.5 Hz, 2H), 1.47 (s, 9H), 1.28 (t, J=7.0 Hz, 3H).

Step 2. Synthesis of 6-tert-butyl 1-ethyl 6-azaspiro[2.5]octane-1, 6-dicarboxylate (C32)

To a solution of trimethylsulfoxonium iodide (140 g, 636 mmol) in dimethyl sulfoxide (800 mL) was added potassium tert-butoxide (71.2 g, 634 mmol) in one portion at 20° C. After the reaction mixture had been stirred at 20° C. for 1.5 hours, a solution of C31 (95.0 g, 353 mmol) in dimethyl sulfoxide (800 mL) was added drop-wise, and stirring was continued at 20° C. for 16 hours. Saturated aqueous sodium chloride solution (2.0 L) was then added; the resulting mixture was neutralized by addition of ammonium chloride, and extracted with ethyl acetate (3.0 L). The combined organic layers were washed sequentially with water (2×1.0 L) and with saturated aqueous sodium chloride solution (2.0 L), dried over sodium sulfate, filtered, and concentrated in vacuo. Purification via silica gel chromatography (Eluent: 10:1 petroleum ether/ethyl acetate) afforded C32 as a yellow oil. $^1$H NMR analysis indicated that extraneous aliphatic material was present. Yield: 80 g, 280 mmol, 79%. $^1$H NMR (400 MHz, chloroform-d), C32 peaks only: δ 4.19-4.09 (m, 2H), 3.55-3.39 (m, 3H), 3.27 (ddd, J=13.0, 7.0, 4.5 Hz, 1H), 1.76-1.64 (m, 2H), 1.56 (dd, J=8.0, 5.5 Hz, 1H, assumed; partially obscured by water peak), 1.47 (s, 9H), 1.47-1.37 (m, 2H), 1.27 (t, J=7.0 Hz, 3H), 1.17 (dd, J=5.0, 5.0 Hz, 1H), 0.93 (dd, J=8.0, 4.5 Hz, 1H).

Step 3. Synthesis of 6-(tert-butoxycarbonyl)-6-azaspiro[2.5]octane-1-carboxylic acid (C33)

To a mixture of C32 (80 g, 280 mmol) in tetrahydrofuran (500 mL) and water (500 mL) was added lithium hydroxide monohydrate (37.4 g, 891 mmol) in one portion. The reaction mixture was stirred at 25° C. for 16 hours, whereupon it was diluted with water (600 mL) and washed with ethyl acetate (3×300 mL). The organic layers were discarded, and the aqueous layer was acidified to pH 3 to 4 by addition of 6 M hydrochloric acid. The resulting mixture was extracted with ethyl acetate (3×600 mL), and the combined organic layers were dried over sodium sulfate, filtered, and concentrated in vacuo. Trituration of the residue with petroleum ether (300 mL) provided C33 as a white solid. Yield: 42.0 g, 164 mmol, 59%. LCMS m/z 278.2 [M+Na$^+$]. $^1$H NMR (400 MHz, DMSO-$d_6$) δ 12.15-12.03 (br s, 1H), 3.43-3.25 (m, 3H, assumed; partially obscured by water peak), 3.23-3.12 (m, 1H), 1.64-1.50 (m, 2H), 1.52 (dd, J=7.5, 5.5 Hz, 1H), 1.39 (s, 9H), 1.39-1.28 (m, 2H), 0.96-0.88 (m, 2H).

Step 4. Synthesis of tert-butyl 1-({4-(methoxycarbonyl)-2-[(2-methoxyethyl) amino] phenyl}carbamoyl)-6-azaspiro[2.5]octane-6-carboxylate (C34)

A solution of C33 (570 mg, 2.23 mmol), C16 (500 mg, 2.23 mmol), and O-(7-azabenzotriazol-1-yl)-N,N,N',N'-tetramethyluronium hexafluorophosphate (HATU; 1.27 g, 3.34 mmol) in N,N-dimethylformamide (10 mL) was stirred at 30° C. for 30 minutes, whereupon triethylamine (902 mg, 8.91 mmol) was added, and stirring was continued at 30° C. for 16 hours. The reaction mixture was then poured into water (60 mL) and extracted with ethyl acetate (3×50 mL). The combined organic layers were washed with saturated aqueous sodium chloride solution (3×50 mL), dried over sodium sulfate, filtered, and concentrated in vacuo. Silica gel chromatography (Eluent: 1:1 petroleum ether/ethyl acetate) afforded C34 as a brown oil, which was taken directly into the following step.

Step 5. Synthesis of methyl 2-[6-(tert-butoxycarbonyl)-6-azaspiro[2.5]oct-1-yl]-1-(2-methoxyethyl)-1H-benzimidazole-6-carboxylate (C35)

A solution of C34 (from the previous step, 52.23 mmol) in acetic acid (15 mL) was stirred at 50° C. for 16 hours, whereupon it was concentrated in vacuo to provide C35 as a brown oil. This material was used directly in the next step. LCMS m/z 444.1 [M+H]$^+$.

Step 6. Synthesis of methyl 2-(6-azaspiro[2.5]oct-1-yl)-1-(2-methoxyethyl)-1H-benzimidazole-6-carboxylate (C36)

Trifluoroacetic acid (5 mL) was added to a solution of C35 (from the previous step; 52.23 mmol) in dichloromethane (10 mL), and the reaction mixture was stirred at 25° C. for 2 hours. After removal of solvents in vacuo, the residue was basified via addition of saturated aqueous potassium carbonate solution (40 mL), and extracted with a mixture of dichloromethane and methanol (10:1, 3×40 mL). The combined organic layers were dried over magnesium sulfate, filtered, concentrated in vacuo, and subjected to silica gel chromatography (Eluent: 10:1:0.1 dichloromethane/methanol/concentrated ammonium hydroxide) to afford C36 as a yellow solid. Yield: 640 mg, 1.86 mmol, 83% over three steps. LCMS m/z 344.1 [M+H]$^+$.

Step 7. Isolation of methyl 2-(6-azaspiro[2.5]oct-1-yl)-1-(2-methoxyethyl)-1H-benzimidazole-6-carboxylate, ENT-1 (P17) and methyl 2-(6-azaspiro [2.5]oct-1-yl)-1-(2-methoxyethyl)-1H-benzimidazole-6-carboxylate, ENT-2 (P18)

Separation of C36 (630 mg, 1.83 mmol) into its component enantiomers was carried out using SFC [Column: Chiral Technologies Chiralpak AD, 10 μm; Mobile phase: 55:45 carbon dioxide/(ethanol containing 0.1% ammonium hydroxide)]. The first-eluting peak was designated as ENT-1 (P17), and the second-eluting enantiomer as ENT-2 (P18); both were isolated as pale yellow solids.

P17 Yield: 300 mg, 0.874 mmol, 48%. LCMS m/z 344.1 $[M+H]^+$. Retention time: 5.10 minutes (Column: Chiral Technologies Chiralpak AD-3, 4.6×150 mm, 3 μm; Mobile phase A: carbon dioxide; Mobile phase B: ethanol containing 0.05% diethylamine; Gradient: 5% to 40% B over 5.5 minutes, then held at 40% B for 3.0 minutes; Flow rate: 2.5 mL/minute).

P18 Yield: 240 mg, 0.699 mmol, 38%. LCMS m/z 344.1 $[M+H]^+$. Retention time: 7.35 minutes (Analytical conditions identical to those used for P17).

Preparation P19

Methyl 4-amino-3-{[(1-ethyl-1H-imidazol-5-yl) methyl]amino}benzoate (P19)

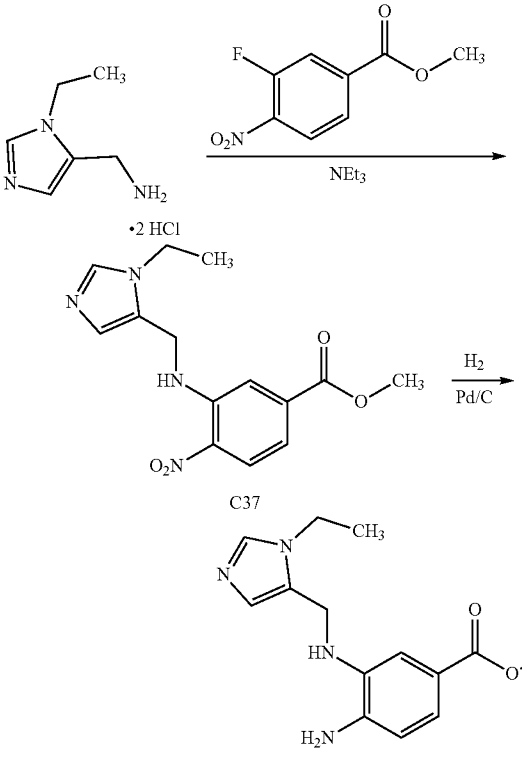

C37

P19

Step 1. Synthesis of methyl 3-{[(1-ethyl-1H-imidazol-5-yl)methyl]amino}-4-nitrobenzoate (C37)

Triethylamine (3.65 mL, 26.2 mmol) was added to a solution of methyl 3-fluoro-4-nitrobenzoate (1.00 g, 5.02 mmol) and 1-(1-ethyl-1H-imidazol-5-yl)methanamine, dihydrochloride salt (1.00 g, 5.05 mmol) in a mixture of tetrahydrofuran (12 mL) and methanol (8 mL). The reaction mixture was stirred at 60° C. for 40 hours, whereupon it was concentrated in vacuo and purified using silica gel chromatography (Gradient: 0% to 2% methanol in dichloromethane) to afford C37 as an orange solid. Yield: 1.27 g, 4.17 mmol, 83%. $^1$H NMR (400 MHz, chloroform-d) δ 8.24 (d, J=8.8 Hz, 1H), 7.98-7.91 (m, 1H), 7.68 (d, J=1.7 Hz, 1H), 7.57 (br s, 1H), 7.33 (dd, J=8.8, 1.7 Hz, 1H), 7.11 (br s, 1H), 4.53 (d, J=4.9 Hz, 2H), 3.99 (q, J=7.3 Hz, 2H), 3.95 (s, 3H), 1.47 (t, J=7.3 Hz, 3H).

Step 2. Synthesis of methyl 4-amino-3-{[(I-ethyl-1H-imidazol-5-yl)methyl]amino}benzoate (P19)

A mixture of wet palladium on carbon (144 mg) and C37 (412 mg, 1.35 mmol) in methanol (13 mL) was stirred under a balloon of hydrogen for 16 hours at 25° C. The reaction mixture was then filtered through a pad of diatomaceous earth and the filtrate was concentrated in vacuo to afford P19 as a gray solid. Yield: 340 mg, 1.24 mmol, 92%. $^1$H NMR (400 MHz, methanol-$d_4$) δ 7.66 (br s, 1H), 7.38-7.29 (m, 2H), 6.97 (br s, 1H), 6.67 (d, J=7.9 Hz, 1H), 4.35 (s, 2H), 4.11 (q, J=7.3 Hz, 2H), 3.81 (s, 3H), 1.44 (t, J=7.3 Hz, 3H).

Preparation P20

Methyl 4-amino-3-(methylamino)benzoate (P20)

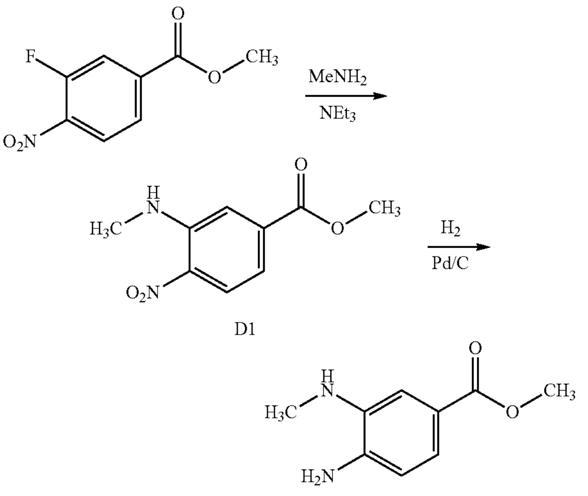

D1

P20

Step 1. Synthesis of methyl 3-(methylamino)-4-nitrobenzoate (D1)

To a solution of methyl 3-fluoro-4-nitrobenzoate (5.10 g, 25.6 mmol) in tetrahydrofuran (60 mL) was added methylamine (38.4 mL, 76.8 mmol, 2 M in tetrahydrofuran), drop-wise, over 10 minutes. The pale yellow solution turned deep orange immediately upon addition and was stirred for 2 hours at room temperature. The reaction mixture was then diluted with diethyl ether (100 mL) and the organic layer was washed sequentially with water (50 mL) and saturated aqueous sodium chloride solution (50 mL). The organic layer was dried over sodium sulfate, filtered, and concentrated under reduced pressure to yield 5.26 g of methyl 3-(methylamino)-4-nitrobenzoate (98%) as a deep orange solid. LCMS m/z 211.1 $[M+H]^+$. $^1$H NMR (400 MHz, chloroform-d) δ 8.22 (d, J=8.9 Hz, 1H), 8.00 (br s, 1H), 7.56 (d, J=1.7 Hz, 1H), 7.25 (dd, J=8.9, 1.7 Hz, 1H, assumed; partially obscured by solvent peak), 3.95 (s, 3H), 3.09 (d, J=5.1 Hz, 3H).

Step 2. Synthesis of methyl 4-amino-3-(methylamino)benzoate (P20)

A solution of D1 (5.26 g, 25.0 mmol) in ethanol (150 mL) was added to a 500 mL Parr® bottle previously charged with 10% palladium on carbon (50% water; 1 g). The mixture was shaken under 50 psi hydrogen atmosphere for 1 hour at room temperature, whereupon it was filtered and the filter cake was rinsed with ethanol (100 mL). The filtrate was concentrated under reduced pressure to yield 4.38 g of P20 (97%) as an off-white solid. LCMS m/z 181.1 $[M+H]^+$. $^1H$ NMR (400 MHz, chloroform-d) δ 7.46 (dd, J=8.0, 1.9 Hz, 1H), 7.34 (d, J=1.8 Hz, 1H), 6.68 (d, J=8.0 Hz, 1H), 3.87 (s, 3H), 3.72 (br s, 2H), 3.21 (br s, 1H), 2.91 (s, 3H).

Preparations P21 and P22

5-Bromo-$N^3$-methylpyridine-2, 3-diamine (P21) and 5-Bromo-$N^3$, 6-dimethylpyridine-2, 3-diamine (P22)

P21

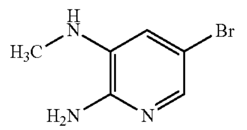

P22

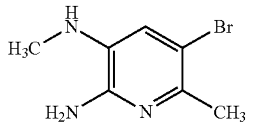

Intermediate P21 was synthesized according to the literature procedure (Choi, J. Y. et al. *J. Med. Chem.* 2012, 55, 852-870). Intermediate P22 was synthesized using the same method.

Preparation P23

Methyl 2-(chloromethyl)-1-[(1-methyl-1H-imidazol-5-yl)methyl]-1H-benzimidazole-6-carboxylate (P23)

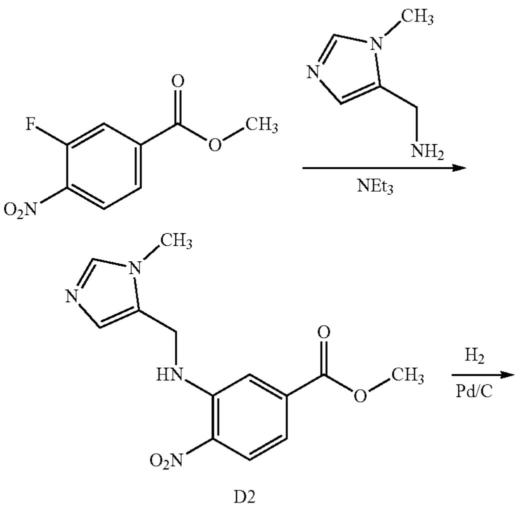

D2

-continued

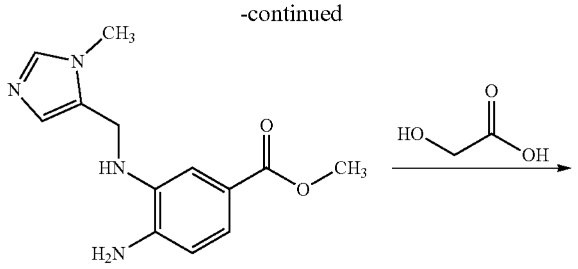

D3

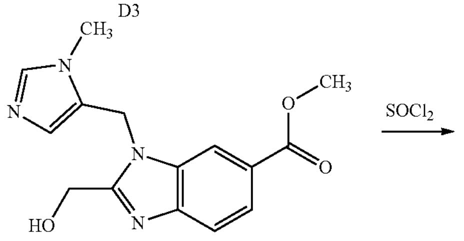

D4

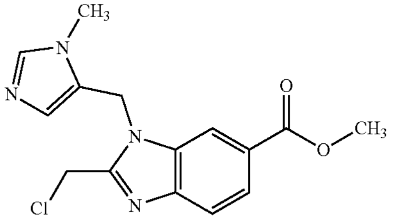

P23

Step 1. Synthesis of methyl 3-{[(1-methyl-1H-imidazol-5-yl)methyl]amino}-4-nitrobenzoate (D2)

To a colorless solution of methyl 3-fluoro-4-nitrobenzoate (1.0 g, 5.0 mmol) in N,N-dimethylformamide (10 mL) was slowly added 1-(1-methyl-1H-imidazol-5-yl)methanamine (670 mg, 6.0 mmol) and triethylamine (762 mg, 7.53 mmol). The reaction mixture was stirred at 60° C. for 16 hours, whereupon it was poured into water (30 mL) and extracted with dichloromethane (3x30 mL). The combined organic layers were dried over sodium sulfate, filtered, and concentrated under reduced pressure. The crude material was purified by silica gel chromatography (Eluent: 20% methanol in dichloromethane). The obtained yellow solid was triturated with 30:1 petroleum ether/ethyl acetate to deliver D2 (1.2 g, 82%) as a yellow solid. LCMS m/z 290.9 $[M+H]^+$. $^1H$ NMR (400 MHz, chloroform-d) δ 8.25 (d, J=8.9 Hz, 1H), 7.98-7.92 (m, 1H), 7.70 (d, J=1.7 Hz, 1H), 7.49 (s, 1H), 7.34 (dd, J=8.9, 1.7 Hz, 1H), 7.12 (s, 1H), 4.54 (d, J=5.0 Hz, 2H), 3.96 (s, 3H), 3.67 (s, 3H).

Step 2. Synthesis of methyl 4-amino-3-{[(1-methyl-1H-imidazol-5-yl)methyl]amino}benzoate (D3)

To a suspension of D2 (5.46 g, 18.8 mmol) in methanol (160 mL) was added wet 10% palladium on carbon (1 g). The mixture was stirred under 1 atmosphere of hydrogen for 36 hours at 20° C. The reaction mixture was filtered and the filter cake was rinsed with methanol (200 mL). The filtrate was concentrated under reduced pressure to deliver D3 (4.8 g, 98%) as a brown solid. LCMS m/z 260.9 $[M+H]^+$. $^1H$ NMR (400 MHz, DMSO-$d_6$) δ 7.56 (s, 1H), 7.18 (br d, J=8.1 Hz, 1H), 7.12 (br s, 1H), 6.87 (s, 1H), 6.55 (d, J=8.2 Hz, 1H), 5.50 (s, 2H), 4.84 (t, J=5.2 Hz, 1H), 4.23 (d, J=5.0 Hz, 2H), 3.73 (s, 3H), 3.63 (s, 3H).

Step 3. Synthesis of methyl 2-(hydroxymethyl)-1-[(1-methyl-1H-imidazol-5-yl)methyl]-1H-benzimidazole-6-carboxylate (D4)

A mixture of D3 (780 mg, 3.00 mmol) and 2-hydroxyacetic acid (342 mg, 4.49 mmol) in 1,3,5-trimethylbenzene (8 mL) was stirred at 140° C. for 14 hours and at 25° C. for 48 hours. The clear yellow solution was decanted off to give a brown residue that was dissolved in methanol (50 mL) and concentrated under reduced pressure. The crude material was purified by silica gel chromatography (Eluent: 20% methanol in dichloromethane) to provide D4 (318 mg, 35%) as a yellow foam. LCMS m/z 300.9 $[M+H]^+$. $^1H$ NMR (400 MHz, DMSO-$d_6$) δ 8.13-8.11 (m, 1H), 7.83 (dd, J=8.4, 1.6 Hz, 1H), 7.71 (d, J=8.5 Hz, 1H), 7.59 (s, 1H), 6.58 (s, 1H), 5.69 (s, 2H), 4.75 (s, 2H), 3.84 (s, 3H), 3.53 (s, 3H).

Step 4. Synthesis of methyl 2-(chloromethyl)-1-[(1-methyl-1H-imidazol-5-yl)methyl]-1H-benzimidazole-6-carboxylate (P23)

To a suspension of D4 (500 mg, 1.66 mmol) in dichloromethane (10 mL) and N,N-dimethylformamide (3 mL) was added thionyl chloride (990 mg, 0.60 mL, 8.32 mmol), drop-wise, at room temperature. The reaction mixture was stirred at room temperature for 1 hour, then concentrated under reduced pressure. The resultant brown residue was triturated with dichloromethane (10 mL). The solids were collected by filtration and rinsed with dichloromethane (5 mL) to provide P23 (431 mg, 73%) as an off-white solid. LCMS m/z 318.9♦ $[M+H]^+$. $^1H$ NMR (400 MHz, DMSO-$d_6$) δ 9.17 (s, 1H), 8.31 (s, 1H), 7.93 (br d, J=8.5 Hz, 1H), 7.82 (d, J=8.5 Hz, 1H), 7.11 (s, 1H), 5.92 (s, 2H), 5.13 (s, 2H), 3.87 (s, 3H), 3.87 (s, 3H).

Preparation P24

5-Chloro-2-(chloromethyl)-3-methyl-3H-imidazo[4,5-b]pyridine (P24)

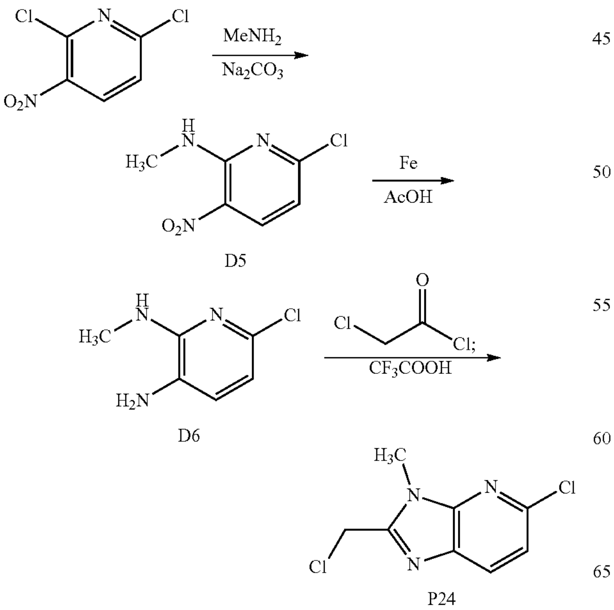

D5

D6

P24

Step 1. Synthesis of 6-chloro-N-methyl-3-nitropyridin-2-amine (D5)

To a suspension of 2,6-dichloro-3-nitropyridine (200 g, 1.04 mol) and $Na_2CO_3$ (132 g, 1.24 mol) in ethanol (1 L) was added a solution of methylamine in tetrahydrofuran (2.0 M; 622 mL, 1.24 mol), drop-wise, at 0° C. via syringe. After completion of the addition, the reaction mixture was stirred at 18° C. for 6 hours. The mixture was filtered and the filtrate was concentrated under reduced pressure to give a yellow solid. The crude material was purified by silica gel chromatography (Gradient: 0% to 5% ethyl acetate in petroleum ether) to afford D5 (158 g, 81% yield) as a yellow solid. $^1H$ NMR (400 MHz, DMSO-$d_6$) δ 8.72 (br s, 1H), 8.41 (d, J=8.6 Hz, 1H), 6.76 (d, J=8.6 Hz, 1H), 3.00 (d, J=4.8 Hz, 3H).

Step 2. Synthesis of 6-chloro-$N^2$-methylpyridine-2,3-diamine (D6)

To a mixture of D5 (15.8 g, 84.2 mmol) in acetic acid (100 mL) was added iron powder (15.4 g, 276 mmol). The reaction mixture was stirred at 80° C. for 3 hours, whereupon it was cooled to room temperature and filtered. The filter cake was washed with ethyl acetate (2×100). The combined organic layers were concentrated under reduced pressure and the crude material was purified by silica gel chromatography (Eluent: 1:1 ethyl acetate/petroleum ether) to afford D6 (8.40 g, 63% yield) as a brown solid. $^1H$ NMR (400 MHz, chloroform-d) δ 6.79 (d, J=7.7 Hz, 1H), 6.49 (d, J=7.7 Hz, 1H), 3.00 (s, 3H).

Step 3. Synthesis of 5-chloro-2-(chloromethyl)-3-methyl-3H-imidazo[4,5-b]pyridine (P24)

To a solution of D6 (50.0 g, 317 mmol) in 1,4-dioxane (1.2 L) was added chloroacetyl chloride (55.5 mL, 698 mmol) and the reaction mixture was stirred at 15° C. for 50 minutes. It was then concentrated under reduced pressure to give a brown solid, which was taken up in trifluoroacetic acid (1.2 L) and stirred at 80° C. for 60 hours. The mixture was concentrated under reduced pressure to give a brown oil, which was diluted with ethyl acetate (1 L) and neutralized by addition of saturated aqueous sodium bicarbonate solution. When carbon dioxide evolution subsided, the layers were separated, and the aqueous layer was extracted with ethyl acetate (200 mL). The organic extracts were combined, dried over sodium sulfate, filtered, and concentrated under reduced pressure. The crude material was purified by silica gel chromatography (Gradient: 10% to 25% ethyl acetate in petroleum ether) to afford P24 (61.0 g, 79% yield) as a yellow solid. LCMS m/z 215.7 (dichloro isotope pattern observed) $[M+H]^+$. $^1H$ NMR (400 MHz, DMSO-$d_6$) 8.13 (d, J=8.3 Hz, 1H), 7.37 (d, J=8.4 Hz, 1H), 5.11 (s, 2H), 3.84 (s, 3H).

Examples 1 and 2

2-({4-[2-(4-Chloro-2-Fluorophenyl)-1,3-Benzodioxol-4-Yl]Piperazin-1-Yl}Methyl)-1-(2-Methoxyethyl)-1H-Benzimidazole-6-Carboxylic Acid, ENT-X1, Trifluoroacetate Salt (1) [from C39]; And 2-({4-[2-(4-Chloro-2-Fluorophenyl)-1,3-Benzodioxol-4-Yl]Piperazin-1-Yl}Methyl)-1-(2-Methoxyethyl)-1H-Benzimidazole-6-Carboxylic Acid, ENT-X2, Trifluoroacetate Salt (2) [from C40]

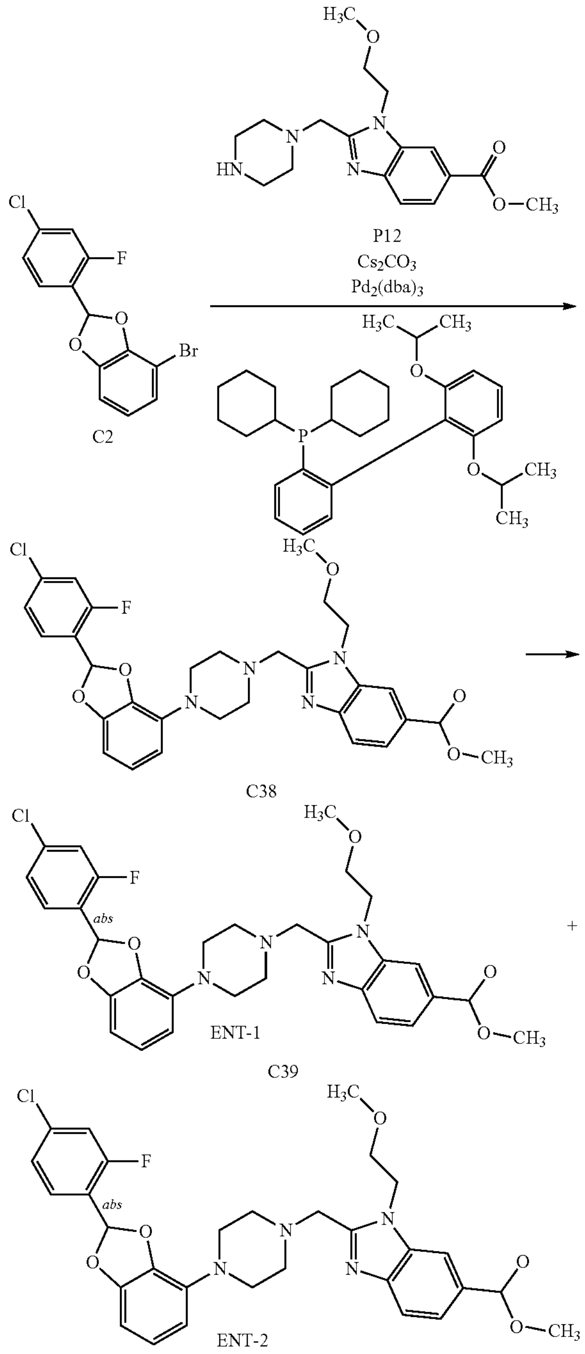

C2

C38

ENT-1

C39

\+

ENT-2

C40

-continued

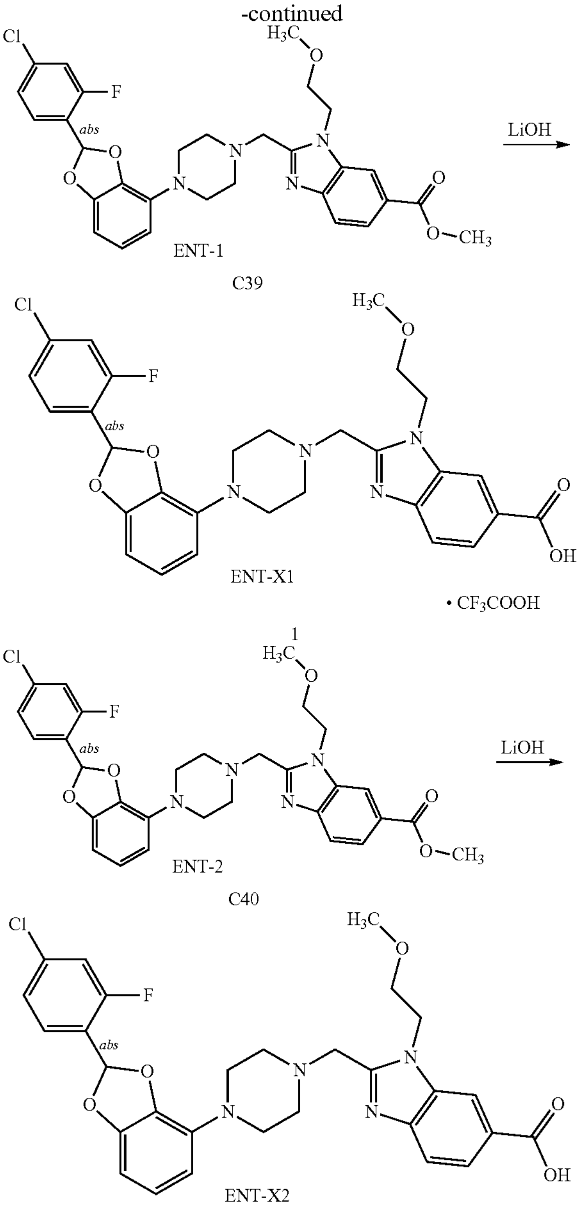

ENT-1

C39

ENT-X1

• $CF_3COOH$

ENT-2

C40

ENT-X2

• $CF_3COOH$

2

Step 1. Synthesis of methyl 2-({4-[2-(4-chloro-2-fluorophenyl)-1,3-benzodioxol-4-yl]piperazin-1-yl}methyl)-1-(2-methoxyethyl)-1H-benzimidazole-6-carboxylate (C38)

This experiment was carried out in two batches of identical scale. A reaction vessel containing a mixture of C2 (500 mg, 1.52 mmol), P12 (530 mg, 1.59 mmol), [2',6'-bis(propan-2-yloxy)biphenyl-2-yl](dicyclohexyl)phosphane (Ruphos; 142 mg, 0.304 mmol), tris(dibenzylideneacetone)dipalladium(0) (139 mg, 0.152 mmol), and cesium carbonate (1.48 g, 4.54 mmol) in toluene (15 mL) was evacuated and charged with nitrogen. This evacuation cycle was repeated twice, whereupon the reaction mixture was stirred at 100° C. for 16 hours, combined with the second batch, and filtered. The filtrate was concentrated, and the residue was subjected to silica gel chromatography (Gradient: 0% to 60% ethyl acetate in petroleum ether) followed by preparative thin-layer chromatography (Eluent: 1:1 petroleum ether/ethyl acetate) to afford C38 as a pale yellow solid. Combined yield: 600 mg, 1.03 mmol, 34%. LCMS m/z 581.0♦ $[M+H]^+$.

Step 2. Isolation of methyl 2-({4-[2-(4-chloro-2-fluorophenyl)-1,3-benzodioxol-4-yl]piperazin-1-yl}methyl)-1-(2-methoxyethyl)-1H-benzimidazole-6-carboxylate, ENT-1 (C39) and methyl 2-({4-[2-(4-chloro-2-fluorophenyl)-1,3-benzodioxol-4-yl]piperazin-1-yl}methyl)-1-(2-methoxyethyl)-1H-benzimidazole-6-carboxylate, ENT-2 (C40)

Separation of C38 (780 mg, 1.34 mmol) into its component enantiomers was effected using SFC [Column: Chiral Technologies Chiralpak AD, 10 μm; Mobile phase: 3:2 carbon dioxide/(ethanol containing 0.1% ammonium hydroxide)]. The first-eluting enantiomer, designated as ENT-1 (C39), was obtained as a white solid. Yield: 282 mg, 0.485 mmol, 36%. LCMS m/z 581.0♦ $[M+H]^+$. Retention time 1.90 minutes (Column: Chiral Technologies Chiralpak AD-3, 4.6×50 mm, 3 μm; Mobile phase A: carbon dioxide; Mobile phase B: ethanol containing 0.05% diethylamine; Gradient: 5% B for 0.20 minutes, then 5% to 40% B over 1.4 minutes, then held at 40% B for 1.05 minutes; Flow rate: 4.0 mL/minute).

The second-eluting enantiomer, designated as ENT-2, (C40), was subjected to a second purification using SFC [Column: Chiral Technologies Chiralpak AD, 10 μm; Mobile phase: 3:2 carbon dioxide/(ethanol containing 0.1% ammonium hydroxide)]. This provided C40 as a pale brown solid. Yield: 280 mg, 0.482 mmol, 36%. LCMS m/z 581.0♦ $[M+H]^+$. Retention time 2.18 minutes (Analytical conditions identical to those used for C39).

Step 3. Synthesis of 2-({4-[2-(4-chloro-2-fluorophenyl)-1,3-benzodioxol-4-yl]piperazin-1-yl}methyl)-1-(2-methoxyethyl)-1H-benzimidazole-6-carboxylic acid, ENT-X1, trifluoroacetate salt (1) [from C39]

Aqueous lithium hydroxide solution (2 M; 0.30 mL, 0.60 mmol) was added to a solution of C39 (70 mg, 0.12 mmol) in a mixture of methanol (3 mL) and tetrahydrofuran (3 mL). After the reaction mixture had been stirred at 25° C. for 16 hours, aqueous lithium hydroxide solution (2 M; 0.30 mL, 0.60 mmol) was again added, and stirring was continued for an additional 20 hours. The reaction mixture was then adjusted to pH 7 via addition of 1 M hydrochloric acid, and subsequently concentrated in vacuo to remove methanol and tetrahydrofuran. The residue was adjusted to a pH of 5 to 6 by addition of trifluoroacetic acid and then purified via reversed-phase HPLC (Column: Agela Durashell C18, 5 μm; Mobile phase A: 0.1% trifluoroacetic acid in water; Mobile phase B: acetonitrile; Gradient: 30% to 60% B) to afford 1 as a white solid. Yield: 40.5 mg, 59.5 μmol, 50%. LCMS m/z 567.0♦ $[M+H]^+$. $^1H$ NMR (400 MHz, methanol-$d_4$) δ 8.37 (br s, 1H), 8.07 (dd, J=8.5, 1.5 Hz, 1H), 7.79 (d, J=8.6 Hz, 1H), 7.59 (dd, J=8.0, 8.0 Hz, 1H), 7.34 (dd, J=10.2, 2.0 Hz, 1H), 7.30 (br dd, J=8.3, 2.0 Hz, 1H), 7.22 (s, 1H), 6.87 (dd, J=8.1, 8.1 Hz, 1H), 6.63 (br d, J=8 Hz, 1H), 6.60 (br d, J=8 Hz, 1H), 4.70 (s, 2H), 4.65 (t, J=4.8 Hz, 2H), 3.75 (t, J=4.8 Hz, 2H), 3.59-3.42 (m, 8H), 3.29 (s, 3H).

Step 4. Synthesis of 2-({4-[2-(4-chloro-2-fluorophenyl)-1,3-benzodioxol-4-yl]piperazin-1-yl}methyl)-1-(2-methoxyethyl)-1H-benzimidazole-6-carboxylic acid, ENT-X2, trifluoroacetate salt (2) [from C40]

Aqueous lithium hydroxide solution (2 M; 0.30 mL, 0.60 mmol) was added to a solution of C40 (69 mg, 0.12 mmol) in a mixture of methanol (3 mL) and tetrahydrofuran (3 mL). After the reaction mixture had been stirred at 25° C. for 16 hours, aqueous lithium hydroxide solution (2 M; 0.30 mL, 0.60 mmol) was again added, and stirring was continued for an additional 20 hours. The reaction mixture was adjusted to pH 7 via addition of 1 M hydrochloric acid, and then concentrated in vacuo to remove methanol and tetrahydrofuran. The residue was adjusted to a pH of 5 to 6 by addition of trifluoroacetic acid and subsequently purified via reversed-phase HPLC (Column: Agela Durashell C18, 5 μm; Mobile phase A: 0.1% trifluoroacetic acid in water; Mobile phase B: acetonitrile; Gradient: 30% to 60% B) to afford 2 as a white solid. Yield: 22.9 mg, 33.6 μmol, 28%. LCMS m/z 567.0♦ $[M+H]^+$. $^1H$ NMR (400 MHz, methanol-$d_4$) δ 8.40-8.35 (m, 1H), 8.07 (dd, J=8.6, 1.5 Hz, 1H), 7.79 (d, J=8.6 Hz, 1H), 7.59 (dd, J=8.0, 8.0 Hz, 1H), 7.35 (dd, J=10.2, 2.0 Hz, 1H), 7.31 (br dd, J=8, 2 Hz, 1H), 7.22 (s, 1H), 6.87 (dd, J=8.3, 8.0 Hz, 1H), 6.63 (br d, J=8 Hz, 1H), 6.60 (br d, J=8 Hz, 1H), 4.68 (s, 2H), 4.65 (t, J=4.9 Hz, 2H), 3.76 (t, J=4.8 Hz, 2H), 3.57-3.40 (m, 8H), 3.29 (s, 3H).

Example 3

2-({4-[2-(4-Chloro-2-fluorophenyl)-2-methyl-1,3-benzodioxol-4-yl]piperidin-1-yl}methyl)-1-(2-methoxyethyl)-1H-imidazo[4,5-b]pyridine-6-carboxylic acid, trifluoroacetate salt (3)

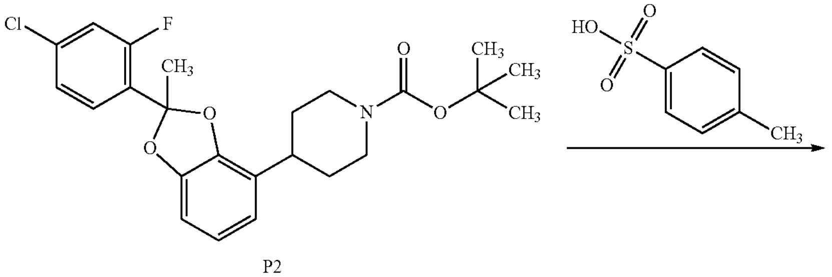

P2

-continued
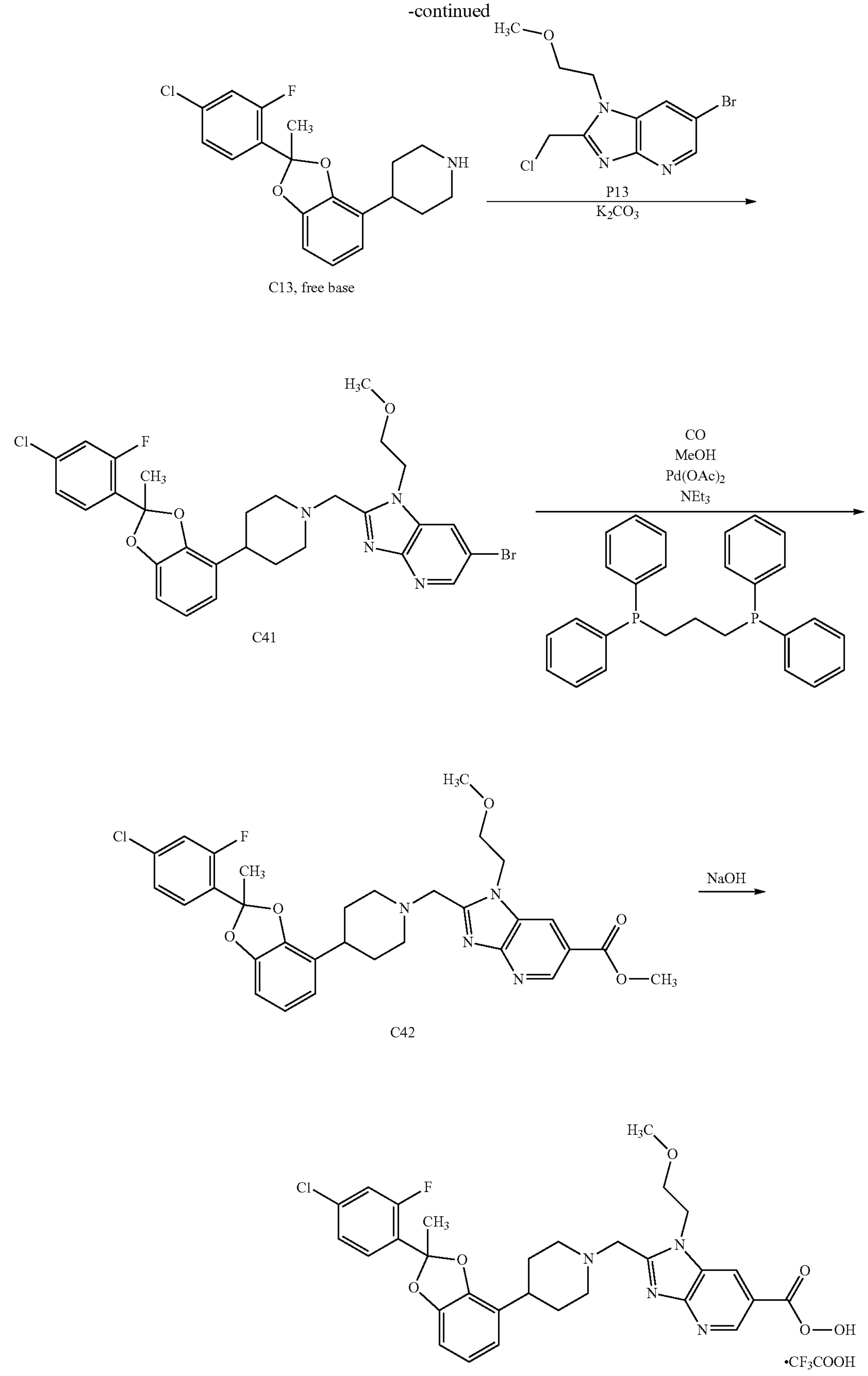
C13, free base
C41
C42
3

Step 1. Synthesis of 4-[2-(4-chloro-2-fluorophenyl)-2-methyl-1,3-benzodioxol-4-yl]piperidine (C13, Free Base)

To a solution of P2 (300 mg, 0.670 mmol) in ethyl acetate (3.5 mL) was added p-toluenesulfonic acid monohydrate (318 mg, 1.67 mmol). The reaction mixture was stirred at 60° C. for 1 hour, whereupon it was basified by addition of saturated aqueous potassium carbonate solution (20 mL) and extracted with a mixture of dichloromethane and methanol (10:1, 3×50 mL). The combined organic layers were dried over magnesium sulfate, filtered, and concentrated in vacuo to provide C13, free base, as a brown solid. Yield: 230 mg, 0.661 mmol, 99%.

Step 2. Synthesis of 6-bromo-2-({4-[2-(4-chloro-2-fluorophenyl)-2-methyl-1,3-benzodioxol-4-yl]piperidin-1-yl}methyl)-1-(2-methoxyethyl)-1H-imidazo[4,5-b]pyridine (C41)

A suspension of C13, free base (130 mg, 0.374 mmol), P13 (130 mg, 0.427 mmol), and potassium carbonate (172 mg, 1.24 mmol) in acetonitrile (2 mL) was stirred at 50° C. for 16 hours. The reaction mixture was then purified using preparative thin-layer chromatography (Eluent: ethyl acetate) to afford C41 as a brown oil. Yield: 114 mg, 0.185 mmol, 49%. LCMS m/z 617.1 (bromine-chlorine isotope pattern observed) $[M+H]^+$.

Step 3. Synthesis of methyl 2-({4-[2-(4-chloro-2-fluorophenyl)-2-methyl-1,3-benzodioxol-4-yl]piperidin-1-yl}methyl)-1-(2-methoxyethyl)-H-imidazo[4,5-b]pyridine-6-carboxylate (C42)

A solution of C41 (114 mg, 0.185 mmol), 1,3-bis(diphenylphosphino)propane (15.3 mg, 37.1 μmol), palladium(II) acetate (8.3 mg, 37 μmol), and triethylamine (187 mg, 1.85 mmol) in a mixture of methanol (5 mL) and N,N-dimethylformamide (1 mL) was stirred at 80° C. under carbon monoxide (50 psi) for 16 hours. After the reaction mixture had been diluted with ethyl acetate (50 mL), it was washed with saturated aqueous sodium chloride solution (2×50 mL), dried over magnesium sulfate, filtered, and concentrated under reduced pressure. Purification using preparative thin-layer chromatography (Eluent: ethyl acetate) provided C42 as a colorless oil. Yield: 60.0 mg, 0.101 mmol, 55%. LCMS m/z 617.2 (chlorine isotope pattern observed $[M+Na^+]$).

Step 4. Synthesis of 2-({4-[2-(4-chloro-2-fluorophenyl)-2-methyl-1,3-benzodioxol-4-yl]piperidin-1-yl}methyl)-1-(2-methoxyethyl)-1H-imidazo[4,5-b]pyridine-6-carboxylic acid, trifluoroacetate salt (3)

To a solution of C42 (60.0 mg, 0.101 mmol) in methanol (2.0 mL) was added aqueous sodium hydroxide solution (3 M; 1.0 mL, 3.0 mmol), and the reaction mixture was stirred at 20° C. for 2 hours. It was then adjusted to pH 7 by addition of 1 M hydrochloric acid, and extracted with a mixture of dichloromethane and methanol (10:1, 3×30 mL). The combined organic layers were dried over magnesium sulfate, filtered, concentrated in vacuo, and purified using reversed-phase HPLC (Column: Boston Green ODS, 5 μm; Mobile phase A: 0.1% trifluoroacetic acid in water; Mobile phase B: acetonitrile; Gradient: 10% to 95% B) to afford 3 as a white solid. Yield: 29.6 mg, 42.6 μmol, 42%. LCMS m/z 581.0♦ $[M+H]^+$. $^1$H NMR (400 MHz, methanol-$d_4$) δ 9.13 (d, J=1.9 Hz, 1H), 8.74 (d, J=1.9 Hz, 1H), 7.63 (dd, J=8.3, 8.3 Hz, 1H), 7.30 (dd, J=10.9, 2.0 Hz, 1H), 7.24 (ddd, J=8.4, 2.0, 0.7 Hz, 1H), 6.89-6.84 (m, 1H), 6.82-6.77 (m, 2H), 4.98-4.89 (m, 2H, assumed; largely obscured by water peak), 4.64 (t, J=4.8 Hz, 2H), 4.04-3.92 (br m, 2H), 3.75 (dd, J=5.4, 4.2 Hz, 2H), 3.51-3.39 (m, 2H), 3.31 (s, 3H), 3.19-3.06 (m, 1H), 2.41-2.24 (m, 2H), 2.24-2.12 (m, 2H), 2.06 (d, J=1.0 Hz, 3H).

Examples 4 and 5

Ammonium 2-({4-[(2R)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (4) and Ammonium 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (5)

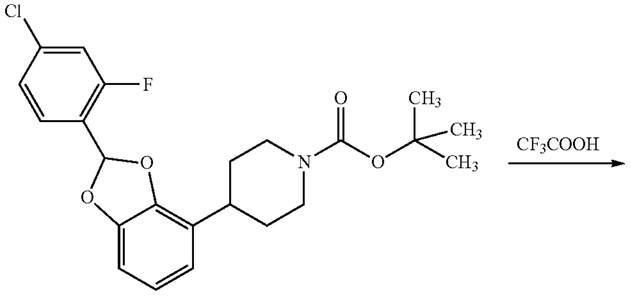

P1

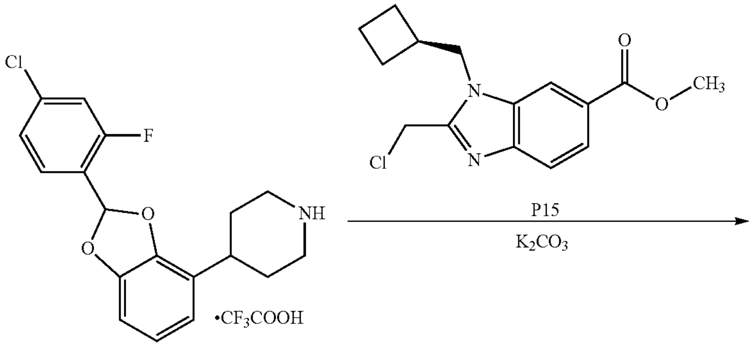

C43

-continued
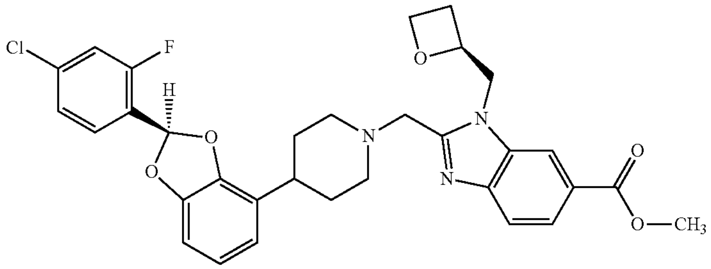
+
C44
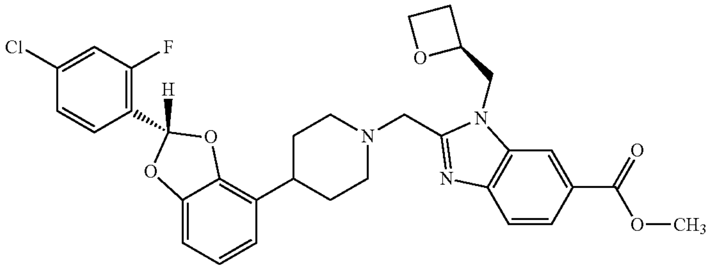
C45
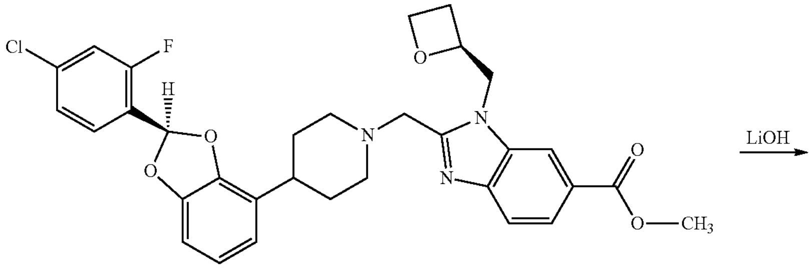
C44
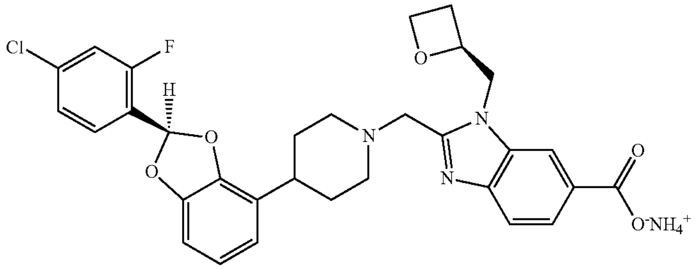
+
4
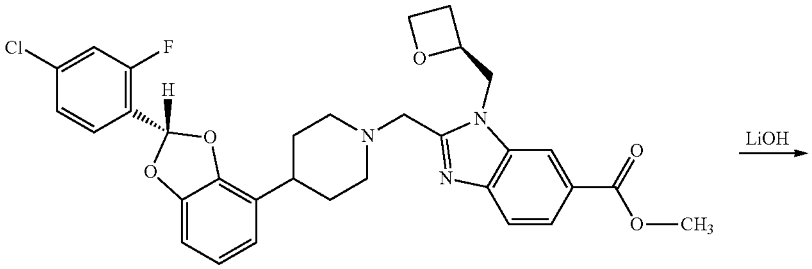
C45

-continued

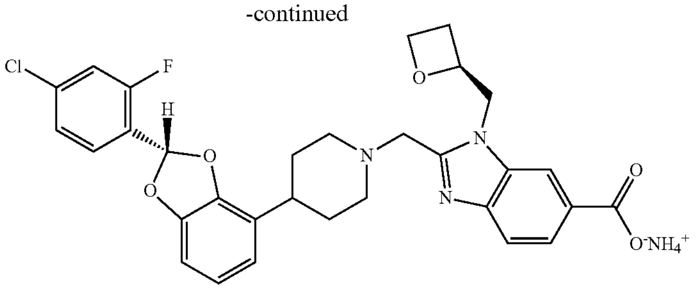

5

Step 1. Synthesis of 4-[2-(4-Chloro-2-Fluorophenyl)-1,3-Benzodioxol-4-Yl]Piperidine, Trifluoroacetate Salt (C43)

To a solution of P1 (300 mg, 0.691 mmol) in dichloromethane (5 mL) was added trifluoroacetic acid (1.3 mL). The reaction mixture was stirred at 29° C. for 2 hours, whereupon it was concentrated in vacuo to afford C43 as a brown oil, which was used directly in the following step.

Step 2. Synthesis of Methyl 2-({4-[(2R)-2-(4-Chloro-2-Fluorophenyl)-1,3-Benzodioxol-4-Yl]Piperidin-1-Yl}Methyl)-1-[(2S)-Oxetan-2-Ylmethyl]-1H-Benzimidazole-6-Carboxylate (C44) and Methyl 2-({4-[(2S)-2-(4-Chloro-2-Fluorophenyl)-1,3-Benzodioxol-4-Yl]Piperidin-1-Yl}Methyl)-1-[(2S)-Oxetan-2-Ylmethyl]-1H-Benzimidazole-6-Carboxylate (C45)

To a solution of C43 (from the previous step, ≤0.691 mmol) in acetonitrile (10 mL) was added P15 (204 mg, 0.692 mmol), followed by potassium carbonate (956 mg, 6.92 mmol). The reaction mixture was stirred at 29° C. for 16 hours, whereupon it was filtered; the filtrate was concentrated in vacuo to give a residue, which was purified by preparative thin-layer chromatography (Eluent: 2:1 petroleum ether/ethyl acetate) to provide a mixture of the diastereomeric products as a yellow gum (178 mg). Separation into the two products was carried out via SFC [Column: Chiral Technologies ChiralCel OD, 5 μm; Mobile phase: 55:45 carbon dioxide/(methanol containing 0.1% ammonium hydroxide)]. The first-eluting diastereomer, obtained as a yellow oil, was designated as C44. Yield: 44.3 mg, 74.8 μmol, 11% over 2 steps. LCMS m/z 592.1♦ $[M+H]^+$. Retention time 4.26 minutes (Column: Chiral Technologies ChiralCel OD-3, 4.6×100 mm, 3 μm; Mobile phase A: carbon dioxide; Mobile phase B: methanol containing 0.05% diethylamine; Gradient: 5% to 40% B over 4.5 minutes, then held at 40% B for 2.5 minutes; Flow rate: 2.8 mL/minute).

The second-eluting diastereomer was subjected to a second purification via SFC [Column: Chiral Technologies ChiralCel OD, 5 μm; Mobile phase: 3:2 carbon dioxide/(methanol containing 0.1% ammonium hydroxide)], providing the second-eluting diastereomer as a colorless oil, which was designated as C45. Yield: 38 mg, 64 μmol, 9% over 2 steps. LCMS m/z 592.1♦ $[M+H]^+$. Retention time 4.41 minutes (Analytical conditions identical to those used for C44).

The indicated absolute stereochemistries at the dioxolane were assigned via potency correlation of 5 with a sample of 5, free acid synthesized from intermediate C48; the absolute stereochemistry of that intermediate was determined via single-crystal X-ray structure determination (see below) of C49, a hemisulfate salt of C48.

Step 3. Synthesis of ammonium 2-({4-[(2R)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (4)

Aqueous lithium hydroxide solution (2 M; 0.80 mL, 1.6 mmol) was added to a solution of C44 (44.3 mg, 74.8 μmol) in a mixture of methanol (1 mL) and tetrahydrofuran (1 mL), and the reaction mixture was stirred at 26° C. for 3 hours. It was then adjusted to pH 7 by addition of trifluoroacetic acid, and the resulting mixture was concentrated in vacuo and purified using reversed-phase HPLC (Column: Agela Durashell C18, 5 μm; Mobile phase A: 0.05% ammonium hydroxide in water; Mobile phase B: acetonitrile; Gradient: 30% to 50% B) to afford 4 as a white solid. Yield: 26.6 mg, 44.7 μmol, 60%. LCMS m/z 578.0♦ $[M+H]^+$. $^1$H NMR (400 MHz, methanol-$d_4$) δ 8.31 (d, J=1.4 Hz, 1H), 7.96 (dd, J=8.5, 1.6 Hz, 1H), 7.66 (d, J=8.5 Hz, 1H), 7.57 (dd, J=8.0, 8.0 Hz, 1H), 7.34 (dd, J=10.1, 2.0 Hz, 1H), 7.29 (br dd, J=8.3, 2.0 Hz, 1H), 7.20 (s, 1H), 6.86-6.79 (m, 1H), 6.77 (br dd, component of ABC pattern, J=7.9, 1.3 Hz, 1H), 6.73 (dd, component of ABC pattern, J=7.5, 1.4 Hz, 1H), 5.29-5.18 (m, 1H), 4.9-4.78 (m, 1H, assumed; partially obscured by water peak), 4.68 (dd, J=15.3, 2.7 Hz, 1H), 4.54 (td, J=8.0, 5.9 Hz, 1H), 4.44 (dt, J=9.2, 5.9 Hz, 1H), 4.02 (AB quartet, $J_{AB}$=13.9 Hz, $\Delta\nu_{AB}$=49.0 Hz, 2H), 3.18-3.08 (m, 1H), 3.05-2.96 (m, 1H), 2.81-2.68 (m, 2H), 2.56-2.45 (m, 1H), 2.45-2.30 (m, 2H), 2.03-1.88 (m, 2H), 1.88-1.79 (m, 2H).

Step 4. Synthesis of ammonium 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (5)

Aqueous lithium hydroxide solution (2 M; 0.80 mL, 1.6 mmol) was added to a solution of C45 (38 mg, 64 μmol) in a mixture of methanol (1 mL) and tetrahydrofuran (1 mL), and the reaction mixture was stirred at 24° C. for 2.5 hours. It was then adjusted to pH 7 by addition of 1 M hydrochloric acid, and the resulting mixture was concentrated in vacuo and purified using reversed-phase HPLC (Column: Agela Durashell C18, 5 μm; Mobile phase A: 0.05% ammonium hydroxide in water; Mobile phase B: acetonitrile; Gradient: 29% to 49% B), providing 5 as a white solid. Yield: 27.9 mg, 46.9 μmol, 73%. LCMS m/z 577.9♦ $[M+H]^+$. $^1$H NMR (400 MHz, methanol-$d_4$) δ 8.32 (d, J=1.4 Hz, 1H), 7.96 (dd, J=8.5, 1.5 Hz, 1H), 7.66 (d, J=8.5 Hz, 1H), 7.56 (dd, J=8.0, 8.0 Hz, 1H), 7.34 (dd, J=10.2, 2.0 Hz, 1H), 7.29 (br dd, J=8.3, 2.0 Hz, 1H), 7.20 (s, 1H), 6.85-6.80 (m, 1H), 6.77 (dd, component of ABC pattern, J=8.0, 1.3 Hz, 1H), 6.73 (dd, component of ABC pattern, J=7.5, 1.4 Hz, 1H), 5.30-5.20 (m, 1H), 4.9-4.79 (m, 1H, assumed; partially obscured by water peak), 4.68 (dd, J=15.4, 2.7 Hz, 1H), 4.62-4.54 (m, 1H), 4.44 (dt, J=9.2, 5.9 Hz, 1H), 4.02 (AB quartet, $J_{AB}$=13.9 Hz, $\Delta v_{AB}$=44.6 Hz, 2H), 3.18-3.09 (m, 1H), 3.06-2.97 (m, 1H), 2.80-2.67 (m, 2H), 2.55-2.30 (m, 3H), 2.02-1.78 (m, 4H).
Alternate Synthesis of Example 5, Free Acid
2-({4-[(2S)-2-(4-Chloro-2-fluorophenyl)-1,3-benzodioxol-4-yl]piperidin-1-yl}methyl)-1-[(2S)-oxetan-2-ylmethyl]-1H-benzimidazole-6-carboxylic acid (5, Free Acid
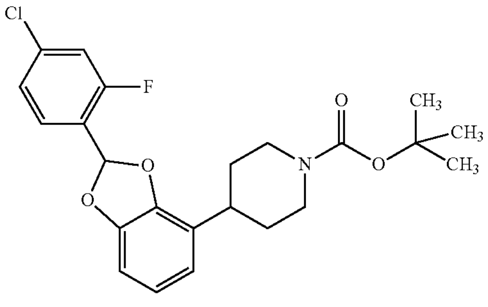
P1
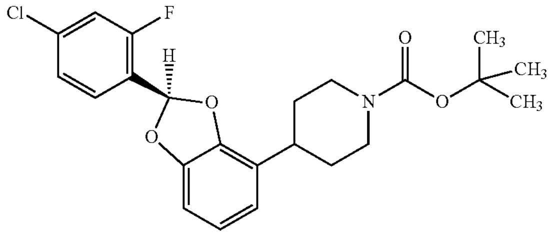
C46
+
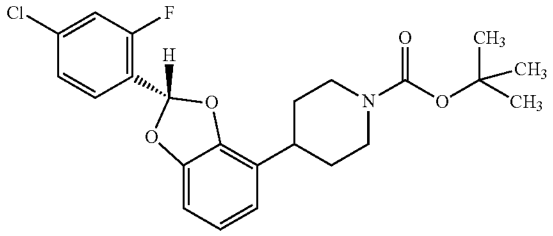
C47
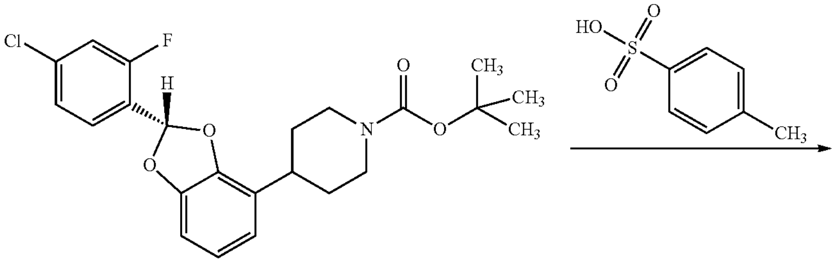
C47
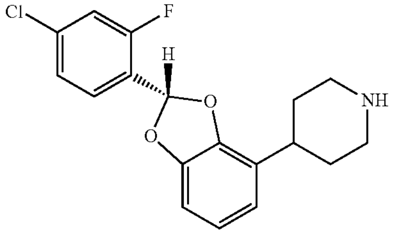
C48
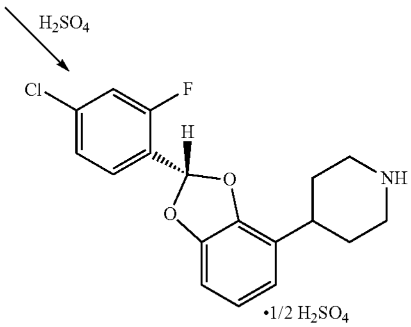
C49

-continued

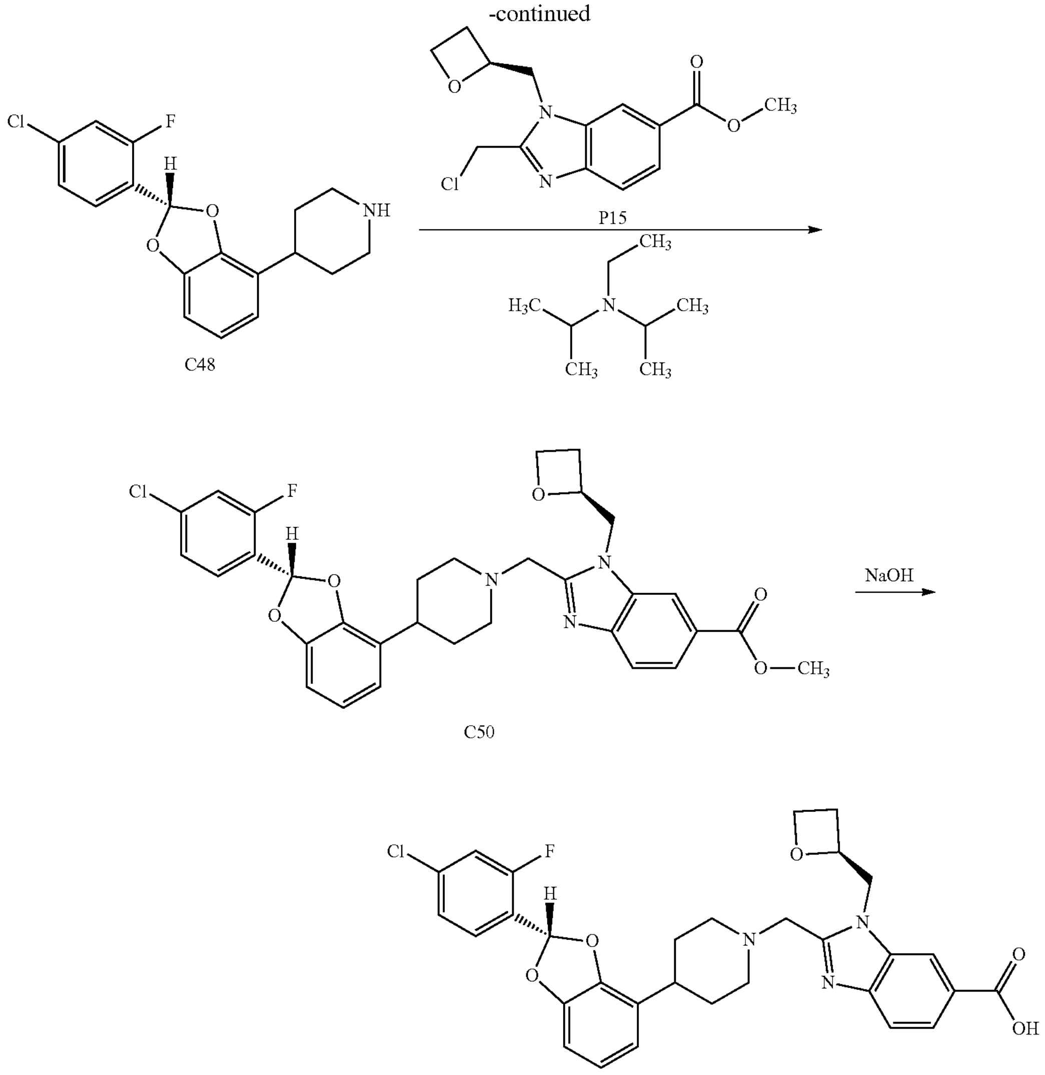

5, free acid

Step 1. Isolation of tert-butyl 4-[(2R)-2-(4-chloro-2-fluorophenyl)-1,3-benzodioxol-4-yl]piperidine-1-carboxylate (C46) and tert-butyl 4-[(2S)-2-(4-chloro-2-fluorophenyl)-1,3-benzodioxol-4-yl] piperidine-1-carboxylate (C47)

Separation of P1 (10 g, 23 mmol) into its component enantiomers was carried out using reversed-phase HPLC [Column: Phenomenex Lux Amylose-1, 5 μm; Mobile phase: 9:1 carbon dioxide/(2-propanol containing 0.2% 1-aminopropan-2-ol)]. The first-eluting enantiomer was designated as C46, and the second-eluting enantiomer as C47; both were obtained as colorless oils. The absolute stereochemistries indicated for C46 and C47 were assigned based on a single-crystal X-ray structure determination carried out on C49, which was synthesized from C47 (see below).

C46 Yield: 4.47 g, 10.3 mmol, 45%. Retention time: 3.98 minutes [Column: Phenomenex Lux Amylose-1, 4.6×250 mm, 5 μm; Mobile phase A: carbon dioxide; Mobile phase B: 2-propanol containing 0.2% 1-aminopropan-2-ol; Gradient: 5% B for 1.00 minute, then 5% to 60% B over 8.00 minutes; Flow rate: 3.0 mL/minute; Back pressure: 120 bar].

C47 Yield: 4.49 g, 10.3 mmol, 45%. Retention time: 4.32 minutes (Analytical SFC conditions identical to those used for C46).

Step 2. Synthesis of 4-[(2S)-2-(4-chloro-2-fluorophenyl)-1,3-benzodioxol-4-yl]piperidine (C48)

p-Toluenesulfonic acid monohydrate (566 mg, 2.98 mmol) was added to a solution of C47 (1.12 g, 2.58 mmol) in ethyl acetate (26 mL). After the reaction mixture had been heated at 45° C. for 16 hours, it was concentrated in vacuo, dissolved in ethyl acetate, and washed with saturated aqueous sodium bicarbonate solution. The aqueous layers were extracted with ethyl acetate, and the combined organic layers were washed with saturated aqueous sodium chloride solution, dried over sodium sulfate, filtered, and concentrated under reduced pressure, affording C48 as a foamy white solid (947 mg), LCMS m/z 334.0♦ $[M+H]^+$. A portion of this material, which still contained some p-toluenesulfonic acid, was used in the synthesis of C50 below.

A second portion of the foamy white solid (440 mg) was dissolved in ethyl acetate (25 mL) and washed with saturated aqueous sodium bicarbonate solution (2×15 mL); the organic layer was dried over magnesium sulfate, filtered, and concentrated in vacuo to afford C48 (350 mg) as a colorless oil that no longer contained p-toluenesulfonic acid. Adjusted yield: 350 mg, 1.05 mmol, 88%. $^1$H NMR (400 MHz, chloroform-d) δ 7.53 (dd, J=8.4, 7.8 Hz, 1H), 7.22-7.13 (m, 3H), 6.87-6.80 (m, 1H), 6.79-6.71 (m, 2H), 3.23-3.14 (m, 2H), 2.86-2.69 (m, 3H), 1.90-1.68 (m, 4H).

Step 3. Synthesis of 4-[(2S)-2-(4-Chloro-2-Fluorophenyl)-1,3-Benzodioxol-4-Yl]Piperidine, Hemisulfate Salt (C49)

A 0.1 M solution of C48 (the colorless oil from above) in ethyl acetate was prepared and subjected to a salt screen. Only the sulfate salt formation is described here. A mixture of sulfuric acid (25 μmol) and the solution of substrate (0.1 M, 250 μL, 25 μmol) was heated to 45° C. for 1 hour, allowed to cool to room temperature, and stirred for 15 hours. The resulting suspension was treated with methanol (approximately 150 μL) until a solution formed; this was allowed to slowly evaporate overnight, until approximately 50 μL of solvent remained. One of the resulting crystals was analyzed by single-crystal X-ray structure determination, establishing the absolute stereochemistry as that shown.

Single-Crystal X-Ray Structural Determination of C49

Single Crystal X-Ray Analysis

Data collection was performed on a Bruker D8 Venture diffractometer at room temperature.

Data collection consisted of omega and phi scans.

The structure was solved by intrinsic phasing using SHELX software suite in the triclinic class space group P1. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

The asymmetric unit is comprised of two molecules of protonated C48, one molecule of doubly deprotonated sulfuric acid, and one molecule full occupancy water. Thus, the structure is a hemisulfate salt and hemihydrate. The chlorofluorophenyl ring is disordered and modeled with occupancy of 60/40, with the ring flipped over two positions.

Analysis of the absolute structure using likelihood methods (Hooft, 2008) was performed using PLATON (Spek). The results indicate that the absolute structure has been correctly assigned; the method calculates that the probability that the structure is correct is 100.0. The Hooft parameter is reported as 0.061 with an esd of 0.004 and the Parson's parameter is reported as 0.063 with an esd of 0.005.

The final R-index was 3.1%. A final difference Fourier revealed no missing or misplaced electron density.

Pertinent crystal, data collection, and refinement information is summarized in Table E. Atomic coordinates, bond lengths, bond angles, and displacement parameters are listed in Tables F—H.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE E

Crystal data and structure refinement for C49.

| | | |
|---|---|---|
| Empirical formula | $C_{36}H_{38}Cl_2F_2N_2O_9S$ | |
| Formula weight | 783.64 | |
| Temperature | 296(2) K | |
| Wavelength | 1.54178 Å | |
| Crystal system | Triclinic | |
| Space group | P1 | |
| Unit cell dimensions | a = 5.9095(2) Å | α = 86.5910(10)° |
| | b = 6.1712(2) Å | β = 89.3680(10)° |
| | c = 25.6096(8) Å | γ = 75.7680(10)° |
| Volume | 903.68(5) Å$^3$ | |
| Z | 1 | |
| Density (calculated) | 1.440 Mg/m$^3$ | |
| Absorption coefficient | 2.743 mm$^{-1}$ | |
| F(000) | 408 | |
| Crystal size | 0.380 × 0.120 × 0.080 mm$^3$ | |
| Theta range for data collection | 3.458 to 72.096° | |
| Index ranges | −7 <= h <= 7, −7 <= k <= 7, −31 <= l <= 31 | |
| Reflections collected | 24619 | |
| Independent reflections | 6399 [$R_{int}$ = 0.0323]] | |
| Completeness to theta = 67.679° | 96.6% | |
| Absorption correction | Empirical | |
| Refinement method | Full-matrix least-squares on F$^2$ | |
| Data/restraints/parameters | 6399/9/495 | |
| Goodness-of-fit on F$^2$ | 1.014 | |
| Final R indices [I > 2σ(I)] | R1 = 0.0305, wR2 = 0.0805 | |
| R indices (all data) | R1 = 0.0310, wR2 = 0.0810 | |
| Absolute structure parameter | 0.058(4) | |
| Extinction coefficient | n/a | |
| Largest diff. peak and hole | 0.167 and −0.184 e · Å$^{-3}$ | |

TABLE F

Atomic coordinates (× 10$^4$) and equivalent isotropic displacement parameters (Å$^2$ × 10$^3$) for C49. U(eq) is defined as one-third of the trace of the orthogonalized $U^{ij}$ tensor.

| | x | y | z | U(eq) |
|---|---|---|---|---|
| S(1) | 8968(1) | 2512(1) | 4774(1) | 33(1) |
| Cl(1) | 2534(3) | 7001(5) | 9863(1) | 161(1) |
| F(1) | 9192(9) | 7761(7) | 8721(2) | 95(1) |
| C(1) | 7533(7) | 6719(7) | 8821(1) | 72(1) |
| C(2) | 6041(9) | 7355(8) | 9230(2) | 92(1) |
| C(3) | 4428(8) | 6206(10) | 9350(2) | 93(2) |
| C(4) | 4276(8) | 4392(9) | 9082(2) | 86(1) |
| C(5) | 5801(7) | 3784(7) | 8678(1) | 69(1) |
| C(6) | 7444(6) | 4930(5) | 8533(1) | 56(1) |
| Cl(1') | 2534(3) | 7001(5) | 9863(1) | 161(1) |
| F(1') | 6045(13) | 1811(12) | 8450(3) | 95(1) |
| C(1') | 5801(7) | 3784(7) | 8678(1) | 69(1) |
| C(2') | 4276(8) | 4392(9) | 9082(2) | 86(1) |
| C(3') | 4428(8) | 6206(10) | 9350(2) | 93(2) |
| C(4') | 6041(9) | 7355(8) | 9230(2) | 92(1) |
| C(5') | 7533(7) | 6719(7) | 8821(1) | 72(1) |
| C(6') | 7444(6) | 4930(5) | 8533(1) | 56(1) |
| Cl(2) | −2047(5) | 12265(3) | 154(1) | 157(1) |
| F(2) | −2662(7) | 5436(7) | 1220(2) | 92(1) |
| C(19) | −1591(6) | 7059(7) | 1154(1) | 68(1) |
| C(20) | −2327(8) | 8653(9) | 752(2) | 88(1) |
| C(21) | −1157(9) | 10260(8) | 665(2) | 88(1) |

TABLE F-continued

Atomic coordinates (× $10^4$) and equivalent isotropic displacement parameters ($Å^2$ × $10^3$) for C49. U(eq) is defined as one-third of the trace of the orthogonalized $U^{ij}$ tensor.

| | x | y | z | U(eq) |
|---|---|---|---|---|
| C(22) | 728(9) | 10361(7) | 964(2) | 80(1) |
| C(23) | 1431(6) | 8731(6) | 1364(1) | 65(1) |
| C(24) | 274(5) | 7058(5) | 1472(1) | 54(1) |
| Cl(2') | −2047(5) | 12265(3) | 154(1) | 157(1) |
| F(2') | 3433(15) | 8441(16) | 1630(4) | 92(1) |
| C(19') | 1431(6) | 8731(6) | 1364(1) | 65(1) |
| C(20') | 728(9) | 10361(7) | 964(2) | 80(1) |
| C(21') | −1157(9) | 10260(8) | 665(2) | 88(1) |
| C(22') | −2327(8) | 8653(9) | 752(2) | 88(1) |
| C(23') | −1591(6) | 7059(7) | 1154(1) | 68(1) |
| C(24') | 274(5) | 7058(5) | 1472(1) | 54(1) |
| N(1) | 4370(3) | 2950(4) | 5713(1) | 41(1) |
| N(2) | 4133(4) | 8236(3) | 4386(1) | 42(1) |
| O(1) | 10923(4) | 2331(5) | 8233(1) | 77(1) |
| O(2) | 7874(4) | 3730(4) | 7651(1) | 64(1) |
| O(3) | 1766(4) | 6201(4) | 2352(1) | 64(1) |
| O(4) | 2966(5) | 3591(4) | 1729(1) | 75(1) |
| O(5) | 9024(3) | 2305(3) | 4214(1) | 50(1) |
| O(6) | 7650(4) | 989(3) | 5024(1) | 63(1) |
| O(7) | 11358(3) | 1934(4) | 4982(1) | 64(1) |
| O(8) | 7789(3) | 4827(3) | 4909(1) | 46(1) |
| O(1W) | 10276(4) | 6879(4) | 5537(1) | 54(1) |
| C(7) | 9086(6) | 4293(6) | 8090(1) | 63(1) |
| C(8) | 9234(4) | 1745(5) | 7490(1) | 44(1) |
| C(9) | 11056(5) | 930(6) | 7834(1) | 54(1) |
| C(10) | 12654(5) | −1059(6) | 7768(1) | 62(1) |
| C(11) | 12316(5) | −2213(6) | 7338(1) | 58(1) |
| C(12) | 10459(4) | −1405(5) | 6994(1) | 47(1) |
| C(13) | 8826(4) | 623(4) | 7066(1) | 38(1) |
| C(14) | 6762(4) | 1637(4) | 6711(1) | 37(1) |
| C(15) | 7243(4) | 3516(4) | 6343(1) | 42(1) |
| C(16) | 5126(4) | 4639(4) | 6009(1) | 44(1) |
| C(17) | 3883(5) | 1105(5) | 6056(1) | 50(1) |
| C(18) | 5997(4) | −38(4) | 6386(1) | 41(1) |
| C(25) | 996(6) | 5296(6) | 1900(1) | 60(1) |
| C(26) | 3848(5) | 4738(4) | 2505(1) | 45(1) |
| C(27) | 4542(6) | 3183(5) | 2133(1) | 52(1) |
| C(28) | 6579(6) | 1567(5) | 2178(1) | 56(1) |
| C(29) | 7932(6) | 1577(5) | 2620(1) | 56(1) |
| C(30) | 7236(5) | 3123(5) | 2992(1) | 51(1) |
| C(31) | 5126(5) | 4786(4) | 2944(1) | 42(1) |
| C(32) | 4261(4) | 6474(4) | 3352(1) | 39(1) |
| C(33) | 6145(5) | 7543(5) | 3544(1) | 51(1) |
| C(34) | 5139(5) | 9272(4) | 3932(1) | 50(1) |
| C(35) | 2313(5) | 7116(5) | 4227(1) | 49(1) |
| C(36) | 3263(4) | 5420(4) | 3826(1) | 42(1) |

TABLE G

Bond lengths [Å] and angles [°] for C49.

| | |
|---|---|
| S(1)—O(5) | 1.4463(18) |
| S(1)—O(7) | 1.4668(19) |
| S(1)—O(6) | 1.475(2) |
| S(1)—O(8) | 1.4863(18) |
| Cl(1)—C(3) | 1.731(4) |
| F(1)—C(1) | 1.314(6) |
| C(1)—C(6) | 1.375(5) |
| C(1)—C(2) | 1.374(6) |
| C(2)—C(3) | 1.343(8) |
| C(2)—H(2) | 0.9300 |
| C(3)—C(4) | 1.369(8) |
| C(4)—C(5) | 1.373(6) |
| C(4)—H(4) | 0.9300 |
| C(5)—C(6) | 1.370(5) |
| C(5)—H(5) | 0.9300 |
| C(6)—C(7) | 1.493(5) |
| Cl(1')—C(3') | 1.731(4) |
| F(1')—C(1') | 1.357(8) |
| C(1')—C(6') | 1.370(5) |
| C(1')—C(2') | 1.373(6) |

TABLE G-continued

Bond lengths [Å] and angles [°] for C49.

| | |
|---|---|
| C(2')—C(3') | 1.369(8) |
| C(2')—H(2') | 0.9300 |
| C(3')—C(4') | 1.343(8) |
| C(4')—C(5') | 1.374(6) |
| C(4')—H(4') | 0.9300 |
| C(5')—C(6') | 1.375(5) |
| C(5')—H(5') | 0.9300 |
| C(6')—C(7) | 1.493(5) |
| Cl(2)—C(21) | 1.739(4) |
| F(2)—C(19) | 1.312(5) |
| C(19)—C(24) | 1.378(5) |
| C(19)—C(20) | 1.378(6) |
| C(20)—C(21) | 1.348(7) |
| C(20)—H(20) | 0.9300 |
| C(21)—C(22) | 1.375(7) |
| C(22)—C(23) | 1.384(6) |
| C(22)—H(22) | 0.9300 |
| C(23)—C(24) | 1.385(5) |
| C(23)—H(23) | 0.9300 |
| C(24)—C(25) | 1.485(5) |
| Cl(2')—C(21') | 1.739(4) |
| F(2')—C(19') | 1.340(9) |
| C(19')—C(20') | 1.384(6) |
| C(19')—C(24') | 1.385(5) |
| C(20')—C(21') | 1.375(7) |
| C(20')—H(20') | 0.9300 |
| C(21')—C(22') | 1.348(7) |
| C(22')—C(23') | 1.378(6) |
| C(22')—H(22') | 0.9300 |
| C(23')—C(24') | 1.378(5) |
| C(23')—H(23') | 0.9300 |
| C(24')—C(25) | 1.485(5) |
| N(1)—C(17) | 1.480(4) |
| N(1)—C(16) | 1.480(3) |
| N(1)—H(1X) | 0.95(2) |
| N(1)—H(1Y) | 0.97(2) |
| N(2)—C(34) | 1.483(4) |
| N(2)—C(35) | 1.487(4) |
| N(2)—H(2X) | 0.96(2) |
| N(2)—H(2Y) | 0.99(2) |
| O(1)—C(9) | 1.368(4) |
| O(1)—C(7) | 1.445(4) |
| O(2)—C(8) | 1.373(3) |
| O(2)—C(7) | 1.443(3) |
| O(3)—C(26) | 1.380(3) |
| O(3)—C(25) | 1.440(3) |
| O(4)—C(27) | 1.369(4) |
| O(4)—C(25) | 1.447(4) |
| O(1W)—H(1WX) | 0.93(2) |
| O(1W)—H(1WY) | 0.94(2) |
| C(7)—H(7) | 0.9800 |
| C(8)—C(9) | 1.374(4) |
| C(8)—C(13) | 1.376(4) |
| C(9)—C(10) | 1.370(5) |
| C(10)—C(11) | 1.387(5) |
| C(10)—H(10) | 0.9300 |
| C(11)—C(12) | 1.390(4) |
| C(11)—H(11) | 0.9300 |
| C(12)—C(13) | 1.400(4) |
| C(12)—H(12) | 0.9300 |
| C(13)—C(14) | 1.514(3) |
| C(14)—C(18) | 1.518(3) |
| C(14)—C(15) | 1.528(3) |
| C(14)—H(14) | 0.9800 |
| C(15)—C(16) | 1.518(3) |
| C(15)—H(15A) | 0.9700 |
| C(15)—H(15B) | 0.9700 |
| C(16)—H(16A) | 0.9700 |
| C(16)—H(16B) | 0.9700 |
| C(17)—C(18) | 1.513(4) |
| C(17)—H(17A) | 0.9700 |
| C(17)—H(17B) | 0.9700 |
| C(18)—H(18A) | 0.9700 |
| C(18)—H(18B) | 0.9700 |
| C(25)—H(25) | 0.9800 |
| C(26)—C(31) | 1.367(4) |
| C(26)—C(27) | 1.379(3) |
| C(27)—C(28) | 1.363(4) |

TABLE G-continued

| Bond lengths [Å] and angles [°] for C49. | |
|---|---|
| C(28)—C(29) | 1.394(5) |
| C(28)—H(28) | 0.9300 |
| C(29)—C(30) | 1.376(4) |
| C(29)—H(29) | 0.9300 |
| C(30)—C(31) | 1.408(4) |
| C(30)—H(30) | 0.9300 |
| C(31)—C(32) | 1.514(3) |
| C(32)—C(33) | 1.527(4) |
| C(32)—C(36) | 1.524(3) |
| C(32)—H(32) | 0.9800 |
| C(33)—C(34) | 1.510(4) |
| C(33)—H(33A) | 0.9700 |
| C(33)—H(33B) | 0.9700 |
| C(34)—H(34A) | 0.9700 |
| C(34)—H(34B) | 0.9700 |
| C(35)—C(36) | 1.515(3) |
| C(35)—H(35A) | 0.9700 |
| C(35)—H(35B) | 0.9700 |
| C(36)—H(36A) | 0.9700 |
| C(36)—H(36B) | 0.9700 |
| O(5)—S(1)—O(7) | 109.68(13) |
| O(5)—S(1)—O(6) | 109.65(13) |
| O(7)—S(1)—O(6) | 109.45(15) |
| O(5)—S(1)—O(8) | 111.22(11) |
| O(7)—S(1)—O(8) | 109.11(11) |
| O(6)—S(1)—O(8) | 107.69(11) |
| F(1)—C(1)—C(6) | 118.6(4) |
| F(1)—C(1)—C(2) | 119.1(4) |
| C(6)—C(1)—C(2) | 122.1(4) |
| C(3)—C(2)—C(1) | 118.9(4) |
| C(3)—C(2)—H(2) | 120.5 |
| C(1)—C(2)—H(2) | 120.5 |
| C(2)—C(3)—C(4) | 121.6(4) |
| C(2)—C(3)—Cl(1) | 119.3(4) |
| C(4)—C(3)—Cl(1) | 119.1(5) |
| C(3)—C(4)—C(5) | 118.2(5) |
| C(3)—C(4)—H(4) | 120.9 |
| C(5)—C(4)—H(4) | 120.9 |
| C(6)—C(5)—C(4) | 122.4(4) |
| C(6)—C(5)—H(5) | 118.8 |
| C(4)—C(5)—H(5) | 118.8 |
| C(5)—C(6)—C(1) | 116.7(3) |
| C(5)—C(6)—C(7) | 122.7(3) |
| C(1)—C(6)—C(7) | 120.6(3) |
| F(1')—C(1')—C(6') | 114.7(4) |
| F(1')—C(1')—C(2') | 122.1(5) |
| C(6')—C(1')—C(2') | 122.4(4) |
| C(3')—C(2')—C(1') | 118.2(5) |
| C(3')—C(2')—H(2') | 120.9 |
| C(1')—C(2')—H(2') | 120.9 |
| C(4')—C(3')—C(2') | 121.6(4) |
| C(4')—C(3')—Cl(1') | 119.3(4) |
| C(2')—C(3')—Cl(1') | 119.1(5) |
| C(3')—C(4')—C(5') | 118.9(4) |
| C(3')—C(4')—H(4') | 120.5 |
| C(5')—C(4')—H(4') | 120.5 |
| C(6')—C(5')—C(4') | 122.1(4) |
| C(6')—C(5')—H(5') | 118.9 |
| C(4')—C(5')—H(5') | 118.9 |
| C(1')—C(6')—C(5') | 116.7(3) |
| C(1')—C(6')—C(7) | 122.7(3) |
| C(5')—C(6')—C(7) | 120.6(3) |
| F(2)—C(19)—C(24) | 119.3(4) |
| F(2)—C(19)—C(20) | 118.1(4) |
| C(24)—C(19)—C(20) | 122.5(4) |
| C(21)—C(20)—C(19) | 118.4(4) |
| C(21)—C(20)—H(20) | 120.8 |
| C(19)—C(20)—H(20) | 120.8 |
| C(20)—C(21)—C(22) | 122.4(4) |
| C(20)—C(21)—Cl(2) | 118.9(4) |
| C(22)—C(21)—Cl(2) | 118.7(4) |
| C(21)—C(22)—C(23) | 117.8(4) |
| C(21)—C(22)—H(22) | 121.1 |
| C(23)—C(22)—H(22) | 121.1 |
| C(22)—C(23)—C(24) | 122.0(4) |
| C(22)—C(23)—H(23) | 119.0 |
| C(24)—C(23)—H(23) | 119.0 |
| C(19)—C(24)—C(23) | 116.8(3) |

TABLE G-continued

| Bond lengths [Å] and angles [°] for C49. | |
|---|---|
| C(19)—C(24)—C(25) | 120.3(3) |
| C(23)—C(24)—C(25) | 122.9(3) |
| F(2')—C(19')—C(20') | 123.5(5) |
| F(2')—C(19')—C(24') | 113.9(5) |
| C(20')—C(19')—C(24') | 122.0(4) |
| C(21')—C(20')—C(19') | 117.8(4) |
| C(21')—C(20')—H(20') | 121.1 |
| C(19')—C(20')—H(20') | 121.1 |
| C(22')—C(21')—C(20') | 122.4(4) |
| C(22')—C(21')—Cl(2') | 118.9(4) |
| C(20')—C(21')—Cl(2') | 118.7(4) |
| C(21')—C(22')—C(23') | 118.4(4) |
| C(21')—C(22')—H(22') | 120.8 |
| C(23')—C(22')—H(22') | 120.8 |
| C(24')—C(23')—C(22') | 122.5(4) |
| C(24')—C(23')—H(23') | 118.7 |
| C(22')—C(23')—H(23') | 118.7 |
| C(23')—C(24')—C(19') | 116.8(3) |
| C(23')—C(24')—C(25) | 120.3(3) |
| C(19')—C(24')—C(25) | 122.9(3) |
| C(17)—N(1)—C(16) | 112.6(2) |
| C(17)—N(1)—H(1X) | 110.7(19) |
| C(16)—N(1)—H(1X) | 108(2) |
| C(17)—N(1)—H(1Y) | 108(2) |
| C(16)—N(1)—H(1Y) | 112.4(19) |
| H(1X)—N(1)—H(1Y) | 105(3) |
| C(34)—N(2)—C(35) | 112.2(2) |
| C(34)—N(2)—H(2X) | 109.7(19) |
| C(35)—N(2)—H(2X) | 109.7(19) |
| C(34)—N(2)—H(2Y) | 107.7(19) |
| C(35)—N(2)—H(2Y) | 110.8(19) |
| H(2X)—N(2)—H(2Y) | 107(3) |
| C(9)—O(1)—C(7) | 106.0(2) |
| C(8)—O(2)—C(7) | 105.9(2) |
| C(26)—O(3)—C(25) | 105.9(2) |
| C(27)—O(4)—C(25) | 105.7(2) |
| H(1WX)—O(1W)—H(1WY) | 105(4) |
| O(2)—C(7)—O(1) | 106.5(3) |
| O(2)—C(7)—C(6) | 110.4(3) |
| O(1)—C(7)—C(6) | 111.2(3) |
| O(2)—C(7)—C(6') | 110.4(3) |
| O(1)—C(7)—C(6') | 111.2(3) |
| O(2)—C(7)—H(7) | 109.6 |
| O(1)—C(7)—H(7) | 109.6 |
| C(6)—C(7)—H(7) | 109.6 |
| C(9)—C(8)—O(2) | 110.0(2) |
| C(9)—C(8)—C(13) | 123.4(2) |
| O(2)—C(8)—C(13) | 126.6(2) |
| O(1)—C(9)—C(10) | 128.1(3) |
| O(1)—C(9)—C(8) | 110.1(3) |
| C(10)—C(9)—C(8) | 121.7(3) |
| C(9)—C(10)—C(11) | 116.3(3) |
| C(9)—C(10)—H(10) | 121.8 |
| C(11)—C(10)—H(10) | 121.8 |
| C(10)—C(11)—C(12) | 122.0(3) |
| C(10)—C(11)—H(11) | 119.0 |
| C(12)—C(11)—H(11) | 119.0 |
| C(11)—C(12)—C(13) | 121.3(3) |
| C(11)—C(12)—H(12) | 119.4 |
| C(13)—C(12)—H(12) | 119.4 |
| C(8)—C(13)—C(12) | 115.3(2) |
| C(8)—C(13)—C(14) | 119.8(2) |
| C(12)—C(13)—C(14) | 124.9(2) |
| C(13)—C(14)—C(18) | 114.2(2) |
| C(13)—C(14)—C(15) | 111.38(19) |
| C(18)—C(14)—C(15) | 108.70(19) |
| C(13)—C(14)—H(14) | 107.4 |
| C(18)—C(14)—H(14) | 107.4 |
| C(15)—C(14)—H(14) | 107.4 |
| C(16)—C(15)—C(14) | 111.7(2) |
| C(16)—C(15)—H(15A) | 109.3 |
| C(14)—C(15)—H(15A) | 109.3 |
| C(16)—C(15)—H(15B) | 109.3 |
| C(14)—C(15)—H(15B) | 109.3 |
| H(15A)—C(15)—H(15B) | 107.9 |
| N(1)—C(16)—C(15) | 109.9(2) |
| N(1)—C(16)—H(16A) | 109.7 |
| C(15)—C(16)—H(16A) | 109.7 |

TABLE G-continued

| Bond lengths [Å] and angles [°] for C49. | |
|---|---|
| N(1)—C(16)—H(16B) | 109.7 |
| C(15)—C(16)—H(16B) | 109.7 |
| H(16A)—C(16)—H(16B) | 108.2 |
| N(1)—C(17)—C(18) | 110.94(19) |
| N(1)—C(17)—H(17A) | 109.5 |
| C(18)—C(17)—H(17A) | 109.5 |
| N(1)—C(17)—H(17B) | 109.5 |
| C(18)—C(17)—H(17B) | 109.5 |
| H(17A)—C(17)—H(17B) | 108.0 |
| C(17)—C(18)—C(14) | 110.6(2) |
| C(17)—C(18)—H(18A) | 109.5 |
| C(14)—C(18)—H(18A) | 109.5 |
| C(17)—C(18)—H(18B) | 109.5 |
| C(14)—C(18)—H(18B) | 109.5 |
| H(18A)—C(18)—H(18B) | 108.1 |
| O(3)—C(25)—O(4) | 106.6(2) |
| O(3)—C(25)—C(24') | 111.0(3) |
| O(4)—C(25)—C(24') | 109.4(3) |
| O(3)—C(25)—C(24) | 111.0(3) |
| O(4)—C(25)—C(24) | 109.4(3) |
| O(3)—C(25)—H(25) | 109.9 |
| O(4)—C(25)—H(25) | 109.9 |
| C(24)—C(25)—H(25) | 109.9 |
| C(31)—C(26)—C(27) | 123.2(3) |
| C(31)—C(26)—O(3) | 127.3(2) |
| C(27)—C(26)—O(3) | 109.5(2) |
| C(28)—C(27)—O(4) | 127.7(2) |
| C(28)—C(27)—C(26) | 121.9(3) |
| O(4)—C(27)—C(26) | 110.3(2) |
| C(27)—C(28)—C(29) | 116.3(2) |
| C(27)—C(28)—H(28) | 121.9 |
| C(29)—C(28)—H(28) | 121.9 |
| C(30)—C(29)—C(28) | 121.8(3) |
| C(30)—C(29)—H(29) | 119.1 |
| C(28)—C(29)—H(29) | 119.1 |
| C(29)—C(30)—C(31) | 121.7(3) |
| C(29)—C(30)—H(30) | 119.2 |
| C(31)—C(30)—H(30) | 119.2 |
| C(26)—C(31)—C(30) | 115.1(2) |
| C(26)—C(31)—C(32) | 121.5(2) |
| C(30)—C(31)—C(32) | 123.4(2) |
| C(31)—C(32)—C(33) | 113.3(2) |
| C(31)—C(32)—C(36) | 111.48(19) |
| C(33)—C(32)—C(36) | 108.02(19) |
| C(31)—C(32)—H(32) | 107.9 |
| C(33)—C(32)—H(32) | 107.9 |
| C(36)—C(32)—H(32) | 107.9 |
| C(34)—C(33)—C(32) | 110.5(2) |
| C(34)—C(33)—H(33A) | 109.6 |
| C(32)—C(33)—H(33A) | 109.6 |
| C(34)—C(33)—H(33B) | 109.6 |
| C(32)—C(33)—H(33B) | 109.6 |
| H(33A)—C(33)—H(33B) | 108.1 |
| N(2)—C(34)—C(33) | 110.6(2) |
| N(2)—C(34)—H(34A) | 109.5 |
| C(33)—C(34)—H(34A) | 109.5 |
| N(2)—C(34)—H(34B) | 109.5 |
| C(33)—C(34)—H(34B) | 109.5 |
| H(34A)—C(34)—H(34B) | 108.1 |
| N(2)—C(35)—C(36) | 110.71(19) |
| N(2)—C(35)—H(35A) | 109.5 |
| C(36)—C(35)—H(35A) | 109.5 |
| N(2)—C(35)—H(35B) | 109.5 |
| C(36)—C(35)—H(35B) | 109.5 |
| H(35A)—C(35)—H(35B) | 108.1 |
| C(35)—C(36)—C(32) | 111.9(2) |
| C(35)—C(36)—H(36A) | 109.2 |
| C(32)—C(36)—H(36A) | 109.2 |
| C(35)—C(36)—H(36B) | 109.2 |
| C(32)—C(36)—H(36B) | 109.2 |
| H(36A)—C(36)—H(36B) | 107.9 |

Symmetry transformations used to generate equivalent atoms.

TABLE H

Anisotropic displacement parameters ($Å^2 \times 10^3$) for C49. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| S(1) | 32(1) | 32(1) | 32(1) | −3(1) | −2(1) | −1(1) |
| Cl(1) | 107(1) | 258(2) | 90(1) | −63(1) | 19(1) | 19(1) |
| F(1) | 111(2) | 91(2) | 98(2) | −30(2) | 6(2) | −46(2) |
| C(1) | 81(2) | 71(2) | 60(2) | −20(2) | −16(2) | −6(2) |
| C(2) | 100(3) | 92(3) | 74(3) | −42(2) | −16(2) | 7(2) |
| C(3) | 70(2) | 134(4) | 53(2) | −27(2) | −7(2) | 19(3) |
| C(4) | 71(2) | 116(3) | 67(2) | 0(2) | −1(2) | −16(2) |
| C(5) | 75(2) | 70(2) | 59(2) | −11(2) | −7(2) | −10(2) |
| C(6) | 65(2) | 54(2) | 42(1) | −8(1) | −18(1) | −1(1) |
| Cl(1') | 107(1) | 258(2) | 90(1) | −63(1) | 19(1) | 19(1) |
| F(1') | 111(2) | 91(2) | 98(2) | −30(2) | 6(2) | −46(2) |
| C(1') | 75(2) | 70(2) | 59(2) | −11(2) | −7(2) | −10(2) |
| C(2') | 71(2) | 116(3) | 67(2) | 0(2) | −1(2) | −16(2) |
| C(3') | 70(2) | 134(4) | 53(2) | −27(2) | −7(2) | 19(3) |
| C(4') | 100(3) | 92(3) | 74(3) | −42(2) | −16(2) | 7(2) |
| C(5') | 81(2) | 71(2) | 60(2) | −20(2) | −16(2) | −6(2) |
| C(6') | 65(2) | 54(2) | 42(1) | −8(1) | −18(1) | −1(1) |
| Cl(2) | 243(2) | 110(1) | 80(1) | 12(1) | −39(1) | 26(1) |
| F(2) | 88(2) | 106(2) | 93(2) | −12(2) | −22(2) | −44(2) |
| C(19) | 62(2) | 77(2) | 62(2) | −26(2) | −12(2) | −5(2) |
| C(20) | 85(3) | 98(3) | 66(2) | −20(2) | −31(2) | 10(2) |
| C(21) | 117(3) | 74(3) | 51(2) | −11(2) | −10(2) | 18(2) |
| C(22) | 104(3) | 70(2) | 60(2) | −9(2) | 8(2) | −8(2) |
| C(23) | 58(2) | 73(2) | 60(2) | −13(2) | −3(1) | −6(2) |
| C(24) | 50(2) | 60(2) | 47(2) | −23(1) | −4(1) | −2(1) |
| Cl(2') | 243(2) | 110(1) | 80(1) | 12(1) | −39(1) | 26(1) |
| F(2') | 88(2) | 106(2) | 93(2) | −12(2) | −22(2) | −44(2) |
| C(19') | 58(2) | 73(2) | 60(2) | −13(2) | −3(1) | −6(2) |
| C(20') | 104(3) | 70(2) | 60(2) | −9(2) | 8(2) | −8(2) |
| C(21') | 117(3) | 74(3) | 51(2) | −11(2) | −10(2) | 18(2) |
| C(22') | 85(3) | 98(3) | 66(2) | −20(2) | −31(2) | 10(2) |
| C(23') | 62(2) | 77(2) | 62(2) | −26(2) | −12(2) | −5(2) |
| C(24') | 50(2) | 60(2) | 47(2) | −23(1) | −4(1) | −2(1) |
| N(1) | 30(1) | 59(1) | 32(1) | −3(1) | −4(1) | −7(1) |
| N(2) | 49(1) | 38(1) | 37(1) | −11(1) | −5(1) | 0(1) |
| O(1) | 58(1) | 107(2) | 55(1) | −23(1) | −26(1) | 6(1) |
| O(2) | 64(1) | 66(1) | 50(1) | −21(1) | −23(1) | 12(1) |
| O(3) | 66(1) | 62(1) | 52(1) | −27(1) | −19(1) | 11(1) |
| O(4) | 92(2) | 64(1) | 56(1) | −32(1) | −20(1) | 10(1) |
| O(5) | 62(1) | 51(1) | 34(1) | −5(1) | −2(1) | −9(1) |
| O(6) | 76(1) | 43(1) | 70(1) | −4(1) | 32(1) | −14(1) |
| O(7) | 45(1) | 68(1) | 69(1) | −29(1) | −22(1) | 13(1) |
| O(8) | 45(1) | 35(1) | 53(1) | −9(1) | −4(1) | 2(1) |
| O(1W) | 56(1) | 50(1) | 51(1) | −3(1) | −12(1) | 1(1) |
| C(7) | 68(2) | 73(2) | 45(2) | −12(1) | −14(1) | −12(2) |
| C(8) | 38(1) | 51(1) | 36(1) | −4(1) | −3(1) | 0(1) |
| C(9) | 42(1) | 76(2) | 39(1) | −1(1) | −9(1) | −4(1) |
| C(10) | 38(1) | 87(2) | 48(2) | 10(1) | −8(1) | 6(1) |
| C(11) | 45(1) | 60(2) | 55(2) | 9(1) | 2(1) | 13(1) |
| C(12) | 41(1) | 46(1) | 47(1) | 0(1) | 3(1) | 0(1) |
| C(13) | 34(1) | 43(1) | 34(1) | 2(1) | −1(1) | −4(1) |
| C(14) | 30(1) | 44(1) | 31(1) | −4(1) | −1(1) | 0(1) |
| C(15) | 41(1) | 38(1) | 45(1) | 0(1) | −12(1) | −7(1) |
| C(16) | 44(1) | 43(1) | 39(1) | −3(1) | −6(1) | 4(1) |
| C(17) | 39(1) | 73(2) | 42(1) | −1(1) | −3(1) | −23(1) |
| C(18) | 41(1) | 46(1) | 39(1) | −4(1) | 2(1) | −14(1) |
| C(25) | 65(2) | 62(2) | 51(2) | −22(1) | −9(1) | −8(1) |
| C(26) | 55(1) | 37(1) | 37(1) | −8(1) | 1(1) | −2(1) |
| C(27) | 72(2) | 41(1) | 39(1) | −9(1) | −2(1) | −6(1) |
| C(28) | 79(2) | 39(1) | 43(1) | −10(1) | 11(1) | 1(1) |
| C(29) | 62(2) | 45(2) | 48(2) | −2(1) | 7(1) | 8(1) |
| C(30) | 58(2) | 45(2) | 42(1) | −1(1) | −1(1) | 1(1) |
| C(31) | 54(1) | 34(1) | 34(1) | −4(1) | 2(1) | −4(1) |
| C(32) | 50(1) | 30(1) | 33(1) | −4(1) | −6(1) | 0(1) |
| C(33) | 63(2) | 45(1) | 54(2) | −9(1) | 17(1) | −28(1) |
| C(34) | 59(2) | 38(1) | 58(2) | −9(1) | −1(1) | −22(1) |
| C(35) | 46(1) | 46(1) | 56(2) | −17(1) | 16(1) | −11(1) |
| C(36) | 39(1) | 36(1) | 53(1) | −15(1) | 12(1) | −13(1) |

Step 4. Synthesis of methyl 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (C50)

A solution of C48 (500 mg of the foamy white solid from above, corrected for p-toluenesulfonic acid: 1.25 mmol) in acetonitrile (6 mL) was treated with N,N-diisopropylethylamine (0.68 mL, 3.9 mmol) and allowed to stir for 5 minutes at 45° C. After addition of P15 (319 mg, 1.08 mmol), stirring at 45° C. was continued for 7.25 hours, whereupon the reaction mixture was diluted with water (6 mL) and acetonitrile (2 mL) at 45° C. The resulting heterogeneous mixture was allowed to cool to room temperature and stir for 72 hours. More water (5 mL) was added, and after a further 30 minutes of stirring, the solid was collected via filtration and washed with a mixture of acetonitrile and water (15:85, 3×5 mL), to afford C50 as a white solid with a slight pink cast. Yield: 605 mg, 1.02 mmol, 82%. LCMS m/z 592.0♦ $[M+H]^+$. $^1H$ NMR (400 MHz, chloroform-d) δ 8.17 (d, J=1.6 Hz, 1H), 7.96 (dd, J=8.5, 1.5 Hz, 1H), 7.73 (d, J=8.4 Hz, 1H), 7.51 (dd, J=8.0, 8.0 Hz, 1H), 7.19 (br s, 1H), 7.18-7.14 (m, 2H), 6.85-6.79 (m, 1H), 6.76-6.71 (m, 2H), 5.26-5.18 (m, 1H), 4.73 (dd, component of ABX pattern, J=15.3, 5.9 Hz, 1H), 4.67 (dd, component of ABX pattern, J=15.3, 3.5 Hz, 1H), 4.63-4.55 (m, 1H), 4.38 (ddd, J=9.1, 6.0, 5.9 Hz, 1H), 3.94 (s, 5H), 3.03-2.89 (m, 2H), 2.77-2.65 (m, 2H), 2.51-2.39 (m, 1H), 2.34-2.20 (m, 2H), 1.91-1.76 (m, 4H).

Step 5. Synthesis of 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid (5, Free Acid)

A suspension of C50 (595 mg, 1.00 mmol) in methanol (10 mL) was heated to 45° C. and treated with aqueous sodium hydroxide solution (1 M; 2.01 mL, 2.01 mmol). After 21 hours at 45° C., the reaction mixture was allowed to cool to room temperature; it was then treated with aqueous citric acid solution (1 M, 1 mL), which brought the pH to 5 to 6. Water (10 mL) was added, and the mixture was stirred for 1 hour, whereupon the solid was collected by filtration. It was washed with a mixture of methanol and water (1:10, 3×5 mL), to afford a solid (433 mg). A portion of this material (300 mg) was stirred with a mixture of heptane and ethyl acetate (1:3, 5 mL) at 40° C. for 1 hour; after cooling to room temperature with continued stirring, the solid was collected via filtration, and washed with a mixture of heptane and ethyl acetate (3:1, 3×3 mL) to afford 5, free acid, as a white solid. Yield: 260 mg, 0.450 mmol, corresponding to 65% for the entire reaction. LCMS m/z 578.0♦ $[M+H]^+$. $^1H$ NMR (400 MHz, DMSO-$d_6$) δ 12.75 (v br s, 1H), 8.26 (br s, 1H), 7.79 (dd, J=8.4, 1.6 Hz, 1H), 7.66-7.56 (m, 3H), 7.40 (dd, J=8.3, 2.0 Hz, 1H), 7.35 (s, 1H), 6.87-6.75 (m, 3H), 5.13-5.03 (m, 1H), 4.76 (dd, component of ABX pattern, J=15.3, 7.2 Hz, 1H), 4.62 (dd, component of ABX pattern, J=15.2, 2.8 Hz, 1H), 4.46-4.38 (m, 1H), 4.34 (ddd, J=9.0, 5.9, 5.8 Hz, 1H), 3.84 (AB quartet, $J_{AB}$=13.5 Hz, $\Delta\nu_{AB}$=67.7 Hz, 2H), 3.00 (br d, J=11.2 Hz, 1H), 2.84 br (d, J=11.3 Hz, 1H), 2.71-2.56 (m, 2H), 2.45-2.34 (m, 1H), 2.28-2.08 (m, 2H), 1.84-1.65 (m, 4H).

This material was determined to be of the same absolute configuration as Example 5 above by comparison of its biological activity with that of both 4 and 5: in Assay 2, this sample of 5, free acid exhibited an $EC_{50}$ of 25 nM (geometric mean of 3 replicates). The activity in Assay 2 for the ammonium salts of Example 4 and Example 5 were >20000 nM (2 replicates) and 20 nM (geometric mean of 3 replicates), respectively.

Synthesis of Example 5, 1,3-dihydroxy-2-(hydroxymethyl)propan-2-aminium salt 1, 3-Dihydroxy-2-(hydroxymethyl)propan-2-aminium 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (5, 1,3-dihydroxy-2-(hydroxymethyl)propan-2-aminium salt)

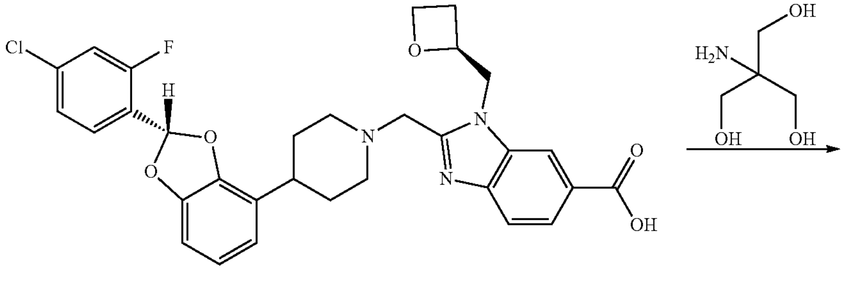

5, free acid

-continued

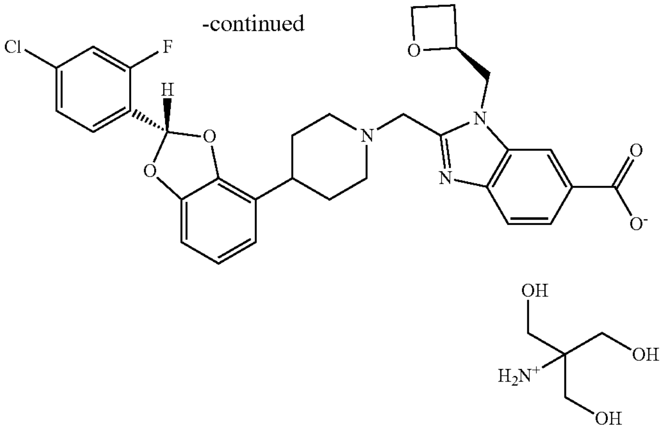

5, 1,3-dihydroxy-2-(hydroxymethyl)propan-2-aminium salt

A mixture of 5, free acid (0.50 g, 0.86 mmol) in tetrahydrofuran (4 mL) was treated with an aqueous solution of 2-amino-2-(hydroxymethyl)propane-1,3-diol (Tris, 1.0 M; 0.5 mL, 1.0 mmol). After 20 hours, the mixture was concentrated in vacuo with ethanol (2×6 mL). The mixture was treated with ethanol (4 mL). After stirring for 48 hours, the solid was collected via filtration, washed with ethanol (2×10 mL) and dried under vacuum to afford 5, 1,3-dihydroxy-2-(hydroxymethyl)propan-2-aminium salt, as a white solid. Yield: 410 mg, 0.586 mmol, 68%. $^1$H NMR (600 MHz, DMSO-$d_6$), characteristic peaks: δ 8.19 (s, 1H), 7.78 (br d, J=8.4 Hz, 1H), 7.62-7.58 (m, 2H), 7.55 (d, J=8.3 Hz, 1H), 7.40 (dd, J=8.4, 2.0 Hz, 1H), 7.35 (s, 1H), 6.85-6.80 (m, 2H), 6.79 (dd, J=6.9, 2.4 Hz, 1H), 5.11-5.05 (m, 1H), 4.73 (dd, J=15.2, 7.2 Hz, 1H), 4.60 (dd, J=15.3, 2.9 Hz, 1H), 4.45-4.39 (m, 1H), 4.34 (ddd, J=9.0, 6.0, 5.8 Hz, 1H), 3.91 (d, J=13.5 Hz, 1H), 3.74 (d, J=13.5 Hz, 1H), 2.99 (br d, J=11.1 Hz, 1H), 2.85 (br d, J=11.3 Hz, 1H), 2.68-2.59 (m, 2H), 2.44-2.37 (m, 1H), 2.25-2.18 (m, 1H), 2.17-2.10 (m, 1H), 1.80-1.69 (m, 4H). mp=168° C. to 178° C.

Examples 6 and 7

Ammonium 2-({4-[(2R)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (6) and Ammonium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (7)

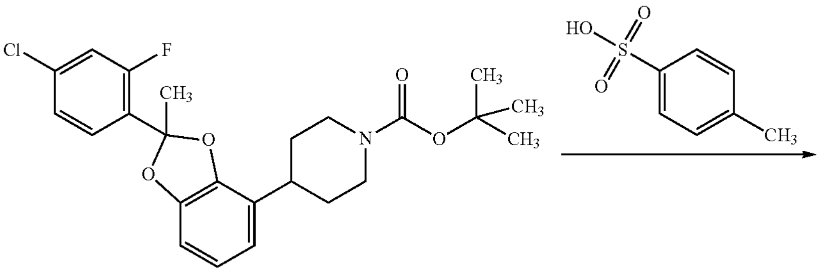

P2

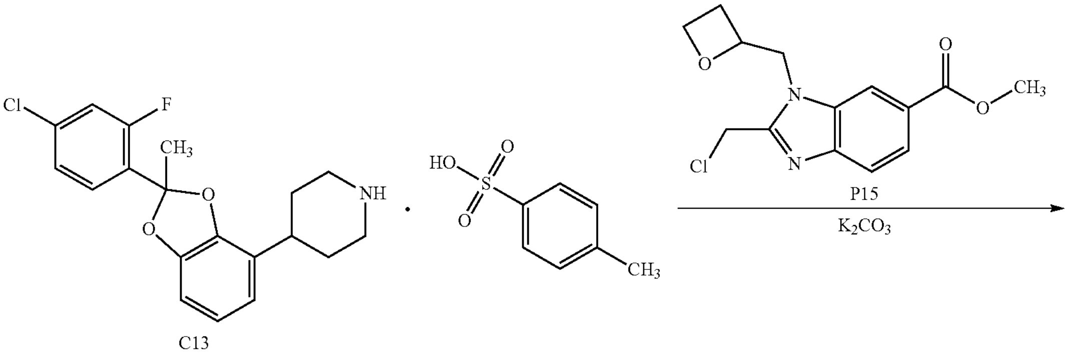

C13

-continued
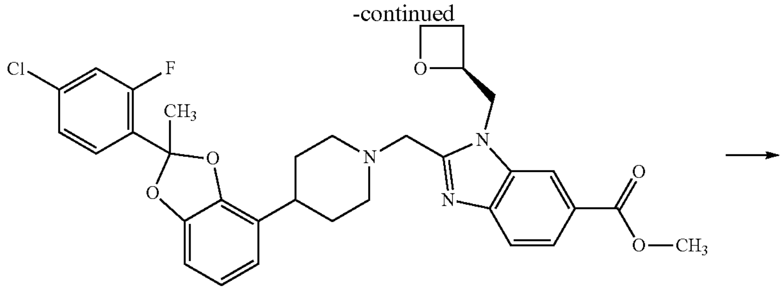
C51
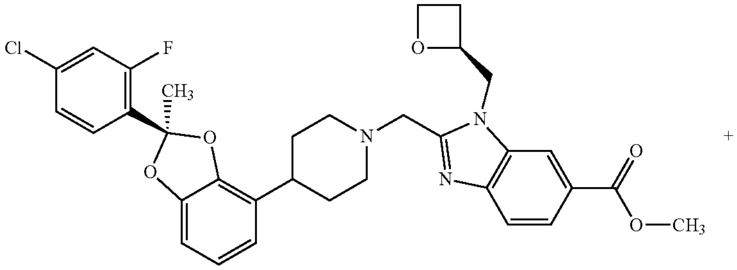
C52
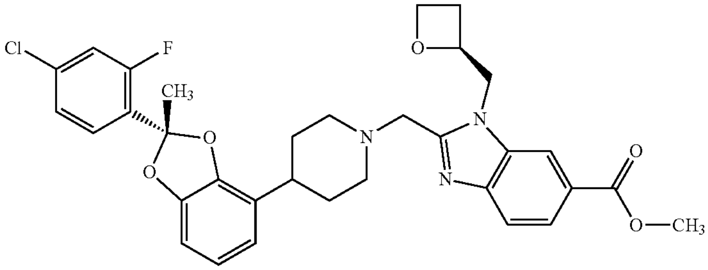
C53
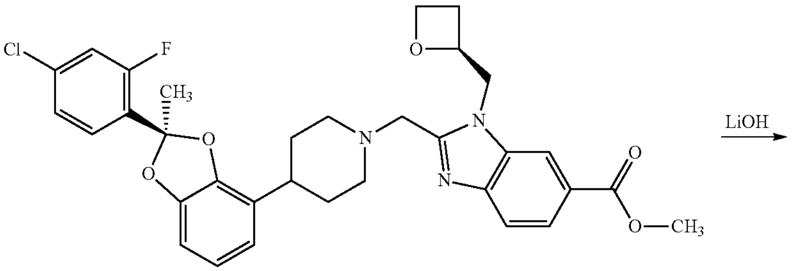
C52
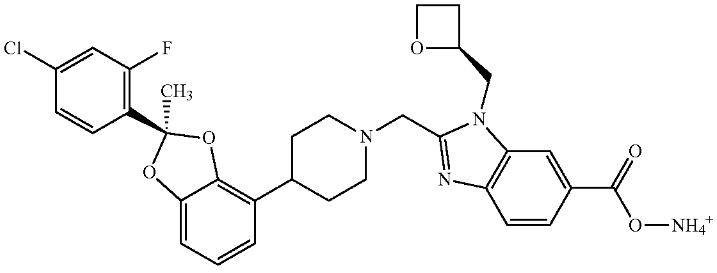
6

-continued

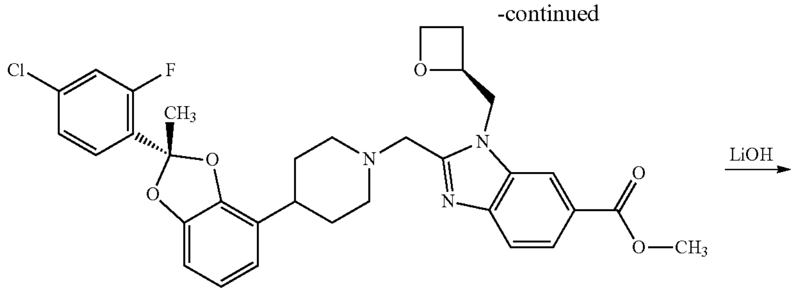

C52

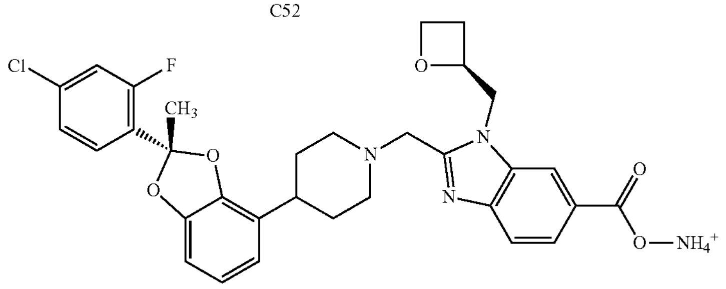

7

Step 1. Synthesis of 4-[2-(4-Chloro-2-Fluorophenyl)-2-Methyl-1,3-Benzodioxol-4-Yl]Piperidine, p-Toluenesulfonate Salt (C13)

A solution of P2 (150 mg, 0.335 mmol) and p-toluenesulfonic acid monohydrate (159 mg, 0.836 mmol) in ethyl acetate (2.0 mL) was stirred at 60° C. for 3.5 hours. The reaction mixture was concentrated in vacuo to afford C13 as a brown oil, which was used directly in the following step. LCMS m/z 348.1♦ $[M+H]^+$.

Step 2. Synthesis of methyl 2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C51)

To a suspension of C13 (from the previous step; 50.335 mmol) and potassium carbonate (232 mg, 1.68 mmol) in acetonitrile (5.0 mL) was added P15 (99.1 mg, 0.336 mmol). The reaction mixture was stirred at 60° C. for 10 hours, whereupon it was filtered, and the filtrate was concentrated in vacuo. After the residue (390 mg) had been combined with the material from a similar reaction carried out using C13 (50.11 mmol), it was diluted with water (20 mL) and extracted with a mixture of dichloromethane and methanol (10:1, 3×30 mL). The combined organic layers were dried over sodium sulfate, filtered, concentrated in vacuo, and subjected to preparative thin-layer chromatography (Eluent: 1:1 dichloromethane/methanol), providing C51, a mixture of diastereomers, as a colorless oil. Combined yield: 80.6 mg, 0.133 mmol, 30% over 2 steps. LCMS m/z 606.2♦ $[M+H]^+$.

Step 3. Isolation of Methyl 2-({4-[(2R)-2-(4-Chloro-2-Fluorophenyl)-2-Methyl-1,3-Benzodioxol-4-Yl]Piperidin-1-Yl}Methyl)-1-[(2S)-Oxetan-2-Ylmethyl]-1H-Benzimidazole-6-Carboxylate (C52) and Methyl 2-({4-[(2S)-2-(4-Chloro-2-Fluorophenyl)-2-Methyl-1,3-Benzodioxol-4-Yl]Piperidin-1-Yl}Methyl)-1-[(2S)-Oxetan-2-Ylmethyl]-1H-Benzimidazole-6-Carboxylate (C53)

Separation of C51 (180 mg, 0.297 mmol) into its component diastereomers was carried out via repeated SFC [Column: Chiral Technologies Chiralpak AD, 10 μm; Mobile phase: 65:35 carbon dioxide/(ethanol containing 0.1% ammonium hydroxide)]. The first-eluting diastereomer was designated as C52. Yield: 61.2 mg, 0.101 mmol, 34%. LCMS m/z 627.9♦ $[M+Na^+]$. Retention time: 5.03 minutes (Column: Chiral Technologies Chiralpak AD-3, 4.6×150 mm, 3 μm; Mobile phase A: carbon dioxide; Mobile phase B: ethanol containing 0.05% diethylamine; Gradient: 5% to 40% B over 5.5 minutes, then held at 40% B for 3.0 minutes; Flow rate: 2.5 mL/minute).

The second-eluting diastereomer was designated as C53. Upon analysis, this material proved to be contaminated with the corresponding ethyl ester; it was taken into the hydrolysis step (to generate 7) as this mixture. Yield: 40.0 mg, 66.0 μmol, 22%. LCMS m/z 606.0♦ $[M+H]^+$. Retention time: 5.19 minutes (Analytical conditions identical to those used for C52).

The indicated absolute stereochemistries at the dioxolane were assigned via potency correlation of 7 with a sample of 7, free acid synthesized from intermediate P3 (see below, Alternate Synthesis of Example 7, free acid); the absolute stereochemistry of P3 was established via single-crystal X-ray structure determination of C8 (see above).

Step 4. Synthesis of ammonium 2-({4-[(2R)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (6)

Aqueous lithium hydroxide solution (2 M; 0.990 mL, 1.98 mmol) was added to a solution of C52 (60 mg, 99 μmol) in a mixture of methanol (1.0 mL) and tetrahydrofuran (1.0 mL), and the reaction mixture was stirred at 20° C. for 16 hours. Trifluoroacetic acid was added until the pH of the reaction mixture reached 7, whereupon it was concentrated in vacuo, and the residue was purified using reversed-phase HPLC (Column: Agela Durashell C18, 5 μm; Mobile phase A: 0.05% ammonium hydroxide in water; Mobile phase B: acetonitrile; Gradient: 29% to 49% B), affording 6 as a white solid. Yield: 14.4 mg. 23.6 μmol, 24%. LCMS m/z 592.0♦ $[M+H]^+$. $^1H$ NMR (400 MHz, methanol-$d_4$), characteristic peaks: δ 8.35 (d, J=1.3 Hz, 1H), 7.97 (dd, J=8.5, 1.5 Hz, 1H), 7.67 (d, J=8.5 Hz, 1H), 7.58 (dd, J=8.3, 8.3 Hz, 1H), 7.28 (dd, J=10.9, 2.0 Hz, 1H), 7.21 (br dd, J=8.4, 1.9 Hz, 1H), 6.81-6.75 (m, 1H), 6.74-6.68 (m, 2H), 5.33-5.25 (m, 1H), 4.72 (dd, J=15.4, 2.7 Hz, 1H), 4.49 (dt, J=9.1, 6.0 Hz, 1H), 4.03 (AB quartet, $J_{AB}$=13.9 Hz, $\Delta v_{AB}$=47.8 Hz, 2H), 3.14 (br d, J=11 Hz, 1H), 3.02 (br d, J=11.5 Hz, 1H), 2.88-2.78 (m, 1H), 2.77-2.68 (m, 1H), 2.60-2.50 (m, 1H), 2.47-2.32 (m, 2H), 2.03 (d, J=1.1 Hz, 3H), 2.01-1.87 (m, 2H), 1.87-1.78 (br m, 2H).

Step 5. Synthesis of ammonium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (7)

Aqueous lithium hydroxide solution (2 M; 0.642 mL, 1.28 mmol) was added to a solution of C53 (38.9 mg, 64.2 μmol) in a mixture of methanol (1.0 mL) and tetrahydrofuran (1.0 mL). After the reaction mixture had been stirred at 20° C. for 16 hours, it was adjusted to pH 7 by addition of trifluoroacetic acid, concentrated in vacuo, and purified using reversed-phase HPLC (Column: Agela Durashell C18, 5 μm; Mobile phase A: 0.05% ammonium hydroxide in water; Mobile phase B: acetonitrile; Gradient: 0% to 80% B), affording 7 as a white solid. Yield: 25.1 mg, 41.2 μmol, 64%. LCMS m/z 591.9♦ $[M+H]^+$. $^1$H NMR (400 MHz, methanol-$d_4$), characteristic peaks: δ 8.34 (d, J=1.5 Hz, 1H), 7.98 (dd, J=8.5, 1.6 Hz, 1H), 7.68 (d, J=8.5 Hz, 1H), 7.58 (dd, J=8.3, 8.3 Hz, 1H), 7.28 (dd, J=10.9, 2.0 Hz, 1H), 7.20 (br dd, J=8.4, 1.9 Hz, 1H), 6.81-6.74 (m, 1H), 6.74-6.67 (m, 2H), 5.33-5.23 (m, 1H), 4.73 (dd, J=15.4, 2.7 Hz, 1H), 4.68-4.61 (m, 1H), 4.48 (dt, J=9.1, 5.9 Hz, 1H), 4.05 (AB quartet, $J_{AB}$=13.9 Hz, $\Delta v_{AB}$=44.1 Hz, 2H), 3.15 (br d, J=11.7 Hz, 1H), 3.03 (br d, J=11.6 Hz, 1H), 2.87-2.69 (m, 2H), 2.60-2.49 (m, 1H), 2.48-2.33 (m, 2H), 2.03 (br s, 3H), 2.01-1.77 (m, 4H).

Alternate Synthesis of Example 7, Free Acid 2-({4-[(2S)-2-(4-Chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid (7, Free Acid

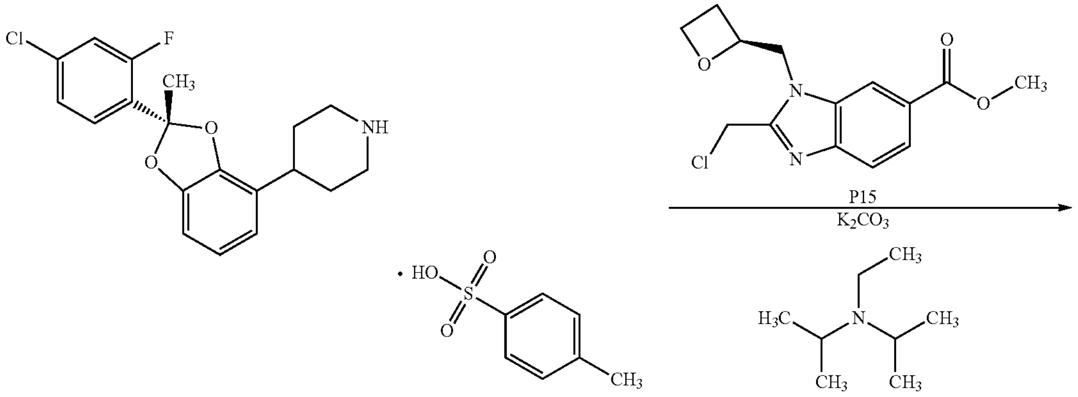

P3

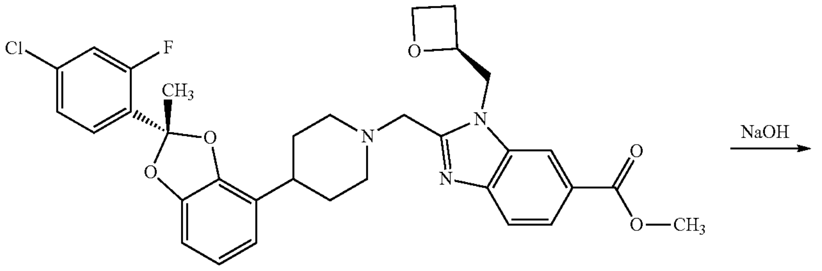

C53

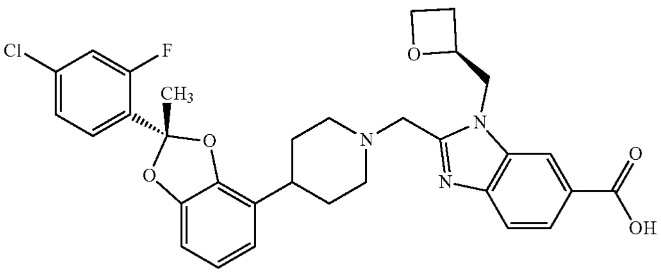

7, free acid

Step 1. Synthesis of methyl 2-({4-[(2S)-2-(4-chloro-2-fluorophenyl)-2-methy-1,3-benzodioxol-4-yl]piperidin-1-yl}methyl)-1 [(2S)-oxetan-2-y/methyl]-1H-benzimidazole-6-carboxylate (C53)

N,N-Diisopropylethylamine (15.1 mL, 86.9 mmol) was added to a mixture of P3 (8.22 g, 15.8 mmol) in acetonitrile (185 mL); after stirring for 5 minutes, P15 (4.57 g, 15.5 mmol) was added, and the reaction mixture was heated at 45° C. After 4 hours, the reaction mixture was concentrated in vacuo to half of its original volume, and the resulting mixture was diluted with water (100 mL) and extracted with ethyl acetate (2×100 mL). The combined organic layers were washed with water (50 mL), dried over magnesium sulfate, filtered, and concentrated in vacuo. Silica gel chromatography (Gradient: 50% to 100% ethyl acetate in heptane) afforded C53 as a white solid. Yield: 8.4 g, 13.9 mmol, 88%. LCMS m/z 606.1♦ $[M+H]^+$. $^1H$ NMR (600 MHz, DMSO-$d_6$) δ 8.30 (s, 1H), 7.82 (br d, J=8.4 Hz, 1H), 7.67 (d, J=8.4 Hz, 1H), 7.58-7.53 (m, 2H), 7.33 (dd, J=8.4, 2.1 Hz, 1H), 6.80-6.76 (m, 2H), 6.76-6.72 (m, 1H), 5.14-5.07 (m, 1H), 4.81 (dd, J=15.2, 7.2 Hz, 1H), 4.67 (dd, J=15.3, 2.8 Hz, 1H), 4.51-4.44 (m, 1H), 4.37 (ddd, J=8.9, 5.9, 5.9 Hz, 1H), 3.97 (d, J=13.6 Hz, 1H), 3.87 (s, 3H), 3.78 (d, J=13.5 Hz, 1H), 3.02 (brd, J=11.1 Hz, 1H), 2.86 (brd, J=11.3 Hz, 1H), 2.74-2.60 (m, 2H), 2.48-2.41 (m, 1H), 2.29-2.22 (m, 1H), 2.21-2.14 (m, 1H), 2.02 (s, 3H), 1.83-1.73 (m, 2H), 1.73-1.64 (m, 2H).

Step 2. Synthesis of 2-({4-[(2S)-2-(4-Chloro-2-Fluorophenyl)-2-Methy-1,3-Benzodioxol-4-Yl]Piperidin-1-Yl}Methyl)-1-[(2S)-Oxetan-2-Ylmethyl]-1H-Benzimidazole-6-Carboxylic Acid (7, Free Acid)

A mixture of C53 (8.40 g, 14.0 mmol) in methanol (135 mL) was heated at 45° C., and treated with aqueous sodium hydroxide solution (1 M; 27.7 mL, 27.7 mmol). After 20 hours, the reaction mixture was concentrated in vacuo to half its original volume. The resulting mixture was diluted with water (100 mL), and aqueous citric acid solution (1 M, 15 mL) was used to adjust the pH to 5 to 6. The resultant solid was filtered, washed with water (2×15 mL), and transferred to a separatory funnel as a solution in ethyl acetate (50 mL); residual water was removed in this way. The organic layer was dried over magnesium sulfate, filtered, combined with four previously prepared batches from a similar procedure (amount of C53 used in these reactions was 987 mg, 1.63 mmol; 1.15 g, 1.90 mmol; 8.57 g, 14.1 mmol; and 12.6 g, 20.8 mmol) and concentrated in vacuo. The resulting sticky solid was treated with 10% ethyl acetate in heptane (500 mL). After 4 hours, the solid was collected via filtration and washed with 10% ethyl acetate in heptane (2×25 mL) to afford 7, free acid, as a white solid. Yield 29.4 g, 0.527 mmol, 74% for combined reactions. LCMS 592.2♦ $[M+H]^+$. $^1H$ NMR (600 MHz, DMSO-$d_6$): δ 12.74 (br s, 1H), 8.28 (s, 1H), 7.80 (br d, J=8.4 Hz, 1H), 7.64 (d, J=8.4 Hz, 1H), 7.59-7.52 (m, 2H), 7.33 (dd, J=8.4, 2.1 Hz, 1H), 6.81-6.76 (m, 2H), 6.76-6.72 (m, 1H), 5.14-5.07 (m, 1H), 4.79 (dd, J=15.3, 7.3 Hz, 1H), 4.65 (dd, J=15.2, 2.8 Hz, 1H), 4.51-4.45 (m, 1H), 4.38 (ddd, J=9.0, 5.9, 5.9 Hz, 1H), 3.96 (br d, J=13.6 Hz, 1H), 3.78 (br d, J=13.5 Hz, 1H), 3.02 (br d, J=11.1 Hz, 1H), 2.86 (br d, J=11.1 Hz, 1H), 2.74-2.60 (m, 2H), 2.48-2.41 (m, 1H), 2.29-2.21 (m, 1H), 2.21-2.14 (m, 1H), 2.02 (s, 3H), 1.83-1.74 (m, 2H), 1.74-1.64 (m, 2H). This material was determined to be of the same absolute configuration as Example 7 above by comparison of its biological activity with that of both 6 and 7: in Assay 2, this sample of 7, free acid exhibited an $EC_{50}$ of 4.3 nM (geometric mean of 3 replicates). The activity in Assay 2 for the ammonium salts of Example 6 and Example 7 were 2400 nM (geometric mean of 5 replicates) and 2.9 nM (geometric mean of 8 replicates), respectively.

Synthesis 7S-1. Synthesis of Example 7, 1,3-dihydroxy-2-(hydroxymethyl)propan-2-aminium salt 1,3-Dihydroxy-2-(hydroxymethyl)propan-2-aminium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (7, 1,3-dihydroxy-2-(hydroxymethyl)propan-2-aminium salt)

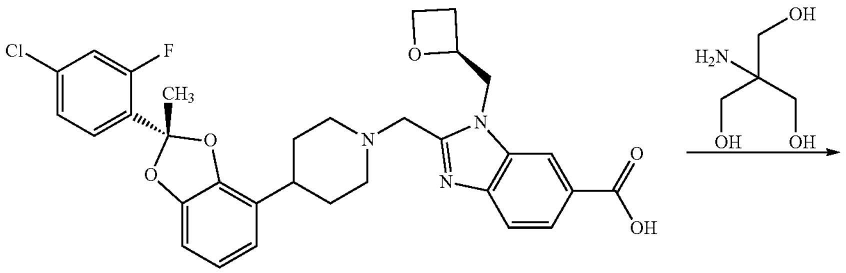

7, free acid

-continued

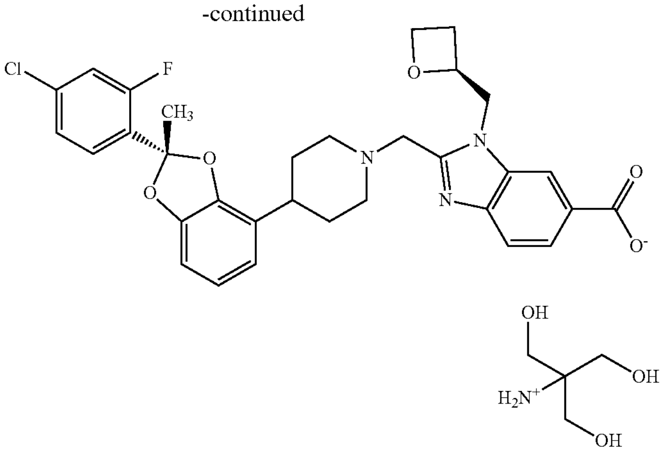

7, 1,3-dihydroxy-2-(hydroxymethyl)propan-2-aminium salt

A mixture of 7, free acid (2.00 g, 3.38 mmol) in tetrahydrofuran (16 mL) was treated with an aqueous solution of 2-amino-2-(hydroxymethyl)propane-1,3-diol (Tris, 1.0 M; 3.55 mL, 3.55 mmol). After 18 hours, the reaction mixture was concentrated in vacuo and treated with ethanol (30 mL). After this mixture had been stirred for 23 hours, the solid was collected via filtration and washed with ethyl acetate (2×10 mL) to afford 7, 1,3-dihydroxy-2-(hydroxymethyl) propan-2-aminium salt as a white solid. Yield: 1.41 g, 1.98 mmol, 59%. LCMS m/z 592.3♦ $[M+H]^+$. $^1H$ NMR (600 MHz, DMSO-$d_6$), characteristic peaks: δ 8.20 (s, 1H), 7.79 (d, J=8.4 Hz, 1H), 7.59-7.52 (m, 3H), 7.33 (br d, J=8.5 Hz, 1H), 6.81-6.72 (m, 3H), 5.14-5.07 (m, 1H), 4.76 (dd, J=15.2, 7.2 Hz, 1H), 4.63 (br d, J=15.4 Hz, 1H), 4.50-4.44 (m, 1H), 4.37 (ddd, J=8.9, 5.9, 5.9 Hz, 1H), 3.94 (d, J=13.4 Hz, 1H), 3.76 (d, J=13.4 Hz, 1H), 3.01 (br d, J=11.1 Hz, 1H), 2.86 (br d, J=11.2 Hz, 1H), 2.73-2.60 (m, 2H), 2.5-2.41 (m, 1H), 2.27-2.20 (m, 1H), 2.20-2.13 (m, 1H), 2.02 (s, 3H), 1.83-1.64 (m, 4H). mp=175° C. to 180° C.

Synthesis 7S-2. Alternative synthesis of Example 7, 1,3-dihydroxy-2-(hydroxymethyl)propan-2-aminium salt A 3.3 M solution of 2-amino-2-(hydroxymethyl)-1,3-propanediol (1.0 equiv., 1.93 L) in water was added to a solution of 7, free acid (3.74 kg) in isopropanol (20 L) at 65° C. Additional isopropanol (19 L) was added followed by methanol (19 L) while maintaining the temperature at 65° C. The mixture was slowly cooled to 45° C. over 2 hours then held for at 45° C. for at least 12 hours. The mixture was then cooled to 5° C. over 3 hours then held at 5° C. for at least 3 hours. The mixture was then filtered and the solid was collected washed with ethyl acetate (2×10 mL) to afford 7, 1,3-dihydroxy-2-(hydroxymethyl)propan-2-aminium salt as a white solid (yield: 3.64 kg, 80.9%). LCMS and $^1H$ NMR data were obtained, which are substantially the same as those in Synthesis 7S-1 shown above.

Acquisition of Powder X-Ray Diffraction (PXRD) Data for Form I of Example 7, 1,3-Dihydroxy-2-(Hydroxymethyl)Propan-2-Aminium Salt The white solid of the tris salt of Example 7 (from both Synthesis 7S-1 and Synthesis 7S-2) was submitted for PXRD analysis and found to be a crystalline material (which is designated as Form I of this anhydrous crystal form). Powder X-ray diffraction analysis was conducted using a Bruker AXS D8 Endeavor diffractometer equipped with a Cu radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected at the Cu wavelength ($CuK_\alpha$=1.5418λ) in the Theta-Theta goniometer from 3.0 to 40.0 degrees 2-Theta using a step size of 0.01 degrees and a step time of 1.0 second. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941). One diffraction pattern was consistently observed and is provided in FIG. 1. A list of diffraction peaks expressed in terms of the degree 2θ and relative intensities with a relative intensity of ≥3.0% of a PXRD from a sample obtained by Synthesis 7S-2 is provided above in Table X1.

TABLE X1

| Angle (2theta) | Relative Intensity (%) |
|---|---|
| 3.7 | 74.3 |
| 7.3 | 83.3 |
| 8.1 | 12.5 |
| 8.5 | 6.5 |
| 10.1 | 6.6 |
| 13.6 | 3.5 |
| 14.7 | 49.8 |
| 15.2 | 7.9 |
| 15.5 | 28.7 |

TABLE X1-continued

| Angle (2theta) | Relative Intensity (%) |
|---|---|
| 15.9 | 18.3 |
| 16.9 | 60.8 |
| 17.4 | 26.3 |
| 17.7 | 11.4 |
| 17.9 | 13.5 |
| 18.9 | 75.4 |
| 19.7 | 18.7 |
| 20.2 | 100.0 |
| 20.9 | 24.8 |
| 21.5 | 14.8 |
| 22.2 | 31.7 |
| 22.9 | 10.1 |
| 23.5 | 34.6 |
| 23.7 | 8.2 |
| 24.4 | 6.5 |
| 24.9 | 8.7 |
| 25.2 | 6.4 |
| 25.9 | 14.7 |
| 26.4 | 48.6 |
| 26.7 | 12.5 |
| 27.5 | 15.8 |
| 27.9 | 6.1 |
| 28.3 | 10.5 |

TABLE X1-continued

| Angle (2theta) | Relative Intensity (%) |
|---|---|
| 29.5 | 15.5 |
| 29.8 | 12.6 |
| 30.2 | 12.1 |
| 30.9 | 3.4 |
| 31.7 | 16.4 |
| 33.3 | 17.2 |
| 34.0 | 14.9 |
| 35.8 | 4.8 |
| 37.5 | 3.2 |
| 38.6 | 5.3 |

Examples 8 and 9

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X1 (8) [from C56]; and 2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (9) [from C57]

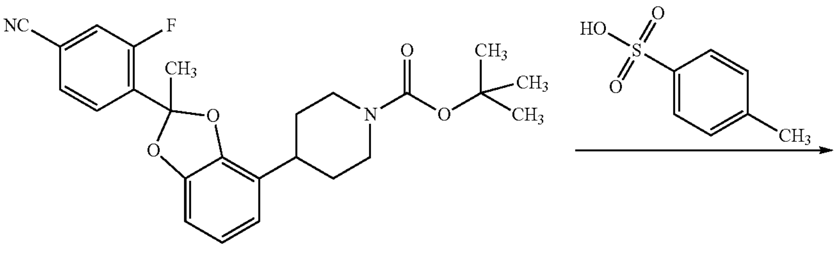

P4

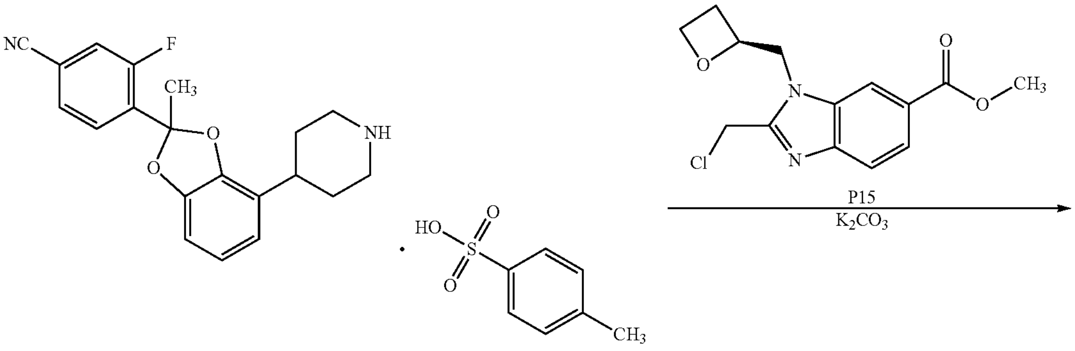

C54

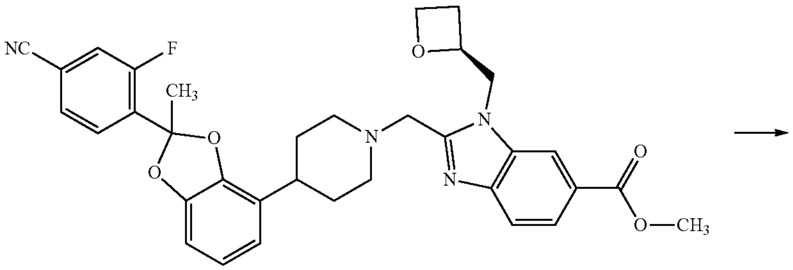

C55

-continued
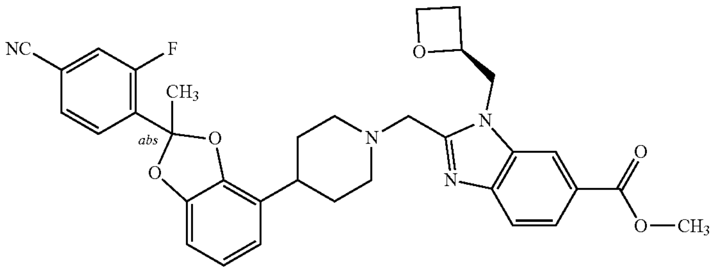
+
ENT-1
C56
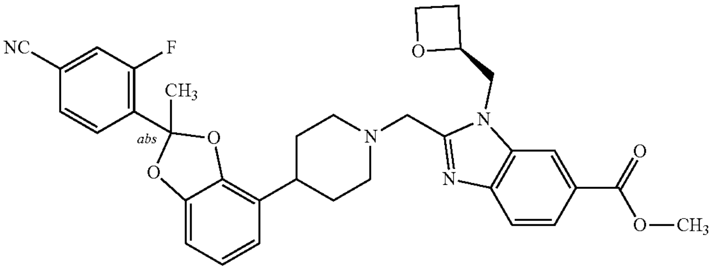
ENT-2
C57
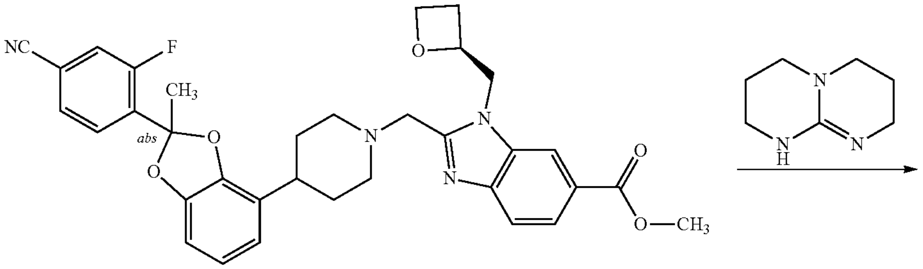
ENT-1
C56
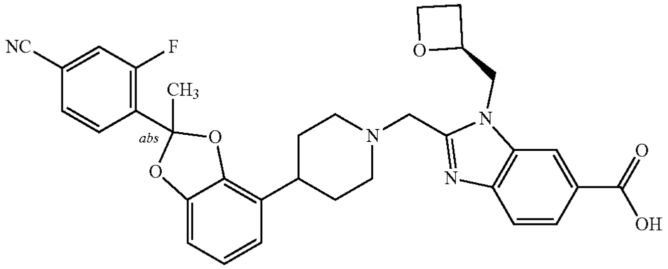
DIAST-X1
8
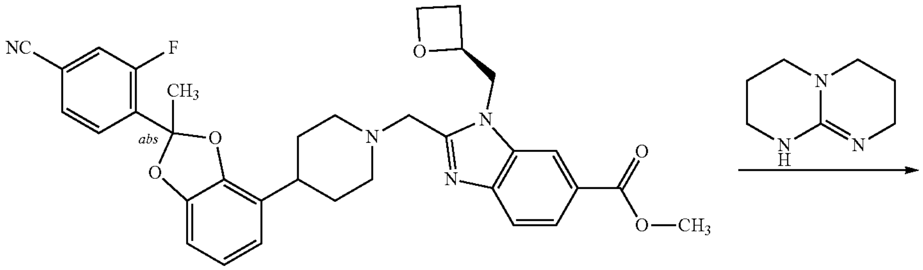
ENT-2
C57

-continued

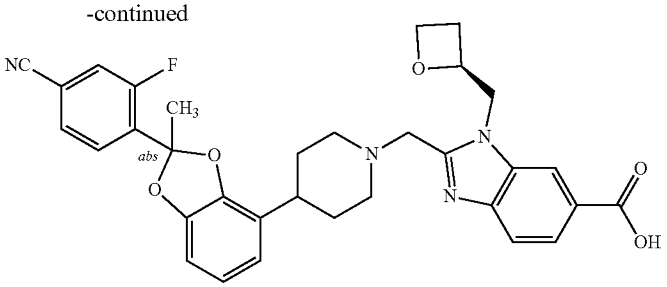

DIAST-X2
9

Step 1. Synthesis of 3-Fluoro-4-[2-Methyl-4-(Piperidin-4-Yl)-1,3-Benzodioxol-2-Yl]Benzonitrile, p-Toluenesulfonate Salt (C54)

To a solution of P4 (161 mg, 0.367 mmol) in ethyl acetate (8 mL) was added p-toluenesulfonic acid (158 mg, 0.919 mmol), and the reaction mixture was stirred at 65° C. for 16 hours. Removal of solvent in vacuo provided C54 as a dark yellow gum; this material was taken directly into the next step.

Step 2. Synthesis of methyl 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C55)

To a solution of C54 (from the previous step; 50.367 mmol) in acetonitrile (3.7 mL) was added potassium carbonate (219 mg, 1.58 mmol), followed by P15 (115 mg, 0.390 mmol). The reaction mixture was stirred at 50° C. for 20 hours, whereupon it was diluted with ethyl acetate (10 mL) and filtered. The filter cake was washed with ethyl acetate (3×10 mL), and the combined filtrates were concentrated in vacuo. Silica gel chromatography (Gradient: 0% to 100% ethyl acetate in petroleum ether) afforded C55 as a dark yellow oil. Yield: 191.0 mg, 0.320 mmol, 87% over 2 steps. LCMS m/z 619.1 $[M+Na^+]$.

Step 3. Isolation of methyl 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylate, ENT-1 (C56) and methyl 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylate, ENT-2 (C57)

Separation of C55 (191 mg, 0.320 mmol) into its component stereoisomers at the dioxolane was carried out via SFC [Column: Chiral Technologies ChiralCel OD, 5 μm; Mobile phase: 3:2 carbon dioxide/2-propanol]. The first-eluting isomer, obtained as a white gum, was designated as ENT-1 (C56). Yield: 114 mg; this material contained residual ethanol. LCMS m/z 597.1 $[M+H]^+$. Retention time 4.40 minutes (Column: Chiral Technologies ChiralCel OD-3, 4.6×100 mm, 3 μm; Mobile phase A: carbon dioxide; Mobile phase B: 2-propanol containing 0.05% diethylamine; Gradient: 5% to 40% B over 4.5 minutes, then held at 40% B for 2.5 minutes; Flow rate: 2.8 mL/minute).

The second-eluting isomer was repurified using SFC [Column: Chiral Technologies ChiralCel OD, 5 μm; Mobile phase: 55:45 carbon dioxide/(2-propanol containing 0.1% ammonium hydroxide)], to afford a colorless gum that was designated as ENT-2 (C57). Yield: 50 mg, 83.8 μmol, 26%. LCMS m/z 597.1 $[M+H]^+$. Retention time 4.74 minutes (Analytical conditions identical to those used for C56).

Step 4. Synthesis of 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X1 (8) [from C56]

A solution of C56 (114 mg, 0.191 mmol) in acetonitrile (10 mL) was treated with an aqueous solution of 1,3,4,6,7,8-hexahydro-2H-pyrimido[1,2-a]pyrimidine (0.97 M, 394 μL, 0.382 mmol), and the reaction mixture was stirred at room temperature for 23 hours. More of the aqueous solution of 1,3,4,6,7,8-hexahydro-2H-pyrimido[1,2-a]pyrimidine (0.97 M, 394 μL, 0.382 mmol) was added, and stirring was continued for 6 hours, whereupon the pH was carefully adjusted to 7 to 8 by addition of 1 M hydrochloric acid. After removal of volatiles in vacuo, purification was carried out using reversed-phase HPLC (Column: Agela Durashell C18, 5 μm; Mobile phase A: 0.05% ammonium hydroxide in water; Mobile phase B: acetonitrile; Gradient: 30% to 50% B) to provide 8 as a white solid. Yield: 22.2 mg, 38.1 μmol, 20%. LCMS m/z 583.3 $[M+H]^+$. $^1H$ NMR (400 MHz, methanol-$d_4$): δ 8.19 (d, J=1.4 Hz, 1H), 7.94 (dd, J=8.4, 1.5 Hz, 1H), 7.77 (dd, J=7.7, 7.7 Hz, 1H), 7.64 (dd, J=10.6, 1.6 Hz, 1H), 7.58 (d, J=8.4 Hz, 1H), 7.57 (dd, J=8.0, 1.5 Hz, 1H), 6.81-6.75 (m, 1H), 6.75-6.68 (m, 2H), 5.34-5.25 (m, 1H), 4.73 (dd, J=15.3, 3.0 Hz, 1H), 4.67-4.59 (m, 1H), 4.49 (dt, J=9.2, 6.0 Hz, 1H), 3.96 (AB quartet, $J_{AB}$=13.7 Hz, $\Delta\nu_{AB}$=41.2 Hz, 2H), 3.06 (br d, J=11 Hz, 1H), 2.95 (br d, J=11 Hz, 1H), 2.87-2.76 (m, 1H), 2.71 (tt, J=12.0, 3.9 Hz, 1H), 2.61-2.50 (m, 1H), 2.36-2.21 (m, 2H), 2.06 (s, 3H), 1.95-1.72 (m, 4H).

Step 5. Synthesis of 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (9) [from C57]

A solution of C57 (50 mg, 84 μmol) in acetonitrile (10 mL) was treated with an aqueous solution of 1,3,4,6,7,8-hexahydro-2H-pyrimido[1,2-a]pyrimidine (0.97 M; 173 μL, 0.168 mmol). The reaction was stirred at room temperature (about 25° C.) for 16 hours, whereupon an additional quantity of an aqueous solution of 1,3,4,6,7,8-hexahydro-2H-pyrimido[1,2-a]pyrimidine (0.97 M; 173 μL, 0.168 mmol) was added, and stirring was continued at 25° C. for 29 hours. The reaction mixture was then carefully adjusted to pH 7 to 8 by addition of 1 M hydrochloric acid; the resulting mixture was concentrated in vacuo and subjected to reversed-phase HPLC (Column: Xtimate™ C18, 5 μm; Mobile phase A: 0.05% ammonium hydroxide in water; Mobile phase B: acetonitrile; Gradient: 27% to 67% B), affording 9 as a white solid. Yield: 18.0 mg, 30.9 μmol, 37%. LCMS m/z 583.3 $[M+H]^+$. $^1H$ NMR (400 MHz, methanol-$d_4$) δ 8.36-8.33 (m, 1H), 7.97 (dd, J=8.5, 1.5 Hz, 1H), 7.78 (dd, J=7.7, 7.7 Hz, 1H), 7.70-7.63 (m, 2H), 7.57 (dd, J=8.0, 1.5 Hz, 1H), 6.83-6.76 (m, 1H), 6.76-6.71 (m, 2H), 5.34-5.25 (m, 1H), 4.95-4.85 (m, 1H, assumed; partially obscured by water peak), 4.73 (dd, component of ABX pattern, J=15.3, 2.7 Hz, 1H), 4.68-4.60 (m, 1H), 4.50 (dt, J=9.2, 6.0 Hz, 1H), 4.02 (AB quartet, $J_{AB}$=13.8 Hz, $\Delta\nu_{AB}$=48.2 Hz, 2H), 3.13 (br d, J=11 Hz, 1H), 3.01 (br d, J=11.5 Hz, 1H), 2.89-2.78 (m, 1H), 2.78-2.68 (m, 1H), 2.60-2.50 (m, 1H), 2.45-2.30 (m, 2H), 2.07 (br s, 3H), 2.00-1.86 (m, 2H), 1.83 (m, 2H).

Example 10

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (10) [from P9]

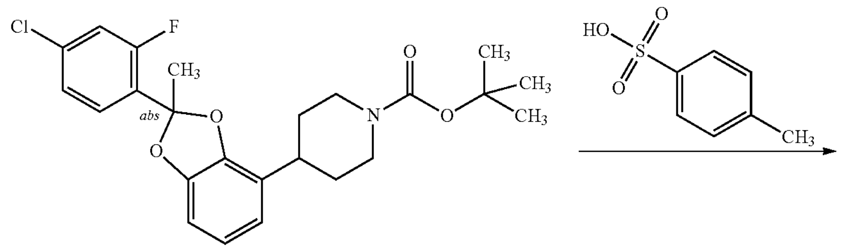

ENT-2

P4

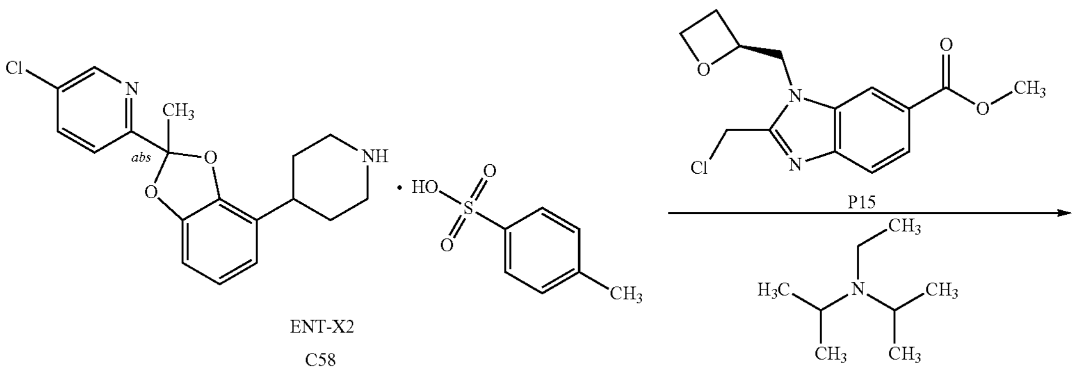

ENT-X2

C58

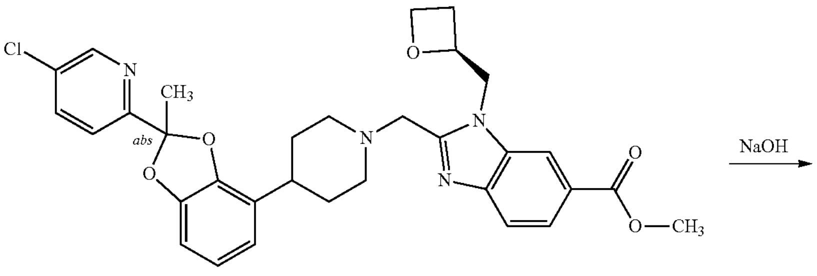

DIAST-Y2

C59

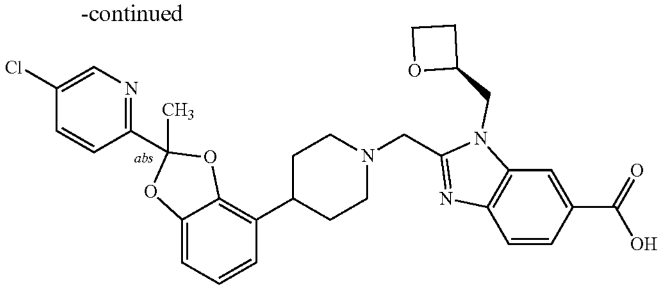

DIAST-X2
10

Step 1. Synthesis of 5-chloro-2-[2-methyl-4-(piperidin-4-yl)-1,3-benzodioxol-2-yl]pyridine, ENT-X2, p-toluenesulfonate salt (C58) [from P9]

A solution of P9 (228 mg, 0.529 mmol) in ethyl acetate (2.7 mL) was treated with p-toluenesulfonic acid monohydrate (116 mg, 0.610 mmol), and the reaction mixture was heated at 50° C. for 16 hours. It was then allowed to stir at room temperature overnight, whereupon the precipitate was collected via filtration and rinsed with a mixture of ethyl acetate and heptane (1:1, 2×20 mL) to provide C58 as a white solid. Yield: 227 mg, 0.451 mmol, 85%. LCMS m/z 331.0♦ [M+H]$^+$. $^1$H NMR (400 MHz, DMSO-d$_6$): δ 8.73 (d, J=2.4 Hz, 1H), 8.61-8.46 (br m, 1H), 8.35-8.18 (br m, 1H), 8.02 (dd, J=8.5, 2.5 Hz, 1H), 7.64 (d, J=8.5 Hz, 1H), 7.47 (d, J=7.8, 2H), 7.11 (d, J=7.8 Hz, 2H), 6.89-6.81 (m, 2H), 6.72 (pentet, J=4.0 Hz, 1H), 3.45-3.27 (m, 2H, assumed; partially obscured by water peak), 3.10-2.91 (m, 3H), 2.28 (s, 3H), 2.02 (s, 3H), 1.97-1.80 (m, 4H).

Step 2. Synthesis of methyl 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylate, DIAST-Y2 (C59) [from P9]

N,N-Diisopropylethylamine (0.234 mL, 1.34 mmol) was added to a solution of C58 (225 mg, 0.447 mmol) in acetonitrile (2.2 mL). After this mixture had been stirred for 5 minutes at 45° C., P15 (120 mg, 0.407 mmol) was added, and stirring was continued at 45° C. for 16 hours, whereupon P15 (11 mg, 37 µmol) was again added. After an additional 3 hours of stirring, the reaction mixture was treated with water (2.5 mL) and allowed to cool to room temperature. More water (5 mL) was added, and the resulting slurry was stirred for 2 hours, whereupon the solid was collected via filtration and washed with a mixture of acetonitrile and water (15:85, 3×5 mL) to afford C59 as an off-white solid (252 mg). This material contained some N,N-diisopropylethylamine by $^1$H NMR analysis, and was taken directly to the following step. LCMS m/z 589.1♦ [M+H]$^+$. $^1$H NMR (400 MHz, chloroform-d) 8.61 (d, J=2.3 Hz, 1H), 8.18 (d, J=1.5 Hz, 1H), 7.96 (dd, J=8.5, 1.5 Hz, 1H), 7.74 (d, J=8.5 Hz, 1H), 7.67 (dd, component of ABX pattern, J=8.4, 2.4 Hz, 1H), 7.59-7.51 (m, 1H), 6.82-6.75 (m, 1H), 6.74-6.66 (m, 2H), 5.28-5.19 (m, 1H), 4.75 (dd, component of ABX pattern, J=15.3, 6.0 Hz, 1H), 4.68 (dd, component of ABX pattern, J=15.3, 3.4 Hz, 1H), 4.67-4.58 (m, 1H), 4.41 (ddd, J=9.1, 5.9, 5.9 Hz, 1H), 3.95 (s, 2H), 3.95 (s, 3H), 3.07-2.89 (m, 2H), 2.81-2.69 (m, 2H), 2.53-2.41 (m, 1H), 2.37-2.22 (m, 2H), 2.05 (s, 3H), 1.93-1.74 (m, 4H).

Step 3. Synthesis of 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (10) [from P9]

A suspension of C59 (from the previous step; 250 mg, 50.407 mmol) in methanol (2 mL) was heated to 40° C., whereupon aqueous sodium hydroxide solution (1 M; 0.81 mL, 0.81 mmol) was added. After 17 hours, the reaction mixture was allowed to cool to room temperature, and the pH was adjusted to 5 to 6 with 1 M aqueous citric acid solution. The resulting mixture was diluted with water (2 mL), stirred for 2 hours, and extracted with ethyl acetate (3×5 mL); the combined organic layers were washed with saturated aqueous sodium chloride solution (5 mL), dried over sodium sulfate, filtered, and concentrated in vacuo to provide a foamy solid. This material was taken up in a mixture of ethyl acetate and heptane (1:1, 4 mL), heated to 50° C., and then allowed to cool and stir overnight. Filtration afforded 10 as a white solid. Yield: 179 mg, 0.311 mmol, 76% over 2 steps. LCMS m/z 575.1♦ [M+H]$^+$. $^1$H NMR (400 MHz, DMSO-d$_6$) δ 12.73 (br s, 1H), 8.71 (d, J=2.5 Hz, 1H), 8.27 (d, J=1.5 Hz, 1H), 8.00 (dd, J=8.5, 2.5 Hz, 1H), 7.80 (dd, J=8.4, 1.6 Hz, 1H), 7.64 (d, J=8.4 Hz, 1H), 7.60 (d, J=8.5 Hz, 1H), 6.83-6.72 (m, 3H), 5.14-5.06 (m, 1H), 4.77 (dd, component of ABX pattern, J=15.2, 7.2 Hz, 1H), 4.63 (dd, component of ABX pattern, J=15.2, 2.8 Hz, 1H), 4.50-4.42 (m, 1H), 4.37 (ddd, J=9.0, 5.9, 5.9 Hz, 1H), 3.85 (AB quartet, J$_{AB}$=13.6 Hz, Δv$_{AB}$=71.5 Hz, 2H), 3.01 (br d, J=11.2 Hz, 1H), 2.85 (br d, J=11.2 Hz, 1H), 2.74-2.57 (m, 2H), 2.47-2.38 (m, 1H), 2.29-2.10 (m, 2H), 2.01 (s, 3H), 1.81-1.64 (m, 4H).

Synthesis 10S-1. Synthesis of Example 10, 1,3-dihydroxy-2-(hydroxymethyl)propan-2-aminium salt Synthesis of 1, 3-dihydroxy-2-(hydroxymethyl)propan-2-aminium 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylate, DIAST-X2 (10, 1,3-dihydroxy-2-(hydroxymethyl)propan-2-aminium salt) [from P9]

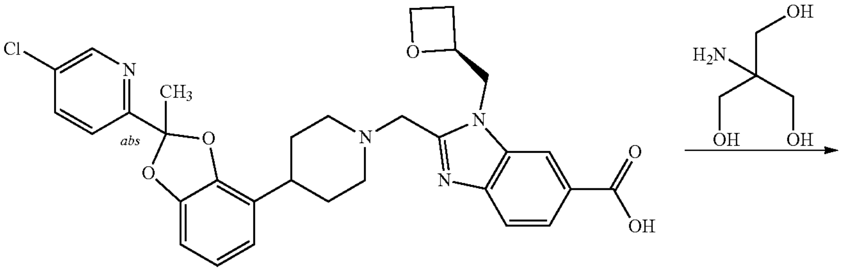

DIAST-X2

10

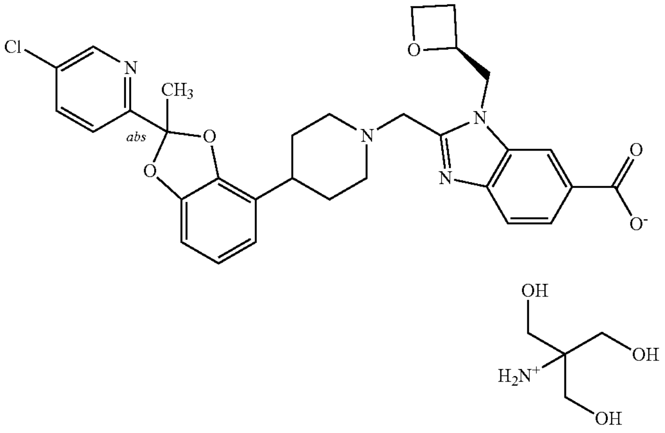

DIAST-X2

10, 1,3-dihydroxy-2-(hydroxymethyl)propan-2-aminium salt

A mixture of 10 (1.54 g, 2.68 mmol) in tetrahydrofuran (10 mL) was treated with an aqueous solution of 2-amino-2-(hydroxymethyl)propane-1,3-diol (Tris, 1.0 M; 2.81 mL, 2.81 mmol). After 24 hours, the reaction mixture was concentrated in vacuo with ethanol (2×50 mL). The residue was treated with ethanol (15 mL). After stirring for 20 hours, the solid was collected via filtration and washed with cold ethanol (5 mL) to afford 10, 1,3-dihydroxy-2-(hydroxymethyl)propan-2-aminium salt as a white solid. Yield: 1.41 g, 2.03 mmol, 76%. LCMS m/z 575.3♦ $[M+H]^+$. $^1H$ NMR (600 MHz, DMSO-$d_6$) δ 8.71 (d, J=2.5 Hz, 1H), 8.21 (br s, 1H), 8.00 (dd, J=8.5, 2.5 Hz, 1H), 7.79 (br d, J=8.4 Hz, 1H), 7.60 (d, J=8.5 Hz, 1H), 7.57 (d, J=8.4 Hz, 1H), 6.82-6.73 (m, 3H), 5.13-5.07 (m, 1H), 4.74 (dd, J=15.3, 7.2 Hz, 1H), 4.61 (dd, J=15.3, 2.9 Hz, 1H), 4.49-4.43 (m, 1H), 4.37 (ddd, J=9.0, 5.9, 5.9 Hz, 1H), 3.93 (d, J=13.6 Hz, 1H), 3.75 (d, J=13.5 Hz, 1H), 3.01 (br d, J=11.3 Hz, 1H), 2.86 (br d, J=11.4 Hz, 1H), 2.73-2.59 (m, 2H), 2.48-2.37 (m, 1H), 2.27-2.20 (m, 1H), 2.19-2.12 (m, 1H), 2.01 (s, 3H), 1.82-1.66 (m, 4H). mp=184° C. to 190° C.

Synthesis 10S-2. Alternative synthesis of Example 10, 1,3-dihydroxy-2-(hydroxymethyl)propan-2-aminium salt A mixture of 10 (8.80 gm, 15.3 mmol) in 2-methyltetrahydrofuran (90 ml) was concentrated in vacuo on a rotary evaporator, in a 37° C. water bath, to reduce the total volume to ~54 ml. Isopropanol (90 ml) was added to the mixture and then again concentrate the resulting mixture to a volume of ~54 ml. Isopropanol (135 ml) was added to the mixture, followed by addition of aqueous tris amine (3M; 5.0 ml, 0.98 equiv). The resulting mixture/solution was stirred at ambient temperature; and a solid precipitate began to form within ~15 min. The mixture was then stirred at ambient temperature for additional 5 hr. The resulting mixture/slurry was cooled to 0° C. and the cooled slurry was stirred for about another 2 hr. The slurry was filtered and washed with cold isopropanol (3×15 ml). The solid collected was allowed to Air dry on the collection funnel for about 90 min and then transfer to the vacuum oven for overnight drying. After ~16 hr at 50° C./23 inHg vacuum (with a slight nitrogen bleed) 8.66 gm of 10, 1,3-dihydroxy-2-(hydroxymethyl)propan-2-aminium salt was obtained as white solid; 99.8 area % by UPLC (yield:12.5 mmol, 81%). LCMS and $^1$H NMR data were obtained, which are substantially the same as those in Synthesis 10S-1 shown above.

Acquisition of Powder X-Ray Diffraction (PXRD) Data for Form a of Example 10, 1,3-Dihydroxy-2-(Hydroxymethyl)Propan-2-Aminium Salt (Also Known as Form a of Anhydrous Tris Salt of Compound Example 10)

The white solid of the tris salt of Example 10 (from both Synthesis 10S-1 and Synthesis 10S-2) was submitted for PXRD analysis and found to be a crystalline material (which is designated as Form A). Powder X-ray diffraction analysis was conducted using a Bruker AXS D8 Endeavor diffractometer equipped with a Cu radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected at the Cu wavelength ($CuK_\alpha$=1.5418λ) in the Theta-Theta goniometer from 3.0 to 40.0 degrees 2-Theta using a step size of 0.01 degrees and a step time of 1.0 second. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941). A list of diffraction peaks expressed in terms of the degree 2θ and relative intensities with a relative intensity of ≥3.0% of a PXRD from a sample obtained by Synthesis 10S-2 is provided above in Table X2.

TABLE X2

| Angle (2 theta) | Relative Intensity (%) |
|---|---|
| 3.9 | 18.4 |
| 7.7 | 36.3 |
| 8.1 | 10.4 |
| 8.7 | 3.4 |
| 10.2 | 4.1 |
| 14.6 | 5.8 |
| 15.2 | 30.1 |
| 15.7 | 45.5 |
| 16.0 | 31.3 |
| 16.8 | 8.7 |
| 17.6 | 86.0 |
| 19.2 | 46.6 |
| 19.5 | 25.4 |
| 19.8 | 31.4 |
| 20.2 | 25.0 |
| 21.1 | 100.0 |
| 21.4 | 40.2 |
| 22.2 | 37.0 |
| 23.0 | 19.8 |
| 24.3 | 43.0 |
| 25.0 | 9.9 |
| 26.0 | 15.8 |
| 27.3 | 35.3 |
| 28.2 | 14.1 |
| 29.3 | 19.7 |
| 29.8 | 11.7 |
| 31.6 | 9.3 |
| 32.8 | 6.0 |
| 34.0 | 14.4 |
| 34.5 | 12.1 |
| 35.4 | 3.0 |
| 36.5 | 4.1 |

Example 11

1-(2-Methoxyethyl)-2-({4-[2-methyl-2-(pyridin-3-yl)-1,3-benzodioxol-4-yl]piperidin-1-yl}methyl)-1H-benzimidazole-6-carboxylic acid, formate salt (11)

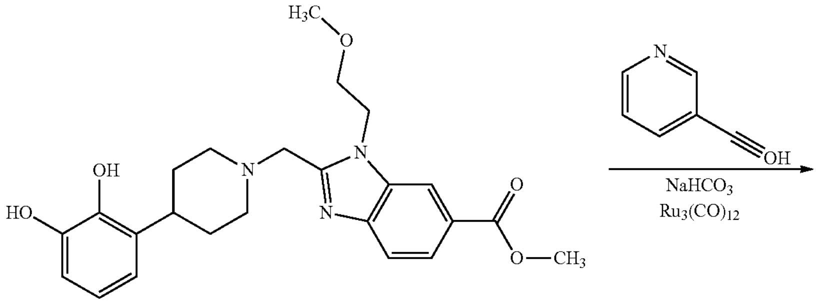

P14

-continued

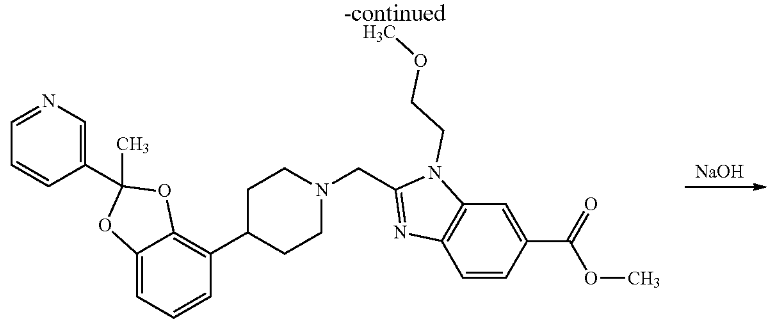

C60

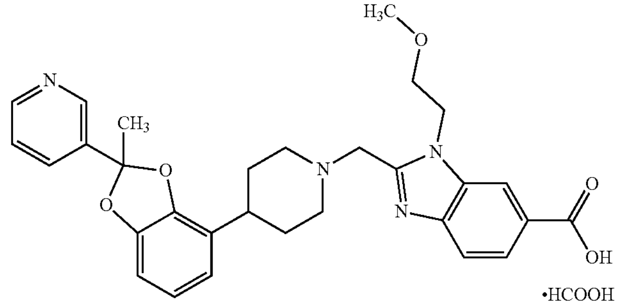

•HCOOH

11

This entire synthetic sequence was carried out in library format.

Step 1. Synthesis of methyl 1-(2-methoxyethyl)-2-({4-[2-methyl-2-(pyridin-3-yl)-1,3-benzodioxol-4-yl]piperidin-1-yl}methyl)-1H-benzimidazole-6-carboxylate (C60)

A mixture of P14 (44 mg, 100 μmol) and 3-ethynylpyridine (21 mg, 200 μmol) in toluene (800 μL) was treated with sodium bicarbonate (100 μmol), followed by triruthenium dodecacarbonyl (6 mg, 9 μmol). The reaction vial was then capped and shaken at 120° C. for 16 hours. Removal of solvent using a Speedvac® concentrator provided C60, which was taken directly into the following step.

Step 2. Synthesis of 1-(2-methoxyethyl)-2-({4-[2-methyl-2-(pyridin-3-yl)-1,3-benzodioxol-4-yl]piperidin-1-yl}methyl)-1H-benzimidazole-6-carboxylic acid, formate salt (11)

An aqueous solution of sodium hydroxide (1.0 M; 200 μL, 200 μmol) was added to a solution of C60 (from the previous step, 5100 μmol) in a mixture of methanol (400 μL) and tetrahydrofuran (400 μL). The reaction vial was capped and shaken at 80° C. for 16 hours, whereupon the reaction mixture was evaporated using a Speedvac® concentrator, and purified using reversed-phase HPLC (Column: Agela Durashell C18, 5 μm; Mobile phase A: 0.225% formic acid in water; Mobile phase B: acetonitrile; Gradient: 12% to 52% B) to afford 11. Yield: 2.2 mg, 4.2 μmol, 4% over 2 steps. LCMS m/z 529 $[M+H]^+$. Retention time: 2.47 minutes (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

Example 12

2-({4-[2-(4-Chloro-2-fluorophenyl)-2-methyl-1,3-benzodioxol-4-yl]piperidin-1-yl}methyl)-1-[2-(dimethylamino)ethyl]-1H-benzimidazole-6-carboxylic acid (12)

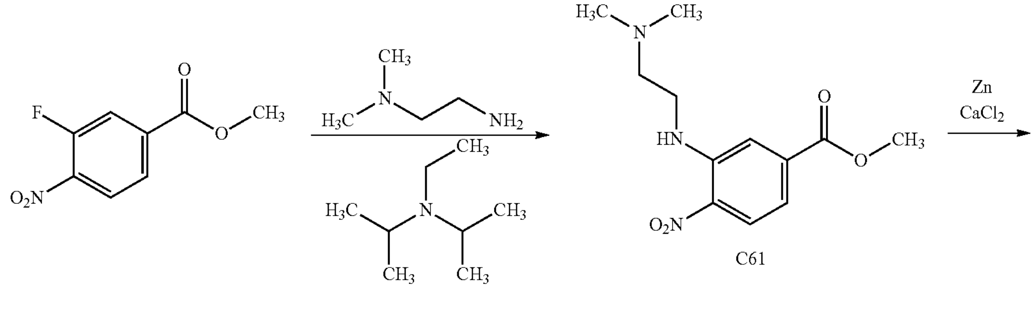

C61

-continued
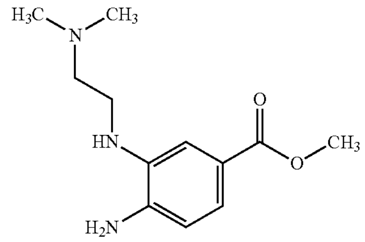
C62
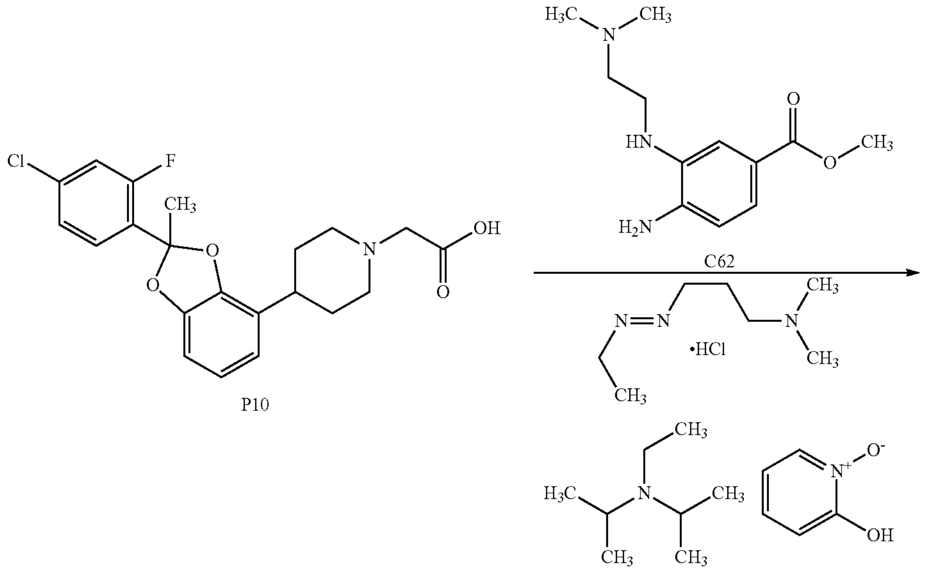
P10
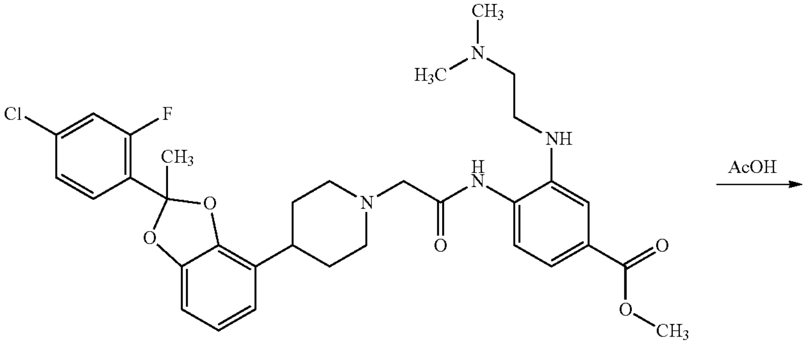
C63
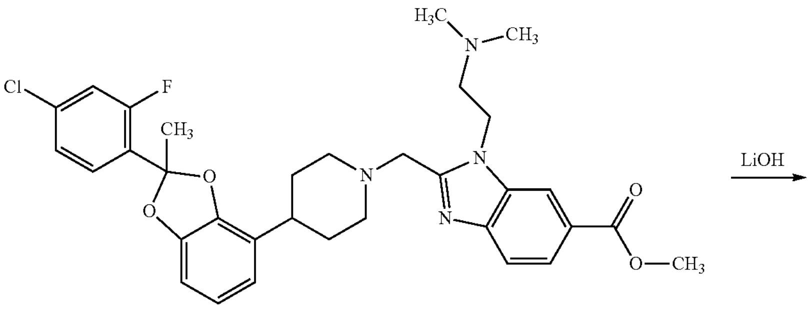
C64

-continued

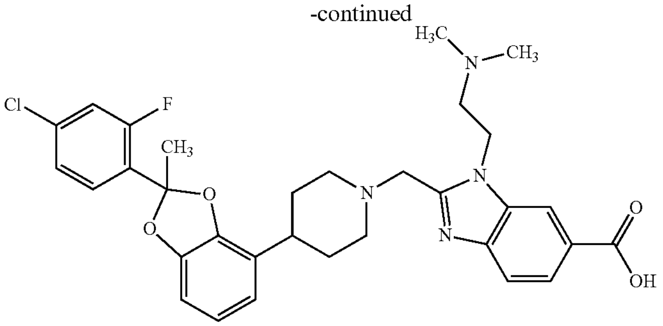

12

This entire synthetic sequence was carried out in library format.

Step 1. Synthesis of methyl 3-{[2-(dimethylamino) ethyl]amino}-4-nitrobenzoate (C61)

Methyl 3-fluoro-4-nitrobenzoate (0.2 M solution in N,N-dimethylformamide; 1 mL, 200 μmol) was treated with N,N-dimethylethane-1,2-diamine (18 mg, 200 μmol) and N,N-diisopropylethylamine (78 mg, 600 μmol). The reaction vial was then capped and shaken at 50° C. for 16 hours, whereupon the reaction mixture was evaporated using a Speedvac® concentrator to afford C61. This material was taken directly to the following step.

Step 2. Synthesis of methyl 4-amino-3-{[2-(dimethylamino)ethyl]amino}benzoate (C62)

Zinc dust was activated using dilute hydrochloric acid. Methanol (2 mL) was added to C61 (from the previous step, 5200 μmol), followed by an aqueous solution of calcium chloride (1.0 M; 200 μL, 200 μmol) and the activated zinc dust (130 mg, 2.0 mmol). The reaction vial was capped and shaken at 70° C. for 16 hours, whereupon the reaction mixture was filtered. The filtrate was concentrated using a Speedvac® concentrator, and the residue was taken up in water (2 mL) and then extracted with ethyl acetate (2×3 mL). The combined organic layers were evaporated using a Speedvac® concentrator to afford C62 (estimated to be 150 μmol), which was used directly in the next step.

Step 3. Synthesis of methyl 4-[({4-[2-(4-chloro-2-fluorophenyl)-2-methyl-1,3-benzodioxol-4-yl]piperidin-1-yl}acetyl)amino]-3-{[2-(dimethylamino)ethyl] amino}benzoate (C63)

Compound P10 (41 mg, 100 μmol) was added to C62 (from the previous step, approximately 150 μmol), and the mixture was treated with an N,N-dimethylacetamide solution of 2-hydroxypyridine 1-oxide and 1-[3-(dimethylamino)propyl]-3-ethylcarbodiimide hydrochloride (0.1 M in each; 1 mL, 100 μmol of each). N,N-Diisopropylethylamine (39 mg, 300 μmol) was then added, and the reaction vial was capped and shaken at 50° C. for 16 hours. The reaction mixture was then concentrated using a Speedvac® concentrator and purified using preparative thin-layer chromatography to provide C63, which was advanced directly to the following step.

Step 4. Synthesis of methyl 2-({4-[2-(4-chloro-2-fluorophenyl)-2-methyl-1,3-benzodioxol-4-yl]piperidin-1-yl}methyl)-1-[2-(dimethylamino)ethyl]-1H-benzimidazole-6-carboxylate (C64)

A mixture of acetic acid (500 μL) and C63 (from the previous step, 5100 μmol) was shaken in a capped vial at 150° C. for 2 hours, whereupon the reaction mixture was evaporated using a Speedvac® concentrator. The resulting C64 was advanced directly to the following step.

Step 5. Synthesis of 2-({4-[2-(4-chloro-2-fluorophenyl)-2-methyl-1,3-benzodioxol-4-yl]piperidin-1-yl}methyl)-1-[2-(dimethylamino)ethyl]-1H-benzimidazole-6-carboxylic acid (12)

A solution of C64 (from the previous step, 5100 μmol) in ethanol (500 μL) was treated with an aqueous solution of lithium hydroxide (2.0 M; 500 μL, 1 mmol), and the reaction mixture was shaken at 50° C. for 2 hours in a sealed vial. After the pH of the mixture had been adjusted to 7 by addition of 1.0 M hydrochloric acid, the resulting mixture was concentrated using a Speedvac® concentrator, and then purified via reversed-phase HPLC [Column: Agela Durashell C18, 5 μm; Mobile phase A: ammonium hydroxide in water (pH 10); Mobile phase B: acetonitrile; Gradient: 25% to 65% B] to afford 12. Yield: 7.0 mg, 12 μmol, 12% over 3 steps. LCMS m/z 593 $[M+H]^+$. Retention time: 2.45 minutes (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute).

Example 13
2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid (13)
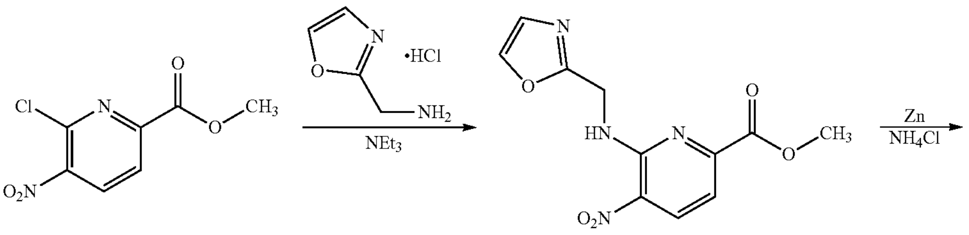
C65
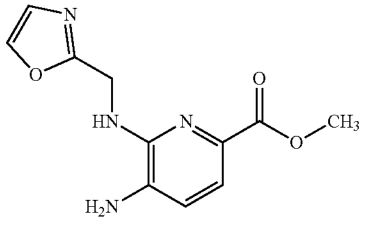
C66
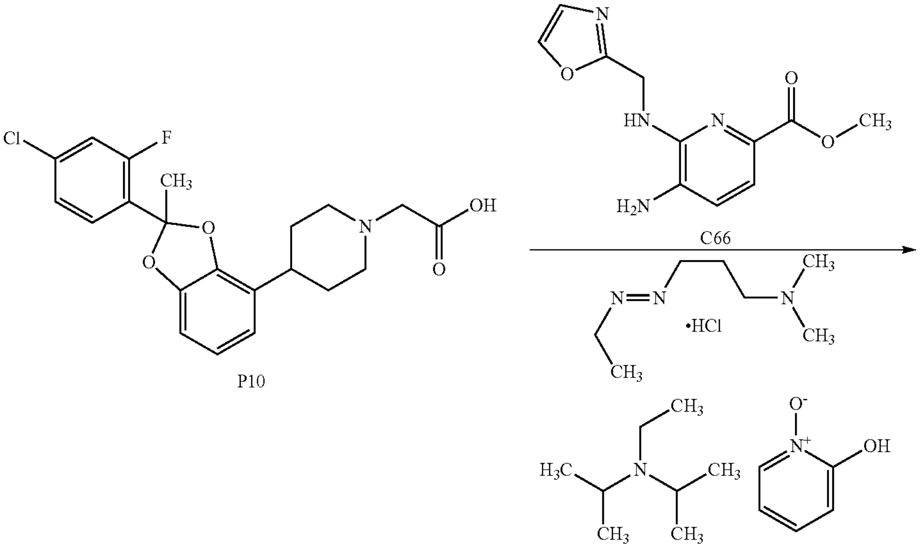
C66
P10
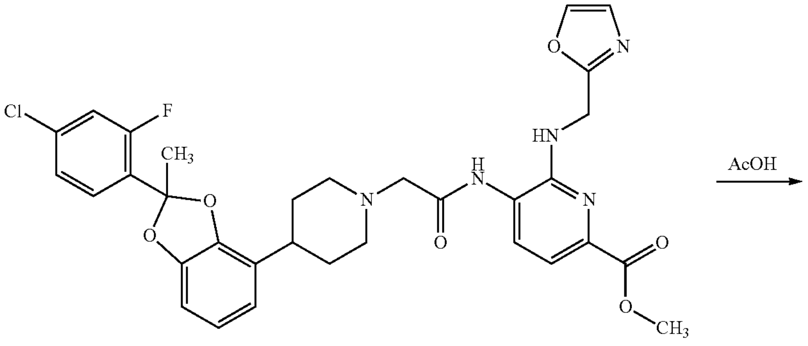
C67

-continued

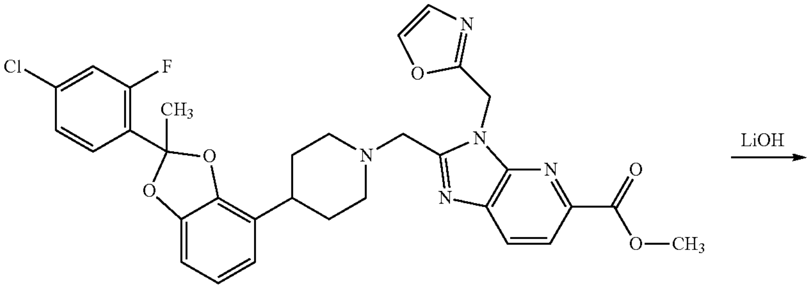

C68

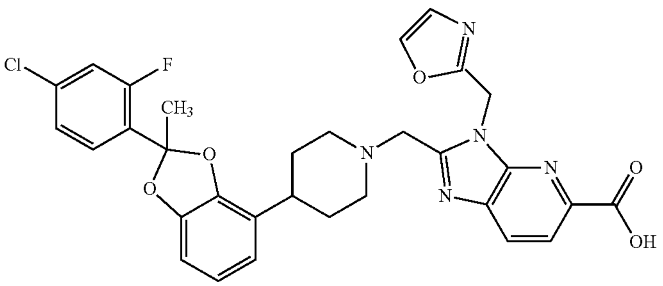

13

Step 1. Synthesis of methyl 6-[(1, 3-oxazol-2-ylmethyl)amino]-5-nitropyridine-2-carboxylate (C65)

Triethylamine (532 mg, 5.26 mmol) was added to a suspension of 1-(1,3-oxazol-2-yl)methanamine, hydrochloride salt (236 mg, 1.75 mmol) and methyl 6-chloro-5-nitropyridine-2-carboxylate (386 mg, 1.78 mmol) in tetrahydrofuran (5 mL). After the reaction mixture had been stirred at 25° C. for 14 hours, it was poured into water (30 mL) and extracted with dichloromethane (2×50 mL). The combined organic layers were dried over magnesium sulfate, filtered, and concentrated in vacuo; silica gel chromatography (Gradient: 0% to 5% methanol in dichloromethane) afforded C65 as a yellow solid. Yield: 310 mg, 1.11 mmol, 63%. LCMS m/z 278.7 $[M+H]^+$. $^1H$ NMR (400 MHz, chloroform-d) δ 8.69-8.61 (br m, 1H), 8.58 (d, J=8.4 Hz, 1H), 7.65 (d, J=0.8 Hz, 1H), 7.46 (d, J=8.4 Hz, 1H), 7.11 (d, J=1.0 Hz, 1H), 5.07 (d, J=5.3 Hz, 2H), 3.97 (s, 3H).
The remainder of this synthetic sequence was carried out in library format.

Step 2. Synthesis of methyl 5-amino-6-[(1,3-oxazol-2-ylmethyl)amino]pyridine-2-carboxylate (C66)

Aqueous ammonium chloride solution (5.0 M; 400 μL, 2.0 mmol), followed by activated zinc (131 mg, 2.0 mmol), was added to a solution of C65 (56 mg, 200 μmol) in methanol (2.0 mL). The reaction vial was then capped and shaken at 30° C. for 16 hours, whereupon the reaction mixture was filtered. The filtrate was concentrated using a Speedvac® concentrator, then mixed with water (1.0 mL) and extracted with dichloromethane (3×1.0 mL); the combined organic layers were evaporated using a Speedvac® concentrator to provide C66, which was taken directly into the following step.

Step 3. Synthesis of methyl 5-[({4-[2-(4-chloro-2-fluorophenyl)-2-methyl-1,3-benzodioxol-4-yl]piperidin-1-yl}acetyl) amino]-6-[(1, 3-oxazol-2-ylmethyl) amino]pyridine-2-carboxylate (C67)

A mixture of P10 (81 mg, 200 μmol) and C66 (from the previous step, 5200 μmol) was mixed with N,N-dimethylacetamide and then treated with N,N-diisopropylethylamine (100 μL, 600 μmol). A solution containing 1-[3-(dimethylamino)propyl]-3-ethylcarbodiimide hydrochloride (0.24 M) and 2-hydroxypyridine 1-oxide (0.1 M) in N,N-dimethylacetamide (1.0 mL, containing 240 μmol 1-[3-(dimethylamino)propyl]-3-ethylcarbodiimide hydrochloride and 100 μmol 2-hydroxypyridine 1-oxide) was added, and the reaction vial was capped and shaken at 50° C. for 16 hours. Volatiles were then removed using a Speedvac® concentrator, and the residue was subjected to preparative thin-layer chromatography to afford C67, which was advanced directly to the next step.

Step 4. Synthesis of methyl 2-({4-[2-(4-chloro-2-fluorophenyl)-2-methyl-1,3-benzodioxol-4-yl]piperidin-1-yl}methyl)-3-(1, 3-oxazol-2-ylmethyl)-3H-imidazo[4,5-b]pyridine-5-carboxylate (C68)

A mixture of acetic acid (1.0 mL) and C67 (from the previous step, 5200 μmol) was shaken at 150° C. for 2 hours, whereupon the reaction mixture was evaporated using a Speedvac® concentrator. The resulting C68 was used directly in the following step.

Step 5. Synthesis of 2-({4-[2-(4-chloro-2-fluorophenyl)-2-methyl-1,3-benzodioxol-4-yl]piperidin-1-yl}methyl)-3-(1, 3-oxazol-2-ylmethyl)-3H-imidazo [4,5-b]pyridine-5-carboxylic acid (13)

Aqueous lithium hydroxide solution (2.0 M; 1.0 mL, 2.0 mmol) was added to a mixture of C68 (from the previous step, 5200 μmol) in tetrahydrofuran (1.0 mL). After addition of methanol (500 μL), the reaction vial was capped and shaken at 50° C. for 16 hours. After removal of volatiles using a Speedvac® concentrator, dimethyl sulfoxide (1.0 mL) was added, and the pH was adjusted to 7 to 8 with concentrated hydrochloric acid. The resulting mixture was purified using reversed-phase HPLC [Column: Agela Durashell C18, 5 μm; Mobile phase A: ammonium hydroxide in water (pH 10); Mobile phase B: acetonitrile; Gradient: 24% to 64% B] to afford 13. Yield: 3.9 mg, 6.5 μmol, 3% over 4 steps. LCMS m/z 604 $[M+H]^+$. Retention time: 3.14 minutes (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

Example 14

2-({4-[(2S)-2-(4-Chloro-2-fluorophenyl)-2-methyl-1,3-benzodioxol-4-yl]piperidin-1-yl}methyl)-1-methyl-1H-benzimidazole-6-carboxylic acid (14)

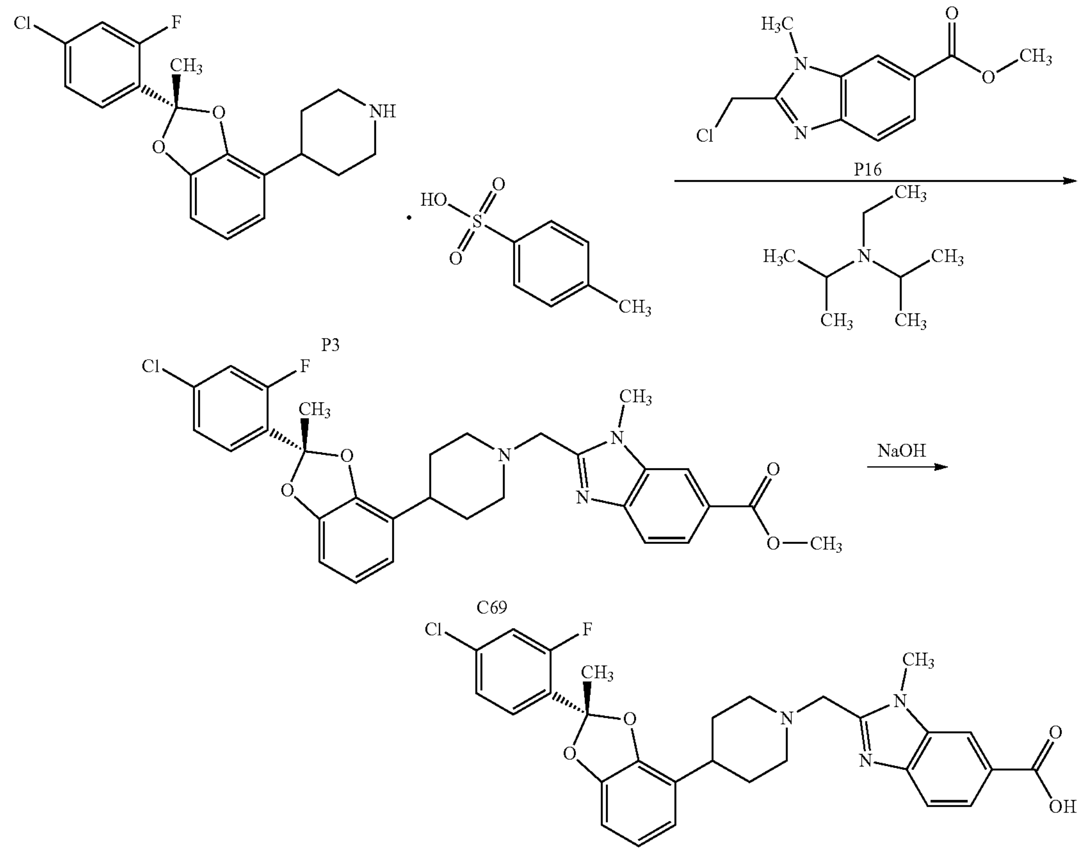

P3

C69

14

Step 1. Synthesis of methyl 2-({4-[(2S)-2-(4-chloro-2-fluorophenyl)-2-methyl-1,3-benzodioxol-4-yl]piperidin-1-yl}methyl)-1-methyl-1H-benzimidazole-6-carboxylate (C69)

N,N-Diisopropylethylamine (683 μL, 3.92 mmol), was added to a mixture of P3 (680 mg, 1.31 mmol) in acetonitrile (5.2 mL); this was allowed to stir for 5 minutes at 45° C., whereupon P16 (319 mg, 1.34 mmol) was added. Stirring was continued at 45° C. for 2.75 hours, and then water (6 mL) was added before allowing the reaction mixture to cool to room temperature and stir for 30 minutes. Solids were collected via filtration and washed with a mixture of acetonitrile and water (1:4, 3×5 mL) to afford C69 as a white solid. Yield: 635 mg, 1.15 mmol, 88%. LCMS m/z 550.1♦ $[M+H]^+$. $^1H$ NMR (400 MHz, chloroform-d) δ 8.15-8.12 (m, 1H), 7.97 (dd, J=8.5, 1.6 Hz, 1H), 7.74 (d, J=8.5 Hz, 1H), 7.50 (dd, J=8.2, 8.2 Hz, 1H), 7.16-7.07 (m, 2H), 6.79-6.73 (m, 1H), 6.72-6.65 (m, 2H), 3.98 (s, 3H), 3.96 (s, 3H), 3.88 (s, 2H), 3.04-2.93 (m, 2H), 2.76-2.66 (m, 1H), 2.37-2.25 (m, 2H), 2.04 (br s, 3H), 1.89-1.78 (m, 4H).

Step 2. Synthesis of 2-({4-[(2S)-2-(4-chloro-2-fluorophenyl)-2-methyl-1,3-benzodioxol-4-yl]piperidin-1-yl}methyl)-1-methyl-1H-benzimidazole-6-carboxylic acid (14)

A mixture of C69 (600 mg, 1.09 mmol) in methanol (11 mL) was heated to 45° C., and then treated with aqueous sodium hydroxide solution (1 M; 2.2 mL, 2.2 mmol). After 24 hours, the reaction mixture was adjusted to pH 5 to 6 via addition of aqueous citric acid (1 M; 1.1 mL), and then diluted with water (10 mL). The resulting mixture was allowed to cool to room temperature and stir for 1 hour, whereupon the precipitated solid was collected via filtration and washed with a mixture of methanol and water (1:4; 3×5 mL). This afforded 14 as a white solid. Yield: 535 mg, 0.998 mmol, 92%. LCMS m/z 536.1♦ $[M+H]^+$. $^1$H NMR (400

MHz, DMSO-$d_6$) δ 8.16 (d, J=1.5 Hz, 1H), 7.81 (dd, J=8.4, 1.6 Hz, 1H), 7.64 (d, J=8.4 Hz, 1H), 7.59-7.52 (m, 2H), 7.33 (dd, J=8.3, 2.1 Hz, 1H), 6.81-6.70 (m, 3H), 3.94 (s, 3H), 3.84 (s, 2H), 3.01-2.91 (m, 2H), 2.70-2.59 (m, 1H), 2.28-2.16 (m, 2H), 2.02 (s, 3H), 1.73 (m, 4H).

Examples 15 and 16

2-{6-[2-(4-Chloro-2-Fluorophenyl)-2-Methyl-1,3-Benzodioxol-4-Yl]-6-Azaspiro[2.5]Oct-1-Yl}-1-(2-Methoxyethyl)-1H-Benzimidazole-6-Carboxylic Acid, DIAST-X1, Trifluoroacetate Salt (15) [from P18 Via C71]; and 2-{6-[2-(4-Chloro-2-Fluorophenyl)-2-Methyl-1,3-Benzodioxol-4-Yl]-6-Azaspiro[2.5]Oct-1-Yl}-1-(2-Methoxyethyl)-1H-Benzimidazole-6-Carboxylic Acid, DIAST-X2, Trifluoroacetate Salt (16) [from P18 Via C72]

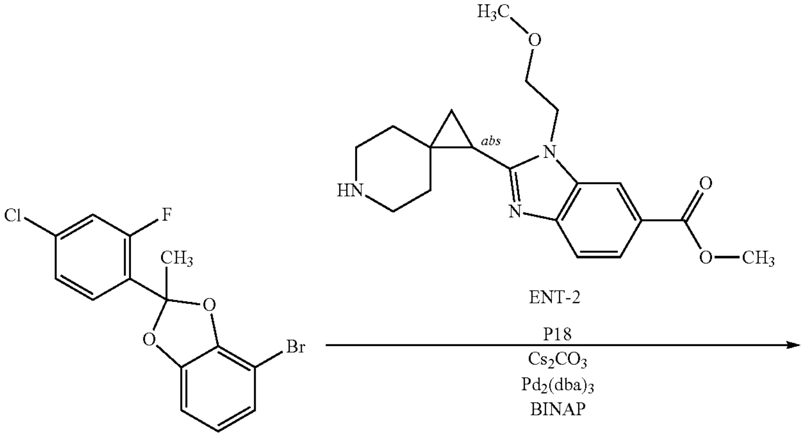

ENT-2

C4

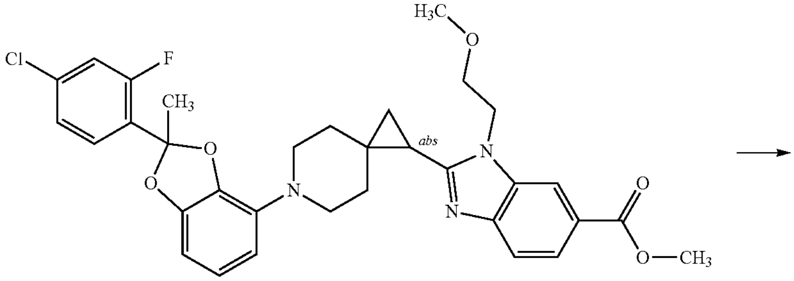

C70 (mixture of diastereomers)

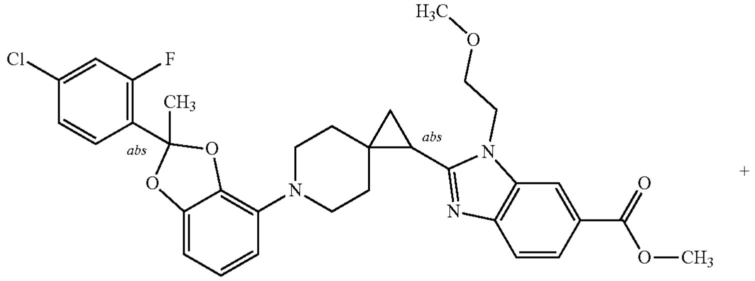

DIAST-Y1

C71 (from P18)

-continued
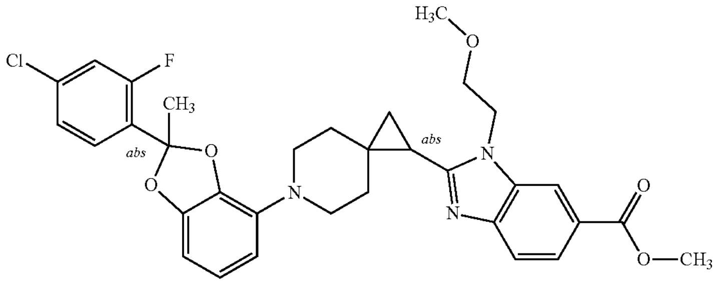
DIAST-Y2
C72 (from P18)
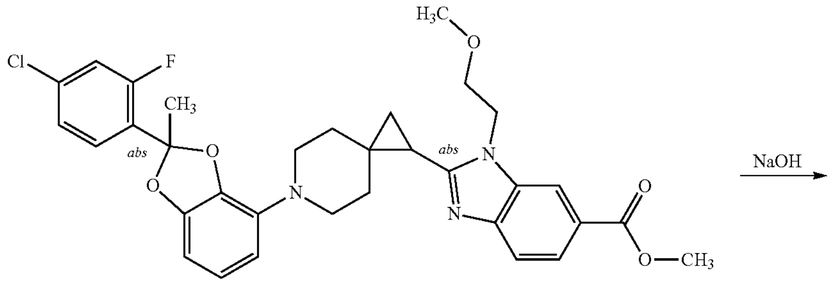
DIAST-Y1
C71 (from P18)
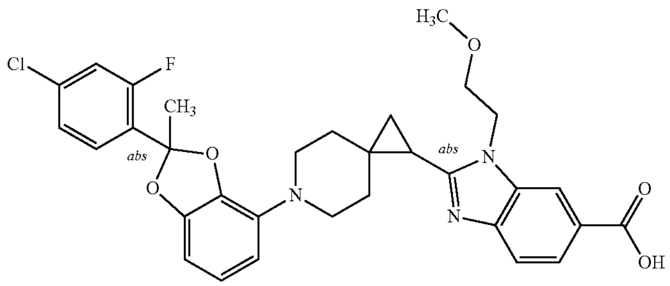
•$CF_3COOH$
DIAST-X1
15
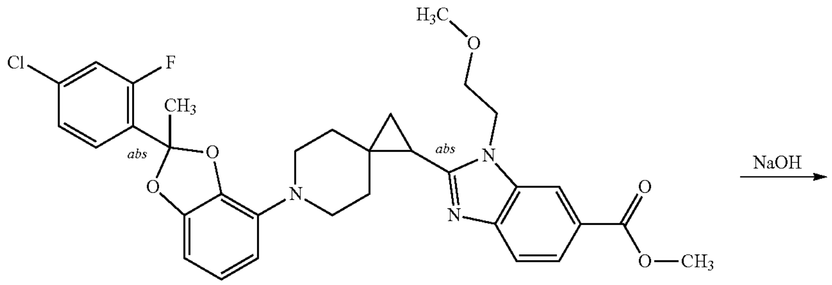
DIAST-Y2
C72 (from P18)

-continued

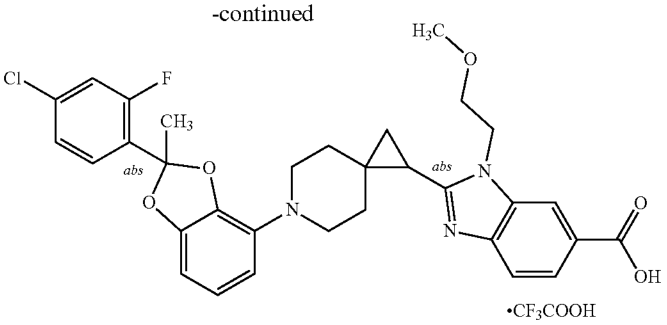

DIAST-X2

16

Step 1. Synthesis of methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate (C70) [from P18]

A mixture of P18 (240 mg, 0.699 mmol), C4 (275 mg, 0.800 mmol), cesium carbonate (455 mg, 1.40 mmol), tris(dibenzylideneacetone)dipalladium(0) (40.0 mg, 43.7 µmol), and 1,1'-binaphthalene-2,2'-diylbis(diphenylphosphane) (BINAP; 52.2 mg, 83.8 µmol) in toluene (5 mL) was degassed with nitrogen for 5 minutes and then stirred at 90° C. for 16 hours. The reaction mixture was filtered, and the filtrate was concentrated in vacuo; preparative thin-layer chromatography (Eluent: 1:1 petroleum ether/ethyl acetate) afforded C70, a mixture of diastereomers, as a yellow oil. Yield: 165 mg, 0.272 mmol, 39%. LCMS m/z 628.1♦ [M+Na$^+$].

Step 2. Isolation of methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate, DIAST-Y1 (C71) [from P18]; and methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate, DIAST-Y2 (C72) [from P18]

Separation of the stereoisomers at the dioxolane in C70 (165 mg, 0.272 mmol) was carried out using SFC [Column: Chiral Technologies Chiralpak AD, 10 µm; Mobile phase: 65:35 carbon dioxide/(ethanol containing 0.1% ammonium hydroxide)]. The first-eluting isomer was designated as DIAST-Y1 (C71), and the second-eluting isomer as DIAST-Y2 (C72); both were isolated as white solids.

C71 Yield: 55.0 mg, 90.7 µmol, 33%. LCMS m/z 605.9♦ [M+H]$^+$. Retention time 4.47 minutes (Column: Chiral Technologies Chiralpak AD-3, 4.6×100 mm, 3 µm; Mobile phase A: carbon dioxide; Mobile phase B: ethanol containing 0.05% diethylamine; Gradient: 5% to 40% B over 4.5 minutes, then held at 40% B for 2.5 minutes; Flow rate: 2.8 mL/minute).

C72 Yield: 58.0 mg, 95.7 µmol, 35%. LCMS m/z 628.0♦ [M+Na$^+$]. Retention time 4.88 minutes (Analytical conditions identical to those used for C71).

Step 3. Synthesis of 2-{6-[2-(4-Chloro-2-Fluorophenyl)-2-Methyl-1,3-Benzodioxol-4-Yl]-6-Azaspiro[2.5]Oct-1-Yl}-1-(2-Methoxyethyl)-1H-Benzimidazole-6-Carboxylic Acid, DIAST-X1, Trifluoroacetate Salt (15) [from P18 Via C71]

To a solution of C71 (55.0 mg, 90.7 µmol) in a mixture of methanol (2.0 mL) and tetrahydrofuran (1.0 mL) was added an aqueous solution of sodium hydroxide (3 M; 1.0 mL, 3.0 mmol). After the reaction mixture had been stirred at 20° C. for 2 hours, the pH was adjusted to 7 by addition of 1 M hydrochloric acid, and the resulting mixture was extracted with a mixture of dichloromethane and methanol (10:1, 3×30 mL). The combined organic layers were dried over magnesium sulfate, filtered, and concentrated in vacuo. Reversed-phase HPLC (Column: Boston Green ODS, 5 µm; Mobile phase A: 0.1% trifluoroacetic acid in water; Mobile phase B: acetonitrile; Gradient: 10% to 95% B) provided 15 as a white solid. Yield: 35.8 mg, 50.7 µmol, 56%. LCMS m/z 592.3♦ [M+H]$^+$. $^1$H NMR (400 MHz, methanol-$d_4$) δ 8.46 (s, 1H), 8.21 (d, J=8.6 Hz, 1H), 7.78 (d, J=8.6 Hz, 1H), 7.54 (dd, J=8.3, 8.3 Hz, 1H), 7.16-7.08 (m, 2H), 6.76 (dd, J=8.2, 8.1 Hz, 1H), 6.55-6.47 (m, 2H), 4.9-4.70 (m, 2H, assumed; partially obscured by water peak), 3.82 (t, J=4.9 Hz, 2H), 3.66-3.56 (m, 1H), 3.50-3.41 (m, 1H), 3.19-3.09 (m, 1H), 3.15 (s, 3H), 3.08-2.99 (m, 1H), 2.63-2.57 (m, 1H), 2.27-2.17 (m, 1H), 2.01 (s, 3H), 1.76-1.66 (m, 2H), 1.62-1.50 (m, 2H), 1.35-1.26 (m, 1H).

Step 4. Synthesis of 2-{6-[2-(4-Chloro-2-Fluorophenyl)-2-Methyl-1,3-Benzodioxol-4-Yl]-6-Azaspiro[2.5]Oct-1-Yl}-1-(2-Methoxyethyl)-1H-Benzimidazole-6-Carboxylic Acid, DIAST-X2, Trifluoroacetate Salt (16) [from P18 Via C72]

To a solution of C72 (58.0 mg, 95.7 µmol) in a mixture of methanol (2.0 mL) and tetrahydrofuran (1.0 mL) was added an aqueous solution of sodium hydroxide (3 M; 1.0 mL, 3.0 mmol). After the reaction mixture had been stirred at 20° C. for 2 hours, the pH was adjusted to 7 by addition of 1 M hydrochloric acid, and the resulting mixture was extracted with a mixture of dichloromethane and methanol (10:1, 3×30 mL). The combined organic layers were dried over magnesium sulfate, filtered, and concentrated in vacuo. Reversed-phase HPLC (Column: Boston Green ODS, 5 µm; Mobile phase A: 0.1% trifluoroacetic acid in water; Mobile phase B: acetonitrile; Gradient: 35% to 95% B) provided 16 as a white solid. Yield: 33.4 mg, 47.3 µmol, 49%. LCMS m/z 592.2♦ [M+H]$^+$. $^1$H NMR (400 MHz, methanol-$d_4$) δ 8.53-8.50 (m, 1H), 8.25 (dd, J=8.6, 1.4 Hz, 1H), 7.80 (br d, J=8.6 Hz, 1H), 7.57 (dd, J=8.4, 8.2 Hz, 1H), 7.25 (dd, J=10.8, 2.0 Hz, 1H), 7.19 (br dd, J=8.4, 2.1 Hz, 1H), 6.77 (dd, J=8.2, 8.1 Hz, 1H), 6.55-6.50 (m, 2H), 4.9-4.72 (m, 2H, assumed; partially obscured by water peak), 3.93-3.80 (m, 2H), 3.68-3.58 (m, 1H), 3.41-3.3 (m, 1H, assumed; partially obscured by solvent peak), 3.25 (s, 3H), 3.22-3.12 (m, 1H), 3.07-2.97

(m, 1H), 2.67 (dd, J=8.3, 5.8 Hz, 1H), 2.28-2.17 (m, 1H), 2.01 (d, J=1.0 Hz, 3H), 1.86-1.71 (m, 2H), 1.69-1.56 (m, 2H), 1.36-1.26 (m, 1H).
Examples 17 and 18
Ammonium 2-({4-[2-(4-chloro-2-fluorophenyl)-2-methyl-1,3-benzodioxol-4-yl]piperidin-1-yl}methyl)-1-[(I-ethyl-1H-imidazol-5-yl)methyl]-1H-benzimidazole-6-carboxylate, ENT-1 (17) and Ammonium 2-({4-[2-(4-chloro-2-fluorophenyl)-2-methyl-1,3-benzodioxol-4-yl]piperidin-1-yl}methyl)-1-[(I-ethyl-1H-imidazol-5-yl)methyl]-1H-benzimidazole-6-carboxylate, ENT-2 (18)
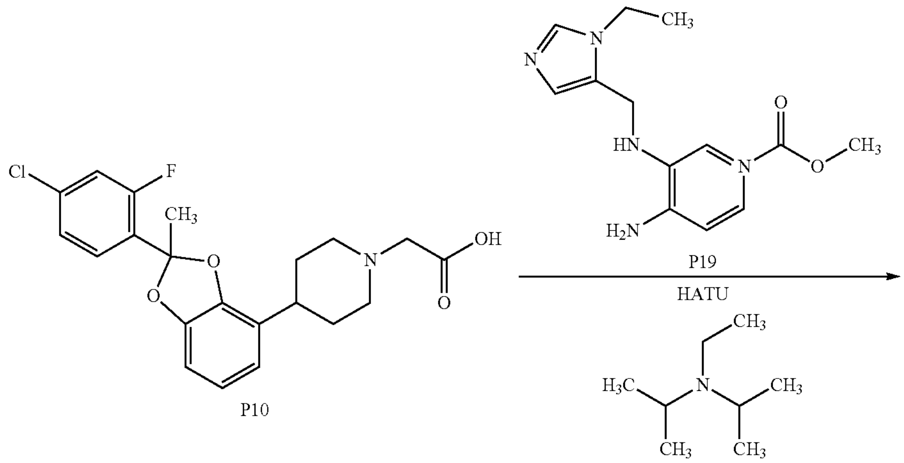
P10
P19
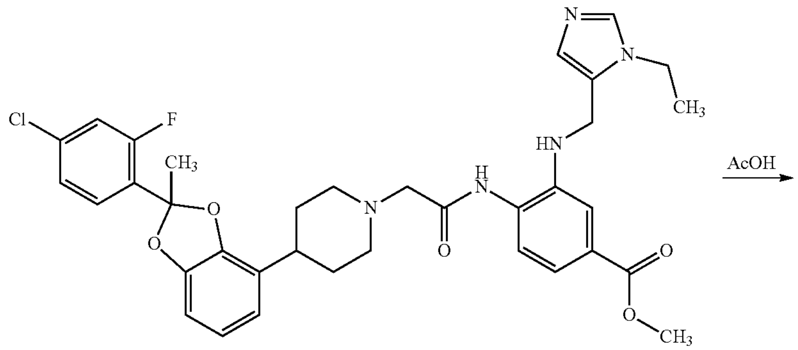
C73
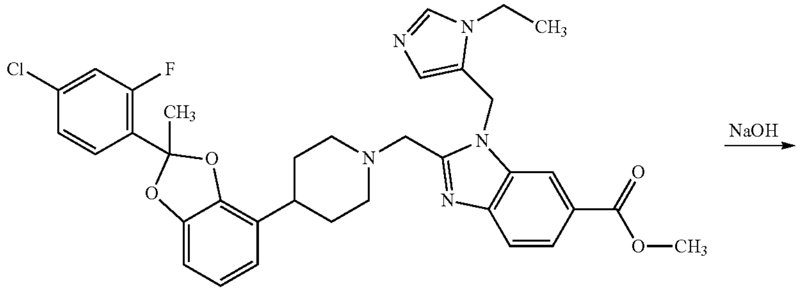
C74

-continued

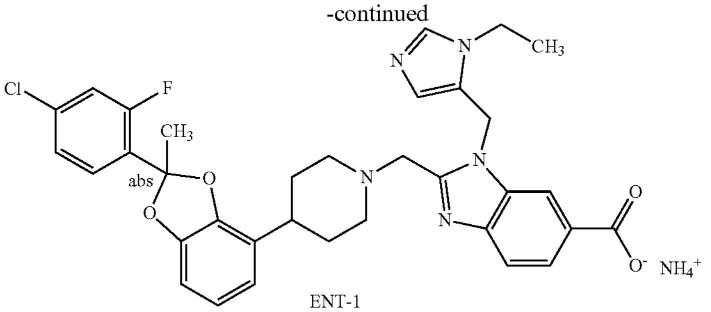

ENT-1

17

+

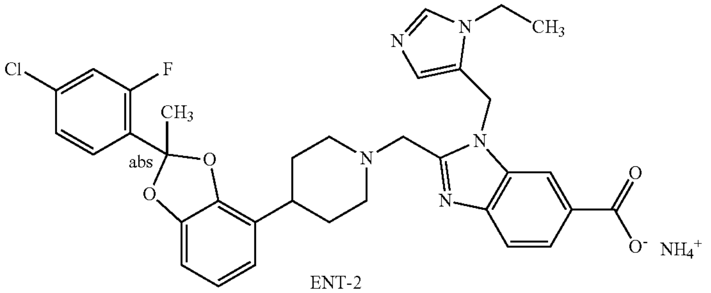

ENT-2

18

Step 1. Synthesis of methyl 4-[({4-[2-(4-chloro-2-fluorophenyl)-2-methyl-1,3-benzodioxol-4-yl]piperidin-1-yl}acetyl)amino]-3-{[(1-ethyl-1H-imidazol-5-yl)methyl]amino}benzoate (C73)

O-(7-Azabenzotriazol-1-yl)-N,N,N',N'-tetramethyluronium hexafluorophosphate (566 mg, 1.49 mmol) was added to a mixture of P19 (340 mg, 1.24 mmol) in N,N-dimethylformamide (10 mL), and the mixture was stirred at 25° C. for 10 minutes. A solution of P10 (503 mg, 1.24 mmol) and N,N-diisopropylethylamine (615 µL, 3.53 mmol) in N,N-dimethylformamide (7.7 mL) was then added, and the reaction mixture was stirred at 25° C. for 16 hours, whereupon it was poured into water (10 mL) and extracted with ethyl acetate (3×50 mL). The combined organic layers were washed sequentially with aqueous ammonium chloride solution (3×20 mL) and saturated aqueous sodium chloride solution (2×20 mL), dried over sodium sulfate, filtered, and concentrated in vacuo. Upon purification using silica gel chromatography (Gradient: 0% to 5% methanol in ethyl acetate), C73 was obtained as a pale brown gum. Yield: 316 mg, 0.477 mmol, 38%. LCMS m/z 662.2♦ $[M+H]^+$.

Step 2. Synthesis of methyl 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate (C74)

A solution of C73 (316 mg, 0.477 mmol) in acetic acid (14 mL) was stirred at 55° C. for 16 hours. Solvent was removed under high vacuum, and the residue was purified using preparative thin-layer chromatography (Eluent: 10:1 dichloromethane/methanol) to afford C74 as a colorless oil. Yield: 200 mg, 0.310 mmol, 65%. LCMS m/z 644.3♦ $[M+H]^+$.

Step 3. Synthesis of ammonium 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate, ENT-1 (17) and ammonium 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate, ENT-2 (18)

A mixture of C74 (150 mg, 0.233 mmol) and aqueous sodium hydroxide solution (2 M; 233 µL, 0.466 mmol) in a mixture of methanol (3 mL) and tetrahydrofuran (3 mL) was stirred at 45° C. for 16 hours. After the reaction mixture had been adjusted to pH 7 by addition of 1 M hydrochloric acid, it was concentrated in vacuo to afford a mixture of 17 and 18. These enantiomers were separated via SFC [Column: Chiral Technologies ChiralCel OD, 10 µm; Mobile phase: 1:1 carbon dioxide/(ethanol containing 0.1% ammonium hydroxide)]. The first-eluting enantiomer was designated as ENT-1 (17), and the second-eluting enantiomer as ENT-2 (18); both were isolated as white solids.

17 Yield: 45.0 mg, 69.5 µmol, 30%. LCMS m/z 630.3♦ $[M+H]^+$. $^1$H NMR (400 MHz, methanol-$d_4$) δ 8.15 (br s, 1H), 8.00 (br d, J=8.4 Hz, 1H), 7.81 (s, 1H), 7.72 (d, J=8.2 Hz, 1H), 7.56 (dd, J=8.3, 8.3 Hz, 1H), 7.28 (dd, J=10.9, 2.0 Hz, 1H), 7.21 (dd, J=8.3, 2.1 Hz, 1H), 6.77 (dd, component of ABC pattern, J=8.0, 7.7 Hz, 1H), 6.69 (dd, component of ABC pattern, J=7.8, 1.2 Hz, 1H), 6.67-6.60 (m, 2H), 5.82 (s, 2H), 4.12 (q, J=7.2 Hz, 2H), 3.89 (AB quartet, $J_{AB}$=14.3 Hz, $\Delta\nu_{AB}$=6.9 Hz, 2H), 3.00-2.90 (m, 2H), 2.74-2.64 (m, 1H), 2.32-2.21 (m, 2H), 2.02 (s, 3H), 1.82-1.61 (m, 4H), 1.29 (t, J=7.3 Hz, 3H). Retention time 5.66 minutes (Column: Chiral Technologies Chiralpak AD-3, 4.6×150 mm, 3 µm; Mobile phase A: carbon dioxide; Mobile phase B: methanol containing 0.05% diethylamine; Gradient: 5% to 40% B over 5.5 minutes, then held at 40% B for 3.0 minutes; Flow rate: 2.5 mL/minute).

18 Yield: 32.8 mg, 50.7 μmol, 22%. LCMS m/z 630.3♦ $[M+H]^+$. $^1H$ NMR (400 MHz, methanol-$d_4$) δ8.15 (s, 1H), 8.00 (d, J=8.5 Hz, 1H), 7.81 (s, 1H), 7.72 (d, J=8.5 Hz, 1H), 7.56 (dd, J=8.3, 8.3 Hz, 1H), 7.28 (dd, J=10.9, 2.0 Hz, 1H), 7.21 (dd, J=8.3, 2.0 Hz, 1H), 6.77 (dd, component of ABC pattern, J=7.8, 7.8 Hz, 1H), 6.69 (dd, component of ABC pattern, J=7.9, 1.2 Hz, 1H), 6.67-6.60 (m, 2H), 5.82 (s, 2H), 4.12 (q, J=7.3 Hz, 2H), 3.89 (AB quartet, $J_{AB}$=14.1 Hz, $\Delta v_{AB}$=7.4 Hz, 2H), 3.01-2.90 (m, 2H), 2.74-2.63 (m, 1H), 2.31-2.21 (m, 2H), 2.02 (s, 3H), 1.82-1.60 (m, 4H), 1.29 (t, J=7.3 Hz, 3H). Retention time 5.34 minutes (Analytical SFC conditions identical to those used for 17).

The compounds listed in Table 1 were prepared using procedures analogous to the examples identified in Table 2 using the appropriate intermediate(s) identified in Table 2. The compounds were purified using methods discussed herein. The final compounds may have been isolated as neutrals or acid or base salts.

TABLE 1

Structure and IUPAC name for Examples 19-102

| Ex. No. | Structure | IUPAC Name |
|---|---|---|
| 19 | 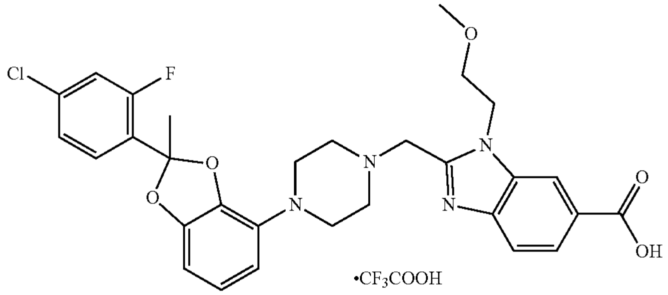 [SMILES: COCCn1c(CN2CCN(c3cccc4c3OC(C)(c3ccc(Cl)cc3F)O4)CC2)nc2ccc(C(=O)O)cc21 ; "·CF3COOH"] •$CF_3COOH$ | 2-({4-[2-(4-chloro-2-fluorophenyl)-2-methyl-1,3-benzodioxol-4-yl]piperazin-1-yl}methyl)-1-(2-methoxyethyl)-1H-benzimidazole-6-carboxylic acid trifluoroacetate salt |
| 20 | 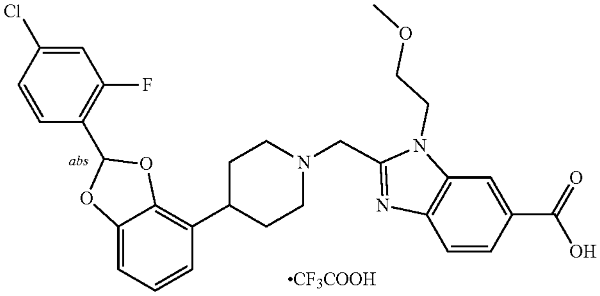 •$CF_3COOH$ ENT-X2 | 2-({4-[2-(4-chloro-2-fluorophenyl)-1,3-benzodioxol-4-yl]piperidin-1-yl}methyl)-1-(2-methoxyethyl)-1H-benzimidazole-6-carboxylic acid, ENT-X2, trifluoroacetate salt, [from C77; footnote 1 in Table 2] |
| 21 | 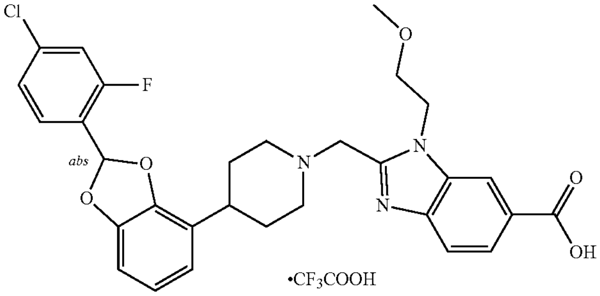 •$CF_3COOH$ ENT-X1 | 2-({4-[2-(4-chloro-2-fluorophenyl)-1,3-benzodioxol-4-yl]piperidin-1-yl}methyl)-1-(2-methoxyethyl)-1H-benzimidazole-6-carboxylic acid, ENT-X1, trifluoroacetate salt, [from C76; footnote 1 in Table 2] |
| 22 | 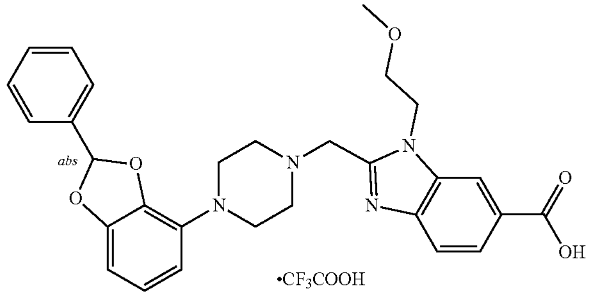 •$CF_3COOH$ ENT-X1 | 1-(2-methoxyethyl)-2-{[4-(2-phenyl-1,3-benzodioxol-4-yl)piperazin-1-yl]methyl}-1H-benzimidazole-6-carboxylic acid, ENT-X1, trifluoroacetate salt, [from P5] |

TABLE 1-continued

| Structure and IUPAC name for Examples 19-102 | | |
|---|---|---|
| Ex. No. | Structure | IUPAC Name |
| 23 | 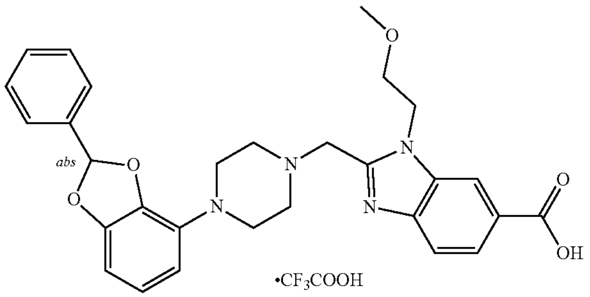 •$CF_3COOH$ ENT-X2 | 1-(2-methoxyethyl)-2-{[4-(2-phenyl-1,3-benzodioxol-4-yl)piperazin-1-yl]methyl}-1H-benzimidazole-6-carboxylic acid, ENT-X2, trifluoroacetate salt, [from P6] |
| 24 | 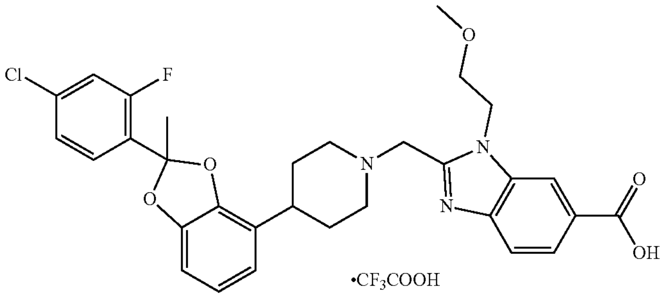 [SMILES: COCCn1c(CN2CCC(c3cccc4c3OC(C)(c3ccc(Cl)cc3F)O4)CC2)nc2ccc(C(=O)O)cc21 ; "·CF3COOH"] •$CF_3COOH$ | 2-({4-[2-(4-chloro-2-fluorophenyl)-2-methyl-1,3-benzodioxol-4-yl]piperidin-1-yl}methyl)-1-(2-methoxyethyl)-1H-benzimidazole-6-carboxylic acid, trifluoroacetate salt |
| 25 | 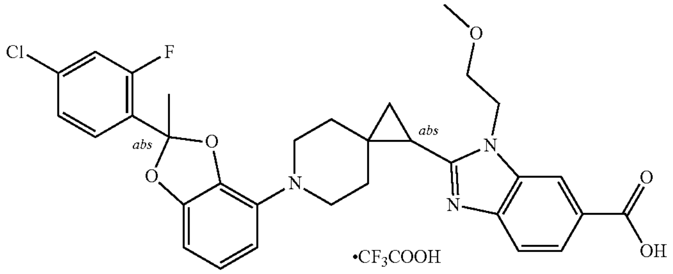 •$CF_3COOH$ DIAST-Z2 | 2-{6-[2-(4-chloro-2-fluorophneyl)-2-methyl-1,3-benzodioxol-4-yl]-6-azaspiro[2.5]oct-1-yl}-1-(2-methoxyethyl)-1H-benzimidazole-6-carboxylic acid, DIAST-Z2, trifluoroacetate salt, [from P17 via C79; footnote 2 in Table 2] |
| 26 | 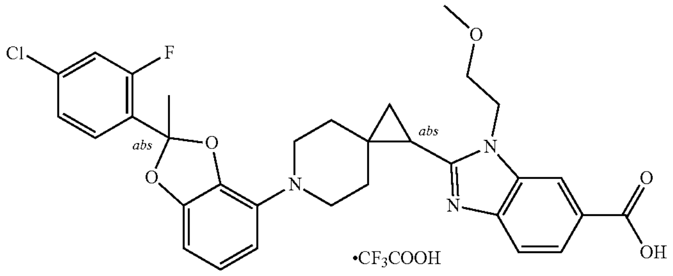 •$CF_3COOH$ DIAST-Z1 | 2-{6-[2-(4-chloro-2-fluorophneyl)-2-methyl-1,3-benzodioxol-4-yl]-6-azaspiro[2.5]oct-1-yl}-1-(2-methoxyethyl)-1H-benzimidazole-6-carboxylic acid, DIAST-Z1, trifluoroacetate salt, [from P17 via C78; footnote 2 in Table 2] |

TABLE 1-continued

| Structure and IUPAC name for Examples 19-102 | | |
|---|---|---|
| Ex. No. | Structure | IUPAC Name |
| 27 | 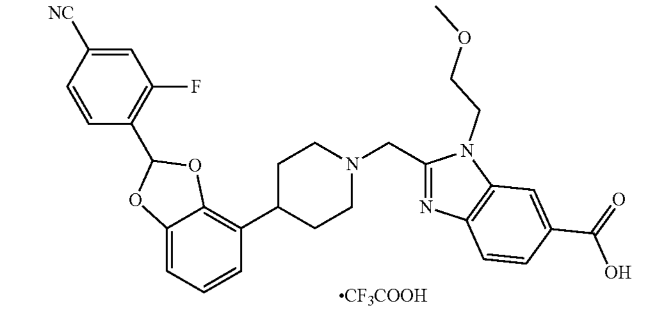 [SMILES: COCCn1c(CN2CCC(c3cccc4c3OC(c3ccc(C#N)cc3F)O4)CC2)nc2ccc(C(=O)O)cc21 ; "·CF3COOH"] | 2-({4-[2-(4-cyano-2-fluorophenyl)-1,3-benzodioxol-4-yl]piperidin-1-yl}methyl)-1-(2-methoxyethyl)-1H-benzimidazole-6-carboxylic acid, trifluoroacetate salt |
| 28 | 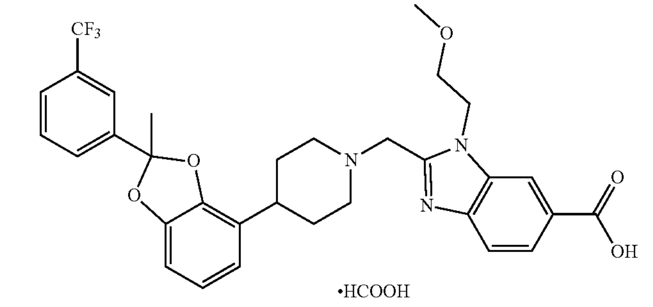 [SMILES: COCCn1c(CN2CCC(c3cccc4c3OC(C)(c3cccc(C(F)(F)F)c3)O4)CC2)nc2ccc(C(=O)O)cc21 ; "·HCOOH"] | 1-(2-methoxyethyl)-2-[(4-{2-methyl-2-[3-(trifluoromethyl)phenyl]-1,3-benzodioxol-4-yl}piperidin-1-yl)methyl]-1H-benzimidazole-6-carboxylic acid, formate salt |
| 29 | 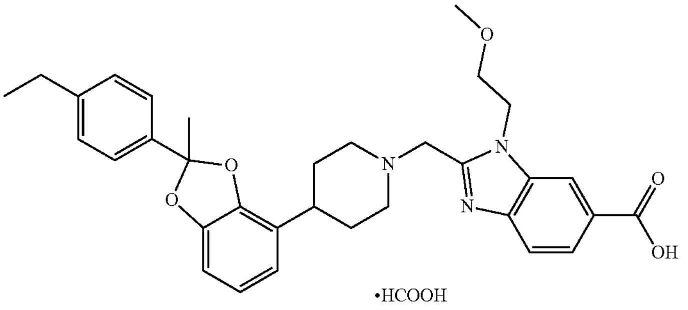 [SMILES: CCc1ccc(C2(C)Oc3cccc(C4CCN(Cc5nc6ccc(C(=O)O)cc6n5CCOC)CC4)c3O2)cc1 ; "·HCOOH"] | 2-({4-[2-(4-ethylphenyl)-2-methyl-1,3-benzodioxol-4-yl]piperidin-1-yl}methyl)-1-(2-methoxyethyl)-1H-benzimidazole-6-carboxylic acid, formate salt |
| 30 | 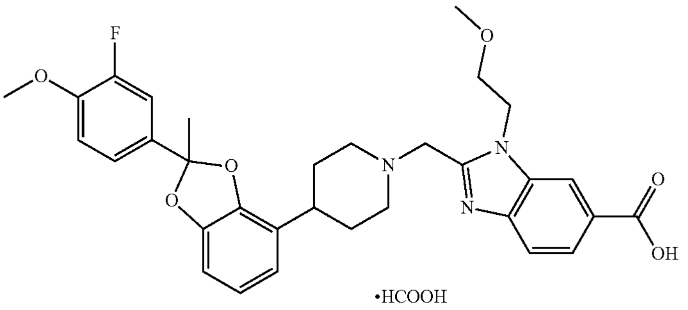 [SMILES: COCCn1c(CN2CCC(c3cccc4c3OC(C)(c3ccc(OC)c(F)c3)O4)CC2)nc2ccc(C(=O)O)cc21 ; "·HCOOH"] | 2-({4-[2-(3-fluoro-4-methoxyphenyl)-2-methyl-1,3-benzodioxol-4-yl]piperidin-1-yl}methyl)-1-(2-methoxyethyl)-1H-benzimidazole-6-carboxylic acid, formate salt |
| 31 | 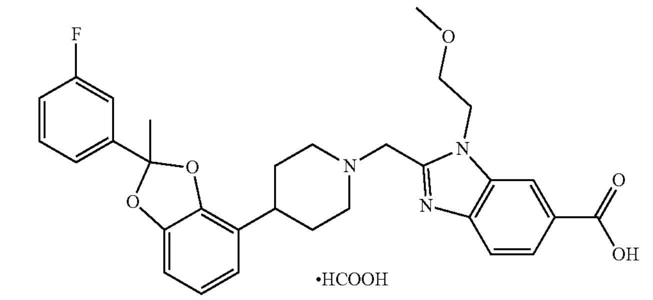 [SMILES: COCCn1c(CN2CCC(c3cccc4c3OC(C)(c3cccc(F)c3)O4)CC2)nc2ccc(C(=O)O)cc21 ; "·HCOOH"] | 2-({4-[2-(3-fluorophenyl)-2-methyl-1,3-benzodioxol-4-yl]piperidin-1-yl}methyl)-1-(2-methoxyethyl)-1H-benzimidazole-6-carboxylic acid, formate salt |

TABLE 1-continued

| Structure and IUPAC name for Examples 19-102 | | |
|---|---|---|
| Ex. No. | Structure | IUPAC Name |
| 32 | 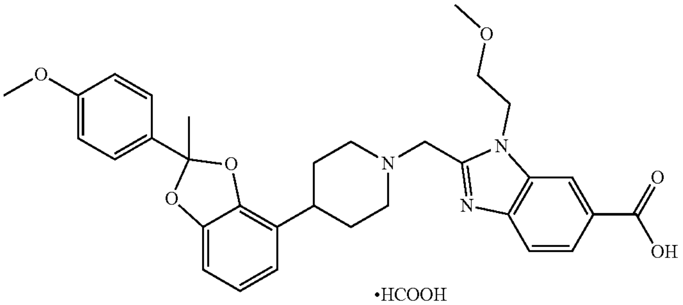 [SMILES: COCCn1c(CN2CCC(c3cccc4c3OC(C)(c3ccc(OC)cc3)O4)CC2)nc2ccc(C(=O)O)cc21 ; "·HCOOH"] •HCOOH | 1-(2-methoxyethyl)-2-({4-[2-(4-methoxyphenyl)-2-methyl-1,3-benzodioxol-4-yl]piperidin-1-yl}methyl)-1H-benzimidazole-6-carboxylic acid, formate salt |
| 33 | 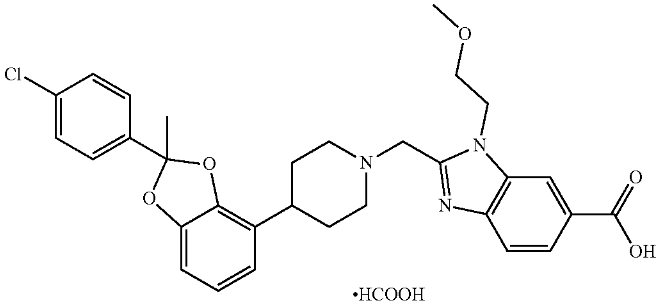 [SMILES: COCCn1c(CN2CCC(c3cccc4c3OC(C)(c3ccc(Cl)cc3)O4)CC2)nc2ccc(C(=O)O)cc21 ; "·HCOOH"] •HCOOH | 2-({4-[2-(4-chlorophenyl)-2-methyl-1,3-benzodioxol-4-yl]piperidin-1-yl}methyl)-1-(2-methoxyethyl)-1H-benzimidazole-6-carboxylic acid, formate salt |
| 34 | 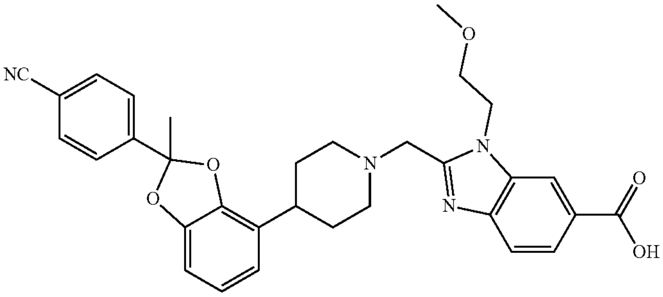 [SMILES: COCCn1c(CN2CCC(c3cccc4c3OC(C)(c3ccc(C#N)cc3)O4)CC2)nc2ccc(C(=O)O)cc21] | 2-({4-[2-(4-cyanophenyl)-2-methyl-1,3-benzodioxol-4-yl]piperidin-1-yl}methyl)-1-(2-methoxyethyl)-1H-benzimidazole-6-carboxylic acid |
| 35 | 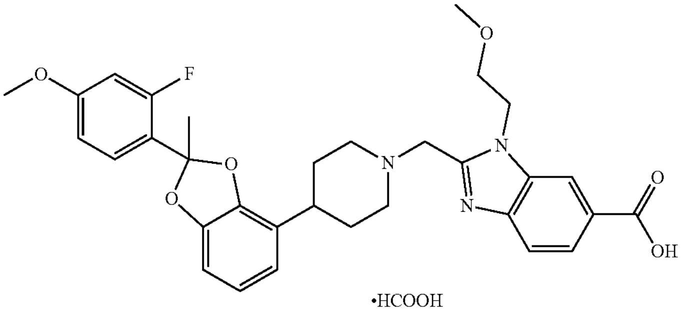 [SMILES: COCCn1c(CN2CCC(c3cccc4c3OC(C)(c3ccc(OC)cc3F)O4)CC2)nc2ccc(C(=O)O)cc21 ; "·HCOOH"] •HCOOH | 2-({4-[2-(2-fluoro-4-methoxyphenyl)-2-methyl-1,3-benzodioxol-4-yl]piperidin-1-yl}methyl)-1-(2-methoxyethyl)-1H-benzimidazole-6-carboxylic acid, formate salt |
| 36 | 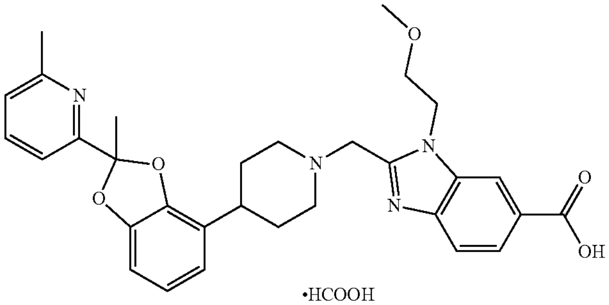 [SMILES: COCCn1c(CN2CCC(c3cccc4c3OC(C)(c3cccc(C)n3)O4)CC2)nc2ccc(C(=O)O)cc21 ; "·HCOOH"] •HCOOH | 1-(2-methoxyethyl)-2-({4-[2-methyl-2-(6-methylpyridin-2-yl)-1,3-benzodioxol-4-yl]piperidin-1-yl}methyl)-1H-benzimidazole-6-carboxylic acid, formate salt |

TABLE 1-continued

| Ex. No. | Structure | IUPAC Name |
|---|---|---|
| | Structure and IUPAC name for Examples 19-102 | |
| 37 | 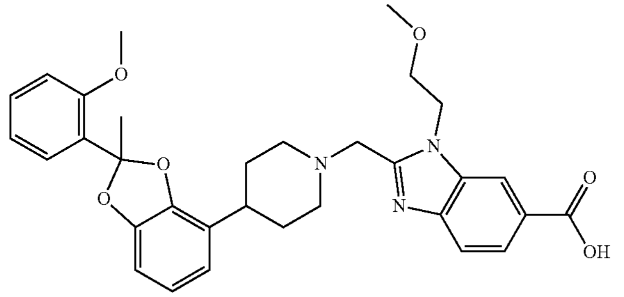 [SMILES: COCCn1c(CN2CCC(c3cccc4c3OC(C)(c3ccccc3OC)O4)CC2)nc2ccc(C(=O)O)cc21] | 1-(2-methoxyethyl)-2-({4-[2-(2-methoxyphenyl)-2-methyl-1,3-benzodioxol-4-yl]piperidin-1-yl}methyl)-1H-benzimidazole-6-carboxylic acid |
| 38 | 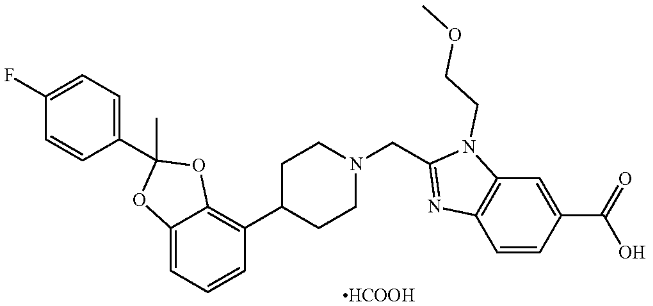 [SMILES: COCCn1c(CN2CCC(c3cccc4c3OC(C)(c3ccc(F)cc3)O4)CC2)nc2ccc(C(=O)O)cc21 ; "·HCOOH"] •HCOOH | 2-({4-[2-(4-fluorophenyl)-2-methyl-1,3-benzodioxol-4-yl]piperidin-1-yl}methyl)-1-(2-methoxyethyl)-1H-benzimidazole-6-carboxylic acid, formate salt |
| 39 | 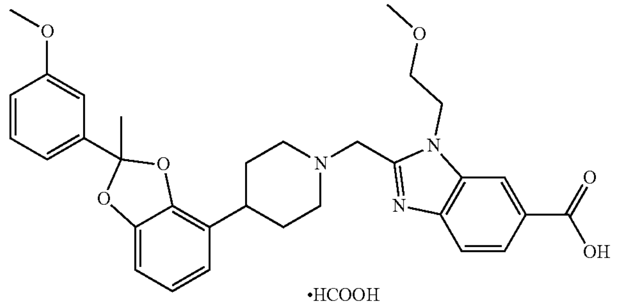 [SMILES: COCCn1c(CN2CCC(c3cccc4c3OC(C)(c3cccc(OC)c3)O4)CC2)nc2ccc(C(=O)O)cc21 ; "·HCOOH"] •HCOOH | 1-(2-methoxyethyl)-2-({4-[2-(3-methoxyphenyl)-2-methyl-1,3-benzodioxol-4-yl]piperidin-1-yl}methyl)-1H-benzimidazole-6-carboxylic acid, formate salt |
| 40 | 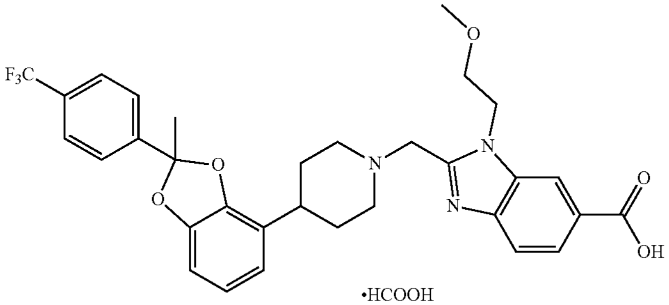 [SMILES: COCCn1c(CN2CCC(c3cccc4c3OC(C)(c3ccc(C(F)(F)F)cc3)O4)CC2)nc2ccc(C(=O)O)cc21 ; "·HCOOH"] •HCOOH | 1-(2-methoxyethyl)-2-[(4-{2-methyl-2-[4-(trifluoromethyl)phenyl]-1,3-benzodioxol-4-yl}piperidin-1-yl)methyl]-1H-benzimidazole-6-carboxylic acid, formate salt |
| 41 | 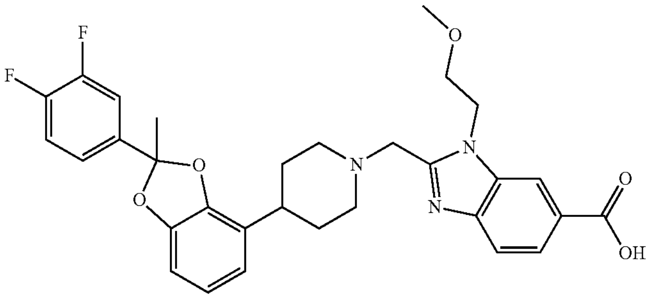 [SMILES: COCCn1c(CN2CCC(c3cccc4c3OC(C)(c3ccc(F)c(F)c3)O4)CC2)nc2ccc(C(=O)O)cc21] | 2-({4-[2-(3,4-difluorophenyl)-2-methyl-1,3-benzodioxol-4-yl]piperidin-1-yl}methyl)-1-(2-methoxyethyl)-1H-benzimidazole-6-carboxylic acid |

TABLE 1-continued

| Structure and IUPAC name for Examples 19-102 | | |
|---|---|---|
| Ex. No. | Structure | IUPAC Name |
| 42 | 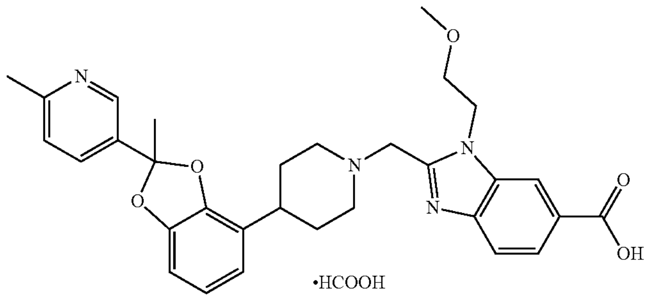 [SMILES: COCCn1c(CN2CCC(c3cccc4c3OC(C)(c3ccc(C)nc3)O4)CC2)nc2ccc(C(=O)O)cc21 ; "·HCOOH"] | 1-(2-methoxyethyl)-2-({4-[2-methyl-2-(6-methylpyridin-3-yl)-1,3-benzodioxol-4-yl]piperidin-1-yl}methyl)-1H-benzimidazole-6-carboxylic acid, formate salt |
| 43 | 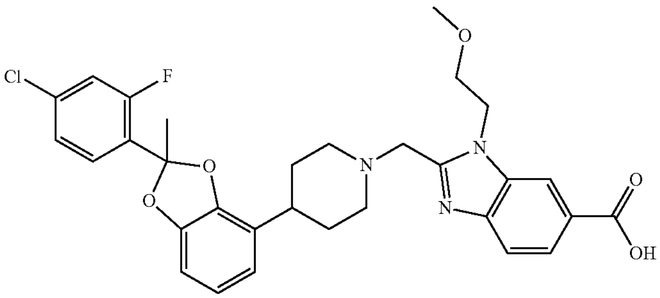 [SMILES: COCCn1c(CN2CCC(c3cccc4c3OC(C)(c3ccc(Cl)cc3F)O4)CC2)nc2ccc(C(=O)O)cc21] | 1-{2-[acetyl(methyl)amino]ethyl}-2-({4-[2-(4-chloro-2-fluorophenyl)-2-methyl-1,3-benzodioxol-4-yl]piperidin-1-yl}methyl)-1H-benzimidazole-6-carboxylic acid |
| 44 | 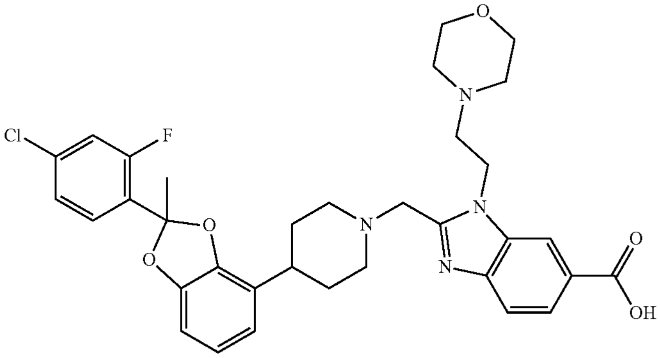 [SMILES: CC1(c2ccc(Cl)cc2F)Oc2cccc(C3CCN(Cc4nc5ccc(C(=O)O)cc5n4CCN4CCOCC4)CC3)c2O1] | 2-({4-[2-(4-chloro-2-fluorophenyl)-2-methyl-1,3-benzodioxol-4-yl]piperidin-1-yl}methyl)-1-[2-(morpholin-4-yl)ethyl]-1H-benzimidazole-6-carboxylic acid |
| 45 | 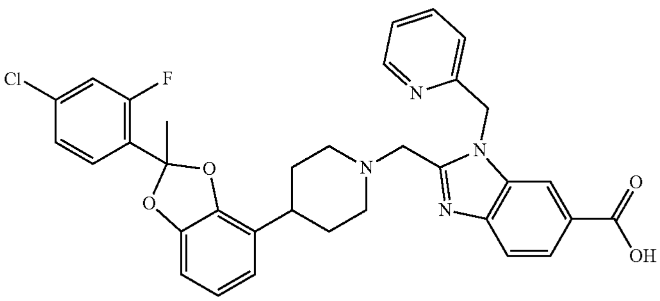 [SMILES: CC1(c2ccc(Cl)cc2F)Oc2cccc(C3CCN(Cc4nc5ccc(C(=O)O)cc5n4Cc4ccccn4)CC3)c2O1] | 2-({4-[2-(4-chloro-2-fluorophenyl)-2-methyl-1,3-benzodioxol-4-yl]piperidin-1-yl}methyl)-1-(pyridin-2-ylmethyl)-1H-benzimidazole-6-carboxylic acid |

TABLE 1-continued

| Ex. No. | Structure | IUPAC Name |
|---|---|---|
| | Structure and IUPAC name for Examples 19-102 | |
| 46 | 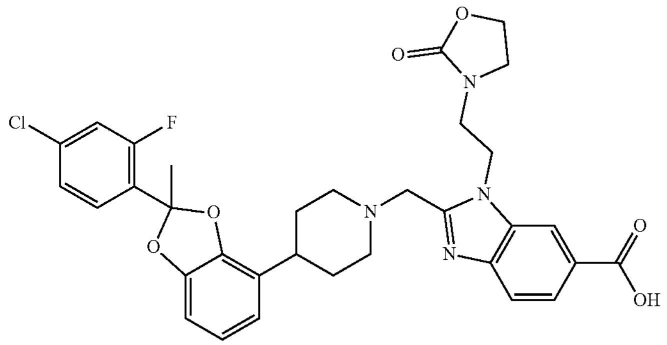 [SMILES: CC1(c2ccc(Cl)cc2F)Oc2cccc(C3CCN(Cc4nc5ccc(C(=O)O)cc5n4CCN4CCOC4=O)CC3)c2O1] | 2-({4-[2-(4-chloro-2-fluorophenyl)-2-methyl-1,3-benzodioxol-4-yl]piperidin-1-yl}methyl)-1-[2-(2-oxo-1,3-oxazolidin-3-yl)ethyl]-1H-benzimidazole-6-carboxylic acid |
| 47 | 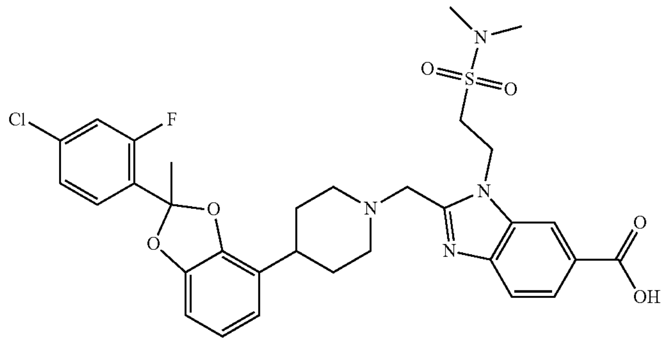 [SMILES: CN(C)S(=O)(=O)CCn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(dimethylsulfamoyl)ethyl]-1H-benzimidazole-6-carboxylic acid |
| 48 | 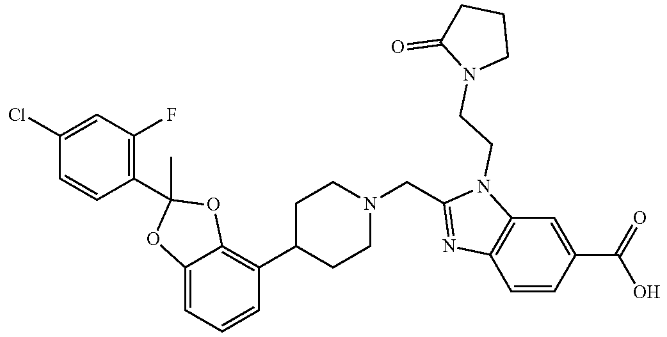 [SMILES: CC1(c2ccc(Cl)cc2F)Oc2cccc(C3CCN(Cc4nc5ccc(C(=O)O)cc5n4CCN4CCCC4=O)CC3)c2O1] | 2-({4-[2-(4-chlorophenyl)-2-methyl-1,3-benzodioxol-4-yl]piperidin-1-yl}methyl)-1-[2-(2-oxopyrrolidin-1-yl)ethyl]-1H-benzimidazole-6-carboxylic acid |
| 49 | 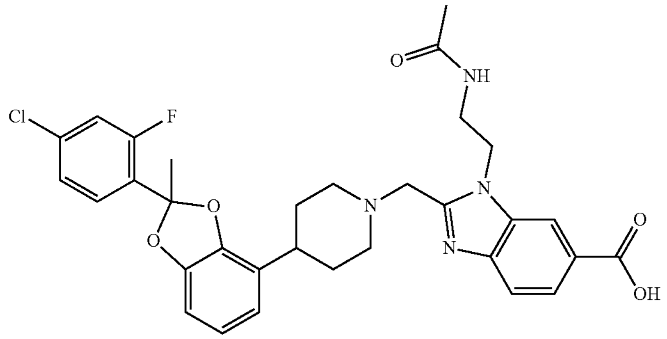 [SMILES: CC(=O)NCCn1c(CN2CCC(c3cccc4c3OC(C)(c3ccc(Cl)cc3F)O4)CC2)nc2ccc(C(=O)O)cc21] | 1-[2-(acetylamino)ethyl]-2-({4-[2-(4-chloro-2-fluorophenyl)-2-methyl-1,3-benzodioxol-4-yl]piperidin-1-yl}methyl)-1H-benzimidazole-6-carboxylic acid |

TABLE 1-continued

| Structure and IUPAC name for Examples 19-102 | | |
|---|---|---|
| Ex. No. | Structure | IUPAC Name |
| 50 | 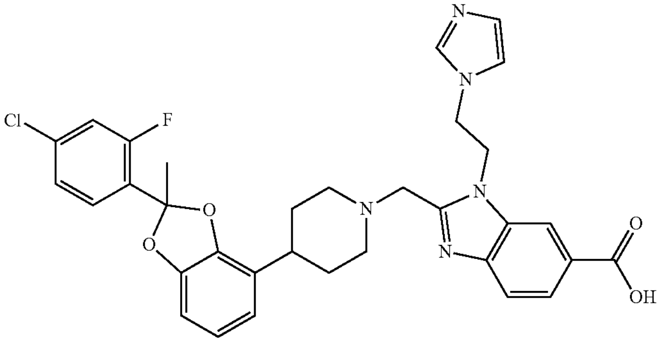 [SMILES: CC1(c2ccc(Cl)cc2F)Oc2cccc(C3CCN(Cc4nc5ccc(C(=O)O)cc5n4CCn4ccnc4)CC3)c2O1] | 2-({4-[2-(4-chloro-2-fluorophenyl)-2-methyl-1,3-benzodioxol-4-yl]piperidin-1-yl}methyl)-1-[2-(1H-imidazol-1-yl)ethyl]-1H-benzimidazole-6-carboxylic acid |
| 51 | 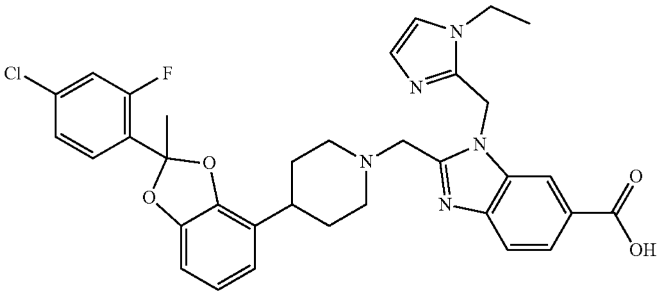 [SMILES: CCn1ccnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(1-ethyl-1H-imidazol-2-yl)methyl]-1H-benzimidazole-6-carboxylic acid |
| 52 | 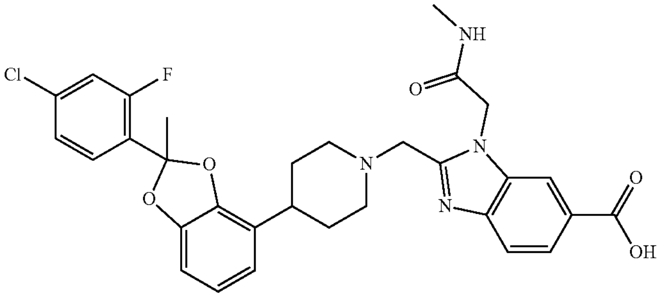 [SMILES: CNC(=O)Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(methylamino)-2-oxoethyl]-1H-benzimidazole-6-carboxylic acid |
| 53 | 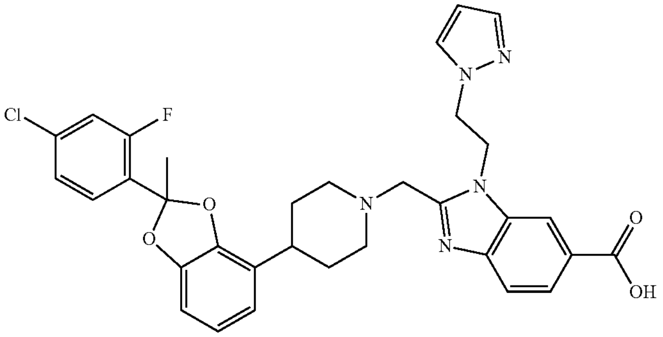 [SMILES: CC1(c2ccc(Cl)cc2F)Oc2cccc(C3CCN(Cc4nc5ccc(C(=O)O)cc5n4CCn4cccn4)CC3)c2O1] | 2-({4-[2-(4-chloro-2-fluorophenyl)-2-methyl-1,3-benzodioxol-4-yl]piperidin-1-yl}methyl)-1-[2-(1H-pyrazol-1-yl)ethyl]-1H-benzimidazole-6-carboxylic acid |

TABLE 1-continued

| Structure and IUPAC name for Examples 19-102 | | |
|---|---|---|
| Ex. No. | Structure | IUPAC Name |
| 54 | 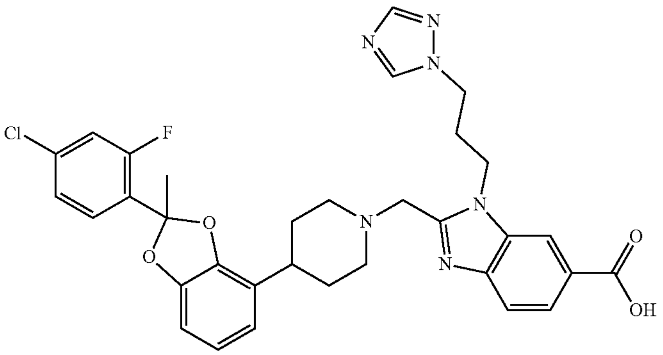 [SMILES: CC1(c2ccc(Cl)cc2F)Oc2cccc(C3CCN(Cc4nc5ccc(C(=O)O)cc5n4CCCn4cncn4)CC3)c2O1] | 2-({4-[2-(4-chloro-2-fluorophenyl)-2-methyl-1,3-benzodioxol-4-yl]piperidin-1-yl}methyl)-1-[3-(1H-1,2,4-triazol-1-yl)propyl]-1H-benzimidazole-6-carboxylic acid |
| 55 | 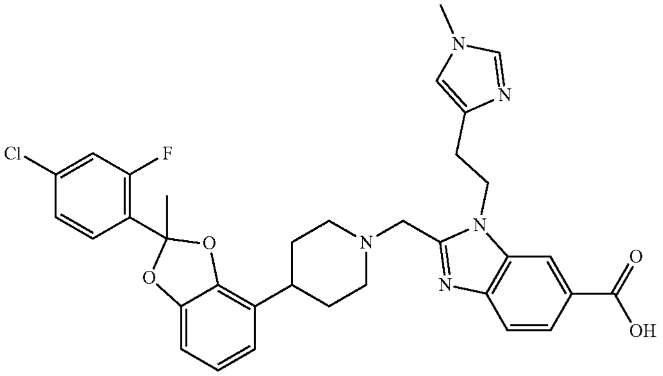 [SMILES: Cn1cnc(CCn2c(CN3CCC(c4cccc5c4OC(C)(c4ccc(Cl)cc4F)O5)CC3)nc3ccc(C(=O)O)cc32)c1] | 2-({4-[2-(4-chloro-2-fluorophenyl)-2-methyl-1,3-benzodioxol-4-yl]piperidin-1-yl}methyl)-1-[2-(1-methyl-1H-imidazol-4-yl)ethyl]-1H-benzimidazole-6-carboxylic acid |
| 56 | 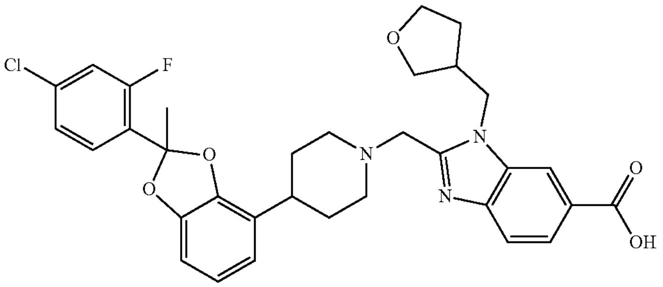 [SMILES: CC1(c2ccc(Cl)cc2F)Oc2cccc(C3CCN(Cc4nc5ccc(C(=O)O)cc5n4CC4CCOC4)CC3)c2O1] | 2-({4-[2-(4-chloro-2-fluorophenyl)-2-methyl-1,3-benzodioxol-4-yl]piperidin-1-yl}methyl)-1-(tetrahydrofuran-3-ylmethyl)-1H-benzimidazole-6-carboxylic acid |
| 57 | 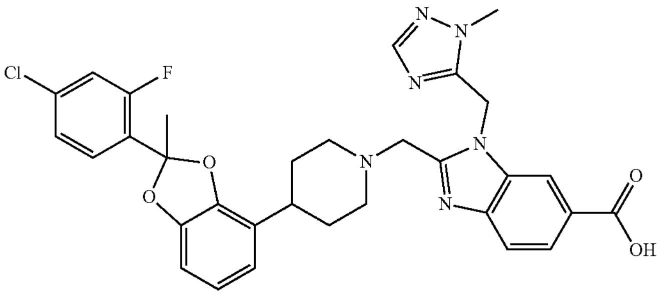 [SMILES: Cn1ncnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(1-methyl-1H-1,2,4-triazol-5-yl)methyl]-1H-benzimidazole-6-carboxylic acid |

TABLE 1-continued

Structure and IUPAC name for Examples 19-102

| Ex. No. | Structure | IUPAC Name |
|---|---|---|
| 58 | 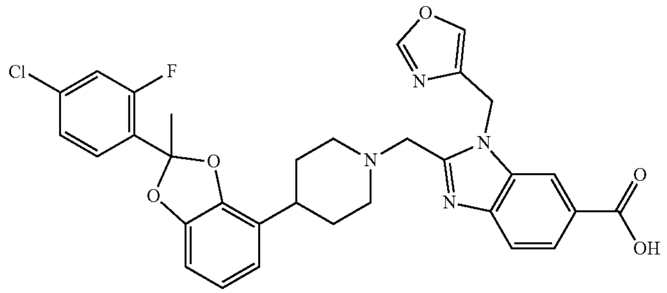 [SMILES: CC1(c2ccc(Cl)cc2F)Oc2cccc(C3CCN(Cc4nc5ccc(C(=O)O)cc5n4Cc4cocn4)CC3)c2O1] | 2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid |
| 59 | 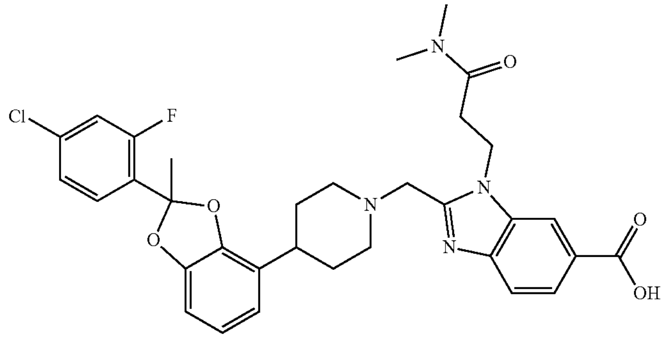 [SMILES: CN(C)C(=O)CCn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[3-(dimethylamino)-3-oxopropyl]-1H-benzimidazole-6-carboxylic acid |
| 60 | 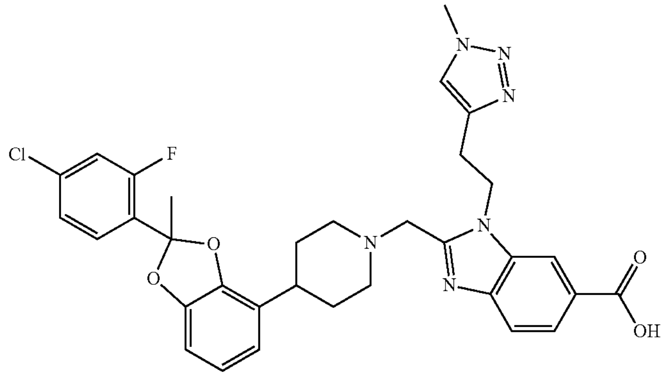 [SMILES: Cn1cc(CCn2c(CN3CCC(c4cccc5c4OC(C)(c4ccc(Cl)cc4F)O5)CC3)nc3ccc(C(=O)O)cc32)nn1] | 2-({4-[2-(4-chloro-2-fluorophenyl)-2-methyl-1,3-benzodioxol-4-yl]piperidin-1-yl}methyl)-1-[2-(1-methyl-1,2,3-yl}methyl)-1-[2-(1-methyl-1H-1,2,3-triazol-4-yl)ethyl]-1H-benzimidazole-6-carboxylic acid |
| 61 | 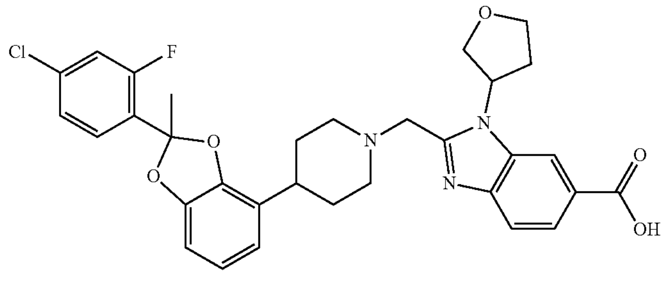 [SMILES: CC1(c2ccc(Cl)cc2F)Oc2cccc(C3CCN(Cc4nc5ccc(C(=O)O)cc5n4C4CCOC4)CC3)c2O1] | 2-({4-[2-(4-chloro-2-fluorophenyl)-2-methyl-1,3-benzodioxol-4-yl]piperidin-1-yl}methyl)-1-(tetrahydrofuran-3-yl)-1H-benzimidazole-6-carboxylic acid |

TABLE 1-continued

| Ex. No. | Structure | IUPAC Name |
|---|---|---|
| 62 | 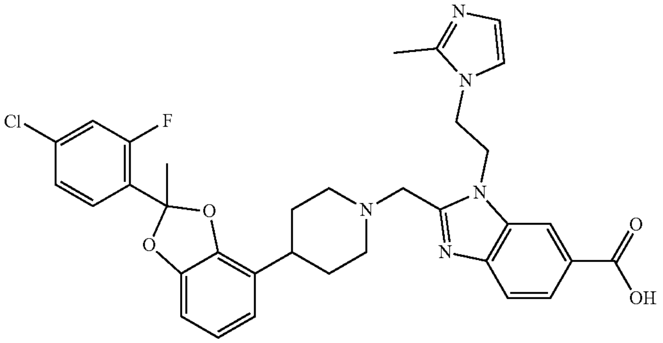 [SMILES: Cc1nccn1CCn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(2-methyl-1H-imidazol-1-yl)ethyl]-1H-benzimidazole-6-carboxylic acid |
| 63 | 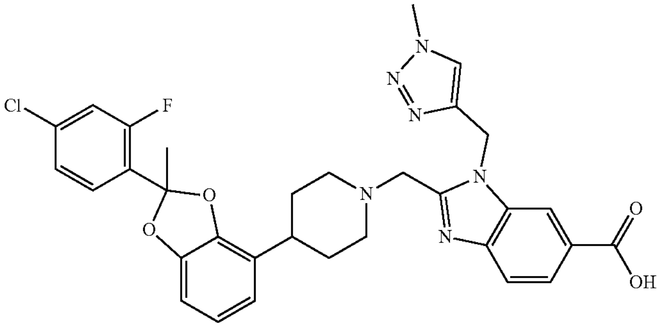 [SMILES: Cn1cc(Cn2c(CN3CCC(c4cccc5c4OC(C)(c4ccc(Cl)cc4F)O5)CC3)nc3ccc(C(=O)O)cc32)nn1] | 2-({4-[2-(4-chloro-2-fluorophenyl)-2-methyl-1,3-benzodioxol-4-yl]piperidin-1-yl}methyl)-1-[(1-methyl-1H-1,2,3-triazol-4-yl)methyl]-1H-benzimidazole-6-carboxylic acid |
| 64 | 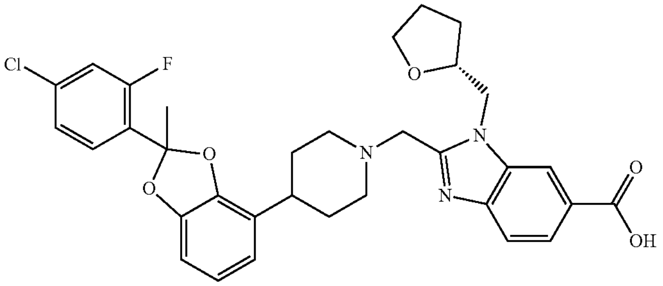 [SMILES: CC1(c2ccc(Cl)cc2F)Oc2cccc(C3CCN(Cc4nc5ccc(C(=O)O)cc5n4C[C@H]4CCCO4)CC3)c2O1] | 2-({4-[2-(4-chloro-2-fluorophenyl)-2-methyl-1,3-benzodioxol-4-yl]piperidin-1-yl}methyl)-1-[(2R)-tetrahydrofuran-2-ylmethyl]-1H-benzimidazole-6-carboxylic acid |
| 65 | 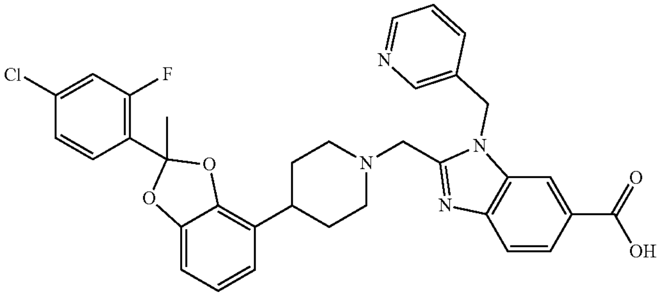 [SMILES: CC1(c2ccc(Cl)cc2F)Oc2cccc(C3CCN(Cc4nc5ccc(C(=O)O)cc5n4Cc4cccnc4)CC3)c2O1] | 2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid |
| 66 | 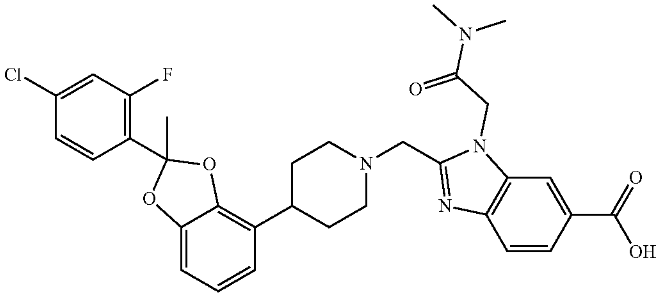 [SMILES: CN(C)C(=O)Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(dimethylamino)-2-oxoethyl]-1H-benzimidazole-6-carboxylic acid |

Structure and IUPAC name for Examples 19-102

TABLE 1-continued

| Structure and IUPAC name for Examples 19-102 | | |
|---|---|---|
| Ex. No. | Structure | IUPAC Name |
| 67 | 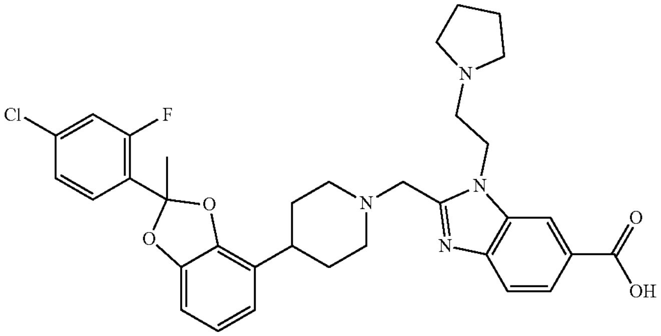 [SMILES: CC1(c2ccc(Cl)cc2F)Oc2cccc(C3CCN(Cc4nc5ccc(C(=O)O)cc5n4CCN4CCCC4)CC3)c2O1] | 2-({4-[2-(4-chloro-2-fluorophenyl)-2-methyl-1,3-benzodioxol-4-yl]piperidin-1-yl}methyl)-1-[2-(pyrrolidin-1-yl)ethyl]-1H-benzimidazole-6-carboxylic acid |
| 68 | 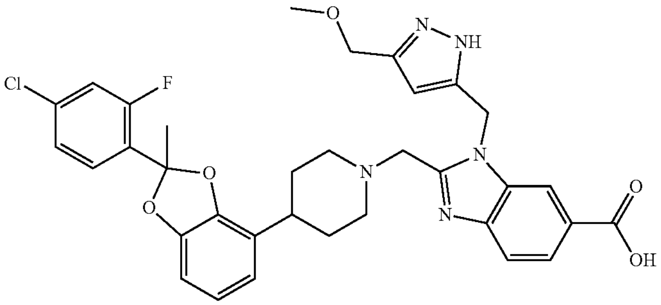 [SMILES: COCc1cc(Cn2c(CN3CCC(c4cccc5c4OC(C)(c4ccc(Cl)cc4F)O5)CC3)nc3ccc(C(=O)O)cc32)[nH]n1] | 2-({4-[2-(4-chloro-2-fluorophenyl)-2-methyl-1,3-benzodioxol-4-yl]piperidin-1-yl}methyl)-1-{[3-(methoxymethyl)-1H-pyrazol-5-yl]methyl}-1H-benzimidazole-6-carboxylic acid |
| 69 | 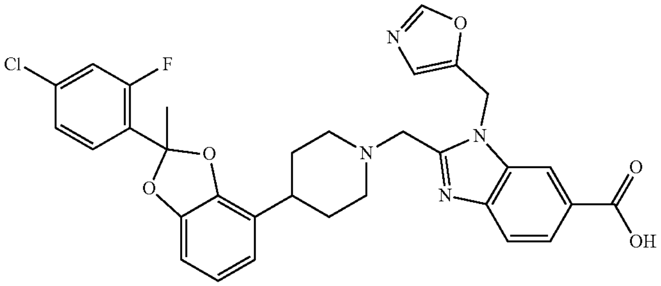 [SMILES: CC1(c2ccc(Cl)cc2F)Oc2cccc(C3CCN(Cc4nc5ccc(C(=O)O)cc5n4Cc4cnco4)CC3)c2O1] | 2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid |
| 70 | 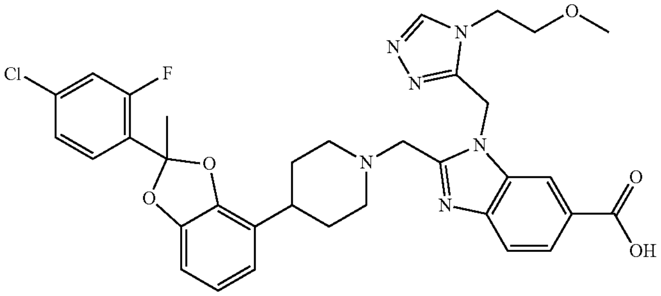 [SMILES: COCCn1cnnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-{[4-(2-methoxyethyl)-4H-1,2,4-triazol-3-yl]methyl}-1H-benzimidazole-6-carboxylic acid |

TABLE 1-continued

| Structure and IUPAC name for Examples 19-102 | | |
|---|---|---|
| Ex. No. | Structure | IUPAC Name |
| 71 | 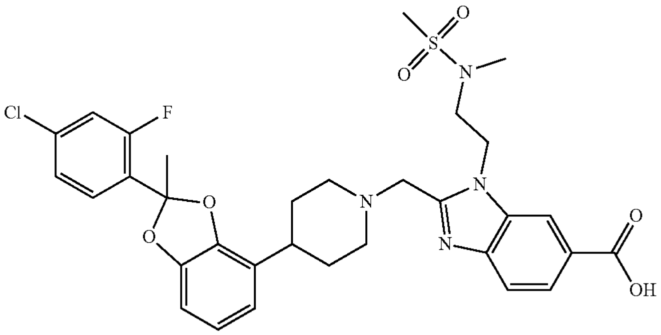 [SMILES: CN(CCn1c(CN2CCC(c3cccc4c3OC(C)(c3ccc(Cl)cc3F)O4)CC2)nc2ccc(C(=O)O)cc21)S(C)(=O)=O] | 2-({4-[2-(4-chloro-2-fluorophenyl)-2-methyl-1,3-benzodioxol-4-yl]piperidin-1-yl}methyl)-1-{2-[methyl(methylsulfonyl)amino]ethyl}-1H-benzimidazole-6-carboxylic acid |
| 72 | 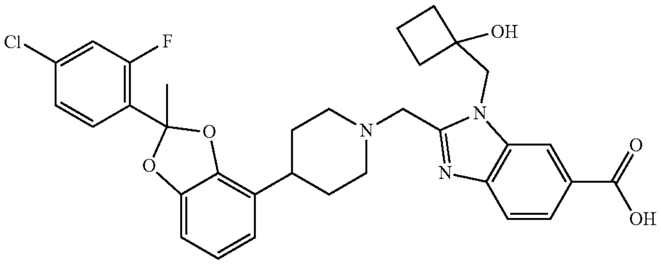 [SMILES: CC1(c2ccc(Cl)cc2F)Oc2cccc(C3CCN(Cc4nc5ccc(C(=O)O)cc5n4CC4(O)CCC4)CC3)c2O1] | 2-({4-[2-(4-chloro-2-fluorophenyl)-2-methyl-1,3-benzodioxol-4-yl]piperidin-1-yl}methyl)-1-[(1-hydroxycyclobutyl)methyl]-1H-benzimidazole-6-carboxylic acid |
| 73 | 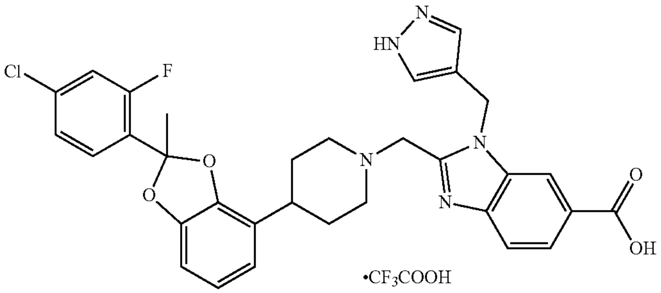 [SMILES: CC1(c2ccc(Cl)cc2F)Oc2cccc(C3CCN(Cc4nc5ccc(C(=O)O)cc5n4Cc4cn[nH]c4)CC3)c2O1 ; "·CF3COOH"] $\cdot CF_3COOH$ | 2-({4-[2-(4-chloro-2-fluorophenyl)-2-methyl-1,3-benzodioxol-4-yl]piperidin-1-yl}methyl)-1-(1H-pyrazol-4-ylmethyl)-1H-benzimidazole-6-carboxylic acid, trifluoroacetate salt |
| 74 | 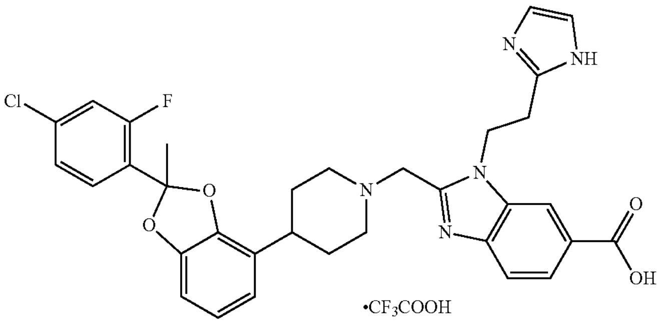 [SMILES: CC1(c2ccc(Cl)cc2F)Oc2cccc(C3CCN(Cc4nc5ccc(C(=O)O)cc5n4CCc4ncc[nH]4)CC3)c2O1 ; "·CF3COOH"] $\cdot CF_3COOH$ | 2-({4-[2-(4-chloro-2-fluorophenyl)-2-methyl-1,3-benzodioxol-4-yl]piperidin-1-yl}methyl)-1-[2-(1H-imidazol-2-yl)ethyl]-1H-benzimidazole-6-carboxylic acid, trifluoroacetate salt |
| 75 | 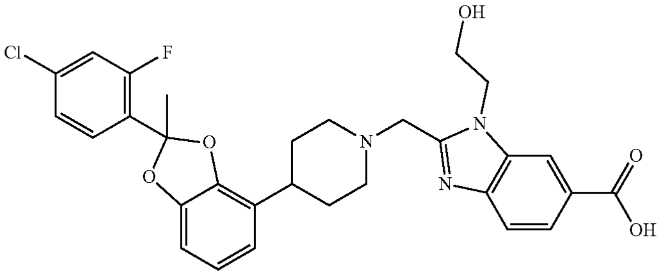 [SMILES: CC1(c2ccc(Cl)cc2F)Oc2cccc(C3CCN(Cc4nc5ccc(C(=O)O)cc5n4CCO)CC3)c2O1] | 2-({4-[2-(4-chloro-2-fluorophenyl)-2-methyl-1,3-benzodioxol-4-yl]piperidin-1-yl}methyl)-1-(2-hydroxyethyl)-1H-benzimidazole-6-carboxylic acid |

TABLE 1-continued

| Structure and IUPAC name for Examples 19-102 | | |
|---|---|---|
| Ex. No. | Structure | IUPAC Name |
| 76 | 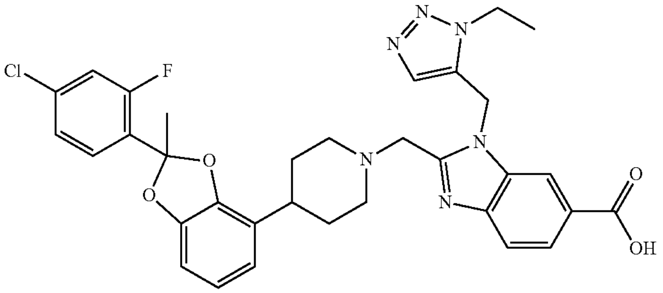 [SMILES: CCn1nncc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid |
| 77 | 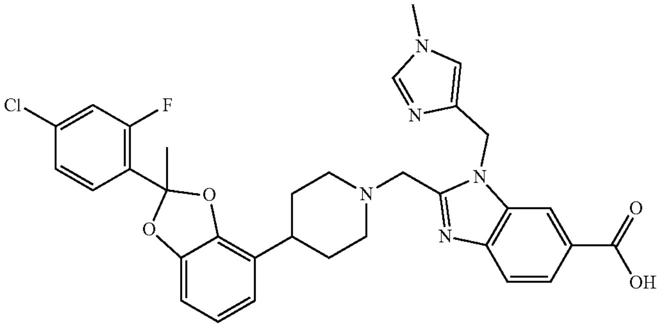 [SMILES: Cn1cnc(Cn2c(CN3CCC(c4cccc5c4OC(C)(c4ccc(Cl)cc4F)O5)CC3)nc3ccc(C(=O)O)cc32)c1] | 2-({4-[2-(4-chloro-2-fluorophenyl)-2-methyl-1,3-benzodioxol-4-yl]piperidin-1-yl}methyl)-1-[(1-methyl-1H-imidazol-4-yl)methyl]-1H-benzimidazole-6-carboxylic acid |
| 78 | 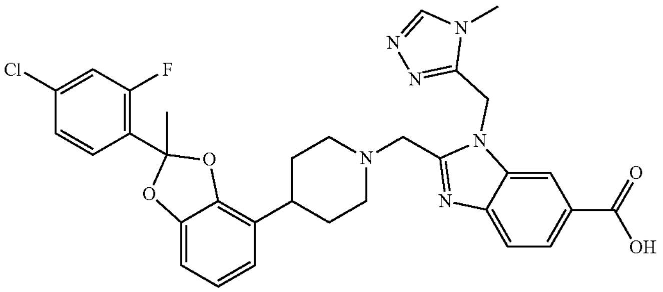 [SMILES: Cn1cnnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(4-methyl-4H-1,2,4-triazol-3-yl)methyl]-1H-benzimidazole-6-carboxylic acid |
| 79 | 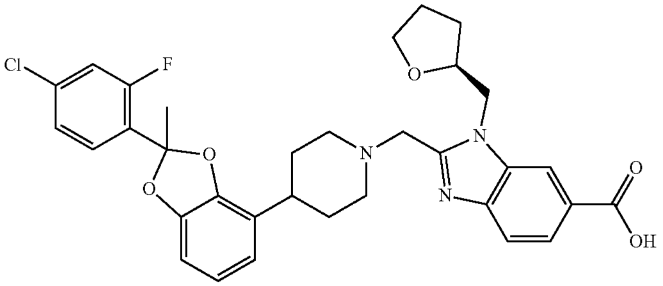 [SMILES: CC1(c2ccc(Cl)cc2F)Oc2cccc(C3CCN(Cc4nc5ccc(C(=O)O)cc5n4C[C@@H]4CCCO4)CC3)c2O1] | 2-({4-[2-(4-chloro-2-fluorophenyl)-2-methyl-1,3-benzodioxol-4-yl]piperidin-1-yl}methyl)-1-[(2S)-tetrahydrofuran-2-ylmethyl]-1H-benzimidazole-6-carboxylic acid |
| 80 | 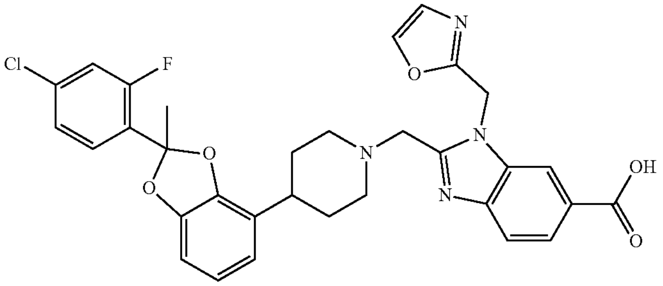 [SMILES: CC1(c2ccc(Cl)cc2F)Oc2cccc(C3CCN(Cc4nc5ccc(C(=O)O)cc5n4Cc4ncco4)CC3)c2O1] | 2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid |

TABLE 1-continued

Structure and IUPAC name for Examples 19-102

| Ex. No. | Structure | IUPAC Name |
| --- | --- | --- |
| 81 | 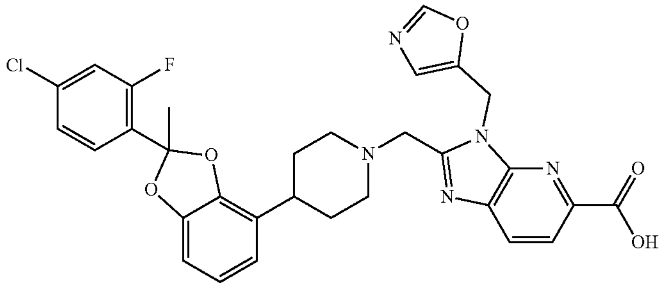 [SMILES: CC1(c2ccc(Cl)cc2F)Oc2cccc(C3CCN(Cc4nc5ccc(C(=O)O)nc5n4Cc4cnco4)CC3)c2O1] | 2-({4-[2-(4-chloro-2-fluorophenyl)-2-methyl-1,3-benzodioxol-4-yl]piperidin-1-yl}methyl)-3-(1,3-oxazol-5-ylmethyl)-3H-imidazo[4,5-b]pyridine-5-carboxylic acid |
| 82 | 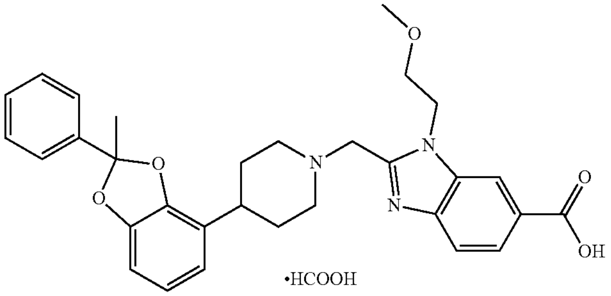 [SMILES: COCCn1c(CN2CCC(c3cccc4c3OC(C)(c3ccccc3)O4)CC2)nc2ccc(C(=O)O)cc21 ; "·HCOOH"] •HCOOH | 1-(2-methoxyethyl)-2-{[4-(2-methyl-2-phenyl-1,3-benzodioxol-4-yl)piperidin-1-yl]methyl}-1H-benzimidazole-6-carboxylic acid, formate salt |
| 83 | 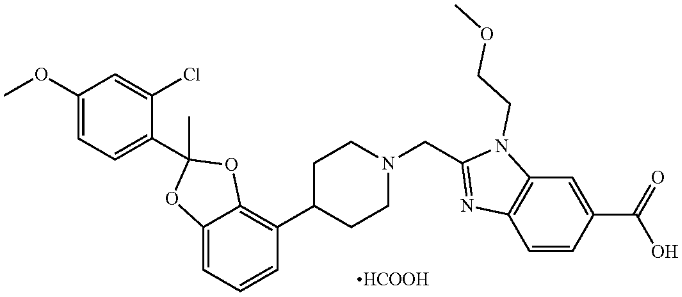 [SMILES: COCCn1c(CN2CCC(c3cccc4c3OC(C)(c3ccc(OC)cc3Cl)O4)CC2)nc2ccc(C(=O)O)cc21 ; "·HCOOH"] •HCOOH | 2-({4-[2-(2-chloro-4-methoxyphenyl)-2-methyl-1,3-benzodioxol-4-yl]piperidin-1-yl}methyl)-1-(2-methoxyethyl)-1H-benzimidazole-6-carboxylic acid, formate salt |
| 84 | 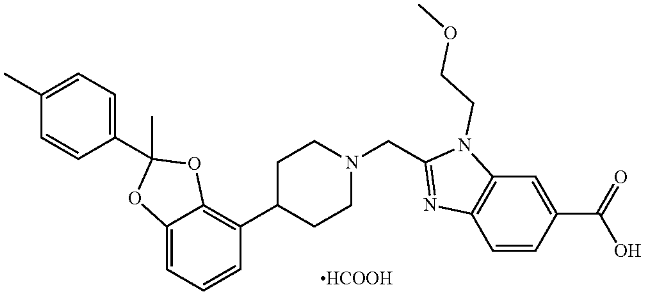 [SMILES: COCCn1c(CN2CCC(c3cccc4c3OC(C)(c3ccc(C)cc3)O4)CC2)nc2ccc(C(=O)O)cc21 ; "·HCOOH"] •HCOOH | 1-(2-methoxyethyl)-2-({4-[2-methyl-2-(4-methylphenyl)-1,3-benzodioxol-4-yl]piperidin-1-yl}methyl)-1H-benzimidazole-6-carboxylic acid, formate salt |
| 85 | 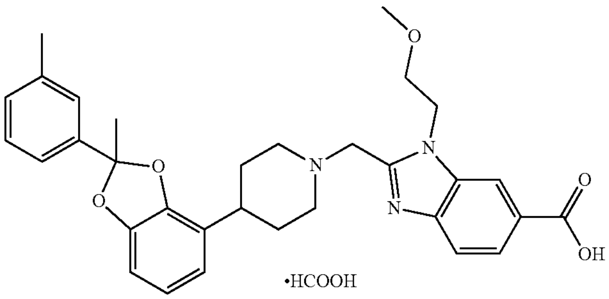 •HCOOH | 1-(2-methoxyethyl)-2-({4-[2-methyl-2-(3-methylphenyl)-1,3-benzodioxol-4-yl]piperidin-1-yl}methyl)-1H-benzimidazole-6-carboxylic acid, formate salt |

TABLE 1-continued

| Structure and IUPAC name for Examples 19-102 | | |
|---|---|---|
| Ex. No. | Structure | IUPAC Name |
| 86 | 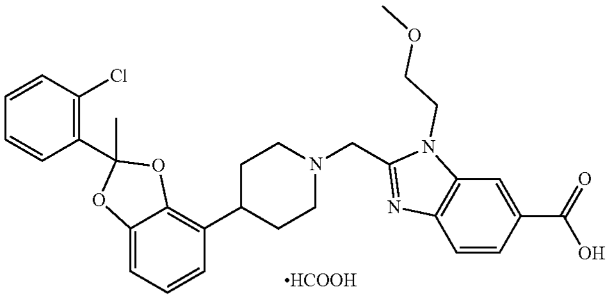 [SMILES: COCCn1c(CN2CCC(c3cccc4c3OC(C)(c3ccccc3Cl)O4)CC2)nc2ccc(C(=O)O)cc21 ; "·HCOOH"] •HCOOH | 2-({4-[2-(2-chlorophenyl)-2-methyl-1,3-benzodioxol-4-yl]piperidin-1-yl}methyl)-1-(2-methoxyethyl)-1H-benzimidazole-6-carboxylic acid, formate salt |
| 87 | 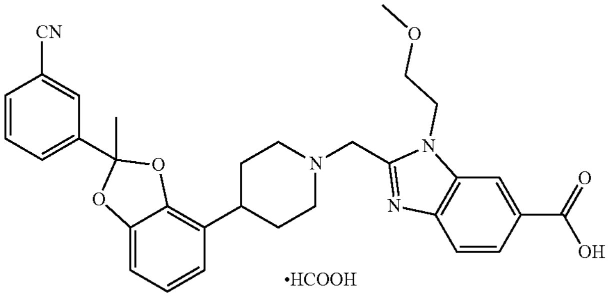 [SMILES: COCCn1c(CN2CCC(c3cccc4c3OC(C)(c3cccc(C#N)c3)O4)CC2)nc2ccc(C(=O)O)cc21 ; "·HCOOH"] •HCOOH | 2-({4-[2-(3-cyanophenyl)-2-methyl-1,3-benzodioxol-4-yl]piperidin-1-yl}methyl)-1-(2-methoxyethyl)-1H-benzimidazole-6-carboxylic acid, formate salt |
| 88 | 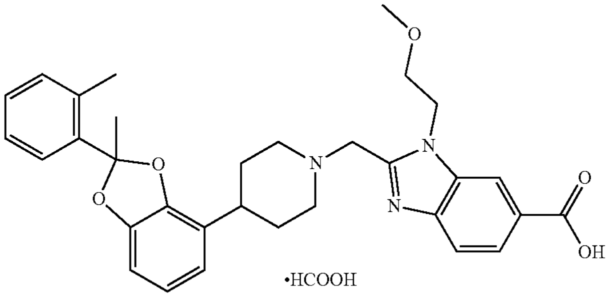 [SMILES: COCCn1c(CN2CCC(c3cccc4c3OC(C)(c3ccccc3C)O4)CC2)nc2ccc(C(=O)O)cc21 ; "·HCOOH"] •HCOOH | 1-(2-methoxyethyl)-2-({4-[2-methyl-2-(2-methylphenyl)-1,3-benzodioxol-4-yl]piperidin-1-yl}methyl)-1H-benzimidazole-6-carboxylic acid, formate acid |
| 89 | 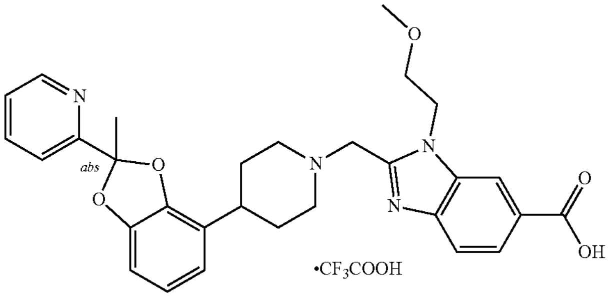 $\bullet CF_3COOH$ ENT-X2 | 1-(2-methoxyethyl)-2-({4-[2-methyl-2-(pyridin-2-yl)-1,3-benzodioxol-4-yl]piperidin-1-yl}methyl)-1H-benzimidazole-6-carboxylic acid, ENT-X2, trifluoroacetate salt [from C81; footnote 7 in Table 2] |

TABLE 1-continued

| Structure and IUPAC name for Examples 19-102 | | |
|---|---|---|
| Ex. No. | Structure | IUPAC Name |
| 90 | 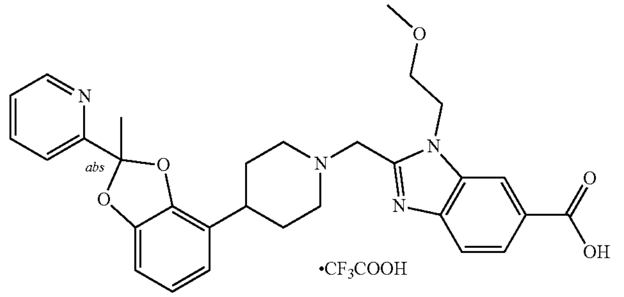 •$CF_3COOH$ ENT-X1 | 1-(2-methoxyethyl)-2-({4-[2-methyl-2-(pyridin-2-yl)-1,3-benzodioxol-4-yl]piperidin-1-yl}methyl)-1H-benzimidazole-6-carboxylic acid, ENT-X1, trifluoroacetate salt [from C80; footnote 7 in Table 2] |
| 91 | 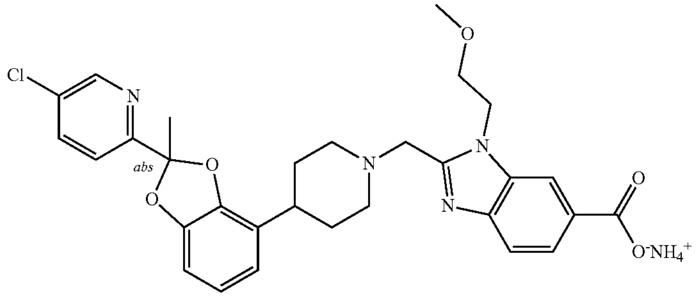 ENT-X1 | ammonium 2-({4-[2-(5-chloropyridin-2-yl)-2-methyl-1,3-benzodioxol-4-yl]piperidin-1-yl}methyl)-1-(2-methoxyethyl)-1H-benzimidazole-6-carboxylate, ENT-X1 [from P8] |
| 92 | 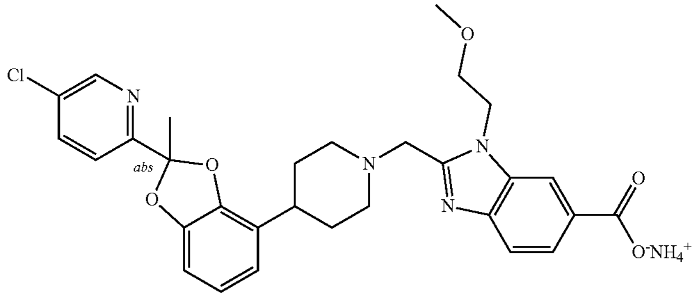 ENT-X2 | ammonium 2-({4-[2-(5-chloropyridin-2-yl)-2-methyl-1,3-benzodioxol-4-yl]piperidin-1-yl}methyl)-1-(2-methoxyethyl)-1H-benzimidazole-6-carboxylate, ENT-X2 [from P9] |
| 93 | 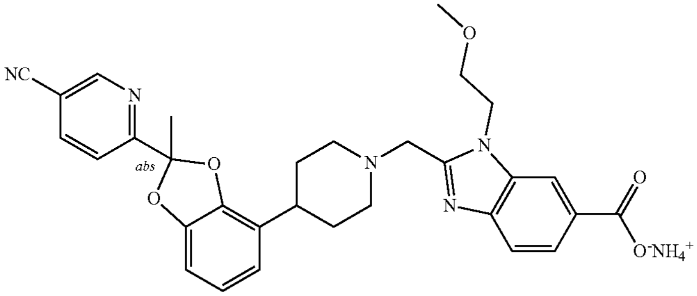 ENT-X1 | ammonium 2-({4-[2-(5-cyanopyridin-2-yl)-2-methyl-1,3-benzodioxol-4-yl]piperidin-1-yl}methyl)-1-(2-methoxyethyl)-1H-benzimidazole-6-carboxylate, ENT-X1 [from P8] |

TABLE 1-continued

| Structure and IUPAC name for Examples 19-102 | | |
|---|---|---|
| Ex. No. | Structure | IUPAC Name |
| 94 | 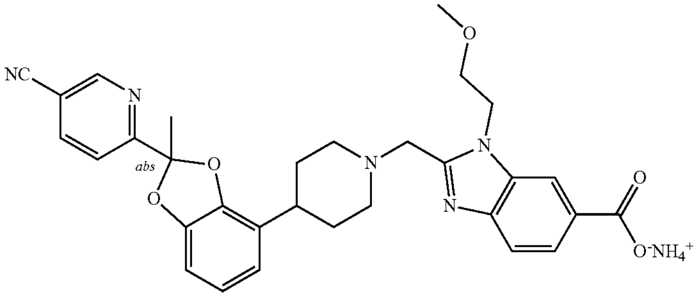 ENT-X2 | ammonium 2-({4-[2-(5-cyanopyridin-2-yl)-2-methyl-1,3-benzodioxol-4-yl)piperidin-1-yl}methyl)-1-(2-methoxyethyl)-1H-benzimidazole-5-carboxylate, ENT-X2 [from P9] |
| 95 | 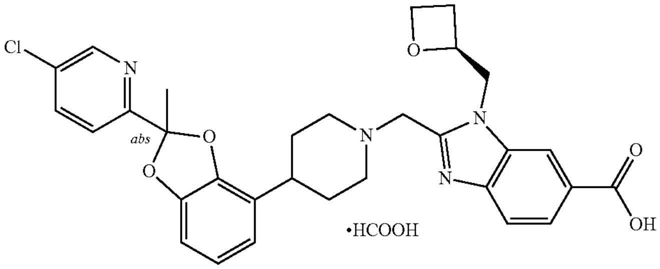 •HCOOH DIAST-X1 | 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylate acid, DIAST-X1 [from P8] |
| 96 | 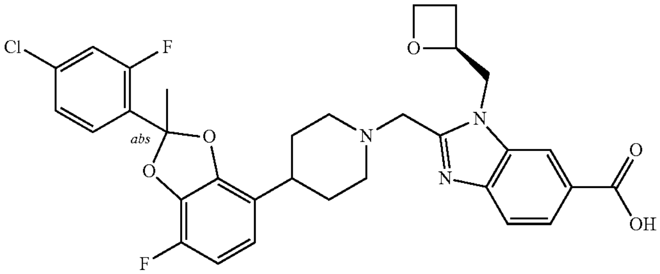 DIAST-1 | 2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid, DIAST-1 [footnote 10 in Table 2] |
| 97 | 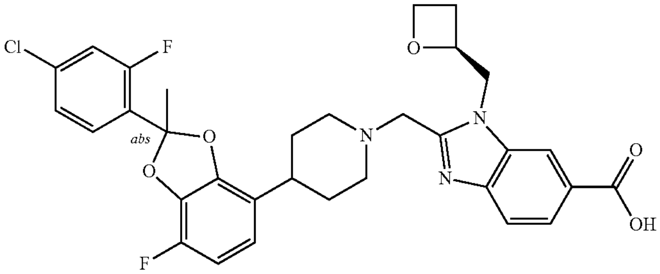 DIAST-2 | 2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid, DIAST-2 [footnote 10 in Table 2] |

TABLE 1-continued

| Ex. No. | Structure | IUPAC Name |
|---|---|---|
| 98 | 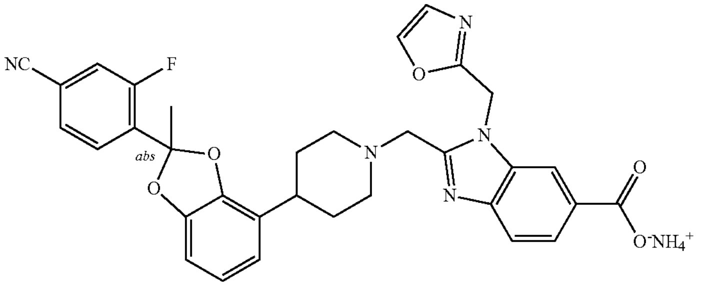 ENT-X2 | ammonium 2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylate, ENT-X2 [from C83; footnote 12 in Table 2] |
| 99 | 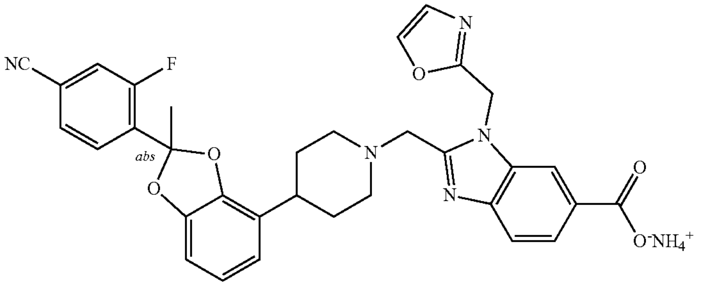 ENT-X1 | ammonium 2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylate, ENT-X1 [from C82; footnote 12 in Table 2] |
| 100 | 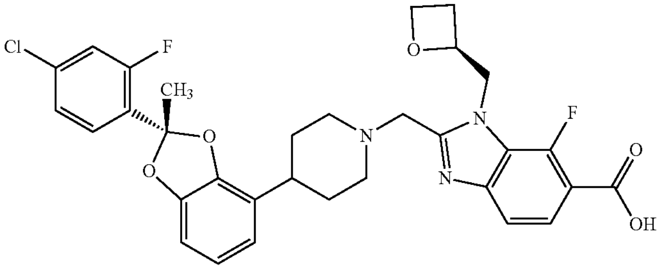 •1/2 citric acid | 2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid, hemicitrate salt [from P3] |
| 101 | 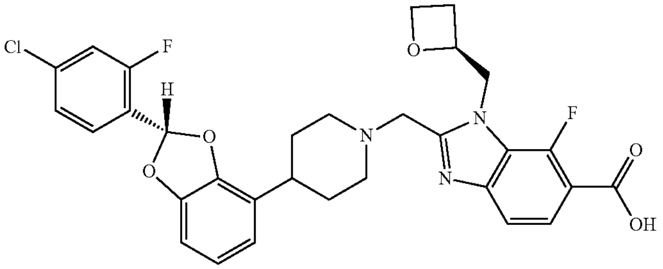 •1/2 citric acid | 2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid, hemicitrate salt [from C48] |

Structure and IUPAC name for Examples 19-102

TABLE 1-continued

| Structure and IUPAC name for Examples 19-102 | | |
|---|---|---|
| Ex. No. | Structure | IUPAC Name |
| 102 | 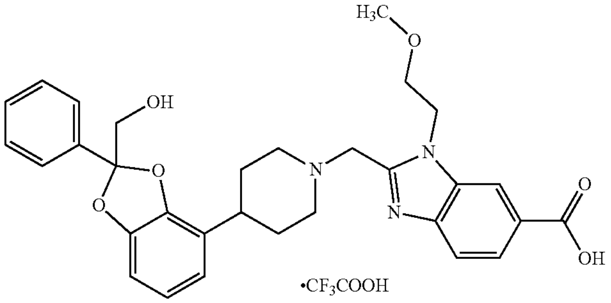 [SMILES: COCCn1c(CN2CCC(c3cccc4c3OC(CO)(c3ccccc3)O4)CC2)nc2ccc(C(=O)O)cc21 ; "·CF3COOH"] •$CF_3COOH$ | 2-({4-[2-(hydroxymethyl)-2-phenyl-1,3-benzodioxol-4-yl]piperidin-1-yl}methyl)-1-(2-methoxyethyl)-1H-benzimidazole-6-carboxylic acid, trifluoroacetate salt |

TABLE 2

Method of preparation and physicochemical data for Examples 19-102.

| Ex. No. | Method | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|
| 19 | Examples 15 and 16; C4, P12 | 8.39 (br s, 1H), 8.08 (d, J = 8.5 Hz, 1H), 7.81 (d, J = 8.6 Hz, 1H), 7.60 (dd, J = 8.3, 8.3 Hz, 1H), 7.28 (dd, J = 10.9, 2.1 Hz, 1H), 7.22 (dd, J = 8.4, 2.0 Hz, 1H), 6.83 (dd, J = 8.1, 8.1 Hz, 1H), 6.60 (d, J = 7.8 Hz, 1H), 6.55 (d, J = 8.4 Hz, 1H), 4.73 (s, 2H), 4.66 (t, J = 4.9 Hz, 2H), 3.77 (t, J = 4.8 Hz, 2H), 3.59-3.43 (m, 8H), 3.30 (s, 3H^^), 2.05 (s, 3H); 581.0 |
| 20 | Examples 4 and 5[1]; C43, P11 | 8.34-8.31 (m, 1H), 8.03 (dd, J = 8.5, 1.5 Hz, 1H), 7.78 (d, J = 8.6 Hz, 1H), 7.60 (dd, J = 8.0, 8.0 Hz, 1H), 7.36 (dd, J = 10.2, 1.9 Hz, 1H), 7.31 (dd, J = 8.4, 1.8 Hz, 1H), 7.25 (s, 1H), 6.90 (dd, component of ABC pattern, J = 8.9, 6.6 Hz, 1H), 6.86-6.80 (m, 2H), 4.79 (s, 2H), 4.60 (br t, J = 4.8 Hz, 2H), 3.95-3.85 (m, 2H), 3.74 (dd, J = 5.3, 4.2 Hz, 2H), 3.44-3.33 (m, 2H), 3.28 (s, 3H), 3.15-3.05 (m, 1H), 2.37-2.12 (m, 4H); 566.0◆ |
| 21 | Examples 4 and 5[1]; C43, P11 | 8.32 (dd, J = 1.6, 0.7 Hz, 1H), 8.03 (dd, J = 8.5, 1.5 Hz, 1H), 7.78 (dd, J = 8.5, 0.7 Hz, 1H), 7.60 (dd, J = 8.1, 7.9 Hz, 1H), 7.36 (dd, J = 10.2, 2.0 Hz, 1H), 7.31 (br dd, J = 8.3, 1.8 Hz, 1H), 7.25 (s, 1H), 6.90 (dd, component of ABC pattern, J = 8.8, 6.7 Hz, 1H), 6.87-6.80 (m, 2H), 4.79 (s, 2H), 4.60 (t, J = 4.8 Hz, 2H), 3.90 (br d, J = 12.3 Hz, 2H), 3.74 (dd, J = 5.3, 4.2 Hz, 2H), 3.38 (br dd, J = 12.6, 12.5 Hz, 2H), 3.28 (s, 3H), 3.10 (tt, J = 11.9, 4.0 Hz, 1H), 2.37-2.11 (m, 4H); 566.0◆ |
| 22 | Examples 1 and 2; P12, P5 | 8.37 (d, J = 1.5 Hz, 1H), 8.07 (dd, J = 8.5, 1.5 Hz, 1H), 7.79 (d, J = 8.6 Hz, 1H), 7.60-7.54 (m, 2H), 7.50-7.42 (m, 3H), 6.98 (s, 1H), 6.86 (dd, J = 8.1, 8.1 Hz, 1H), 6.61 (dd, J = 7.9, 0.9 Hz, 1H), 6.59 (dd, J = 8.4, 0.9 Hz, 1H), 4.73 (s, 2H), 4.64 (t, J = 4.8 Hz, 2H), 3.75 (dd, J = 5.4, 4.3 Hz, 2H), 3.61-3.44 (m, 8H), 3.28 (s, 3H); 515.1 |
| 23 | Examples 1 and 2; P12, P6 | 8.37 (br s, 1H), 8.07 (dd, J = 8.6, 1.5 Hz, 1H), 7.79 (d, J = 8.5 Hz, 1H), 7.61-7.54 (m, 2H), 7.51-7.42 (m, 3H), 6.98 (s, 1H), 6.86 (dd, J = 8.2, 8.1 Hz, 1H), 6.61 (br d, J = 8 Hz, 1H), 6.59 (br d, J = 8.5 Hz, 1H), 4.69 (s, 2H), 4.64 (t, J = 4.9 Hz, 2H), 3.75 (t, J = 4.9 Hz, 2H), 3.59-3.43 (m, 8H), 3.29 (s, 3H); 515.1 |
| 24 | Examples 4 and 5; C13, P11 | 8.33 (dd, J = 1.5, 0.6 Hz, 1H), 8.03 (dd, J = 8.5, 1.5 Hz, 1H), 7.79 (dd, J = 8.5, 0.5 Hz, 1H), 7.62 (dd, J = 8.4, 8.3 Hz, 1H), 7.29 (dd, J = 10.9, 2.0 Hz, 1H), 7.22 (ddd, J = 8.4, 2.0, 0.7 Hz, 1H), 6.88-6.82 (m, 1H), 6.82-6.76 (m, 2H), 4.83 (s, 2H), 4.63 (t, J = 4.8 Hz, 2H), 3.98-3.88 (m, 2H), 3.75 (dd, J = 5.3, 4.2 Hz, 2H), 3.47-3.36 (m, 2H), 3.31 (s, 3H^^), 3.10 (tt, J = 12.0, 4.1 Hz, 1H), 2.36-2.10 (m, 4H), 2.05 (d, J = 1.0 Hz, 3H); 580.1◆ |

TABLE 2-continued

Method of preparation and physicochemical data for Examples 19-102.

| Ex. No. | Method | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|
| 25 | Examples 15 and 16[2]; C4, P17 | 8.51 (dd, J = 1.5, 0.7 Hz, 1H), 8.25 (dd, J = 8.6, 1.4 Hz, 1H), 7.79 (dd, J = 8.6, 0.7 Hz, 1H), 7.57 (dd, J = 8.3, 8.3 Hz, 1H), 7.25 (dd, J = 10.8, 2.0 Hz, 1H), 7.19 (ddd, J = 8.4, 2.0, 0.7 Hz, 1H), 6.80-6.73 (m, 1H), 6.55-6.50 (m, 2H), 4.9-4.73 (m, 2H^), 3.92-3.81 (m, 2H), 3.66-3.58 (m, 1H), 3.41-3.3 (m, 1H^^), 3.25 (s, 3H), 3.20-3.12 (m, 1H), 3.05-2.97 (m, 1H), 2.70-2.63 (m, 1H), 2.27-2.17 (m, 1H), 2.01 (d, J = 1.0 Hz, 3H), 1.84-1.71 (m, 2H), 1.67-1.58 (m, 2H), 1.31 (br d, J = 13 Hz, 1H); 592.3◆ |
| 26 | Examples 15 and 16[2]; C4, P17 | 8.53-8.50 (m, 1H), 8.26 (dd, J = 8.6, 1.4 Hz, 1H), 7.81 (d, J = 8.6 Hz, 1H), 7.55 (dd, J = 8.3, 8.2 Hz, 1H), 7.16-7.08 (m, 2H), 6.77 (dd, J = 8.3, 7.9 Hz, 1H), 6.52 (br d, J = 8.3 Hz, 1H), 6.51 (br d, J = 7.7 Hz, 1H), 4.9-4.74 (m, 2H^), 3.83 (t, J = 4.8 Hz, 2H), 3.68-3.60 (m, 1H), 3.54-3.46 (m, 1H), 3.18-3.09 (m, 1H), 3.14 (s, 3H), 3.09-3.01 (m, 1H), 2.69-2.62 (m, 1H), 2.31-2.21 (m, 1H), 2.01 (br s, 3H), 1.78-1.69 (m, 2H), 1.63-1.52 (m, 2H), 1.33-1.25 (m, 1H); 592.3◆ |
| 27 | Examples 4 and 5[3]; P11 | 8.32 (br s, 1H), 8.02 (dd, J = 8.5, 1.5 Hz, 1H), 7.82-7.76 (m, 2H), 7.73 (br d, J = 10.0 Hz, 1H), 7.67 (br d, J = 8.0 Hz, 1H), 7.35 (s, 1H), 6.96-6.89 (m, 1H), 6.88-6.83 (m, 2H), 4.76 (s, 2H), 4.61 (t, J = 4.8 Hz, 2H), 3.87 (br d, J = 12.3 Hz, 2H), 3.74 (t, J = 4.8 Hz, 2H), 3.39-3.3 (m, 2H^^), 3.29 (s, 3H), 3.15-3.05 (m, 1H), 2.35-2.10 (m, 4H); 557.1 |
| 28 | Example 11; P14 | 3.08 minutes[4]; 596 |
| 29 | Example 11; P14 | 3.12 minutes[4]; 556 |
| 30 | Example 11; P14 | 2.90 minutes[4]; 576 |
| 31 | Example 11; P14 | 2.92 minutes[4]; 546 |
| 32 | Example 11; P14 | 2.88 minutes[4]; 558 |
| 33 | Example 11; P14 | 3.04 minutes[4]; 562 |
| 34 | Example 11; P14 | 2.99 minutes[5]; 553 |
| 35 | Example 11; P14 | 2.92 minutes[4]; 576 |
| 36 | Example 11; P14 | 2.81 minutes[5]; 543 |
| 37 | Example 11; P14 | 2.90 minutes[4]; 558 |
| 38 | Example 11; P14 | 2.91 minutes[4]; 546 |
| 39 | Example 11; P14 | 2.89 minutes[4]; 558 |
| 40 | Example 11; P14 | 3.11 minutes[4]; 596 |
| 41 | Example 11; P14 | 2.97 minutes[4]; 564 |
| 42 | Example 11; P14 | 2.40 minutes[5]; 543 |
| 43 | Example 12; P10 | 2.70 minutes[4]; 621 |
| 44 | Example 12; P10 | 2.49 minutes[4]; 635 |
| 45 | Example 12; P10 | 2.79 minutes[4]; 613 |
| 46 | Example 12; P10 | 2.71 minutes[4]; 635 |
| 47 | Example 12; P10 | 2.85 minutes[4]; 657 |
| 48 | Example 12; P10 | 2.71 minutes[4]; 633 |
| 49 | Example 12; P10 | 2.66 minutes[4]; 607 |

TABLE 2-continued

| Method of preparation and physicochemical data for Examples 19-102. | | |
|---|---|---|
| Ex. No. | Method | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| 50 | Example 12; P10 | 2.43 minutes[4]; 616 |
| 51 | Example 12; P10 | 2.74 minutes[4]; 630 |
| 52 | Example 12; P10 | 2.73 minutes[4]; 593 |
| 53 | Example 12; P10 | 2.79 minutes[4]; 616 |
| 54 | Example 12; P10 | 2.67 minutes[4]; 631 |
| 55 | Example 12; P10 | 2.44 minutes[4]; 630 |
| 56 | Example 12; P10 | 2.77 minutes[4]; 606 |
| 57 | Example 12; P10 | 2.72 minutes[4]; 617 |
| 58 | Example 12; P10 | 2.78 minutes[4]; 603 |
| 59 | Example 12; P10 | 2.82 minutes[4]; 621 |
| 60 | Example 12; P10 | 2.74 minutes[4]; 631 |
| 61 | Example 12; P10 | 2.76 minutes[4]; 592 |
| 62 | Example 12; P10 | 2.45 minutes[4]; 630 |
| 63 | Example 12; P10 | 2.78 minutes[4]; 617 |
| 64 | Example 12; P10 | 2.84 minutes[4]; 606 |
| 65 | Example 12; P10 | 2.56 minutes[4]; 613 |
| 66 | Example 12; P10 | 2.75 minutes[4]; 607 |
| 67 | Example 12; P10 | 2.48 minutes[4]; 619 |
| 68 | Example 12; P10 | 2.75 minutes[4]; 646 |
| 69 | Example 12; P10 | 2.73 minutes[4]; 603 |
| 70 | Example 12; P10 | 2.86 minutes[5]; 661 |
| 71 | Example 12; P10 | 2.77 minutes[4]; 657 |
| 72 | Example 12; P10 | 2.79 minutes[4]; 606 |
| 73 | Example 12; P10 | 2.70 minutes[4]; 602 |
| 74 | Example 12; P10 | 2.45 minutes[4]; 616 |
| 75 | Example 13; P10 | 2.92 minutes[4]; 566 |
| 76 | Example 13; P10 | 2.99 minutes[4]; 631 |
| 77 | Example 13; P10 | 2.94 minutes[4]; 616 |
| 78 | Example 13; P10 | 3.08 minutes[5]; 617 |
| 79 | Example 13; P10 | 3.09 minutes[4]; 606 |
| 80 | Example 13; P10 | 3.02 minutes[4]; 603 |
| 81 | Example 13; P10 | 3.10 minutes[5]; 604 |
| 82 | Example 11; P14 | 2.87 minutes[4]; 528 |
| 83 | Example 11; P14 | 3.00 minutes[4]; 592 |
| 84 | Example 11; P14 | 2.99 minutes[4]; 542 |
| 85 | Example 11; P14 | 2.98 minutes[4]; 542 |
| 86 | Example 11; P14 | 2.97 minutes[4]; 562 |

TABLE 2-continued

| Method of preparation and physicochemical data for Examples 19-102. | | |
|---|---|---|
| Ex. No. | Method | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| 87 | Example 11; P14 | 2.97 minutes[5]; 553 |
| 88 | Example 11; P14 | 2.90 minutes[4]; 542 |
| 89 | Examples 4 and 5[6,7]; P11 | 8.63 (ddd, J = 4.9, 1.8, 0.9 Hz, 1H), 8.34 (dd, J = 1.6, 0.7 Hz, 1H), 8.03 (dd, J = 8.5, 1.5 Hz, 1H), 7.90 (ddd, J = 7.8, 7.8, 1.7 Hz, 1H), 7.80 (dd, J = 8.5, 0.7 Hz, 1H), 7.74 (ddd, J = 7.9, 1.1, 1.0 Hz, 1H), 7.45 (ddd, J = 7.6, 4.9, 1.2 Hz, 1H), 6.88-6.83 (m, 1H), 6.83-6.76 (m, 2H), 4.83 (s, 2H), 4.63 (t, J = 4.8 Hz, 2H), 3.99-3.88 (m, 2H), 3.75 (dd, J = 5.3, 4.2 Hz, 2H), 3.45-3.34 (m, 2H), 3.31 (s, 3H), 3.15-3.03 (m, 1H), 2.41-2.20 (m, 2H), 2.19-2.08 (m, 2H), 2.05 (5, 3H); 529.3 |
| 90 | Examples 4 and 5[6,7]; P11 | 8.63 (ddd, J = 4.9, 1.8, 0.9 Hz, 1H), 8.34 (dd, J = 1.6, 0.7 Hz, 1H), 8.04 (dd, J = 8.5, 1.5 Hz, 1H), 7.90 (ddd, J = 7.8, 7.8, 1.7 Hz, 1H), 7.80 (dd, J = 8.5, 0.7 Hz, 1H), 7.73 (ddd, J = 8.0, 1.1, 1.0 Hz, 1H), 7.45 (ddd, J = 7.6, 4.9, 1.2 Hz, 1H), 6.88-6.83 (m, 1H), 6.83-6.75 (m, 2H), 4.83 (s, 2H), 4.63 (t, J = 4.9 Hz, 2H), 3.98-3.88 (m, 2H), 3.75 (t, J = 4.8 Hz, 2H), 3.44-3.34 (m, 2H), 3.32 (s, 3H^^), 3.15-3.03 (m, 1H), 2.40-2.19 (m, 2H), 2.18-2.08 (m, 2H), 2.05 (s, 3H); 529.3 |
| 91 | Examples 6 and 7; P8, P11 | 8.59 (d, J = 2.4 Hz, 1H), 8.26 (d, J = 1.4 Hz, 1H), 7.96 (dd, J = 8.5, 1.5 Hz, 1H), 7.87 (dd, J = 8.5, 2.5 Hz, 1H), 7.68-7.61 (m, 2H), 6.83-6.75 (m, 1H), 6.75-6.67 (m, 2H), 4.67 (t, J = 5.2 Hz, 2H), 4.00 (5, 2H), 3.82 (t, J = 5.1 Hz, 2H), 3.29 (s, 3H), 3.13-3.05 (m, 2H), 2.81-2.70 (m, 1H), 2.45-2.34 (m, 2H), 2.01 (s, 3H), 1.98-1.77 (m, 4H); 563.3◆ |
| 92 | Examples 6 and 7; P9, P11 | 8.59 (d, J = 2.3 Hz, 1H), 8.26 (d, J = 1.4 Hz, 1H), 7.96 (dd, J = 8.5, 1.5 Hz, 1H), 7.87 (dd, J = 8.5, 2.5 Hz, 1H), 7.68-7.62 (m, 2H), 6.82-6.76 (m, 1H), 6.74-6.68 (m, 2H), 4.67 (t, J = 5.2 Hz, 2H), 4.00 (s, 2H), 3.82 (t, J = 5.1 Hz, 2H), 3.29 (s, 3H), 3.13-3.04 (m, 2H), 2.76 (tt, J = 11.8, 4 Hz, 1H), 2.45-2.34 (m, 2H), 2.01 (s, 3H), 1.97-1.78 (m, 4H); 563.3◆ |
| 93 | Examples 8 and 9[8]; P8, P11 | 8.97 (dd, J = 2.1, 0.9 Hz, 1H), 8.27-8.25 (m, 1H), 8.21 (dd, J = 8.2, 2.1 Hz, 1H), 7.96 (dd, J = 8.5, 1.5 Hz, 1H), 7.81 (dd, J = 8.3, 0.9 Hz, 1H), 7.64 (d, J = 8.6 Hz, 1H), 6.83-6.77 (m, 1H), 6.76-6.68 (m, 2H), 4.68 (t, J = 5.2 Hz, 2H), 3.95 (s, 2H), 3.83 (t, J = 5.2 Hz, 2H), 3.30 (s, 3H), 3.08-2.99 (m, 2H), 2.79-2.69 (m, 1H), 2.39-2.28 (m, 2H), 2.04 (s, 3H), 1.96-1.76 (m, 4H); 554.4 |
| 94 | Examples 8 and 9[8]; P9, P11 | 8.97 (dd, J = 2.2, 0.9 Hz, 1H), 8.26 (br s, 1H), 8.21 (dd, J = 8.2, 2.1 Hz, 1H), 7.96 (dd, J = 8.4, 1.4 Hz, 1H), 7.81 (dd, J = 8.2, 0.9 Hz, 1H), 7.64 (br d, J = 8.5 Hz, 1H), 6.83-6.77 (m, 1H), 6.76-6.69 (m, 2H), 4.68 (t, J = 5.3 Hz, 2H), 3.95 (s, 2H), 3.83 (t, J = 5.2 Hz, 2H), 3.30 (s, 3H), 3.08-2.99 (m, 2H), 2.79-2.69 (m, 1H), 2.39-2.28 (m, 2H), 2.04 (s, 3H), 1.96-1.76 (m, 4H); 554.4 |
| 95 | Example 10; P8, P15 | 8.61 (dd, J = 2.5, 0.7 Hz, 1H), 8.41 (s, 1H), 8.33 (dd, J = 1.6, 0.7 Hz, 1H), 7.97 (dd, J = 8.5, 1.5 Hz, 1H), 7.88 (dd, J = 8.5, 2.5 Hz, 1H), 7.66 (dd, J = 8.5, 0.6 Hz, 1H), 7.65 (dd, J = 8.5, 0.7 Hz, 1H), 6.82-6.77 (m, 1H), 6.76-6.69 (m, 2H), 5.32-5.24 (m, 1H), 4.9-4.83 (m, 1H^), 4.71 (dd, J = 15.4, 2.6 Hz, 1H), 4.65-4.58 (m, 1H), 4.48 (ddd, J = 9.2, 6.0, 5.9 Hz, 1H), 4.03 (AB quartet, $J_{AB}$ = 13.9 Hz, $\Delta\nu_{AB}$ = 49.7 Hz, 2H), 3.18-3.11 (m, 1H), 3.06-2.98 (m, 1H), 2.87-2.69 (m, 2H), 2.60-2.49 (m, 1H), 2.46-2.31 (m, 2H), 2.02 (s, 3H), 1.98-1.79 (m, 4H); 574.9◆ |

TABLE 2-continued

Method of preparation and physicochemical data for Examples 19-102.

| Ex. No. | Method | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|
| 96 | Examples 6 and 7[9,10]; P15 | 7.01 minutes[11]; 610.5♦ |
| 97 | Examples 6 and 7[9,10]; P15 | 7.89 minutes[11]; 610.5♦ |
| 98 | C54[12] | 8.25-8.23 (m, 1H), 8.00 (dd, J = 8.5, 1.5 Hz, 1H), 7.89 (d, J = 0.9 Hz, 1H), 7.76 (dd, J = 7.9, 7.6 Hz, 1H), 7.70 (d, J = 8.5 Hz, 1H), 7.64 (dd, J = 10.6, 1.5 Hz, 1H), 7.57 (dd, J = 8.0, 1.5 Hz, 1H), 7.14 (d, J = 0.9 Hz, 1H), 6.78 (dd, component of ABC pattern, J = 7.9, 7.8 Hz, 1H), 6.70 (dd, component of ABC pattern, J = 7.8, 1.2 Hz, 1H), 6.66 (br d, component of ABC pattern, J = 7.9 Hz, 1H), 5.94 (AB quartet, $J_{AB}$ = 17.2 Hz, $\Delta\nu_{AB}$ = 6.5 Hz, 2H), 3.96 (s, 2H), 3.02-2.92 (m, 2H), 2.74-2.63 (m, 1H), 2.31-2.21 (m, 2H), 2.05 (br s, 3H), 1.80-1.58 (m, 4H); 594.3 |
| 99 | C54[12] | 8.23 (d, J = 1.4 Hz, 1H), 8.00 (dd, J = 8.5, 1.5 Hz, 1H), 7.89 (d, J = 0.9 Hz, 1H), 7.76 (dd, J = 7.9, 7.6 Hz, 1H), 7.69 (d, J = 8.5 Hz, 1H), 7.64 (dd, J = 10.6, 1.5 Hz, 1H), 7.57 (dd, J = 8.1, 1.5 Hz, 1H), 7.14 (d, J = 0.9 Hz, 1H), 6.78 (dd, component of ABC pattern, J = 7.8, 7.8 Hz, 1H), 6.70 (dd, component of ABC pattern, J = 7.8, 1.2 Hz, 1H), 6.66 (br d, component of ABC pattern, J = 7.9 Hz, 1H), 5.94 (AB quartet, $J_{AB}$ = 17.1 Hz, ΔνAB = 6.6 Hz, 2H), 3.96 (s, 2H), 3.01-2.92 (m, 2H), 2.74-2.63 (m, 1H), 2.30-2.20 (m, 2H), 2.05 (br s, 3H), 1.80-1.58 (m, 4H); 594.3 |
| 100 | Example 7, free acid[13]; P3, C29 | characteristic peaks: 7.80 (dd, J = 8.5, 6.6 Hz, 1H), 7.59 (dd, J = 8.3, 8.3 Hz, 1H), 7.51 (d, J = 8.6 Hz, 1H), 7.28 (dd, J = 10.9, 2.0 Hz, 1H), 7.21 (br dd, J = 8.4, 2.0 Hz, 1H), 6.83-6.77 (m, 1H), 6.76-6.71 (m, 2H), 5.32-5.23 (m, 1H), 4.99 (dd, J = 15.5, 7.1 Hz, 1H), 4.79 (dd, J = 15.6, 2.8 Hz, 1H), 4.72-4.63 (m, 1H), 4.47 (ddd, J = 9.1, 6.0, 6.0 Hz, 1H), 4.31 (AB quartet, $J_{AB}$ = 14.4 Hz, $\Delta\nu_{AB}$ = 33.3 Hz, 2H), 3.40 (br d, J = 11.9 Hz, 1H), 2.92-2.65 (m, 4H), 2.82 (AB quartet, $J_{AB}$ = 15.5 Hz, $\Delta\nu_{AB}$ = 37.5 Hz, 2H), 2.61-2.49 (m, 1H), 2.13-1.87 (m, 4H), 2.04 (s, 3H); 610.0♦ |
| 101 | Example 5, free acid[13]; C48, C29 | characteristic peaks: 7.79 (dd, J = 8.5, 6.6 Hz, 1H), 7.57 (dd, J = 8.0, 8.0 Hz, 1H), 7.49 (d, J = 8.5 Hz, 1H), 7.35 (dd, J = 10.2, 1.9 Hz, 1H), 7.30 (br d, J = 8.4 Hz, 1H), 7.22 (s, 1H), 6.88-6.82 (m, 1H), 6.82-6.74 (m, 2H), 5.30-5.21 (m, 1H), 4.95 (dd, J = 15.4, 7.1 Hz, 1H), 4.77 (br d, J = 15.1 Hz, 1H), 4.67-4.59 (m, 1H), 4.44 (ddd, J = 9.1, 5.9, 5.9 Hz, 1H), 4.28 (AB quartet, $J_{AB}$ = 14.4 Hz, $\Delta\nu_{AB}$ = 31.7 Hz, 2H), 3.37 (br d, J = 12.3 Hz, 1H^^), 2.92-2.61 (m, 4H), 2.82 (AB quartet, $J_{AB}$ = 15.6 Hz, $\Delta\nu_{AB}$ = 37.1 Hz, 2H), 2.58-2.47 (m, 1H), 2.12-1.89 (m, 4H); 596.1♦ |

TABLE 2-continued

Method of preparation and physicochemical data for Examples 19-102.

| Ex. No. | Method | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|
| 102 | Examples 4 and 5[14]; P11 | 8.34 (dd, J = 1.6, 0.7 Hz, 1H), 8.04 (dd, J = 8.5, 1.5 Hz, 1H), 7.80 (dd, J = 8.5, 0.7 Hz, 1H), 7.66-7.60 (m, 2H), 7.46-7.36 (m, 3H), 6.84-6.76 (m, 2H), 6.74 (dd, J = 7.2, 2.0 Hz, 1H), 4.84 (s, 2H), 4.63 (t, J = 4.7 Hz, 2H), 4.01-3.91 (m, 4H), 3.76 (dd, J = 5.3, 4.2 Hz, 2H), 3.47-3.37 (m, 2H), 3.32 (s, 3H), 3.19-3.08 (m, 1H), 2.41-2.26 (m, 2H), 2.26-2.13 (m, 2H); 544.2 |

^area is assumed, peak is partially obscured by water peak

^^area is assumed, peak is partially obscured by solvent peak

♦chlorine isotope pattern observed

[1]The racemic methyl ester [methyl 2-({4-[2-(4-chloro-2-fluorophenyl)-1,3-benzodioxol-4-yl]piperidin-1-yl}methyl)-1-(2-methoxyethyl)-1H-benzimidazole-6-carboxylate] was separated into its component enantiomers via SFC [Column: Chiral Technologies ChiralCel OD-H, 5 μm; Mobile phase: 7:3 carbon dioxide/(2-propanol containing 0.1% ammonium hydroxide)]. The first-eluting enantiomer, ENT-1 (C76), was used in the synthesis of Example 21, and the second-eluting enantiomer, ENT-2 (C77), was converted to Example 20. C76 retention time: 5.72 minutes (Column: Chiral Technologies Chiralpak OD-3, 4.6 × 150 mm, 3 μm; Mobile phase A: carbon dioxide; Mobile phase B: 2-propanol containing 0.05% diethylamine; Gradient: 5% to 40% B over 5.5 minutes, then held at 40% B for 3.0 minutes; Flow rate: 2.5 mL/minute). C77 retention time: 6.01 minutes (Analytical SFC conditions identical to those used for C76).

[2]The methyl ester (methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate) derived from coupling of C4 and P17 was separated into its component stereoisomers at the dioxolane via SFC [Column: Chiral Technologies Chiralpak AD, 10 μm; Mobile phase: 65:35 carbon dioxide/(ethanol containing 0.1% ammonium hydroxide)]. The first-eluting isomer, DIAST-1 (C78), was converted to Example 26; by examination of $^1H$ NMR data, this material was the enantiomer of Example 15. The second-eluting isomer, DIAST-2 (C79), was used in the synthesis of Example 25; by examination of $^1H$ NMR data, this material was the enantiomer of Example 16. C78 retention time: 3.60 minutes (Column: Chiral Technologies Chiralpak AD-3, 4.6 × 100 mm, 3 μm; Mobile phase A: carbon dioxide; Mobile phase B: ethanol containing 0.05% diethylamine; Gradient: 5% to 40% B over 4.5 minutes, then held at 40% B for 2.5 minutes; Flow rate: 2.8 mL/minute). C79 retention time: 3.82 minutes (Analytical SFC conditions identical to those used for C78).

[3]4-(4-Bromo-1,3-benzodioxol-2-yl)-3-fluorobenzonitrile was prepared via treatment of 3-fluoro-4-formylbenzonitrile and 3-bromobenzene-1,2-diol with p-toluenesulfonic acid in toluene, with removal of water using a Dean-Stark apparatus. This material was then reacted with [1-(tert-butoxycarbonyl)piperidin-4-yl](iodo)zinc in the presence of [1,1'-bis(diphenylphosphino)ferrocene]dichloropalladium(II) and copper(i) iodide, followed by ester cleavage using p-toluene- sulfonic acid, to afford the requisite 3-fluoro-4-[4-(piperidin-4-yl)-1,3-benzodioxol-2-yl]benzonitrile.

[4]Conditions for analytical HPLC. Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.

[5]Conditions for analytical HPLC. Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

[6]tert-Butyl 4-[2-methyl-2-(pyridin-2-yl)-1,3-benzodioxol-4-yl]-3,6-dihydropyridine-1(2H)-carboxylate was synthesized from 3-bromobenzene-1,2-diol and 2-ethynylpyridine using the procedure described for synthesis of C12 in Preparation P7. Subsequent hydrogenation over palladium on carbon, followed by treatment with hydrogen chloride in ethyl acetate, afforded the requisite 2-[2-methyl-4-(piperidin-4-yl)-1,3-benzodioxol-2-yl]pyridine, hydrochloride salt.

[7]The racemic methyl ester [methyl 1-(2-methoxyethyl)-2-({4-[2-methyl-2-(pyridin-2-yl)-1,3-benzodioxol-4-yl]piperidin-1-yl}methyl)-1H-benzimidazole-6-carboxylate] was separated into its component enantiomers via SFC [Column: Chiral Technologies Chiralpak AD, 10 μm; Mobile phase: 65:35 carbon dioxide/(ethanol containing 0.1% ammonium hydroxide)]. The first-eluting enantiomer ENT-1 (C80) was used in the synthesis of Example 90, and the second-eluting enantiomer ENT-2 (C81) was converted to Example 89. C80 retention time: 4.11 minutes (Column: Chiral Technologies Chiralpak AD-3, 4.6 × 100 mm, 3 μm; Mobile phase A: carbon dioxide; Mobile phase B: ethanol containing 0.05% diethylamine; Gradient: 5% to 40% B over 4.5 minutes, then held at 40% B for 2.5 minutes; Flow rate: 2.8 mL/minute). C81 retention time: 4.62 minutes (Analytical SFC conditions identical to those used for C80).

[8]Conversion of P8 and P9 to the corresponding cyano-substituted derivatives was carried out using the method described for synthesis of P4 from P2 in Preparation P4.

[9]Treatment of 1-(4-chloro-2-fluorophenyl)ethanone with trimethyl orthoformate and p-toluene-sulfonic acid provided 4-chloro-1-(1,1-dimethoxyethyl)-2-fluorobenzene, which was reacted with 3-bromo-6-fluorobenzene-1,2-diol in the presence of p-toluenesulfonic acid to afford 4-bromo-2-(4-chloro-2-fluorophenyl)-7-fluoro-2-methyl-1,3-benzodioxole. This material was converted to the requisite tert-butyl 4-[2-(4-chloro-2-fluorophenyl)-7-fluoro-2-methyl-1,3-benzodioxol-4- yl]piperidine-1-carboxylate using the method described in Preparation P1 for synthesis of P1 from C2.

[10]Separation of the stereoisomers at the dioxolane in 96 and 97 was carried out using SFC [Column: Chiral Technologies Chiralpak IG, 5 μm; Mobile phase: 3:1 carbon dioxide/(2-propanol containing 0.2% ammonium hydroxide)]. The first-eluting isomer was designated as DIAST-1 (96) and the second-eluting isomer as DIAST-2 (97).

[11]Conditions for analytical SFC. Column: Chiral Technologies Chiralpak IG, 4.6 × 100 mm, 5 μm; Mobile phase: 7:3 carbon dioxide/(2-propanol containing 0.2% ammonium hydroxide); Flow rate: 1.5 mL/minute; Back pressure: 150 bar.

[12]tert-Butyl 2-(chloromethyl)-1-(1,3-oxazol-2-ylmethyl)-1H-benzimidazole-6-carboxylate was synthesized from tert-butyl 3-fluoro-4-nitrobenzoate and 1-(1,3-oxazol-2-yl)methanamine, using the method described for synthesis of P11. Subsequent reaction with C54 was carried out using triethylamine to afford ter-butyl 2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylate, which was separated into its component enantiomers using SFC [Column: Chiral Technologies ChiralCel OD-H, 5 μm; Mobile phase: 55:45 carbon dioxide/(ethanol containing 0.1% ammonium hydroxide)]. The first-eluting enantiomer ENT-1 (C82) was used in the synthesis of 99, and the second-eluting enantiomer ENT-2 (C83) was converted to 98. C82 retention time: 1.47 minutes (Column: Chiral Technologies Chiralpak OD-3, 4.6 × 50 mm, 3 μm; Mobile phase A: carbon dioxide; Mobile phase B: methanol containing 0.05% diethylamine; Gradient: 5% B for 0.2 minutes, then 5% to 40% B over 1.4 minutes, then held at 40% B for 1.05 minutes; Flow rate: 4 mL/minute). C83 retention time: 1.85 minutes (Analytical SFC conditions identical to those used for C82).

[13]Reaction of 1-bromo-2,3-difluoro-4-nitrobenzene with copper(I) cyanide in 1-methylpyrrolidin-2-one at elevated temperature provided 2,3-difluoro-4-nitrobenzonitrile, which was subjected to thionyl chloride and methanol to afford methyl 2,3-difluoro-4-nitrobenzoate. This material was converted, through use of C29, to the requisite methyl 2-(chloromethyl)-7-fluoro-1-[(2S)-oxetan-2-ylmethyl]-1H-benzimidazole-6-carboxylate, via the method described in Preparation P11 for synthesis of P11 from methyl 3-fluoro-4-nitrobenzoate.

[14]The requisite [2-phenyl-4-(piperidin-4-yl)-1,3-benzodioxol-2-yl]methanol was synthesized from 2-oxo-2-phenylethyl acetate, by analogy to the method described for synthesis of C13.

CHO GLP-1R Clone H6-Assay 1

GLP-1R-mediated agonist activity was determined with a cell-based functional assay utilizing an HTRF (Homogeneous Time-Resolved Fluorescence) cAMP detection kit (cAMP HI Range Assay Kit; CisBio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either standard or experimental sample.

The human GLP-1R coding sequence (NCBI Reference Sequence NP_002053.3, including naturally-occurring variant Gly168Ser) was subcloned into pcDNA3 (Invitrogen)

and a cell line stably expressing the receptor was isolated (designated Clone H6). Saturation binding analyses (filtration assay procedure) using $^{125}I$-GLP-$1_{7-36}$ (Perkin Elmer) showed that plasma membranes derived from this cell line express a high GLP-1R density ($K_d$: 0.4 nM, $B_{max}$: 1900 fmol/mg protein).

Cells were removed from cryopreservation, re-suspended in 40 mL of Dulbecco's Phosphate Buffered Saline (DPBS-Lonza Cat #17-512Q) and centrifuged at 800×g for 5 minutes at 22° C. The cell pellet was then re-suspended in 10 mL of growth medium [DMEM/F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100×L-Glutamine (Gibco Cat #25030-081) and 500 μg/mL Geneticin (G418) (Invitrogen #10131035)]. A 1 mL sample of the cell suspension in growth media was counted on a Becton Dickinson ViCell to determine cell viability and cell count per mL. The remaining cell suspension was then adjusted with growth media to deliver 2000 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment in 5% carbon dioxide.

Varying concentrations of each compound to be tested (in DMSO) were diluted in assay buffer (HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E) containing 100 μM 3-isobutyl-1-methylxanthin (IBMX; Sigma cat #15879). The final DMSO concentration is 1%.

After 48 hours, the growth media was removed from the assay plate wells, and the cells were treated with 20 μL of the serially diluted compound in assay buffer for 30 minutes at 37° C. in a humidified environment in 5% carbon dioxide. Following the 30 minute incubation, 10 μL of labeled d2 cAMP and 10 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-$1_{7-36}$ (1 PM) included on each plate. $EC_{50}$ determinations were made from agonist dose-response curves analyzed with a curve fitting program using a 4-parameter logistic dose response equation.

CHO GLP-1R Clone C6-Assay 2

GLP-1R-mediated agonist activity was determined with a cell-based functional assay utilizing an HTRF (Homogeneous Time-Resolved Fluorescence) cAMP detection kit (cAMP HI Range Assay Kit; Cis Bio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either a standard or an experimental sample.

The human GLP-1R coding sequence (NCBI Reference Sequence NP_002053.3, including naturally-occurring variant Leu260Phe) was subcloned into pcDNA5-FRT-TO and a clonal CHO cell line stably expressing a low receptor density was isolated using the Flp-In™ T-Rex™ System, as described by the manufacturer (ThermoFisher). Saturation binding analyses (filtration assay procedure) using $^{125}I$-GLP-1 (Perkin Elmer) showed that plasma membranes derived from this cell line (designated clone C6) express a low GLP-1R density ($K_d$: 0.3 nM, $B_{max}$: 240 fmol/mg protein), relative to the clone H6 cell line.

Cells were removed from cryopreservation, re-suspended in 40 mL of Dulbecco's Phosphate Buffered Saline (DPBS-Lonza Cat #17-512Q) and centrifuged at 800×g for 5 minutes at 22° C. The DPBS was aspirated, and the cell pellet was re-suspended in 10 mL of complete growth medium (DMEM:F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100×L-Glutamine (Gibco Cat #25030-081), 700 μg/mL Hygromycin (Invitrogen Cat #10687010) and 15 μg/mL Blasticidin (Gibco Cat #R21001). A 1 mL sample of the cell suspension in growth media was counted on a Becton Dickinson ViCell to determine cell viability and cell count per mL. The remaining cell suspension was then adjusted with growth media to deliver 1600 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment (95% $O_2$, 5% $CO_2$)

Varying concentrations of each compound to be tested (in DMSO) were diluted in assay buffer [HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E)] containing 100 μM 3-isobutyl-1-methylxanthin (IBMX; Sigma cat #15879). The final DMSO concentration in the compound/assay buffer mixture is 1%.

After 48 hours, the growth media was removed from the assay plate wells, and the cells were treated with 20 μL of the serially diluted compound in assay buffer for 30 minutes at 37° C. in a humidified environment (95% $O_2$, 5% $CO_2$). Following the 30 minute incubation, 10 μL of labeled d2 cAMP and 10 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1 (1 μM) included on each plate. $EC_{50}$ determinations were made from agonist dose response curves analyzed with a curve fitting program using a 4-parameter logistic dose response equation.

In Table 3, assay data are presented to two (2) significant figures as the geometric mean ($EC_{50}$s) and arithmetic mean (Emax) based on the number of replicates listed (Number). A blank cell means there was no data for that Example or the Emax was not calculated.

TABLE 3

Biological activity for Examples 1-102.

| Ex. No. | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| 1 | 880 | 99 | 3 | >20000 | | 1 |
| 2* | 6.6 | 81 | 5 | 260 | 100 | 4 |
| 3 | 1.3 | 94 | 3 | 45 | 120 | 3 |
| 4 | 1600 | 87 | 3 | >20000 | | 1 |
| 5** | 1.3 | 89 | 6 | 23 | 97 | 7 |
| 6 | 140 | 89 | 7 | 2400 | 89 | 5 |
| 7** | 0.26 | 98 | 3 | 3.1 | 93 | 12 |
| 8*** | 0.30 | 92 | 6 | 3.6 | 91 | 6 |
| 9*** | 73 | 88 | 9 | 1600 | 90 | 4 |
| 10**** | 0.96 | 99 | 5 | 17 | 96 | 8 |
| 11 | 290 | 78 | 3 | | | |
| 12 | 29 | 83 | 3 | 690 | 92 | 3 |
| 13 | 4.5 | 95 | 3 | 38 | 110 | 3 |
| 14 | 7 | 95 | 6 | 79 | 85 | 5 |
| 15 | >18000 | 100 | 3 | >20000 | | 1 |
| 16 | 7.7 | 90 | 3 | 120 | 64 | 3 |
| 17 | 0.079 | 97 | 3 | 1.1 | 96 | 4 |
| 18 | 210 | 97 | 3 | 1000 | 87 | 3 |
| 19 | 1.2 | 87 | 3 | 25 | 100 | 3 |
| 20 | 17 | 85 | 3 | 270 | 100 | 3 |
| 21 | >20000 | | 1 | >20000 | | 1 |
| 22 | >20000 | | 1 | | | |
| 23 | 680 | 76 | 3 | | | |
| 24 | 1.4 | 82 | 3 | 49 | 110 | 3 |
| 25 | >20000 | | 1 | >20000 | | 1 |
| 26 | >20000 | | 1 | >20000 | | 1 |
| 27 | 61 | 98 | 3 | 1000 | 100 | 3 |
| 28 | 480 | 87 | 3 | | | |
| 29 | 5.3 | 87 | 4 | 150 | 93 | 3 |
| 30 | 45 | 86 | 4 | 1100 | 77 | 4 |
| 31 | 190 | 88 | 3 | 1900 | 65 | 3 |
| 32 | 18 | 86 | 3 | 450 | 87 | 3 |
| 33 | 2.6 | 85 | 3 | 100 | 86 | 3 |
| 34 | 7.8 | 98 | 3 | 110 | 88 | 3 |
| 35 | 6.6 | 86 | 3 | 170 | 89 | 3 |
| 36 | 760 | 85 | 3 | | | |
| 37 | 81 | 100 | 3 | 1000 | 83 | 3 |
| 38 | 10 | 87 | 3 | 240 | 73 | 3 |
| 39 | 200 | 83 | 3 | | | |
| 40 | 14 | 88 | 3 | 130 | 73 | 3 |
| 41 | 91 | 78 | 3 | 2000 | 74 | 2 |
| 42 | 120 | 93 | 3 | 1700 | 83 | 3 |
| 43 | 3.5 | 88 | 4 | 65 | 86 | 3 |
| 44 | 160 | 78 | 4 | | | |
| 45 | 9.9 | 81 | 3 | 220 | 79 | 3 |
| 46 | 5.2 | 95 | 4 | 57 | 96 | 3 |
| 47 | 42 | 75 | 3 | 1400 | 76 | 4 |
| 48 | 14 | 81 | 3 | 280 | 73 | 3 |
| 49 | 230 | 93 | 3 | | | |
| 50 | 12 | 87 | 4 | 140 | 92 | 4 |
| 51 | 19 | 80 | 3 | 280 | 81 | 3 |
| 52 | 32 | 85 | 3 | 570 | 80 | 3 |
| 53 | 3.1 | 87 | 3 | 52 | 84 | 4 |
| 54 | 18 | 82 | 3 | 160 | 64 | 3 |
| 55 | 74 | 81 | 3 | 1100 | 50 | 3 |
| 56 | 1.2 | 87 | 4 | 11 | 81 | 3 |
| 57 | 15 | 86 | 3 | 500 | 98 | 3 |
| 58 | 4 | 98 | 3 | 23 | 88 | 4 |
| 59 | 74 | 85 | 3 | 680 | 53 | 3 |
| 60 | 15 | 82 | 3 | 240 | 60 | 3 |
| 61 | 10 | 79 | 3 | 240 | 85 | 3 |
| 62 | 2.2 | 94 | 3 | 82 | 95 | 3 |
| 63 | 5.2 | 91 | 3 | 66 | 96 | 3 |
| 64 | 9.2 | 94 | 3 | 91 | 80 | 3 |
| 65 | 1.2 | 99 | 3 | 11 | 99 | 6 |
| 66 | 51 | 82 | 3 | 850 | 74 | 3 |
| 67 | 710 | 83 | 3 | | | |
| 68 | 73 | 89 | 3 | 1200 | 94 | 3 |
| 69 | 10 | 100 | 3 | 8.3 | 98 | 3 |
| 70 | 2.8 | 100 | 4 | 97 | 100 | 4 |
| 71 | 6.8 | 80 | 4 | 74 | 80 | 3 |
| 72 | 14 | 76 | 3 | 310 | 80 | 3 |
| 73 | 1.7 | 98 | 3 | 10 | 100 | 3 |

TABLE 3-continued

Biological activity for Examples 1-102.

| Ex. No. | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| 74 | 460 | 90 | 3 | | | |
| 75 | 65 | 82 | 3 | 1000 | 71 | 3 |
| 76 | 0.77 | 93 | 3 | 7.6 | 100 | 3 |
| 77 | 53 | 89 | 3 | 1700 | 92 | 3 |
| 78 | 4.5 | 89 | 4 | 78 | 100 | 3 |
| 79 | 1.4 | 85 | 3 | 21 | 85 | 3 |
| 80 | 1.1 | 87 | 3 | 6.9 | 96 | 4 |
| 81 | 29 | 110 | 3 | 54 | 110 | 3 |
| 82 | 47 | 83 | 3 | 1000 | 83 | 3 |
| 83 | 3.4 | 85 | 4 | 44 | 88 | 4 |
| 84 | 9.1 | 93 | 3 | 100 | 86 | 3 |
| 85 | 230 | 80 | 3 | | | |
| 86 | 24 | 91 | 3 | 410 | 100 | 3 |
| 87 | 570 | 89 | 3 | | | |
| 88 | 17 | 86 | 3 | 360 | 91 | 3 |
| 89 | 130 | 85 | 3 | 2900 | 87 | 3 |
| 90 | >20000 | | 1 | | | |
| 91 | 14000 | 100 | 3 | >20000 | | 1 |
| 92 | 4.2 | 90 | 5 | 72 | 83 | 3 |
| 93 | >6500 | 84 | 5 | >20000 | | 1 |
| 94 | 12 | 89 | 5 | 360 | 87 | 3 |
| 95**** | 220 | 77 | 3 | >13000 | | 5 |
| 96 | 1.1 | 85 | 3 | 11 | 93 | 4 |
| 97 | 14 | 86 | 3 | 140 | 93 | 4 |
| 98 | 50 | 97 | 3 | 440 | 95 | 3 |
| 99 | 2.8 | 99 | 4 | 5.4 | 91 | 2 |
| 100 | | | | 7.6 | 99 | 1 |
| 101 | | | | 19 | 74 | 1 |
| 102 | 600 | 86 | 4 | | | |

*Tested as ammonium and trifluoroacetate salts

**Tested as ammonium and 1,3-dihydroxy-2-(hydroxymethyl)propan-2-aminium (Tris) salts, and free acid

***Tested as ammonium salt and free acid

****Tested as formate salt and free acid

All patents, patent applications and references referred to herein are hereby incorporated by reference in their entirety.

What is claimed is:

1. A compound of Formula 1,

I

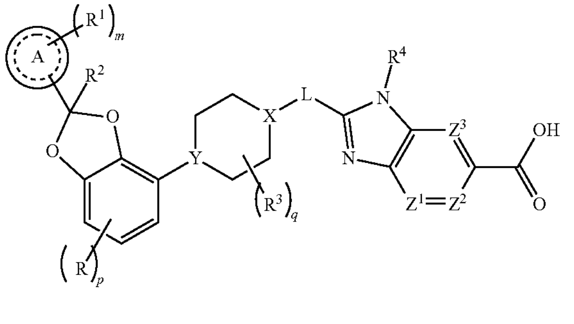

or a pharmaceutically acceptable salt thereof, wherein R is F, Cl, or —CN;

p is 0 or 1;

Ring A is phenyl or a 6-membered heteroaryl;

m is 0, 1, 2, or 3;

each $R^1$ is independently selected from halogen, —CN, —$C_{1-3}$alkyl, or $OC_{1-3}$alkyl, wherein the alkyl of $C_{1-3}$alkyl and $OC_{1-3}$alkyl is substituted with 0 to 3 F atoms;

$R^2$ is H or —$C_{1-3}$alkyl, wherein alkyl is substituted with 0 to 1 OH;

each $R^3$ is independently F, —OH, —CN, —$C_{1-3}$alkyl, $OC_{1-3}$alkyl, or —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;

q is 0, 1, or 2;

X-L is N—$CH_2$, $CHCH_2$, or cyclopropyl;

Y is CH or N;

$R^4$ is —$C_{1-3}$alkyl, —$C_{0-3}$alkylene-$C_{3-6}$cycloalkyl, —$C_{0-3}$ alkylene-$R^5$, or —$C_{1-3}$alkylene-$R^6$, wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^o$, —$SO_2$—$N(R^N)_2$, —N(C=(O)($R^N$)$_2$, —N(C=O)($R^N$), and —$N(R^N)_2$, and wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^o$, and —N($R^N$)2;

$R^5$ is a 4- to 6-membered heterocycloalkyl, wherein said heterocycloalkyl may be substituted with 0 to 2 substituents as valency allows independently selected from:

0 to 1 oxo (=O), 0 to 1 —CN, 0 to 2 F atoms, and 0 to 2 substituents independently selected from —$C_{1-3}$ alkyl and $OC_{1-3}$alkyl, wherein the alkyl of $C_{1-3}$alkyl and $OC_{1-3}$alkyl may be substituted with 0 to 3 substituents as valency allows independently selected from:

0 to 3 F atoms, 0 to 1 —CN, and 0 to 1 —$OR^o$;

$R^6$ is a 5- to 6-membered heteroaryl, wherein said heteroaryl may be substituted with 0 to 2 substituents as valency allows independently selected from:

0 to 2 halogens, 0 to 1 substituent selected from —$OR^o$ and —$N(R^N)_2$, and 0 to 2 —$C_{1-3}$alkyl, wherein the alkyl may be substituted with 0 to 3 substituents as valency allows independently selected from:

0 to 3 F atoms, and 0 to 1 —$OR^o$;

each $R^o$ is independently H, or —$C_{1-3}$alkyl, wherein $C_{1-3}$alkyl may be substituted with 0 to 3 F atoms;

each $R^N$ is independently H, or —$C_{1-3}$alkyl;

$Z^1$, $Z^2$, and $Z^3$ are each —$CR^z$, or one of $Z^1$, $Z^2$, and $Z^3$ is N and the other two are —$CR^z$; and each $R^z$ is independently H, F, Cl, or —$CH_3$.

2. The compound of claim 1, wherein the compound is a compound of Formula II

II

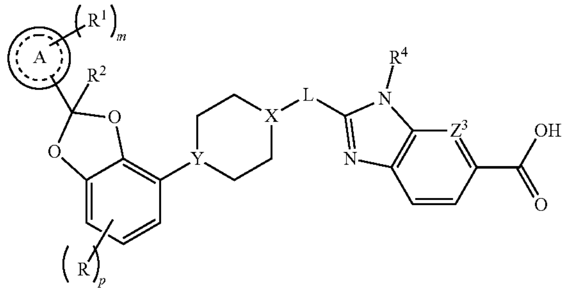

or a pharmaceutically acceptable salt thereof, wherein R is F;

p is 0 or 1;

Ring A is phenyl or pyridinyl;

m is 0, 1, or 2;

each $R^1$ is independently selected from halogen, —CN, —$C_{1-3}$alkyl, or —$OC_{1-3}$alkyl, wherein the alkyl of $C_{1-3}$alkyl and $OC_{1-3}$alkyl is substituted with 0 to 3 F atoms;

$R^2$ is H or $CH_3$;

X-L is N—$CH_2$, or cyclopropyl;

Y is CH or N;

$Z^3$ is —$CR^z$ or N; and $R^z$ is H, F, Cl, or —$CH_3$.

3. The compound of claim 2, wherein the compound is a compound of Formula III

III

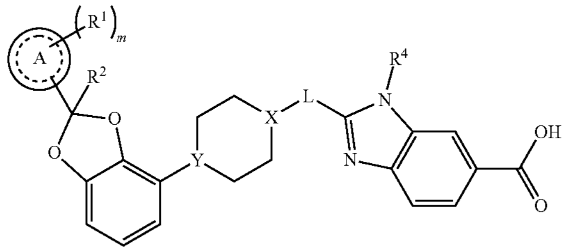

or a pharmaceutically acceptable salt thereof, wherein

Ring A is phenyl or pyridinyl;

m is 0, 1, or 2;

each $R^1$ is independently selected from F, Cl, or —CN;

$R^2$ is H or $CH_3$; and

Y is CH or N.

4. The compound of claim 3, wherein $R^4$ is —$CH_2$—$R^5$, wherein $R^5$ is the 4- to 5-membered heterocycloalkyl, wherein said heterocycloalkyl may be substituted with 0 to 2 substituents as valency allows independently selected from:

0 to 2 F atoms, and 0 to 1 substituent selected from —$OCH_3$ and —$CH_2OCH_3$; or a pharmaceutically acceptable salt thereof.

5. The compound of claim 3, wherein $R^4$ is —$CH_2$—$R^6$, wherein $R^6$ is the 5-membered heteroaryl, wherein said heteroaryl may be substituted with 0 to 2 substitutents as valency allows independently selected from:

0 to 2 halogens, wherein the halogen is independently selected from F and Cl, 0 to 1 —$OCH_3$, and 0 to 1 —$CH_3$, —$CH_2CH_3$, —$CF_3$, or —$CH_2CH_2OCH_3$; or a pharmaceutically acceptable salt thereof.

6. The compound of claim 3, wherein $R^2$ is H, or a pharmaceutically acceptable salt thereof.

7. The compound of claim 6, wherein the compound is 2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid; or 2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid, or a pharmaceutically acceptable salt thereof.

8. The compound of claim 3, wherein $R^2$ is $CH_3$, or a pharmaceutically acceptable salt thereof.

9. The compound of claim 8, wherein the compound is 2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yllmethyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-R2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-R2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-R2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-R2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-R2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-R2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-R2R)-2-(4-Cyano-2-fluorophenyl)-2-methyl-1,3-benzodioxol-4-yl]piperidin-1-yllmethyl)-1-[(2S)-oxetan-2-ylmethyl]-1H-benzimidazole-6-carboxylic acid;

2-({4-R2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; or 2-({4-R2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid, or a pharmaceutically acceptable salt thereof.

10. A crystal form (Form I) of anhydrous 1,3-dihydroxy-2-(hydroxymethyl)propan-2-aminium salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid having a powder X-ray diffraction pattern (CuKa radiation) comprising at least two characteristic peaks, in terms of 2θ, selected from at 3.7±0.2°; 7.3±0.2°; 8.5±0.2°; 10.1±0.2°; 14.7±0.2°; and 16.9±0.2°.

11. The crystal form of claim 10 having a powder X-ray diffraction pattern comprising peaks, at least three characteristic peaks, in terms of 2θ, selected from at 3.7±0.2°; 7.3±0.2°; 8.5±0.2°; 10.1±0.2°; 14.7±0.2°; and 16.9±0.2°.

12. A crystal form (Form A) of anhydrous 1,3-dihydroxy-2-(hydroxymethyl)propan-2-aminium salt of 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 having a powder X-ray diffraction pattern (CuKα radiation) comprising at least two characteristic peaks, in terms of 2θ, selected from at 7.7±0.2°; 15.2±0.2°; 15.7±0.2°; and 17.6±0.2°.

13. The crystal form of claim 12 having a powder X-ray diffraction pattern comprising at least three characteristic peaks, in terms of 2θ, selected from at 7.7±0.2°; 15.2±0.2°; 15.7±0.2°; and 17.6±0.2°.

14. A pharmaceutical composition comprising the compound of claim 1, or a pharmaceutically acceptable salt thereof, and a pharmaceutically acceptable excipient.

15. A pharmaceutical composition comprising the crystal form of claim 10 and a pharmaceutically acceptable excipient.

16. A pharmaceutical composition comprising the crystal form of claim 12 and a pharmaceutically acceptable excipient.

* * * * *